(12) United States Patent
Altier et al.

(10) Patent No.: US 7,205,453 B2
(45) Date of Patent: Apr. 17, 2007

(54) CROP PLANT CYSTATIN PROTEINASE INHIBITORS ENCODING NUCLEIC ACIDS AND METHODS OF USE

(75) Inventors: Daniel J. Altier, Granger, IA (US); Zhongmeng Bao, Urbandale, IA (US); Guihua Lu, Johnston, IA (US); Pedro A. Navarro Acevedo, Ankeny, IA (US); Vincent J. H. Sewalt, West Des Moines, IA (US); Carl R. Simmons, Des Moines, IA (US); Nasser Yalpani, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 278 days.

(21) Appl. No.: 10/947,979

(22) Filed: Sep. 23, 2004

(65) Prior Publication Data

US 2005/0102717 A1 May 12, 2005

Related U.S. Application Data

(60) Provisional application No. 60/505,948, filed on Sep. 25, 2003.

(51) Int. Cl.
*C12N 15/09* (2006.01)
*C12N 15/29* (2006.01)
*C12N 15/82* (2006.01)
*A01H 5/00* (2006.01)
*A01H 5/10* (2006.01)

(52) U.S. Cl. .................. 800/279; 536/23.6; 435/468; 435/430.1; 435/320.1; 800/278; 800/298; 800/295; 800/320; 800/317

(58) Field of Classification Search ............... 800/278, 800/279, 298, 295, 320.1, 317; 536/23.6; 435/468
See application file for complete search history.

(56) References Cited

U.S. PATENT DOCUMENTS 5,494,813 A 2/1996 Hepher et al.
6,703,224 B2 3/2004 Presnell et al.

FOREIGN PATENT DOCUMENTS

WO WO 97/32007 9/1997

OTHER PUBLICATIONS

Corre-Menguy. et. al, Triticum aestivum cystatin mRNA, Database EMBL-EBI, (2002), XP-002329517, Accession # AF364099.
Abe, et. al, Corn kernel cysteine proteinase inhibitor as a novel cystatin superfamily member of plant origin, Eur. J. Biochem, (1992), 209:933-937.
Belenghi, et. al, AtCYS1, a cystatin from *Arabidopsis thaliana*, suppresses hypersensitive cell death, Eur. J. Biochem., (2003), 270: 2593-2604.
Choi, et. al, Cholecystokinin mediates depression of feed intake in dairy cattle fed high fat diets, Domestic Animal Endocrinology, (2000), 19(3): 159-175.
Yamada, et. al, A Cysteine Protease from Maize Isolated in a Complex with Cystatin, Plant Cell Physiol., (2000), 41(2): 185-191.
Fox, et. al, Effects of Ostertagia ostertagi and omeprazole treatment on feed intake and gastrin-related responses in the calf, Veterinary Parasitology, (2002), 105: 285-301.
Schwartz, et. al, Treatment with an Oral Proteinase Inhibitor Slows Gastric Emptying and Acutely Reduces Glucose and Insulin Levels after a Liquid Meal in Type II Diabetic Patents, Diabetes Care, (1994), 17(4): 255-262.
Goke, et. al, Increased CCK-Response to Proteinase Inhibitor Feeding after Induction of Pancreatic Hypertropy in Rats, Pancreas, (1988), 3(5): 576-579.
Garlicki, et al, Cholecystokinin receptors and vagal nerves in control of food intake in rats, American Journal of Physiology, (1990), 258(1): E40-E45.
Elsasser, et al, Stimulation of pancreatic secretory process in the rat by low-molecular weight proteinase inhibitor, Cell Tissue Res, (1990), 262: 143-148.
Poulle, et. al, A Proteinase from Germinating Barley, Plant Physiol., (1988), 88: 1454-1460.
Muramatsu, et. al, A high-order structure of plant storage proprotein allows its second conversion by an asparagine-specific cysteine protease, a novel proteolytic enzyme, Eur. J. Biochem., (1993), 215: 123-132.
deBarros, et al., Cloning of a cDNA encoding a putative cysteine protease from germinating maize seeds, Plant Science, (1994), 99: 189-197.
Koehler, et al, A Major Gibberellic Acid-Induced Barley Aleurone Cysteine Proteinase Which Digests Hordein, Plant Physiol., (1990), 94: 251-258.
Drake, et al, Isolation and analysis of cDNAs encoding tomato cysteine proteases expressed during leaf senescence, Plant Molecular Biology, (1996), 30: 755-767.
D'Silva, et al, Activation of Cysteine Proteases in Cowpea Plants during the Hypersensitive Response—A Form of Programmed Cell Death, Experimental Cell Research, (1998), 245: 389-399.
Bjork, et. al, Differential changes in the association and dissociation rate constatns for binding of cystatins to target proteinases occurring on N-terminal truncation of the inhibitors indicate that the interaction mechanism varies with different enzymes, Biochem J., (1994), 299: 219-225.
Valpuesta, et. al., Up-regulation of a cysteine protease accompanies the ethylene-insensitive senescence of daylily (Hemerocallis) flowers, Plant Molecular Biology, (1995), 28: 575-582.

(Continued)

Primary Examiner—Medina A. Ibrahim

(57) ABSTRACT

Methods and compositions for modulating development and defense responses are provided. Nucleotide sequences encoding *maize*, soybean, wheat and rice cystatin proteins are provided. The sequences can be used in expression cassettes for modulating development, developmental pathways, and defense responses. Transformed plants, plant cells, tissues, and seed are also provided.

19 Claims, 1 Drawing Sheet

OTHER PUBLICATIONS

Orr, et. al., Inhibition of Diabrotica Larval Growth by a Multicystatin from Potato Tubers, J. Insect Physiol. (1994), 40(10): 893-900.

Misaka, et al., Soyacystatin, a novel cysteine proteinase inhibitor in soybean, is distinct in protein structure and gene organization from other cystatins of animal and plant origin, Eur. J. Biochem., (1996), 240: 609-614.

Kouzuma et. al., Purification, Characterization, and Sequencing of Two Cystein Proteinase Inhibitors, Sca and Scb, from Sunflower (*Helianthus annuus*) Seeds, J. Biochem, (1996), 119: 1106-1113.

Margis, et. al, Structural and Phylogenetic Relationships among Plant and Animal Cystatins, Archives of Biochemistry and Biophysics, (1998), 359(1): 24-30.

Matsumoto, et. al., Phytocystatins and Their Target Enzymes: From Molecular Biology to Practical Application: A Review, Journal of Food Biochemistry, (1998), 22: 287-299.

Urwin, et. al, Engineered oryzacystatin-I expressed in transgenic hairy roots confers resistance to *Globodera pallida*, The Plant Journal, (1995), 8(1): 121-131.

Koiwa, et al., Phage display selection can differentiate insecticidal activity of soybean cystatins, The Plant Journal, (1998), 14(3): 371-379.

Eason, et. al, Programmed cell death during flower senescene: isolation and characterization of cysteine proteinases from *Sandersonia aurantiaca*, Funct. Plant Biol., (2002), 29: 1055-1064.

Bown, et al, Characterisation of cysteine proteinases responsible for digestive proteolysis in guts of larval western corn rootworm (*Diabrotica virgifera*) by expression in the yeast *Pichia pastoris*, Insect Biochemistry and Molecular Biology, (2004), 34: 305-320.

Bouchard, et. al, Molecular interactions between an insect predator and its herbivore prey on transgenic potato expressing a cysteine proteinase inhibitor from rice, Molecular Ecology, (2003), 12(9): 2429-2437.

Mikola, et al., Electrophoretic and 'In Solution' Analyses of Endoproteinases Extracted from Germinated Oats, Journal of Cereal Science, (2000), 31(1): 15-23.

Ho, et al., Multiple Mode Regulation of a Cysteine Proteinase Gene Expression in Rice, Plant Physiol., (2000), 122(1): 57-66.

Yamada, et al., A Slow Maturation of a Cysteine Protease with a Granulin Domain in the Vacuoles of Senescing *Arabidopsis* Leaves, Plant Physiol., (2001), 127(4): 1626-1634.

Tiwari, et al., Oxidative Stress Increased Respiration and Generation of Reactive Oxygen Species, Resulting in ATP Depletion, Opening of Mitochondrial Permeability Transition, and Programmed Cell Death, Plant Physiol., (2002), 128(4): 1271-1281.

Chen, et al., Molecular Characterization of a Senescence-Associated Gene Encoding Cysteine Proteinase and its Gene Expression during Leaf Senescence in Sweet Potato, Plant Cell Physiol., (2002), 43(9): 984-991.

Gruis, et al., Redundant Proteolytic Mechanisms Process Seed Storage Proteins in the Absence of Seed-Type Members of the Vacuolar Processing Enzyme Family of Cysteine Proteases, Plant Cell, (2002), 14(11): 2863-2882.

Pechan, et al., A Unique 33-kD Cysteine Proteinase Accumulates in Response to Larval Feeding in Maize Genotypes Resistant to Fall Armyworm and Other Lepidoptera, Plant Cell, (2000), 12(7): 1031-1040.

Solomon, et al., The Involvement of Cysteine Proteases and Protease Inhibitor Genes in the Regulation of Programmed Cell Death in Plants, Plant Cell, (1999), 11(3): 431-443.

Wan, et al., Early stages of seed development in *Brassica napus*: a seed coat-specific cysteine proteinase associated with programmed cell death of the inner integument, Plant J, (2002), 30(1): 1-10.

Xu, et al., Expression of cysteine proteinase during development events associated with programmed cell death in brinjal, Plant J, (1999), 17(3): 321-327.

Pechan, et al., Characterization of three distinct cDNA clones encoding cysteine proteinases from maize (*Zea mays* L.) callus, Plant Molecular Biology, (1999), 40(1): 111-119.

Corre-Menguy, et al., Characterization of the expression of a wheat cystatin gene during caryopsis development, Plant Molecular Biology, (2002), 50(4-5): 687-698.

Young, et. al. Programmed cell death during endosperm development, Plant Molecular Biology, (2000), 44(3): 283-301.

Noh, et al., Identification of a promoter region responsible for the senescence-specific expression of SAG12, Plant Molecular Biology, (1999), 41(2): 181-194.

Huckelhoven, et al., Differential expression of putative cell death regulator genes in near-isogenic, resistant and susceptible barley lines during interaction with the powdery mildew fungus, Plant Molecular Biology, (2001), 47(6): 739-748.

Griffiths, et al., Sequencing, expression pattern and RFLP mapping of a senescence-enhanced cDNA from *Zea mays* with high homology to oryzain $↑^3$ aleurain, Plant Molecular Biology, (1997), 34(5): 815-821.

Ojima, et al., An extracellular insoluble inhibitor of cysteine proteinases in cell cultures and seeds of carrot, Plant Molecular Biology, (1997), 34(1): 99-109.

Kondo. et. al, Cloning and sequence analysis of the genomic DNA fragment encoding oryzacystatin, GENE, (1989), 81: 259-265.

Abe, et. al, Two Distinct Species of Corn Cystatin in Corn Kernels, Biosci. Biotech. Biochem., (1995), 59(4):756-758.

Blankenvoorde, et al, Cystatin and Cystatin-Derived Peptides Have Antibacterial Activity against the Pathogen *Porphyromonas gingivalis*, Biol. Chem., (1998), 379: 1371-1375.

Irie, et. al, Transgenic rice established to express corn cystatin exhibits strong inhibitory activity against insect gut proteinases, Plant Mol. Biol., (1996), 30: 149-157.

Chen, et al, Rice Cystatin: Bacterial Expression, Purification, Cysteine Proteinase Inhibitory Activity, and Insect Growth Suppressing Activity of a Truncated Form of the Protein, Protein Expression and Purification, (1992), 3:41-49.

Urwin, et. al, Characterization of two cDNAs encoding cysteine proteinases from the soybean cyst nematode *Heterodera glycines*, Parasitology, (1997), 114: 605-613.

Koiwa, et al, A plant defensive cystatin (soyacystatin) targets cathepsin L-like digestive cysteine proteinases (DvCALs) in the larval midgut of western corn rootworm (*Diabrotica virgifera virgifera*), FEBS Letters, (2000), 471: 67-70.

Fabrick, et. al, Effects of a potato cysteine proteinase inhibitor on midgut proteolytic enzyme activity and growth of the southern corn rootworm, *Diabrotica undecimpunctata howardi* (*Coleoptera: Chrysomelidae*), Insect Biochem. and Molec. Biol., (2002), 32: 405-415.

Delledonne, et al., Transformation of white poplar (*Populus alba* L.) with a novel *Arabidopsis thaliana* cysteine proteinase inhibitor and analysis of insect pest resistance, Molecular Breeding, (2001), 7: 35-42.

Duvick, et al, Purification and Characterization of a Novel Antimicrobial Peptide from Maize (*Zea mays* L.) Kernels, J Biol. Chem., (1992), 267(26): 18814-18820.

Pernas, et. al, Antifungal Activity of a Plant Cystatin, Molecular Plant-Microbe Interactions, (1999), 12(7): 624-627.

Soares-Costa, et. al, A sugarcane cystatin: recombinant expression, purification, and antifungal activity, Biochem and Biophys. Res. Commun, (2002), 296: 1194-1199.

Arai, et al, Plant Seed Cystatins and Their Target Enzymes of Endogenous and Exogenous Origin, J. Agric. Food Chem., (2002), 50: 6612-6617.

Brown. et. al, Friends and relations of the cystatin superfamily—new members and their evolution, Protein Science, (1997), 6: 5-12.

Kondo, et. al, Gene organization of oryzacystatin-II, a new cystatin superfamily member of plant origin, is closely related to that of oryzacystatin-I but different from those of animal cystatins, FEBS Letters, (1991), 278(1): 87-90.

Urwin, et. al, Enhanced transgenic plant resistance to nematodes by dual proteinase inhibitor constructs, Planta, (1998), 204: 472-479.

Urwin, et. al, Resistance to both cyst and root-knot nematodes conferred by transgenic *Arabidopsis* expressing a modified plant cystatin, Plant J, (1997), 12(2): 455-461.

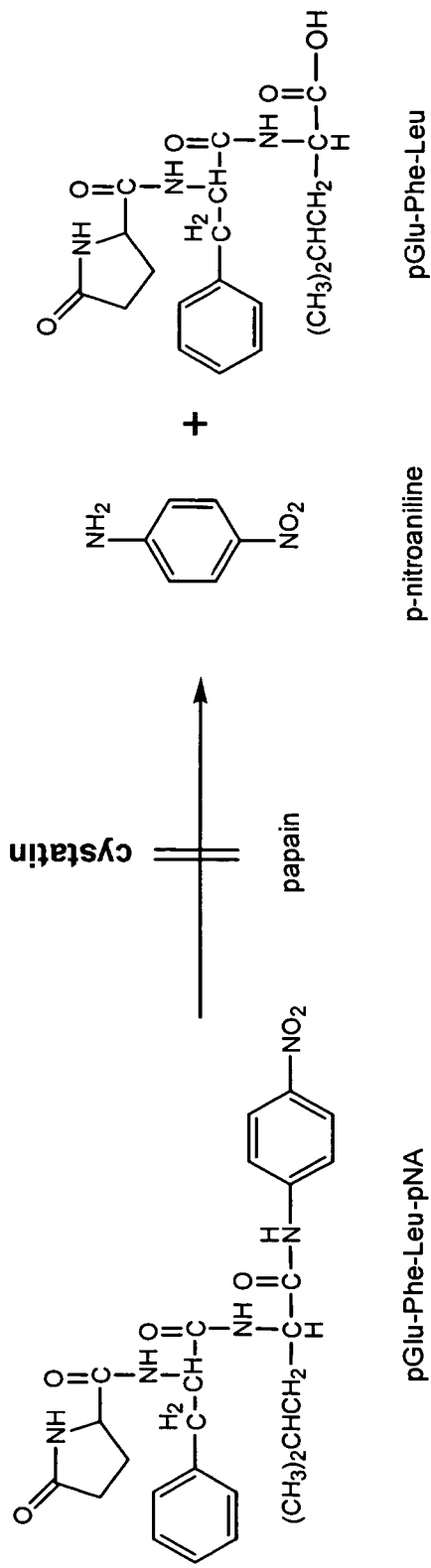
Figure 1. Reaction inhibited by cystatins.

US 7,205,453 B2

CROP PLANT CYSTATIN PROTEINASE INHIBITORS ENCODING NUCLEIC ACIDS AND METHODS OF USE

CROSS-REFERENCE TO RELATED APPLICATIONS

This application claims priority to and the benefit of U.S. Provisional Application No. 60/505,948, filed Sep. 25, 2003, which is hereby incorporated in its entirety by reference.

FIELD OF THE INVENTION

The invention relates to the field of the genetic manipulation of plants, particularly the modulation of gene activity and development in plants resulting in improvements in agronomic traits.

BACKGROUND OF THE INVENTION

Agronomic traits, such as disease resistance, nutritional quality, senescence and cell proliferation, have been subject to improvement attempts by various methods in the past. Often, improvements are attempted through plant breeding methods, which are often very expensive and of uncertain success. More recently, genetic modifications, such as those creating transgenic plants, have been used in attempts to reach these trait improvement goals. These approaches are meeting with varied success. No one strategy or gene has proven to be a panacea, although some show promise. Successful broad improvement of crop disease resistance, among other traits, will require multiple strategies. The addition of novel genes and methods is especially of value in the area of disease resistance, where pathogens are continually evolving and no single-gene method will have sustained success for long. Thus multiple genes and strategies for genetic improvement of agronomic traits are sought. This invention provides novel genes and methods of use through which agronomic traits can be improved.

SUMMARY OF THE INVENTION

Compositions and methods relating to disease resistance and other plant agronomic traits are provided. Particularly, the nucleotide and amino acid sequences for cystatin homologs from *maize*, soybean, wheat and rice are provided. The nucleotide sequences of the invention encode proteinase inhibitors of the cystatin cysteine proteinase inhibitor class.

The cystatin genes of the present invention may find use in enhancing agronomic traits of plants, including a wide variety of crop plants. The compositions and methods of the invention can be used to manipulate the plant pathogen defense system, the control of senescence, the control of cell proliferation and cell death, and the nutritional quality of plant seeds intended for human and animal consumption. The methods involve stably transforming a plant with a nucleotide sequence capable of modulating the production of one or more cystatins in the plant, operably linked with a promoter capable of driving expression of a gene in a plant cell.

Specifically, the present invention is directed to an isolated polynucleotide set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, and 75, isolated polynucleotides encoding the amino acid sequences set forth in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, and 76, 48, 50, 52, 54, 56, 58, 60, 62, 64, 66, 68, 70, 72, 74, and 76, isolated polypeptides having the sequences set forth in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, and 76, variant polynucleotide and amino acid sequences, DNA constructs comprising the sequences of the present invention, and host cells having incorporated such DNA constructs. Transformed plants, plant cells, and seeds, as well as methods for making such plants, plant cells, and seeds are additionally provided. It is recognized that a variety of promoters will be useful in the invention, the choice of which will depend in part upon the desired level of expression of the disclosed genes. It is recognized that the levels of expression can be controlled to modulate the levels of expression in the plant cell.

Further embodiments of the invention include methods of enhancing disease resistance of plants; methods of modulating the timing of plant maturation; methods of reducing cell death in plant tissue culture preparations; and methods of modulating protein digestibility and energy availability in plant products; wherein the preceding methods use plants transformed with the nucleotide sequences of the present invention.

BRIEF DESCRIPTION OF THE DRAWINGS

FIG. 1 shows the chemical reaction inhibited by the cystatins of the present invention.

DETAILED DESCRIPTION OF THE INVENTION

Units, prefixes, and symbols are denoted in their SI accepted form. Unless otherwise indicated, nucleic acids are written left to right in 5' to 3' orientation and amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms below are more fully defined by reference to the specification as a whole.

"Amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

"Encoding" or "encoded", with respect to a specified nucleic acid, means comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both *monocotyledonous* and *dicotyledonous* plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the *maize* preferred codon for a particular amino acid may be derived from known gene sequences from *maize*. *Maize* codon usage for 28 genes from *maize* plants is listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous," in reference to a nucleic acid, is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

"Host cell" means a cell which contains a vector and supports the replication and/or expression of the vector. Host cells may be prokaryotic cells such as *E. coli*, or eukaryotic cells such as yeast, insect, amphibian, or mammalian cells, excluding human cells. Preferably, host cells are monocotyledonous or dicotyledonous plant cells. A particularly preferred monocotyledonous plant cell is a *maize* host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as it is found in its naturally occurring environment. The isolated material optionally comprises material not found with it in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" and "polynucleotide" are used interchangeably and include reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

"Nucleic acid library" means a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989) (hereinafter Sambrook); and *Current Protocols in Molecular Biology*, F. M. Ausubel et al., Eds., Current Protocols, a joint venture between Greene Publishing Associates, Inc. and John Wiley & Sons, Inc. (1994) (hereinafter Ausubel).

As used herein, "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The classes of plants which can be used in the methods of the invention include both monocotyledonous and dicotyledonous plants. A particularly preferred plant is *Zea mays*.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is from a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue," "amino acid residue," and "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, 90% sequence identity, 95% or 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, and optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of a destabilizing agent such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C. for at least 4 hours, more preferably up to 12 hours or longer, and a final wash in 0.1×SSC at 60 to 65° C. for 30 minutes.

Specificity is typically a function of post-hybridization washes, the critical factors being the ionic strength and temperature of the final wash solution. For DNA-DNA hybrids, the $T_m$ (thermal melting point) can be approximated from the equation of Meinkoth and Wahl, *Anal. Biochem.*, 138:267–284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C.

Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and Ausubel.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in the introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, a "reference sequence" is a defined sequence used as a basis for sequence comparison with a polynucleotide/polypeptide of the present invention. A reference sequence may be a subset of, or the entirety of a specified sequence; for example, as a segment of a full-length cDNA or gene sequence, or the complete cDNA or gene sequence.

(b) As used herein, a "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotide or amino acid residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Thus, the determination of percent identity between any two sequences can be accomplished using a mathematical algorithm. Optimal alignment of sequences for comparison may be conducted by the local alignment algorithm of Smith and Waterman, *Adv. Appl. Math.* 2: 482 (1981); by the global alignment algorithm of Needleman and Wunsch, *J. Mol. Biol.* 48: 443 (1970); by the local alignment method of Pearson and Lipman, *Proc. Natl. Acad. Sci.* 85: 2444 (1988), by the algorithm of Karlin and Altschul (1990) *Proc Natl Acad Sci USA* 87: 2264, modified as in Karlin and Altschul (1993) *Proc Natl Acad Sci USA* 90: 5873–5877.; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package®, Genetics Computer Group (GCG®), (Accelrys, Inc., San Diego, Calif.). The CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Software for performing BLAST analyses is publicly available, e.g., through the National Center for Biotechnology Information website, located on the world wide web at the address ncbi.nlm.nih.gov, preceded by the www prefix. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877, 1993). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput Chem.*, 17:149–163, 1993) and XNU (Claverie and States, *Comput Chem.*, 17:191–201, 1993) low-complexity filters can be employed alone or in combination.

GAP can also be used to compare a polynucleotide or polypeptide of the present invention with a reference sequence. GAP uses the algorithm of Needleman and Wunsch (*J. Mol. Biol.* 48:443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each independently be: 0, 1, 2, 3, 4, 5, 6, 7, 8, 9, 10, 15, 20, 30, 40, 50, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89: 10915).

Unless otherwise stated, sequence identity/similarity values provided herein refer to the value obtained using the BLAST 2.0 suite of programs using default parameters (Altschul et al., *Nucleic Acids Res.* 25:3389–3402, 1997; Altschul et al., J. Mol. Bio. 215: 403–410, 1990) or to the value obtained using the GAP program using default parameters (see the Wisconsin Genetics Software Package, (Accelrys, Inc., San Diego, Calif.)).

(c) As used herein, "sequence identity" or "identity" in the context of two nucleic acid or polypeptide sequences includes reference to the residues in the two sequences which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) As used herein, "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

The present invention provides, inter alia, compositions and methods for modulating the total level of proteins of the present invention and/or altering their ratios in a plant. "Modulation" is intended to mean an increase or decrease in a particular character, quality, substance, or response.

The compositions comprise the nucleotide and amino acid sequence for 38 homologs of cysteine proteinases from *maize*, wheat, rice, and soybean, as presented in Table 1. These plant cystatin genes are characterized by their cysteine proteinase inhibitory activity. "Plant cystatin genes" is intended to mean genes that are structurally related to plant cystatins, also known as plant cysteine proteinases. As is well known in the art, "proteinases" are also called "proteases" and "peptidases" interchangeably. Thus, "cystatin-like" activity is intended to include the activity of peptides that inhibit the activity of cysteine proteinases in plants. In addition, at least some of these peptides also retain antifungal and/or antibacterial activity. The genes of the present invention are called cystatins after a structural classification of proteins (SCOP) classification system.

TABLE 1

The Cystatin Genes of the Present Invention

| Plant | Gene Name | Nucleotide SEQ ID NO: | Corresponding Peptide SEQ ID NO: | Full Length Nucleotide Sequence Length (nt) | Full Length Peptide Sequence Length (aa) |
|---|---|---|---|---|---|
| Maize | Zm-Cys1 | 1 | 2 | 786 | 135 |
| Maize | Zm-Cys3 | 3 | 4 | 915 | 134 |
| Maize | Zm-Cys4 | 5 | 6 | 915 | 134 |
| Maize | Zm-Cys5 | 7 | 8 | 1102 | 245 |
| Maize | Zm-Cys6 | 9 | 10 | 944 | 176 |
| Maize | Zm-Cys7 | 11 | 12 | 688 | 116 |
| Maize | Zm-Cys8 | 13 | 14 | 622 | 110 |
| Maize | Zm-Cys9 | 15 | 16 | 802 | 157 |
| Maize | Zm-Cys10 | 17 | 18 | 871 | 174 |
| Maize | Zm-Cys11 | 19 | 20 | 716 | 174 |
| Maize | Zm-Cys12 | 21 | 22 | 1102 | 245 |
| Maize | Zm-Cys13 | 23 | 24 | 761 | 127 |
| Maize | Zm-Cys14 | 25 | 26 | 749 | 150 |
| Soybean | Gm-Cys1 | 27 | 28 | 1140 | 245 |
| Soybean | Gm-Cys2 | 29 | 30 | 552 | 97 |
| Soybean | Gm-Cys3 | 31 | 32 | 484 | 103 |
| Soybean | Gm-Cys4 | 33 | 34 | 814 | 92 |
| Soybean | Gm-Cys5 | 35 | 36 | 504 | 112 |
| Soybean | Gm-Cys6 | 37 | 38 | 708 | 104 |
| Soybean | Gm-Cys7 | 39 | 40 | 505 | 97 |
| Soybean | Gm-Cys8 | 41 | 42 | 573 | 142 |
| Soybean | Gm-Cys9 | 43 | 44 | 473 | 114 |
| Rice | Os-Cys1 | 45 | 46 | 797 | 102 |
| Rice | Os-Cys2 | 47 | 48 | 1091 | 250 |
| Rice | Os-Cys3 | 49 | 50 | 744 | 108 |
| Rice | Os-Cys4 | 51 | 52 | 919 | 184 |
| Rice | Os-Cys5 | 53 | 54 | 798 | 151 |
| Rice | Os-Cys6 | 55 | 56 | 780 | 123 |
| Wheat | Ta-Cys1 | 57 | 58 | 626 | 142 |
| Wheat | Ta-Cys2 | 59 | 60 | 609 | 125 |
| Wheat | Ta-Cys3 | 61 | 62 | 557 | 128 |
| Wheat | Ta-Cys4 | 63 | 64 | 608 | 107 |
| Wheat | Ta-Cys6 | 65 | 66 | 622 | 107 |
| Wheat | Ta-Cys8 | 67 | 68 | 750 | 152 |
| Wheat | Ta-Cys9 | 69 | 70 | 801 | 152 |

TABLE 1-continued

The Cystatin Genes of the Present Invention

| Plant | Gene Name | Nucleotide SEQ ID NO: | Corresponding Peptide SEQ ID NO: | Full Length Nucleotide Sequence Length (nt) | Full Length Peptide Sequence Length (aa) |
|---|---|---|---|---|---|
| Wheat | Ta-Cys10 | 71 | 72 | 1149 | 243 |
| Wheat | Ta-Cys11 | 73 | 74 | 959 | 180 |
| Wheat | Ta-Cys13 | 75 | 76 | 518 | 127 |

Cystatins are a group of proteins which inhibit the activity of cysteine proteinases. The cystatins identified in vertebrates, insects, and plants have been classified into four groups, all belonging to a cystatin superfamily. Groups 1 through 3 are primarily vertebrate cystatin molecules, while group 4 comprises all the known plant cystatins. Group 1 cystatins are referred to as the stefins, single chain proteins with molecular weights of about 11 kDa, which contain no disulfide bonds or carbohydrates. The second group is referred to as the cystatins, and comprise single chain proteins of about 13 kDa, with two disulfide bonds located toward the carboxyl terminus. The kininogens, group 3, are the largest of the cystatins. They are characterized by having three Type 2-like domains, bound carbohydrates, and an additional polypeptide (kinin) unrelated to the cystatin segments.

The cysteine proteinase inhibitors of plant origin have been grouped into a fourth cystatin family, the "phytocystatins," or "plant cystatins" based on their sequence similarity and absence of disulfide bonds or cysteine residues. The phytocystatins are single polypeptide chains with molecular weights ranging from 10 to 16 kDa. Many share several reported conserved sequence motifs, including glycine residue(s) in the vicinity of the N-terminal region, a Gln-Xaa-Val-Xaa-Gly (SEQ ID NO: 77) motif in the first hairpin loop, and a Pro-Trp in the second hairpin loop. In addition, many also share a longer conserved sequence at a part of the N-terminal α-1 helix identified as Leu-Ala-Arg-[Phe or Tyr]-Ala-[Val or Ile]-Xaa-Xaa-Xaa-Asn (SEQ ID NO: 78) (Margis et al (1998) Arch Biochem Biophys 359(1): 24–30). After an examination of 32 members of the plant cystatin family, Margis et al. (supra) indicate this conserved region of the N-terminal α-1 helix can be rewritten as [Leu or Val or Ile]-[Ala or Gly or Thr]-[Arg or Lys or Glu]-[Phe or Tyr]-[Ala or Ser]-[Val or Ile]-Xaa-[Glu or Asp or Gln or Val]-[His or Tyr or Phe or Gln]-Asn (SEQ ID NO: 79).

Analysis of the 38 plant cystatins (see Table 62—multiple sequence alignment) of the present invention when compared with those analyzed by Margis et al. (supra) shows this N-terminal domain analysis to be generally consistent across the plant cystatin group. The sequences examined by Margis et at were primarily dicot sequences, only 5 of 32 sequences were monocot species. The present analysis (Table 62) shows some trends that are more particular to monocot species. In particular, Table 62 shows that the fourth residue of the N-terminal α-1 helix, shown by Margis et al. to be [Phe or Tyr], should be expanded to be [Phe or Tyr or Trp]. This is supported by the fact that all eight of the sequences of the instant invention not having a phenylalanine or tyrosine at position 4 had a tryptophan residue instead, and is further supported by the chemical similarity of tryptophan to both phenylalanine and tyrosine, which are often referred to as the aromatics group of amino acids. Similarly, in the first hairpin loop, while the Margis et al. analysis showed the consensus sequence of the final six amino acids to be Thr-Met-Tyr-Tyr-Ile-Thr (SEQ ID NO: 80), the present analysis showed this consensus to be Thr-Leu-Tyr-Tyr-Leu-Thr (SEQ ID NO: 81), in which quite often the Tyr-Tyr was replaced with His-His. The replacement of the methionine residue with a leucine and the isoleucine residue with a leucine is not surprising in view of the fact that methionine, leucine, isoleucine and valine are all in the same family and are considered to be conservative substitutes for each other.

Table 2 shows the sequences of the first and second hairpin loops and their locations in the cystatin sequences of the present invention. In particular, the highly conserved nature of the QXVXG (SEQ ID NO: 77) motif within the first hairpin loop is evident. Furthermore, the second hairpin loop, while less highly conserved than the first, generally presents a tryptophan residue at the end of the motif.

TABLE 2

First Hairpin Loop (FHL) and Second Hairpin Loop (SHL) Motifs of Plant Cystatin Genes

| Full Protein SEQ ID NO: | Gene Name | FHL Motif | FHL Motif SEQ ID NO: | FHL Start Amino Acid Position | SHL Motif | SHL Motif SEQ ID NO: | SHL Start Amino Acid Position |
|---|---|---|---|---|---|---|---|
| 28 | gm-cys1 | QVVAGTLHHLT | 82 | 93 | EAKVWVKPW | 120 | 116 |
| 30 | gm-cys2 | QVVSGTLYTIT | 83 | 49 | EAKVWEKSW | 121 | 72 |
| 32 | gm-cys3 | QVVSGTLYYIT | 84 | 49 | ETKVLEKPW | 122 | 72 |

TABLE 2-continued

First Hairpin Loop (FHL) and Second Hairpin Loop
(SHL) Motifs of Plant Cystatin Genes

| Full Protein SEQ ID NO: | Gene Name | FHL Motif | FHL Motif SEQ ID NO: | FHL Start Amino Acid Position | SHL Motif | SHL Motif SEQ ID NO: | SHL Start Amino Acid Position |
|---|---|---|---|---|---|---|---|
| 34 | gm-cys4 | QVVEGFIYYIT | 85 | 40 | ETKVWVRSW | 123 | 63 |
| 36 | gm-cys5 | QVVSGTNYRLV | 86 | 68 | EAIVWEKPW | 124 | 91 |
| 38 | gm-cys6 | QVVSGMKYYLK | 87 | 54 | TSVVVVKPW | 125 | 77 |
| 40 | gm-cys7 | QVVSGTLYTIT | 88 | 49 | EAKVWEKAW | 126 | 72 |
| 42 | gm-cys8 | QVVSGMKYYLK | 89 | 80 | NSVVVVKPW | 127 | 103 |
| 44 | gm-cys9 | QVVAGLNYRLS | 90 | 70 | QAIVYEKAW | 128 | 90 |
| 46 | os-cys1 | QVVAGTLYYFT | 91 | 53 | EAKVWEKPW | 129 | 76 |
| 48 | os-cys2 | QVVAGTLHHLT | 92 | 93 | EAKVWVKPW | 130 | 116 |
| 50 | os-cys3 | QVVGGFMHYLT | 93 | 59 | EAKVWERAW | 131 | 83 |
| 52 | os-cys4 | QVVTGTLHDLM | 94 | 90 | SAKVWVKPW | 132 | 113 |
| 54 | os-cys5 | QVVSDVAYYLK | 95 | 96 | DAVVVVKAW | 133 | 127 |
| 56 | os-cys6 | QVVSGMNYRLV | 96 | 76 | VAVVYEQSW | 134 | 100 |
| 58 | ta-cys1 | QTVAGTMHYIT | 97 | 93 | EAKVWEKPW | 135 | 116 |
| 72 | ta-cys10 | QTVAGTVHHLT | 98 | 86 | EAKVWVKPW | 136 | 109 |
| 74 | ta-cys11 | QVVAGTLHDLM | 99 | 85 | KAKVWVKPW | 137 | 108 |
| 76 | ta-cys13 | QVVAGTMYYLT | 100 | 78 | EAKVWEKPW | 138 | 101 |
| 60 | ta-cys2 | QTVAGTMHYIT | 101 | 76 | EAKVWEKPW | 139 | 99 |
| 62 | ta-cys3 | QLVSGMNYELI | 102 | 83 | KAEVYEQTW | 140 | 107 |
| 64 | ta-cys4 | QVVAGCMHYFT | 103 | 63 | EAKVWEKAW | 141 | 86 |
| 66 | ta-cys6 | QVVAGCMHYFT | 104 | 63 | EAKVWEKAW | 142 | 86 |
| 68 | ta-cys8 | QVVSGIKYYLR | 105 | 98 | DAVVVVKPW | 143 | 129 |
| 70 | ta-cys9 | QVVSGIKYYLR | 106 | 98 | DAVVVVKPW | 144 | 129 |
| 2 | ZmCys1 | QVVAGTMYYLT | 107 | 86 | EAKVWEKPW | 145 | 109 |
| 18 | ZmCys10 | QVVTGTLHDLI | 108 | 77 | RAKVWVKSW | 146 | 100 |
| 20 | ZmCys11 | QVVAGTNYKLN | 109 | 131 | QAVVFDPLP | 147 | 152 |
| 22 | ZmCys12 | QVVAGTLHHLT | 110 | 87 | EAKVWVKPW | 148 | 110 |
| 24 | ZmCys13 | QIVAGKNYRLR | 111 | 83 | RAVVYEQLT | 149 | 107 |
| 26 | ZmCys14 | QVVSGLKYYLR | 112 | 99 | DAVVVVKPW | 150 | 127 |
| 4 | ZmCys3 | QVVAGTMYYLT | 113 | 85 | EAKVWEKPW | 151 | 108 |
| 6 | ZmCys4 | QVVAGTMYYLT | 114 | 85 | EAKVWEKPW | 152 | 108 |
| 8 | ZmCys5 | QVVAGTLHHLT | 115 | 87 | EAKVWVKPW | 153 | 110 |
| 10 | ZmCys6 | QVVTGTLHDLI | 116 | 80 | RAKVWVKPW | 154 | 103 |
| 12 | ZmCys7 | QVVSGMNYKLV | 117 | 71 | GAFVYEQSW | 155 | 95 |

TABLE 2-continued

First Hairpin Loop (FHL) and Second Hairpin Loop (SHL) Motifs of Plant Cystatin Genes

| Full Protein SEQ ID NO: | Gene Name | FHL Motif | FHL Motif SEQ ID NO: | FHL Start Amino Acid Position | SHL Motif | SHL Motif SEQ ID NO: | SHL Start Amino Acid Position |
|---|---|---|---|---|---|---|---|
| 14 | ZmCys8 | QVVAGTLHHFT | 118 | 59 | EAKVWEKAW | 156 | 84 |
| 16 | ZmCys9 | QVVSGMNYRLY | 119 | 81 | VAVVYEQVW | 157 | 105 |

Table 3 shows the conserved region of the N-terminal alpha-1-helix in each of the sequences of the present invention.

TABLE 3

N-terminal Alpha-1 Helix Motif

| Full Protein SEQ ID NO: | Gene Name | Motif Sequence | Motif SEQ ID NO: | Motif Start Amino Acid Position |
|---|---|---|---|---|
| 28 | gm-cys1 | LARFAVDEHN | 158 | 66 |
| 30 | gm-cys2 | LARFAVEEHN | 159 | 22 |
| 32 | gm-cys3 | LARFAVDEHN | 160 | 22 |
| 34 | gm-cys4 | LARFAVEEQN | 161 | 13 |
| 36 | gm-cys5 | IANYALSEYD | 162 | 41 |
| 38 | gm-cys6 | LGRFAVEEYN | 163 | 20 |
| 40 | gm-cys7 | LARFAVEEHN | 164 | 22 |
| 42 | gm-cys8 | LGRFAVEEYN | 165 | 42 |
| 44 | gm-cys9 | IANFAVTEYD | 166 | 43 |
| 46 | os-cys1 | LARFAVTEHN | 167 | 26 |
| 48 | os-cys2 | LARFAVDEHN | 168 | 66 |
| 50 | os-cys3 | LARFAVAEHN | 169 | 32 |
| 52 | os-cys4 | AARFAVAEYN | 170 | 63 |
| 54 | os-cys5 | LGRFAVAEHN | 171 | 57 |
| 56 | os-cys6 | LGGWAVERHA | 172 | 49 |
| 58 | ta-cys1 | LARFAVSEHN | 173 | 66 |
| 72 | ta-cys10 | LARFAVDEHN | 174 | 59 |
| 74 | ta-cys11 | AARFAVAEHN | 175 | 58 |
| 76 | ta-cys13 | LARFAVDEHN | 176 | 51 |
| 60 | ta-cys2 | LARFAVSEHN | 177 | 49 |
| 62 | ta-cys3 | LGRWAVLEFG | 178 | 56 |
| 64 | ta-cys4 | LARFAVAEHN | 179 | 36 |
| 66 | ta-cys6 | LARFAVAEHN | 180 | 36 |

TABLE 3-continued

N-terminal Alpha-1 Helix Motif

| Full Protein SEQ ID NO: | Gene Name | Motif Sequence | Motif SEQ ID NO: | Motif Start Amino Acid Position |
|---|---|---|---|---|
| 68 | ta-cys8 | LGRYSVEEHN | 181 | 61 |
| 70 | ta-cys9 | LGRYSVEEHN | 182 | 61 |
| 2 | ZmCys1 | LARFAVNEHN | 183 | 59 |
| 18 | ZmCys10 | AARFAVAHYN | 184 | 50 |
| 20 | ZmCys11 | VGEWAVKEHN | 185 | 104 |
| 22 | ZmCys12 | LGRFAVDEHN | 186 | 60 |
| 24 | ZmCys13 | IGRWAVSEHI | 187 | 56 |
| 26 | ZmCys14 | LGRFSVAEYN | 188 | 66 |
| 4 | ZmCys3 | LARFAVDEHN | 189 | 58 |
| 6 | ZmCys4 | LARFAVDEHN | 190 | 58 |
| 8 | ZmCys5 | LGRFAVDEHN | 191 | 60 |
| 10 | ZmCys6 | AARFAVAYHN | 192 | 53 |
| 12 | ZmCys7 | LGGWAVTEHV | 193 | 44 |
| 14 | ZmCys8 | LARFAVAEHN | 194 | 32 |
| 16 | ZmCys9 | LGGWALGQAK | 195 | 35 |

The protein sequences of the present invention were analyzed for percent identities and similarities using the GAP algorithm. These analyses were performed by species, such that the *maize* sequences were compared to the other *maize* sequences, and so on for each of soybean, rice, and wheat. It is evident from the tables that follow that the sequences of the present invention, although they are all cystatins, can vary markedly at the protein level while still retaining cystatin activity. In Tables 4 through 11, sequence similarities and identities among crop plant sequence groups are presented. Those SEQ ID NOs: for which activity data are provided in the instant application are shown in bold faced type (see Examples).

TABLE 4

GAP Analysis: Maize Amino Acid Sequence Percent Identities

| SEQ ID NO: | 3 | 5 | 7 | 9 | 11 | 13 | 15 | 18 | 20 | 22 | 24 | 26 |
|---|---|---|---|---|---|---|---|---|---|---|---|---|
| 1 | 90.3 | 90.3 | 44.2 | 38.7 | 36.2 | 56.0 | 33.0 | 37.3 | 34.1 | 44.3 | 35.2 | 33.3 |
| 3 | | 100 | 45.0 | 38.2 | 39.1 | 56.0 | 33.9 | 37.3 | 33.3 | 45.0 | 37.1 | 33.3 |
| 5 | | | 45.0 | 38.2 | 39.1 | 56.0 | 33.9 | 37.3 | 33.3 | 45.0 | 37.1 | 33.3 |
| 7 | | | | 38.9 | 33.9 | 50.5 | 28.7 | 36.9 | 32.3 | 100 | 29.5 | 37.6 |
| 9 | | | | | 36.8 | 44.9 | 25.5 | 88.4 | 32.5 | 39.0 | 24.6 | 38.1 |
| 11 | | | | | | 29.0 | 57.4 | 33.9 | 37.5 | 33.9 | 53.9 | 38.8 |
| 13 | | | | | | | 25.2 | 43.5 | 32.3 | 50.5 | 34.7 | 36.9 |
| 15 | | | | | | | | 28.0 | 35.2 | 28.7 | 43.0 | 36.7 |
| 18 | | | | | | | | | 29.9 | 36.9 | 22.5 | 34.9 |
| 20 | | | | | | | | | | 32.3 | 44.3 | 29.6 |
| 22 | | | | | | | | | | | 29.5 | 37.6 |
| 24 | | | | | | | | | | | | 37.1 |

TABLE 5

GAP Analysis: Maize Amino Acid Sequence Percent Similarities

| SEQ ID NO: | 3 | 5 | 7 | 9 | 11 | 13 | 15 | 18 | 20 | 22 | 24 | 26 |
|---|---|---|---|---|---|---|---|---|---|---|---|---|
| 1 | 92.5 | 92.5 | 53.4 | 48.1 | 44.2 | 69.2 | 40.3 | 46.8 | 40.0 | 53.4 | 44.0 | 43.2 |
| 3 | | 100 | 54.2 | 46.9 | 47.8 | 70.1 | 42.7 | 45.2 | 41.7 | 54.2 | 48.4 | 43.4 |
| 5 | | | 54.2 | 46.9 | 47.8 | 70.1 | 42.7 | 45.2 | 41.7 | 54.2 | 48.4 | 43.4 |
| 7 | | | | 46.5 | 40.0 | 57.0 | 35.3 | 44.6 | 35.4 | 100 | 40.2 | 44.8 |
| 9 | | | | | 44.7 | 49.5 | 34.6 | 91.3 | 37.5 | 46.5 | 38.5 | 45.2 |
| 11 | | | | | | 38.0 | 61.1 | 42.6 | 45.5 | 40.0 | 64.3 | 46.6 |
| 13 | | | | | | | 32.7 | 47.2 | 38.4 | 57.0 | 46.5 | 45.6 |
| 15 | | | | | | | | 36.7 | 43.4 | 35.3 | 49.6 | 42.2 |
| 18 | | | | | | | | | 36.8 | 44.6 | 33.3 | 41.5 |
| 20 | | | | | | | | | | 35.4 | 54.9 | 35.2 |
| 22 | | | | | | | | | | | 40.2 | 44.8 |
| 24 | | | | | | | | | | | | 48.4 |

TABLE 6

GAP Analysis: *Glycine max* Amino Acid Sequence Percent Identities

| SEQ ID NO: | 30 | 32 | 34 | 36 | 38 | 40 | 42 | 44 |
|---|---|---|---|---|---|---|---|---|
| 28 | 67.0 | 55.3 | 45.7 | 33.9 | 41.2 | 65.0 | 37.8 | 27.7 |
| 30 | | 69.1 | 61.4 | 41.3 | 42.2 | 94.9 | 38.0 | 30.8 |
| 32 | | | 67.4 | 39.1 | 34.0 | 69.1 | 33.0 | 32.2 |
| 34 | | | | 34.5 | 37.8 | 60.2 | 35.9 | 32.9 |
| 36 | | | | | 34.4 | 41.3 | 32.1 | 59.6 |
| 38 | | | | | | 42.2 | 82.7 | 31.8 |
| 40 | | | | | | | 38.0 | 31.9 |
| 42 | | | | | | | | 28.4 |

TABLE 7

GAP Analysis: *Glycine max* Amino Acid Sequence Percent Similarities

| SEQ ID NO: | 30 | 32 | 34 | 36 | 38 | 40 | 42 | 44 |
|---|---|---|---|---|---|---|---|---|
| 28 | 77.3 | 63.1 | 59.8 | 44.6 | 55.7 | 75.3 | 48.8 | 38.4 |
| 30 | | 78.4 | 68.2 | 48.9 | 51.1 | 94.9 | 47.8 | 42.9 |
| 32 | | | 72.8 | 48.9 | 47.4 | 78.4 | 42.7 | 41.1 |
| 34 | | | | 44.0 | 47.8 | 67.0 | 44.6 | 40.2 |
| 36 | | | | | 42.2 | 48.9 | 39.3 | 67.0 |
| 38 | | | | | | 51.1 | 85.6 | 42.0 |
| 40 | | | | | | | 47.8 | 44.0 |
| 42 | | | | | | | | 36.7 |

TABLE 8

GAP Analysis: *Oryza sativa* Amino Acid Sequence Percent Identities

| SEQ ID NO: | 48 | 50 | 52 | 54 | 56 |
|---|---|---|---|---|---|
| 46 | 54.9 | 60.0 | 40.2 | 34.7 | 31.3 |
| 48 |  | 48.1 | 37.0 | 40.2 | 34.7 |
| 50 |  |  | 38.3 | 34.9 | 36.9 |
| 52 |  |  |  | 31.3 | 25.0 |
| 54 |  |  |  |  | 42.3 |

TABLE 9

GAP Analysis: *Oryza sativa* Amino Acid Sequence Percent Similarities

| SEQ ID NO: | 48 | 50 | 52 | 54 | 56 |
|---|---|---|---|---|---|
| 46 | 62.7 | 71.0 | 49.0 | 44.9 | 40.4 |
| 48 |  | 57.5 | 42.0 | 46.5 | 41.3 |
| 50 |  |  | 46.7 | 44.3 | 40.8 |
| 52 |  |  |  | 36.7 | 31.7 |
| 54 |  |  |  |  | 48.0 |

TABLE 10

GAP Analysis: Wheat Amino Acid Sequence Percent Identities

| SEQ ID NO: | 60 | 62 | 64 | 66 | 68 | 70 | 72 | 74 | 76 |
|---|---|---|---|---|---|---|---|---|---|
| 58 | 92.8 | 28.6 | 61.7 | 61.7 | 29.9 | 31.3 | 46.7 | 38.8 | 63.8 |
| 60 |  | 33.3 | 63.6 | 63.6 | 31.4 | 33.1 | 48.7 | 38.0 | 62.6 |
| 62 |  |  | 33.6 | 33.6 | 29.7 | 29.7 | 30.3 | 24.4 | 35.0 |
| 64 |  |  |  | 98.1 | 34.0 | 34.9 | 47.6 | 43.0 | 63.2 |
| 66 |  |  |  |  | 33.0 | 34.0 | 47.6 | 42.1 | 63.2 |
| 68 |  |  |  |  |  | 91.5 | 38.8 | 43.4 | 37.2 |
| 70 |  |  |  |  |  |  | 35.7 | 40.0 | 33.1 |
| 72 |  |  |  |  |  |  |  | 38.3 | 47.9 |
| 74 |  |  |  |  |  |  |  |  | 39.5 |

TABLE 11

GAP Analysis: Wheat Amino Acid Sequence Percent Similarities

| SEQ ID NO: | 60 | 62 | 64 | 66 | 68 | 70 | 72 | 74 | 76 |
|---|---|---|---|---|---|---|---|---|---|
| 58 | 93.6 | 34.1 | 66.4 | 65.4 | 41.8 | 41.8 | 54.1 | 47.8 | 70.9 |
| 60 |  | 39.3 | 67.3 | 66.4 | 43.0 | 43.8 | 57.1 | 47.1 | 68.3 |
| 62 |  |  | 40.2 | 40.2 | 37.5 | 39.1 | 41.0 | 34.4 | 44.2 |
| 64 |  |  |  | 98.1 | 42.5 | 43.4 | 57.1 | 51.4 | 70.8 |
| 66 |  |  |  |  | 41.5 | 42.5 | 57.1 | 50.5 | 70.8 |
| 68 |  |  |  |  |  | 94.1 | 46.5 | 50.0 | 47.1 |
| 70 |  |  |  |  |  |  | 44.2 | 47.7 | 46.0 |
| 72 |  |  |  |  |  |  |  | 43.4 | 57.0 |
| 74 |  |  |  |  |  |  |  |  | 51.6 |

The phytocystatins play a role in a wide range of plant physiological processes, including plant defense mechanisms. Plant cystatins have been found in various tissues in numerous plant species, including, but not limited to, crop plants such as rice (Abe et al. (1987) J Biol Chem 262: 16793–16797; Kondo et al. (1990) J Biol Chem 265: 15832–15837), tomato (Wu et al. (2000) Comp Biochem Phys C 127: 209–220), maize (Yamada et al. (2000) Plant Cell Physiol 42(7): 710–716), sunflower (Doi-Kawano et al. (1998) J Biochem 124: 11–916), soybean (Misaka et al. (1996) Eur J Biochem 240: 609–614) and potato (Rowan et al. (1990) FEBS Lett 269: 328–330; Waldron et al. (1993) Plant Mol Biol 23: 801–812). Information on their amino acid sequences has been obtained through either protein or cDNA sequencing.

Cystatins play a role in many plant physiological functions, including defense, more specifically plant defense against pathogens. A range of functions performed by plant cystatins are responsible for enhancing plant defense against different pathogens. While not wishing to be bound by any one mechanism of action, the sequences and related genes of the present invention encode proteins with antimicrobial and antifungal activity. These proteins may inhibit the proteinases of the pathogen, so as to thwart their utilization of the plant tissue. In addition, cystatins which are expressed around disease-induced lesions may control symptom development, as in a hypersensitive response (HR), by controlling the proteinase-mediated cell death mechanism.

Compositions of the present invention include the sequences for maize, soybean, rice and wheat nucleotide sequences which have been identified as cystatins that are involved in plant defense response and development. In particular, the present invention provides for isolated nucleic acid molecules comprising nucleotide sequences encoding the amino acid sequences shown in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, and 76. Further provided are polypeptides having an amino acid sequence encoded by a nucleic acid molecule described herein, for example those nucleotide sequences set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, and 75.

The nucleotide sequences of the invention are maize, soybean, rice and wheat sequences comprising plant cysteine proteinases. The claimed sequences are members of the plant cystatin class of genes and polypeptides. These plant cystatins are identified herein as "Zm-Cys", "Ta-Cys", "Gm-Cys" and "Os-Cys" for cystatins originating from *Zea mays, Triticum aestivum, Glycine max* and *Oryza sativa*, respectively, and are numbered for easy reference (e.g. Zm-Cys10 or Gm-Cys8). These sequences represent a diverse and conserved supergene family in plants.

The compositions of the invention can be used in a variety of methods whereby the protein products can be expressed in crop plants to function as antimicrobial proteins. Such expression results in the alteration or modulation of the level, tissue, or timing of expression to achieve enhanced disease or stress resistance. The compositions of the invention may be expressed in the same species from which the particular cystatin originates, or alternatively, can be expressed in any plant of interest. In this manner, the coding sequence for the cystatin can be used in combination with a promoter that is introduced into a crop plant. In one embodiment, a high-level expressing constitutive promoter may be utilized and would result in high levels of expression of the cystatin. In other embodiments, the coding sequence may be operably linked to a tissue-specific promoter to direct the expression to a plant tissue known to be susceptible to a pathogen. Likewise, manipulation of the timing of expression may be utilized. For example, by judicious choice of promoter, expression can be enhanced early in plant growth to prime the plant to be responsive to pathogen attack. Likewise, pathogen inducible promoters can be used wherein expression of the cystatin is turned on in the presence of the pathogen.

The cystatin genes of the present invention additionally find use in enhancing the plant pathogen defense system. The compositions and methods of the invention can be used for enhancing resistance to plant pathogens including fungal pathogens, plant viruses, and the like. The method involves stably transforming a plant with a nucleotide sequence capable of modulating the plant pathogen defense system operably linked with a promoter capable of driving expression of a gene in a plant cell. "Enhancing resistance" means that the plant's tolerance to pathogens is increased. That is, the cystatin may slow or prevent pathogen infection and spread.

In specific embodiments, methods for increasing pathogen resistance in a plant comprise stably transforming a plant with a DNA construct comprising an anti-pathogenic nucleotide sequence of the invention operably linked to a promoter that drives expression in a plant. Such methods find use in agriculture, particularly in limiting the impact of plant pathogens on crop plants. While the choice of promoter will depend on the desired timing and location of expression of the anti-pathogenic nucleotide sequences, preferred promoters include constitutive and pathogen-inducible promoters.

Additionally, the compositions can be used in formulations used for their disease resistance activities. The proteins of the invention can be formulated with an acceptable carrier into a pesticidal composition(s) that is for example, a suspension, a solution, an emulsion, a dusting powder, a dispersible granule, a wettable powder, an emulsifiable concentrate, an aerosol, an impregnated granule, an adjuvant, a coatable paste, or an encapsulation in, for example, polymer substances.

Transformed plants, plant cells, plant tissues and seeds thereof are additionally provided.

It is recognized that the present invention is not dependent upon a particular mechanism of defense. Rather, the genes and methods of the invention work to increase resistance of the plant to pathogens independent of how that resistance is increased or achieved.

It is understood in the art that plant DNA viruses and fungal pathogens remodel the control of the host replication and gene expression machinery to accomplish their own replication and effective infection. The present invention may be useful in preventing such corruption of the cell.

The cystatin sequences find use in disrupting cellular function of plant pathogens or insect pests as well as altering the defense mechanisms of a host plant to enhance resistance to disease or insect pests. While the invention is not bound by any particular mechanism of action to enhance disease resistance, the gene products, probably proteins or polypeptides, function to inhibit or prevent diseases in a plant.

The methods of the invention can be used with other methods available in the art for enhancing disease resistance in plants. For example, any one of a variety of second nucleotide sequences may be utilized, embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome. Other plant defense proteins include those described in PCT patent publications WO 99/43823 and WO 99/43821, both of which are herein incorporated by reference.

Plant senescence is an important trait affecting life cycle duration or maturity, seed dry down, the disease resistance profile, and 'stay green', which in turn affect yield, stalk strength, appearance, and nutritional value (silage quality). All of these factors, which relate to cell death processes, are considered in *maize* breeding efforts. Plant proteinases have been implicated in these processes and thus comprise an area of active research.

In particular, cysteine proteinases are induced upon plant organ senescence, such as in tomato leaves (Drake et al. (1996) Plant Mol Biol 30(4): 755–767), sweet potato (Chen et al. (2002) Plant and Cell Phys 43(9): 984–991), and day-lily flowers (Valpuesta et al. (1995) Plant Mol Biol 28(3): 575–582). Furthermore, the *maize* cysteine proteinase See 1 ("Senescence enhanced") has been linked to the stay green phenotype in *maize* (Griffiths et al. (1997) Plant Mol Biol 34: 815–821). Cysteine proteinase inhibitors have also been shown to delay flower senescence (Eason et al. (2002) Functional Plant Biol 29(9): 1055–1064). While the biology is undoubtedly complex in senescence, to the extent that the cysteine proteinases are involved in senescence related processes, then their cognate proteinase inhibitors, here cystatins, are involved in the control of the timing and onset of senescence as well. Modulation of cystatins can provide agronomic advantages by promoting or delaying senescence and other developmental signals.

In a plant breeding effort, the position of the starting breeding material relative to the desired outcome, will dictate what direction one will want to push a trait. For example, one may want increase or decrease maturity time; generally decrease. To increase senescence one may want to suppress cystatin expression, and to decrease senescence one may want to increase cystatin expression. Methods for increasing or decreasing cystatin expression are outlined elsewhere in this specification. However, tissue-targeted or developmental-targeted expression may be desirable to reach these ends. The proteinase promoters, such as those from See1, can be useful in conjunction with forward or antisense constructs of the proteinase inhibitor gene in question, to coordinately augment or cancel, respectively, the death-promoting capacity of the cysteine proteinase.

The proteinase inhibitor genes herein are useful for controlling the senescence of special crop plant tissues. For certain crops particular tissue or organs are desired to senesce. This includes controlled dropping of cotton leaves to facilitate cotton boll harvesting. Sometimes organs are desired not to senesce, as in the petioles of fruit; premature fruit drop can cause loss of yield. For *maize*, delay of senescence of the pedicel/hilum region of kernels may be desirable to allow for prolonged kernel fill or delayed maturation of seed, with higher yield and/or higher digestibility as possible outcomes.

Over-expression or transgenic expression of proteinase inhibitors provides effective control of both cyst and root knot nematodes. The primary mechanism by which cystatins confer nematode resistance is most likely associated with disruption of nematode development. Currently over-expression of proteinase inhibitors (PIs) offers the most advanced approach for nematode control. Furthermore, transgenic expression of PIs provides effective control of both cyst and root knot nematodes. Recent research has shown the value of using proteinase inhibitors in controlling certain species of nematodes.

Oryzacystatin-I (Oc-I) is a cysteine proteinase inhibitor from rice seeds (Abe et al. (1987) Supra), while Oc-1 D86 is a modified form of Oc-1 which has shown stronger inhibitory activity (Urwin et al. (1995) Plant J 8: 121–131). When expressed in tomato hairy roots both Oc-1 and Oc-ID86 had a detrimental effect on the growth and development of potato cyst nematode *G. pallida* (Id.). Similarly, when expressed in transgenic *Arabidopsis thaliana* Oc-ID86 had a profound effect on the size and fecundity of females of both the beet-cyst nematode *Heterodera schachtii* and the root-knot nematode *Meloidogyne incognita* as well as reniform nematode *Rotylenchulus reniformis* (Urwin et al. (1997) Plant J 12: 455–461; Urwin et al. (1998) Planta 204: 472–479; Urwin et al. (2000) Mol Breeding 6: 257–264). Compositions of the instant invention indicate that cystatins can also confer resistance to soybean cyst nematode (SCN) in soybean and other crops, by inhibiting nematode growth and development.

The recovery of viable transgenic plants from crop plants, in particular for monocot cereal crop plants such as *maize*, rice and wheat, is still a laborious and expensive process. This can be a particular problem when transformation-recalcitrant varieties, often those with desirable breeding characteristics, perform poorly in the transgenic production transformation process. Methods are consequently sought to identify new methods that will improve the transformation and recovery of viable plants.

One of the chief problems is cell death in tissue culture. This is caused not only by the general poor viability of some lines in culture, but also by the fact that in order to select for the transformants, often antibiotics are added that kill the non-transformed cells. Amidst this cell death the positively transformed lines are also killed. Recalcitrance to death, or the signals of death, and as well positive cell growth, are thus desirable features.

To the extent that these proteinase inhibitors can retard cell death by suppressing proteinase inhibitor activity, they can be used to help transformed cells survive. Cysteine proteinases are known to be induced in the plant HR response, and transgenic ectopically expressed cystatins can counteract this response (Pechan et al. (2000) Plant Cell 12(7): 1031–1040; Solomon et al., (1999) Plant Cell 11(3): 431–443). The transformed cells receive a copy of one or more of these proteinase inhibitor coding region(s) driven by an appropriate promoter. Promoter choices are discussed elsewhere in this application, however, this embodiment can benefit from the use of a constitutive promoter, or by a transiently expressed promoter targeted to the cell culture phase or induced by plant hormones used in culture. Constitutive expression may help disease resistance generally, and as such, constitutive promoters, for example the ubiquitin promoter, can be useful beyond cell culture. Of course a variety of promoters would be effective. The resulting transformed cells would be more viable. This would effect a cleaner separation of the dying non-transformed cells and allow for cleaner and more rapid growth of the transformed line. Plant transformation techniques would be improved as a result.

It should also be recognized that plants can be wounded abiotically, as by drought stress, wind stress (which includes damage by wind-blown soil particles), and chemical and nutrient stress. Such stresses can precipitate cell death that can reduce plant yield. To the extent that these proteinase inhibitors may retard cell death by thwarting proteinase inhibitor activity, they can retard the symptom development of necrosis resulting from these stresses when driven by a death-induced promoter.

Second, the proteinase inhibitor genes can have application in the development and implementation of herbicide resistance mechanisms in crop plants. Ectopic expression of the proteinase inhibitors, as in leaves, can result in a retardation of cell death following the application of herbicides. This would be subject to the kind of herbicide used and its mode of action, but it is an area of utility for these genes. Herbicides and herbicide resistance systems are often used as selectable markers in plant transformation experiments. Thus, in a way similar to the herbicide resistance application, these proteinase inhibitor genes can be used as selectable markers—only cells expressing the proteinase inhibitor genes (ectopically) would grow or stay alive in the face of an antibiotic/herbicide medium. This application of course bears direct overlap with the examples given above for improving plant transformation.

Cell death can also be a mechanism of male infertility. Consequently similar methods, probably with anther- or tapetum- or pollen-preferred expression, could be a means of enhancing or controlling male fertility. For example, expressing cystatins can suppress cell death and thus suppress sterility, rendering the plants male fertile. This could be used in a conditional situation, where the plants would be sterile until induced to be fertile.

Many proteinase inhibitors, including some of the present invention, are expressed in seeds. The chief biological role of seed expression of proteinase inhibitors is to inhibit, or otherwise control, proteinase activities in the seeds. This is especially important during seed development/maturation, in order to regulate protein processing by proteinases. Cereal cysteine proteinases play a chief role in the digestion of seed storage proteins, especially during germination (Gruis et al. (2002) Plant Cell 14(11):2863–2882; Debarros & Larkins (1994) Plant Sci 99(2) 189–197; Koehler & Ho (1990) Plant Physiol 94(1):251–258; Poulle & Jones (1988) Plant Physiol 88(4): 1454–1460). Regulating the activity of cysteine proteinases in seeds prevents undesirable loss of seed proteins, including storage proteins, and also prevents premature germination (Corre et al (2002) Plant Mol Biol 50(4–5): 687–698). Furthermore, regulating the processing of proteins can serve as an anti-nutritional/protective agent against microbes, insects, and herbivores. However, crop plant seeds, such as *maize* caryopses, are mostly intended for animal consumption as feed grain, and some also for human food consumption. As such, the proteinase inhibitors from the seed can inhibit digestive proteinases in the gastrointestinal tract of livestock and humans. This can change the site and extent of digestion of protein and other grain components within, as well as elicit hyper-secretion of pancreatic enzymes. The impact on overall nutritional status may either be positive or negative.

Lowering the digestibility of grain proteins lowers the effectiveness of the grain for weight gain for monogastric animals and humans. The reduced protein digestibility will also reduce access of starch-degrading enzymes to starch granules (which are encompassed by a protein matrix), thereby reducing digestible energy content in addition to digestible protein. Moreover, various proteinase inhibitors induce the release of pancreatic cholecystokinin, a known satiety factor resulting in lower feed or food intake (Elsaesser et al. (1990) Cell Tissue Res 262(1): 143–148; Garlicki et al (1990) Am J Physiol 258: E40–45; Schwartz et al. (1994) Diabetes Care 17(4): 255–262; Choi et al. (2000) Domest Anim Endocrin 19(3): 159–175). For livestock, this is clearly a negative factor, as well as for undernourished humans in developing countries; reduced caloric value and reduced food intake may be very positive, however, for overweight people.

Lowering fermentative proteolysis to reduce the formation of non-protein-nitrogen (NPN) is beneficial, however, for ruminant livestock (dairy and beef cattle, sheep and goats), especially if the protein is of high Biological Value (i.e., of balanced amino acid composition, containing especially lysine, tryptophan, threonine, and methionine). First, silage made of various forages, such as ryegrass and *alfalfae*, is subject to excessive proteolysis during the ensiling process. Total protein losses can amount to 50% and the dairy cow poorly utilizes the resulting NPN. Proteinase inhibitors can be employed to reduce these proteolytic losses. Second, lowering the proteolysis in the rumen is beneficial to allow otherwise easily digestible high-protein concentrates (such as fat-extracted soybean & canola meals) and high-protein forages (such as *alfalfae*) to bypass rumen fermentation. Rapid and extensive ruminal breakdown of protein leads to decreased protein efficiency because 1) the rumen microbes do not use the degraded protein as fast as it is broken down, leading to excessive formation of ammonia, much of which will be excreted in the urine as urea, and 2) the microbial protein that is re-synthesized from ammonia is generally of lower biological value than soybean or canola protein.

Consequently, to the extent that these cystatin proteinase inhibitors can alter digestion characteristics of the grain, it would be desirable to reduce the level of their expression to increase protein digestibility and energy availability for monogastric livestock and humans. On the other hand, given the reasoning above, it would be desirable to increase the level of cystatin expression to reduce proteolysis in silage and generate rumen by-pass protein for ruminant livestock, and to produce diet foods by reducing the caloric value of cereals and/or inducing satiety.

It is this over-expression that would be the best mode of using these cystatin genes, which would be achieved by over-expression of one or more of the cystatin genes. The various advantages and disadvantages of using different promoters to drive such over-expression is well known by those skilled in the art. However, by way of example, a constitutive promoter could drive the expression, but a more ideal promoter would target tissues, such as the grain. For silage production, a high-level vegetative promoter would be desirable. Over-expression of one or several of the cystatins would be technically more easy to achieve than suppression of most of these cystatins, especially given their sequence diversity.

The different proteinase inhibitor genes have somewhat different expression profiles. Based upon the *maize* EST library distributions, Zm-Cys5, Zm-Cys6, Zm-Cys9, Zm-Cys10, Zm-Cys13, and Zm-Cys14 are abundant in, or specific to, *maize* endosperm or other kernel tissues. Generally, the best mode for this invention (in *maize* or cereals) is to express the sense version of the proteinase inhibitor genes under the control of a seed-preferred, especially endosperm-preferred, especially R3-R5-preferred promoter, or, in the case of *alfalfae*, a constitutive promoter. Thus when the sense transcript is produced, it will result in either over-expression or silencing of the targeted proteinase inhibitor gene. There are other methods for suppression of gene expression that may be applied. This strategy could be applied to one or several of the proteinase inhibitor genes in the same crop plant.

Sequences of the invention, as discussed in more detail below, encompass coding sequences, antisense sequences, and fragments and variants thereof. Expression of the sequences of the invention can be used to modulate or regulate the expression of corresponding cystatin proteins. The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. "Fragment" means a portion of the nucleotide sequence or a portion of the amino acid sequence and hence protein encoded thereby. Fragments of a nucleotide sequence may encode protein fragments that retain the biological activity of the native protein and hence have cystatin-like activity and thereby affect development, developmental pathways, and defense responses. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a cystatin nucleotide sequence that encodes a biologically active portion of a cystatin protein of the invention will encode at least 15, 25, 30, 50, 100, 150, 200, or 250 contiguous amino acids, or up to the total number of amino acids present in a full-length protein of the invention (for example, 135, 134, 134, 245, 176, 116, 110 or 157 amino acids for SEQ ID NO:2, 4, 6, 8, 10, 12, 14, or 16, respectively). Fragments of a cystatin nucleotide sequence that are useful as hybridization probes for PCR primers generally need not encode a biologically active portion of a cystatin protein.

Thus, a fragment of a cystatin nucleotide sequence may encode a biologically active portion of a cystatin protein, or it may be a fragment that can be used as a hybridization probe or PCR primer using methods disclosed below. A biologically active portion of a cystatin protein can be prepared by isolating a portion of one of the cystatin nucleotide sequences of the invention, expressing the encoded portion of the cystatin protein (e.g., by recombinant expression in vitro), and assessing the activity of the encoded portion of the cystatin protein. Nucleic acid molecules that are fragments of a cystatin nucleotide sequence comprise at least 16, 20, 50, 75, 100, 150, 200, 250, 300, 350, 400, 450, 500, 550, 600, 650, 700, or 800 nucleotides, or up to the number of nucleotides present in a full-length cystatin nucleotide sequence disclosed herein (for example, 408, 405, 405, 738, 531, 351, 333, or 474 nucleotides for SEQ ID NO:1, 3, 5, 7, 9, 11, 13, or 15, respectively).

"Variants" is intended to mean substantially similar sequences. For nucleotide sequences, conservative variants include those sequences that, because of the degeneracy of the genetic code, encode the amino acid sequence of one of the cystatin polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a cystatin protein of the invention. Generally, variants of a particular nucleotide sequence of the invention will have at least about 50%, 60%, 65%, 70%, generally at least about 75%, 80%, 85%, 90%, 91%, 92%, 93%, 94%, 95%, 96%, 97%, 98%, 99% or more sequence identity to that particular nucleotide sequence as determined by sequence alignment programs described elsewhere herein using default parameters.

These variant nucleotide sequences can also be evaluated by comparison of the percent sequence identity shared by the polypeptides they encode. For example, isolated nucleic acids which encode a polypeptide with a given percent sequence identity to the polypeptide of SEQ ID NO: 2, 4, 6, 8 and 10 are disclosed. Identity can be calculated using, for example, the BLAST, CLUSTALW, or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%.

A "variant" protein is intended to mean a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, cystatin-like activity as described herein. Such variants may result from, for example, genetic polymorphism or from human manipulation. Biologically active variants of a native cystatin protein of the invention will have at least about 40%, 50%, 60%, 65%, 70%, 75%, 80%, 85%, 90%, 91%, 92%, 93%, 94%, 95%, 96%, 97%, 98%, 99% or more sequence identity to the amino acid sequence of the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The polypeptides of the invention may be altered in various ways including amino acid substitutions, deletions, truncations, and insertions. Novel proteins having properties of interest may be created by combining elements and fragments of proteins of the present invention as well as other proteins. Methods for such manipulations are generally known in the art. For example, amino acid sequence variants of the cystatin proteins can be prepared by mutations in the DNA. Methods for mutagenesis and nucleotide sequence alterations are well known in the art. See, for example, Kunkel (1985) Proc Nat Acad Sci USA 82:488–492; Kunkel et al. (1987) Method Enzymol 154: 367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest are well known in the art and may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred. Table 12, below, shows potential amino acid substitution groups which are considered to be highly conserved.

TABLE 12

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired developmental activity, or defense response activity. Obviously, the mutations that will be made in the DNA encoding the variant must not place the sequence out of reading frame and preferably will not create complementary regions that could produce secondary mRNA structures. See, EP Patent Application Publication No. 0075444.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but not further processing yet is called a "propeptide" or "proprotein". The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect can be evaluated by routine screening assays. That is, the activity can be evaluated by cystatin activity assays. Additionally, differences in the expression of specific genes between uninfected and infected plants can be determined using gene expression profiling.

Variant nucleotide sequences and proteins also encompass sequences and proteins derived from a mutagenic and recombinogenic procedure such as DNA shuffling. With such a procedure, one or more different cystatin coding sequences can be manipulated to create a new cystatin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the cystatin genes and partial sequences of the invention and other known cystatin genes to obtain a new gene coding for a protein with an improved property of interest, such as an increased $K_m$ in the case of an enzyme. Such shuffling of domains may also be used to assemble novel proteins having novel properties. Strategies for such DNA shuffling are known in the art. See, for example, Stemmer (1994) Proc Natl Acad Sci USA 91: 10747–10751; Stemmer (1994) Nature 370: 389–391; Crameri et al. (1997) Nature Biotech 15: 436–438; Moore et al. (1997) J Mol Biol 272: 336–347; Zhang et al. (1997) Proc Natl Acad Sci USA 94: 4504–4509; Crameri et al. (1998) Nature 391: 288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire cystatin sequences set forth herein or to fragments thereof are encompassed by the present invention. Such sequences include sequences that are orthologs of the disclosed sequences. "Orthologs" means genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, for example, Sambrook. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the cystatin sequences of the invention. Methods for preparation of probes for hybridization and for construction of cDNA and genomic libraries are generally known in the art and are disclosed in Sambrook.

For example, an entire cystatin sequence disclosed herein, or one or more portions thereof, may be used as a probe capable of specifically hybridizing to corresponding cystatin sequences and messenger RNAs. To achieve specific hybridization under a variety of conditions, such probes include sequences that are unique among cystatin sequences and are preferably at least about 10 nucleotides in length, and most preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook.

Thus, isolated sequences that encode for a cystatin polypeptide and which hybridize under stringent conditions to the cystatin sequences disclosed herein, or to fragments thereof, are encompassed by the present invention.

Biological activity of the cystatin polypeptides (i.e., influencing the plant defense response and various developmental pathways, including, for example, influencing cell division) can be assayed by any method known in the art. Biological activity of the polypeptides of the present invention can be assayed by any method known in the art. For example, most published cystatin activity assays are based on inhibition of papain-mediated substrate hydrolysis. A variety of synthetic papain substrates are known in the art and can be used for this purpose, such as N-benzoyl-asparaginyl-p-nitroanilide (Schlereth et al. (2001) Planta 212: 718–727), α-N-benzoyl-L-arginine-p-nitroanilide (Masoud et al. (1993) Plant Mol Biol 21: 655–663), N-Cbz-Phe-Arg-7-amido-4-methylcoumarin (Urwin et al. (1998) Supra), and Z-Phe-Arg-7-(4-methylcoumarylamide) (Barrett & Kirschke (1981) Method Enzymol 80: 535–561), all of which are herein incorporated by reference. Furthermore, papain could be substituted by a cysteine proteinase that is more relevant to the biological system studied (e.g., a *Fusarium* cysteine proteinase). Assays to detect cystatin-like activity include, for example, assessing antifungal and/or antimicrobial activity (Soares-Costa et al. (2002) Biochem Biophys Res Comm 296: 1194–1199; Duvick et al. (1992) J Biol Chem 267(26): 18814–18820; Pernas-Monica et al. (1999) Mol Plant Microbe In 12 (7): 624–627; Blankenvoorde-Michiel et al. (1998) Biol Chem 379(11): 1371–1375, all of which are herein incorporated by reference).

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Compositions and methods for controlling pathogenic agents are provided. The anti-pathogenic compositions comprise *maize*, soybean, rice and wheat cystatin nucleotide and amino acid sequences. Particularly, the nucleic acid and amino acid sequences and fragments and variants thereof set forth herein. Accordingly, the compositions and methods are also useful in protecting plants against fungal pathogens, viruses, nematodes, insects and the like.

"Plant pathogen" or "plant pest" is intended to mean any microorganism that can cause harm to a plant, such as by inhibiting or slowing the growth of a plant, by damaging the tissues of a plant, by weakening the immune system of a plant or the resistance of a plant to abiotic stresses, and/or by causing the premature death of the plant, etc. Plant pathogens and plant pests include microbes such as fungi, viruses, bacteria, and nematodes.

"Disease resistance" or "pathogen resistance" is intended to mean that the organisms avoid the disease symptoms which are the outcome of organism-pathogen interactions. That is, pathogens are prevented from causing diseases and the associated disease symptoms, or alternatively, the disease symptoms caused by the pathogen is minimized or lessened. The methods of the invention can be utilized to protect plants from disease, particularly those diseases that are caused by plant pathogens. "Anti-pathogenic compositions" is intended to mean that the compositions of the invention are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

An "antimicrobial agent," a "pesticidal agent," a "cystatin," and/or a "fungicidal agent" will act similarly to suppress, control, and/or kill the invading pathogen. A defensive agent will possess defensive activity. "Defensive activity" means an antipathogenic, antimicrobial, or antifungal activity.

"Antipathogenic compositions" is intended to mean that the compositions of the invention have activity against pathogens; including fungi, microorganisms, viruses, and nematodes, and thus are capable of suppressing, controlling, and/or killing the invading pathogenic organism. An antipathogenic composition of the invention will reduce the disease symptoms resulting from plant pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect organisms, particularly plants, from disease, particularly those diseases that are caused by invading pathogens.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, *maize* dwarf mosaic virus, etc. Specific fungal and viral pathogens for the major crops include, but are not limited to: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines, Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfae: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v.

syringae, Alternaria alternata, Cladosporium herbarum, Fusarium graminearum, Fusarium avenaceum, Fusarium culmorum, Ustilago tritci, Ascochyta tritci, Cephalosporium gramineum, Collotetrichum graminicola, Erysiphe graminis f.sp. tritici, Puccinia graminis f.sp. tritici, Puccinia recondita f.sp. tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis var. tritici, Pythium aphanidermatum, Pythium arrhenomanes, Pythium ultimum, Bipolaris sorokiniana, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, Claviceps purpurea, Tilletia tritici, Tilletia laevis, Tilletia indica, Pythium gramicola, High Plains Virus, European wheat striate virus; Sunflower: Broomrape, *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, *Maize* Dwarf Mosaic Virus A & B, Wheat Streak Mosaic Virus, *Maize* Chlorotic Dwarf Virus, *Claviceps sorghi, Pseudonomas avenae, Erwinia chrysanthemi* pv. *zea*, *Erwinia* carotovora, Corn stunt spiroplasma, *Diplodia macrospora, Sclerophthora macrospora, Peronosclerospora sorghi, Peronosclerospora philippinensis, Peronosclerospora maydis, Peronosclerospora saccharin, Sphacelotheca reiliana, Physopella zeae, Cephalosporium maydis, Cephalosporium acremonium, Maize* Chlorotic Mottle Virus, High Plains Virus, *Maize* Mosaic Virus, *Maize* Rayado Fino Virus, *Maize* Streak Virus, *Maize* Stripe Virus, *Maize* Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosponum sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, *Maize* Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*; Rice: rice brownspot fungus (*Cochliobolus miyabeanus*), rice blast fungus—*Magnaporthe grisea* (*Pyricularia grisea*), *Magnaporthe salvinii* (*Sclerotium oryzae*), *Xanthomomas oryzae* pv. *oryzae, Xanthomomas oryzae* pv. *oryzicola, Rhizoctonia* spp. (including but not limited to *Rhizoctonia solani, Rhizoctonia oryzae* and *Rhizoctonia oryzae-sativae*), *Pseudomonas* spp. (including but not limited to *Pseudomonas plantarii, Pseudomonas avenae, Pseudomonas glumae, Pseudomonas fuscovaginae, Pseudomonas alboprecipitans, Pseudomonas syringae* pv. *panici, Pseudomonas syringae* pv. *syringae, Pseudomonas syringae* pv. *oryzae* and *Pseudomonas syringae* pv. *aptata*), *Erwinia* spp. (including but not limited to *Erwinia herbicola, Erwinia amylovaora, Erwinia chrysanthemi* and *Erwinia carotovora*), *Achyla* spp. (including but not limited to *Achyla conspicua* and *Achyla klebsiana*), *Pythium* spp. (including but not limited to *Pythium dissotocum, Pythium irregulare, Pythium arrhenomanes, Pythium myriotylum, Pythium catenulatum, Pythium graminicola* and *Pythium spinosum*), *Saprolegnia* spp., *Dictyuchus* spp., *Pythiogeton* spp., *Phytophthora* spp., *Alternaria padwickii, Cochliobolus miyabeanus, Curvularia* spp. (including but not limited to *Curvularia lunata, Curvularia affinis, Curvularia clavata, Curvularia eragrostidis, Curvularia fallax, Curvularia geniculata, Curvularia inaequalis, Curvularia intermedia, Curvularia oryzae, Curvularia oryzae-sativae, Curvularia pallescens, Curvularia senegalensis, Curvularia tuberculata, Curvularia uncinata* and *Curvularia verruculosa*), *Sarocladium oryzae, Gerlachia oryzae, Fusarium* spp. (including but not limited *Fusarium graminearum, Fusarium nivale* and to different pathovars of *Fusarium monoliforme*, including pvs. *fujikuroi* and *zeae*), *Sclerotium rolfsii, Phoma exigua, Mucor fragilis, Trichoderma viride, Rhizopus* spp., *Cercospora oryzae, Entyloma oryzae, Dreschlera gigantean, Sclerophthora macrospora, Mycovellosiella oryzae, Phomopsis oryzae-sativae, Puccinia graminis, Uromyces coronatus, Cylindrocladium scoparium, Gaeumannomyces graminis* pv. *graminis, Myrothecium verrucaria, Pyrenochaeta oryzae, Ceratobasidium oryzae-sativae, Microdochium oryzae* (*Rhynchosporium oryzae*), *Cercospora janseana, Thanatephorus cucumeris, Ustilaginoidea virens, Neovossia* spp. (including but not limited to *Neovossia horrida*), *Tilletia* spp., *Balansia oryzae-sativae, Phoma* spp. (including but not limited to *Phoma sorghina, Phoma insidiosa, Phoma glumarum, Phoma glumicola* and *Phoma oryzina*), *Nigrospora* spp. (including but not limited to *Nigrospora oryzae, Nigrospora sphaerica, Nigrospora panici* and *Nigrospora padwickii*), *Epiococcum nigrum, Phyllostica* spp., *Wolkia decolorans, Monascus purpureus, Aspergillus* spp., *Penicillium* spp., *Absidia* spp., *Mucor* spp., *Chaetomium* spp., *Dematium* spp., *Monilia* spp., *Streptomyces* spp., *Syncephalastrum* spp., *Verticillium* spp., *Nematospora coryli, Nakataea sigmoidea, Cladosporium* spp., *Bipolaris* spp., *Coniothyrium* spp., *Diplodia oryzae, Exserophilum rostratum, Helococera oryzae, Melanomma glumarum, Metashaeria* spp., *Mycosphaerella* spp., *Oidium* spp., *Pestalotia* spp., *Phaeoseptoria* spp., *Sphaeropsis* spp., *Trematosphaerella* spp., rice black-streaked dwarf virus, rice dwarf virus, rice gall dwarf virus, barley yellow dwarf virus, rice grassy stunt virus, rice hoja blanca virus, rice necrosis mosaic virus, rice ragged stunt virus, rice stripe virus, rice stripe necrosis virus, rice transitory yellowing virus, rice tungro bacilliform virus, rice tungro spherical virus, rice yellow mottle virus, rice tarsonemid mite virus, *Echinochloa* hoja blanca virus, *Echinochloa* ragged stunt virus, rice bunchy stunt virus, rice giallume virus, orange leaf mycoplasma-like organism, yellow dwarf mycoplasma-like organism, *Aphelenchoides besseyi*, *Ditylenchus angustus*, *Hirschmanniella* spp., *Criconemella* spp., *Meloidogyne* spp., *Heterodera* spp., *Pratylenchus* spp., *Hoplolaimus indicus*.

Nematodes include plant-parasitic nematodes such as root-knot, cyst, and lesion nematodes, including *Heterodera* and *Globodera* spp. such as *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include, but are not limited to:Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicomis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, two-spotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis* grandis, boll weevil; *Aphis gossypii*, cotton aphid; *Pseudatomoscelis seriatus*, cotton fleahopper; *Trialeurodes abutilonea*, banded-winged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, two-spotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrostemum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

The cystatin sequences of the invention are provided in expression cassettes or DNA constructs for expression in the plant of interest. The cassette will include 5' and 3' regulatory sequences operably linked to a cystatin sequence of the invention. The cassette may additionally contain at least one additional gene to be cotransformed into the organism. Alternatively, the additional gene(s) can be provided on multiple expression cassettes.

Such an expression cassette is provided with a plurality of restriction sites for insertion of the cystatin sequence to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

While it may be preferable to express the sequences using heterologous promoters, the native promoter sequences may be used. Such constructs would change expression levels of cystatin in the host cell (i.e., plant or plant cell). Thus, the phenotype of the host cell (i.e., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot(1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986) *Virology* 154: 9–20); and human immunoglobulin heavy-chain binding protein (BiP), (Macejak et al. (1991) *Nature* 353:90–94); untranslated leader from the coat protein mRNA of *alfalfae* mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and *maize* chlorotic mottle virus leader (MCMV) (Lommel et al. (1991) *Virology* 81:382–385). See also, Della-Cioppa et al. (1987) *Plant Physiol.* 84:965–968. Other methods known to enhance transcription can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate, glyphosate, ammonium, bromoxynil, imidazolinones, and 2,4-dichlorophenoxyacetate (2,4-D). See generally, Yarranton (1992) *Curr. Opin. Biotech.* 3:506–511; Christopherson et al., (1992) *Proc. Natl. Acad. Sci. USA* 89:6314–6318; Yao et a. (1992) *Cell* 71:63–72; Reznikoff (1992) *Mol. Microbiol.* 6:2419–2422; Barkley et a. (1980) in *The Operon*, pp. 177–220; Hu et al. (1987) *Cell* 48:555–566; Brown et a. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) Proc. Natl. Acad. Sci. USA 89:5547–5551; Oliva et al., (1992) *Antimicrob. Agents Chemother.* 36:913–919; Hlavka et al. (1985) *Handbook of Experimental Pharmacology, Vol. 78* (Springer-Verlag, Berlin); Gill et al. (1988) *Nature* 334: 721–724; and WO Publication No. 02/36782. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV $^{35}$S promoter (Odell et al. (1985) *Nature* 313:810–812); rice actin (McElroy et al. (1990) *Plant Cell* 2:163–171); ubiquitin (Christensen et al., (1989) *Plant Mol. Biol.* 12:619–632 and Christensen et al. (1992) *Plant Mol.*

*Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et a. (1992) *Plant Cell* 4:645–656; and Van Loon (1985) *Plant Mol. Virol.* 4:111-116. See also, U.S. application Ser. No. 09/257,583 and WO 99/43819, herein incorporated by reference.

Of interest are promoters that are expressed locally at or near the site of pathogen infection. See, for example, Marineau et a. (1987) *Plant Mol. Biol.* 9:335–342; Matton et a. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et a. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990)*Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991)*Mol. Gen. Genet.* 227:229–237, and U.S. Pat. Nos. 5,814,618 and 5,789,156), herein incorporated by reference.

Tissue-preferred promoters can be utilized to target enhanced cystatin expression within a particular plant tissue. Tissue-preferred promoters include those disclosed in Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Just as expression of an antipathogenic polypeptide of the invention may be targeted to specific plant tissues or cell types through the use of appropriate promoters, it may also be targeted to different locations within the cell through the use of targeting information or "targeting labels". Unlike the promoter, which acts at the transcriptional level, such targeting information is part of the initial translation product. Depending on the mode of infection of the pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel N, Chrispeels M J (2000) Protein sorting and vesicle traffic. In B Buchanan, W Gruissem, R Jones, eds, Biochemistry and Molecular Biology of Plants. American Society of Plant Physiologists, Rockville, Md., pp 160–201, herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606), *Agrobacterium*-mediated transformation (Townsend et al., U.S. Pat. No. 5,563,055 and Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) In vitro *Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563. (*maize*); Tomes, U.S. Pat. No. 5,240,855; Buising et al., U.S. Pat. Nos. 5,322,783 and 5,324,646; Klein et al. (1988) *Plant Physiol.* 91:440–444 (*maize*); Fromm et al. (1990) *Biotechnology* 8:833–839 (*maize*); Hooykaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (*maize* via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plans that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those *Brassica* species useful as sources of seed oil, alfalfae (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setara italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulchernima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesil*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfae, sunflower, *Brassica*, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229–235 and Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention. Such antimicrobial proteins can be used for any application including coating surfaces to target microbes. In this manner, target microbes include human pathogens or microorganisms.

Synthesis of heterologous nucleotide sequences in yeast is well known. Sherman, F., et al. (1982) *Methods in Yeast Genetics*, Cold Spring Harbor Laboratory is a well recognized work describing the various methods available to produce a protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider, *J. Embryol. Exp. Morphol.* 27:353–365 (1987)).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al. (1983) *J. Virol.* 45:773–781). Additionally, gene sequences to control replication in the host cell may be incorporated into the vector such as those found in bovine papilloma virus type-vectors. See, Saveria-Campo, M., (1985) Bovine Papilloma Virus DNA a Eukaryotic Cloning Vector in *DNA Cloning Vol. II a Practical Approach*, D. M. Glover, Ed., IRL Press, Arlington, Va. pp. 213–238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. See, Kuchler, R. J. (1997) *Biochemical Methods in Cell Culture and Virology*, Dowden, Hutchinson and Ross, Inc.

It is recognized that with these nucleotide sequences, antisense constructions, complementary to at least a portion of the messenger RNA (mRNA) for the cystatin sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The present invention further provides a method for modulating (i.e., increasing or decreasing) the concentration or composition of the polypeptides of the present invention in a plant or part thereof. Increasing or decreasing the concentration and/or the composition of polypeptides in a plant can affect modulation. For example, increasing the ratio of polypeptides of the invention to native polypeptides can affect modulation. The method comprises: introducing a polynucleotide of the present invention into a plant cell with a recombinant expression cassette as described above to obtain a transformed plant cell, culturing the transformed plant cell under appropriate growing conditions, and inducing or repressing expression of a polynucleotide of the present invention in the plant for a time sufficient to modulate the concentration and/or the composition of polypeptides in the plant or plant part.

In some embodiments, the content and/or composition of polypeptides of the present invention in a plant may be modulated by altering, in vivo or in vitro, the promoter of the nucleotide sequence to up- or down-regulate expression. For instance, an isolated nucleic acid comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, concentration or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In preferred embodiments, the polypeptides of the present invention are modulated in monocots, particularly *maize*.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of the *maize*, soybean, rice and wheat cystatin sequences presented (SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57; 59, 61, 63, 65, 67, 69, 71, 73, and 75), or with other genes implicated in disease resistance pathways, especially those that have antimicrobial activity like cystatins, such as: (a) other proteinase inhibitors, such as trypsin proteinase inhibitors (Chen et al. (1999) Appl Environ Microb 65(3): 1320–1324.), subtilisin/chymotrypsin inhibitors (Cordero et al. (1994) Plant J 6(2): 141–150), trypsin/alpha-amylase inhibitors (Wen et al. (1992) Plant Mol. Biol. 18(4): 813–814), and Bowman-Birk proteinase inhibitors (Prakash et al. (1996) J Mol Evol 1996; 42 (5): 560–569); (b) small cysteine-rich antimicrobial proteins, such as defensins (Thomma et al. (2002) Planta 261(2): 193–202) or gamma-thionins (Nitti et al. (1995) Eur J Biochem 228(2): 250–6), kistrin-like cysteine-rich proteins (Segura, et al. (1999) Mol Plant Microbe Interact 12: 16–23), cyclotides (Craik et al. (1999) J Mol Biol 294(5):1327–36), and basal layer antifungal peptides (Hueros et al. (1995) Plant Cell 7: 747–757); (c) antimicrobial enzymes, such as endo-1,3-beta-glucanases, chitinases (Simmons (1994) CRC Cr Rev Plant Sci 13: 325–387), RNAses (Hugot et al. (2002) Mol Plant Microbe Interact 15(3): 243–250); (d) other pathogenesis-related proteins, such as PR-1 homologs (Tornero et al. (1997) Mol Plant Microbe Interact 10(5): 624–34), PR-10/ocatin/major latex protein homologs (McGee et al. (2001) Mol Plant Microbe Interact 14(7): 877–86), PR-5/thaumatin/osmotin homologs (Barre et al. (2000) Planta. 211 (6): 791–9); (e) and other antimicrobial proteins such as lipid transfer proteins (Park et al. (2002) Plant Mol. Biol. 48(3): 243–54), puroindolines (Krishnamurthy et al. (2001). Mol Plant Microbe Interact 14: 1255–1260), alpha- and beta-thionins (Rodriguez-Palenzuela et al. (1988) Gene 70: 271–281; Van Campenhout et al. (1998) Theor Appl Genet 96: 80–86), *maize* basic proteins (Duvick et al. (1992) J Biol Chem 267(26): 18814–18820), and small histidine-glycine rich proteins (Park et al. (2000) Plant Mol Biol 44: 187–197) and the like, the disclosures of which are herein incorporated by reference. It is understood that other genes and their products that are not themselves antimicrobial, but which contribute to the disease response by a number mechanisms, could also be employed in conjunction, among them LRR-proteins (Mondragon-Palomino et al. (2002) Genome Res (9): 1305–15) and other R gene analogues, transcription factors such as WRKY (Eulgem et al. (2000) Trends Plant Sci (5): 199–206), multidrug transporters (Diener et al. (2001) Plant Cell 13(7): 1625–38), phenylpropanoid pathway enzymes (Dixon et al. (1996) Gene 179(1):61–71), and polygalacturonase inhibitor proteins (Berger et al. (2000).

Phys Mol Plant Pathol. 57 (1): 5–14). Such genes could come from *maize* or non-maize sources, including non-plant sources.

The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409)); barley high lysine (Williamson et al. (1987) Eur. J. Biochem. 165:99–106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001)); and thioredoxins (U.S. application Ser. No. 10/005, 429, filed Dec. 3, 2001), the disclosures of which are herein incorporated by reference.

The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593, 881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266: 789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene)); and traits desirable for processing or process products such as high oil (U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (U.S. Pat. No. 5,602,321); beta-ketothiolase, polyhydroxybutyrate synthase, and acetoacetyl-CoA reductase (Schubert et al. (1988) J. Bacteriol. 170:5837–5847), which facilitate expression of polyhydroxyalkanoates (PHAs)), the disclosures of which are herein incorporated by reference. One could also combine the polynucleotides of the present invention with polynucleotides providing agronomic traits such as male sterility (see U.S. Pat. No. 5,583,210), stalk strength, flowering time, or transformation technology traits such as cell cycle regulation or gene targeting (see, WO 99/61619; WO 00/17364; WO 99/25821), the disclosures of which are herein incorporated by reference.

These stacked combinations can be created by any method including, but not limited to, polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in plants (Ed., Andrew H. Paterson) by Academic Press/R.G. Lands Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes hybridize, under selective hybridization conditions, to a gene encoding a polynucleotide of the present invention. In preferred embodiments, the probes are selected from polynucleotides of the present invention. Typically, these probes are cDNA probes or restriction enzyme treated (e.g., PST I genomic clones. The length of the probes is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome compliment. Some exemplary restriction enzymes employed in RFLP mapping are EcoRI, EcoRV, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present invention of the genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a *maize* polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

The methods of the invention can be used with other methods available in the art for enhancing disease resistance in plants. Similarly, the antimicrobial compositions described herein may be used alone or in combination with other nucleotide sequences, polypeptides, or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens.

Proteins, peptides, and lysozymes that naturally occur in insects (Jaynes et al. (1987) *Bioassays* 6:263–270), plants (Broekaert et al. (1997) *Critical Reviews in Plant Sciences* 16:297–323), animals (Vunnam et al. (1997) *J. Peptide Res.* 49:59–66), and humans (Mitra and Zang (1994) *Plant Physiol.* 106:977–981; Nakajima et al. (1997) *Plant Cell Reports* 16:674–679) are also a potential source of plant disease resistance (Ko, K. (2000) www.scisoc.org/feature/BioTechnology/antimicrobial.html). Examples of such plant resistance-conferring sequences include those encoding sunflower rhoGTPase-Activating Protein (rhoGAP), lipoxygenase (LOX), Alcohol Dehydrogenase (ADH), and *Sclerotinia*-Inducible Protein-1 (SCIP-1) described in U.S. application Ser. No. 09/714,767, herein incorporated by reference. These nucleotide sequences enhance plant disease resistance through the modulation of development, developmental pathways, and the plant pathogen defense system. Other plant defense proteins include those described in WO 99/43823 and WO 99/43821, all of which are herein incorporated by reference. It is recognized that such second nucleotide sequences may be used in either the sense or antisense orientation depending on the desired outcome.

In another embodiment, the cystatins comprise isolated polypeptides of the invention. The cystatins of the invention find use in the decontamination of plant pathogens during the processing of grain for animal or human food consumption; during the processing of feedstuffs, and during the processing of plant material for silage. In this embodiment, the cystatins of the invention, are presented to grain, plant material for silage, or a contaminated food crop, or during an appropriate stage of the processing procedure, in amounts effective for anti-microbial activity. The compositions can be applied to the environment of a plant pathogen by, for example, spraying, atomizing, dusting, scattering, coating or pouring, introducing into or on the soil, introducing into irrigation water, by seed treatment, or dusting at the time when the plant pathogen has begun to appear or before the appearance of pests as a protective measure. It is recognized that any means to bring the defensive agent polypeptides in contact with the plant pathogen can be used in the practice of the invention.

Additionally, the compositions can be used in formulations used for their antimicrobial activities. Methods are provided for controlling plant pathogens comprising applying a decontaminating amount of a polypeptide or composition of the invention to the environment of the plant pathogen. The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The decontaminating concentration will vary depending upon the nature of the particular formulation, specifically, whether it is a concentrate or to be used directly.

In a further embodiment, the compositions, as well as the polypeptides of the present invention can be treated prior to formulation to prolong their activity when applied to the environment of a plant pathogen as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W. H. Freeman and Co.)).

In an embodiment of the invention, the compositions of the invention comprise a microbe having stably integrated the nucleotide sequence of a defensive agent. The resulting microbes can be processed and used as a microbial spray. Any suitable microorganism can be used for this purpose. See, for example, Gaertner et al. (1993) in *Advanced Engineered Pesticides*, Kim (Ed.). In one embodiment, the nucleotide sequences of the invention are introduced into microorganisms that multiply on plants (epiphytes) to deliver the cystatins to potential target crops. Epiphytes can be, for example, gram-positive or gram-negative bacteria.

It is further recognized that whole, i.e., unlysed, cells of the transformed microorganism can be treated with reagents that prolong the activity of the polypeptide produced in the microorganism when the microorganism is applied to the environment of a target plant. A secretion signal sequence may be used in combination with the gene of interest such that the resulting enzyme is secreted outside the microorganism for presentation to the target plant.

In this manner, a gene encoding a defensive agent of the invention may be introduced via a suitable vector into a microbial host, and said transformed host applied to the environment, plants, or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the detoxifying polypeptide, and for improved protection of the enzymes of the invention from environmental degradation and inactivation.

Such microorganisms include bacteria, algae, and fungi. Of particular interest are microorganisms, such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes*; fungi, particularly yeast, e.g., *Saccharomyces, Pichia, Cryptococcus, Kluyveromyces, Sporobolomyces, Rhodotorula, Aureobasidium,* and *Gliocladium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pullulans*.

Illustrative prokaryotes, both Gram-negative and -positive, include Enterobacteriaceae, such as *Escherichia, Erwinia, Shigella, Salmonella,* and *Proteus*; Bacillaceae; Rhizobiaceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae; and Nitrobacteraceae. Among eukaryotes are fungi, such as *Phycomycetes* and *Ascomycetes*, which includes yeast, such as *Saccharomyces* and *Schizosaccharomyces*; and Basidiomycetes yeast, such as *Rhodotorula, Aureobasidium, Sporobolomyces,* and the like.

In an embodiment of the invention, the cystatins of the invention may be used as a pharmaceutical compound for treatment of fungal and microbial pathogens in humans and other animals. Diseases and disorders caused by fungal and microbial pathogens include but are not limited to fungal meningoencephalitis, superficial fungal infections, ringworm, Athlete's foot, histoplasmosis, candidiasis, thrush, coccidioidoma, pulmonary cryptococcus, trichosporonosis, piedra, tinea nigra, fungal keratitis, onychomycosis, tinea capitis, chromomycosis, aspergillosis, endobronchial pulmonary aspergillosis, mucormycosis, chromoblastomycosis, dermatophytosis, tinea, fusariosis, pityriasis, mycetoma, pseudallescheriasis, and sporotrichosis.

The compositions of the invention may be used as pharmaceutical compounds to provide treatment for diseases and disorders associated with, but not limited to, the following fungal pathogens: *Histoplasma capsulatum, Candida* spp. (*C. albicans, C. tropicalis, C. parapsilosis, C. guilliermondii, C. glabrata/Torulopsis glabrata, C. krusei, C. lusitaniae*), *Aspergillus fumigatus, A. flavus, A. niger, Rhizopus* spp., *Rhizomucor* spp., *Cunninghamella* spp., *Apophysomyces* spp., *Saksenaee* spp., *Mucor* spp., and *Absidia* spp. Efficacy of the compositions of the invention as anti-fungal treatments may be determined through anti-fungal assays known to one of skill in the art.

The cystatins may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

The cystatins of the invention can be used for any application including coating surfaces to target microbes. In this manner, target microbes include human pathogens or microorganisms. Surfaces that might be coated with the cystatins of the invention include carpets and sterile medical facilities. Polymer bound polypeptides of the invention may be used to coat surfaces. Methods for incorporating compositions with anti-microbial properties into polymers are known in the art. See U.S. Pat. No. 5,847,047 herein incorporated by reference.

An isolated polypeptide of the invention can be used as an immunogen to generate antibodies that bind cystatins using standard techniques for polyclonal and monoclonal antibody preparation. The full-length cystatins can be used or, alternatively, the invention provides antigenic peptide fragments of cystatins for use as immunogens. The antigenic peptide of a defensive agent comprises at least 8, preferably 10, 15, 20, or 30 amino acid residues of the amino acid sequence shown in any of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, and 76, and encompasses an epitope of a cystatin such that an antibody raised against the peptide forms a specific immune complex with the anti-microbial polypeptides. Preferred epitopes encompassed by the antigenic peptide are regions of cystatins that are located on the surface of the protein, e.g., hydrophilic regions.

Accordingly, another aspect of the invention pertains to anti-cystatin polyclonal and monoclonal antibodies that bind a cystatin. Polyclonal cystatin-like antibodies can be prepared by immunizing a suitable subject (e.g., rabbit, goat, mouse, or other mammal) with an defensive agent-like immunogen. The anti-cystatin antibody titer in the immunized subject can be monitored over time by standard techniques, such as with an enzyme linked immunosorbent assay (ELISA) using immobilized anti-microbial polypeptides. At an appropriate time after immunization, e.g., when the anti-defensive agent antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies* and *Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternatively to preparing monoclonal antibody-secreting hybridomas, a monoclonal anti-cystatin-like antibody can be identified and isolated by screening a recombinant combinatorial immunoglobulin library (e.g., an antibody phage display library) with a cystatin to thereby isolate immunoglobulin library members that bind the defensive agent. Kits for generating and screening phage display libraries are commercially available (e.g., the Pharmacia Recombinant Phage Antibody System, Catalog No. 27–9400–01; and the Stratagene SurfZAP™ Phage Display Kit, Catalog No. 240612). Additionally, examples of methods and reagents particularly amenable for use in generating and screening an antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Anti-bod. Hybridomas* 3:81–85; Huse et al. (1989) *Science* 246:1275–1281; Griffiths et al. (1993) *EMBO J.* 12:725–734. The antibodies can be used to identify homologs of the cystatins of the invention.

The following examples are offered by way of illustration and not by way of limitation.

The following stock solutions and media were used for transformation and regeneration of soybean roots:

Stock Solutions (per Liter):
10×B-5 Majors: 25.00 g $KNO_3$, 1.34 g $(NH_4)_2 SO_4$, 2.50 g $MgSO_4.7H_2O$, 1.50 g $CaCl_2.2H_2O$, 1.31 g $NaH_2PO_4$ (anhydrous).
100×B-5 Minors: 1.00 g $MnSO_4.H_2O$, 0.30 g $H_3BO_3$, 0.20 g $ZnSO_4.7H_2O$, 0.075 g KI.
100×B-5 Vitamins with Thiamine: 10.00 g myo-Inositol, 1.00 g Thiamine*HCl, 0.10 g Nicotinic acid, 0.10 g Pyridoxine HCl.
100×Iron Mix: 3.73 g. $Na_2EDTA$, 2.78 g $FeSO_4 7H_2O$.

Media (per Liter):
Minimal A medium: 10.5 g $K_2HPO_4$, 4.5 g $KH_2PO_4$, 1.0 g $(NH_4)_2SO_4$, 0.5 g $(Na)_2C_6H_5O_7 2H_2O$, 246.5 mg $MgSO_4 7H_2O$, 2 g sucrose, 15 g agar.
0 B-5 medium: 0.6 g MES [2-(N-Morpholino) ethanesulfonic acid (Sigma, M5287), 20 g sucrose, 10 mL 100×B-5 minors, 100 mL 10×B-5 majors, 10 mL 100×B-5 vitamins with Thiamine, 10 mL 100×Iron mix.
MXB medium: Murashige and Skoog Basal nutrient salts (M5524, Sigma), 10 mL 100×B-5 Vitamins with thiamine, 30 g sucrose, 3 g gelrite, pH 5.7.
SOC medium: 20 g bactotryptone, 5 g yeast extract (Difco), 2 mL 5 M NaCl, 2.5 mL 1 M KCl, 10 mL 1 M $MgCl_2$, 10 mL 2 M glucose, 10 mL 1 M $MgSO_4$.

EXAMPLE 1

Transformation and Regeneration of Transgenic Plants

Immature *maize* embryos from greenhouse donor plants are bombarded with a plasmid containing the cystatin sequences of the present invention operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

Preparation of DNA

This plasmid DNA plus plasmid DNA containing a PAT selectable marker is precipitated onto 1.1 μm (average diameter) tungsten pellets using a $CaCl_2$ precipitation procedure as follows:
  100 μL prepared tungsten particles in water
  10 μL (1 μg) DNA in Tris EDTA buffer (1 μg total DNA)
  100 μL 2.5 M $CaCl_2$
  10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 μL 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for and altered level of expression of the cystatin sequence of the invention. Alternatively, the cysteine proteinase activity can be assayed.

Bombardment and Culture Media

Bombardment medium (560Y) comprises 4.0 g/L N6 basal salts (SIGMA C-1416), 1.0 mL/L Eriksson's Vitamin Mix (1000×SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 111117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) *Physiol. Plant* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleaceatic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

EXAMPLE 2

*Agrobacterium*-Mediated Transformation

For *Agrobacterium*-mediated transformation of *maize* with a cystatin nucleotide sequence of the invention, operably linked to a ubiquitin promoter, preferably the method of Zhao is employed (U.S. Pat. No. 5,981,840, and PCT patent publication WO98/32326; the contents of which are hereby incorporated by reference). Briefly, immature embryos are isolated from *maize* and the embryos contacted with a suspension of *Agrobacterium*, where the bacteria are capable of transferring the DNA construct containing the cystatin nucleotide sequence to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 3

Identification of the Gene from a Computer Homology Search

Gene identities were determined by conducting BLAST (Basic Local Alignment Search Tool; Altschul, S. F., et al. (1993) *J. Mol. Biol.* 215:403–410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases).

The cDNA sequences of the present invention were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI.

In some cases, the sequencing data from two or more clones containing overlapping segments of DNA were used to construct contiguous DNA sequences.

Sequence alignments and percent identity calculations were performed using GAP, as well as the Megalign program of the LASERGENE bioinformatics computing suite (DNASTAR Inc., Madison, Wis.). Multiple alignments of the sequences were performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

EXAMPLE 4

Soybean Embryo Transformation

Soybean embryos are bombarded with a plasmid containing the cystatin sequence operably linked to a ubiquitin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures are maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the cystatin sequence operably linked to the ubiquitin promoter can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 5

Sunflower Meristem Tissue Transformation

Sunflower meristem tissues are transformed with an expression cassette containing the cystatin sequence operably linked to a ubiquitin promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 mL of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant,* 15: 473–497), Shepard's vitamin additions (Shepard (1980) in *Emergent Techniques for the Genetic Improvement of Crops* (University of Minnesota Press, St. Paul, Minn.), 40 mg/L adenine sulfate, 30 g/L sucrose, 0.5 mg/L 6-benzyl-aminopurine (BAP), 0.25 mg/L indole-3-acetic acid (IAA), 0.1 mg/L gibberellic acid ($GA_3$), pH 5.6, and 8 g/L Phytagar.

The explants are subjected to microprojectile bombardment prior to *Agrobacterium* treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 mL of sterile TE buffer (10 mM Tris HCl, 1 mM EDTA, pH 8.0) and 1.5 mL aliquots are used per bombardment. Each plate is bombarded twice through a 150 mm nytex screen placed 2 cm above the samples in a PDS 1000® particle acceleration device.

Disarmed *Agrobacterium tumefaciens* strain EHA 105 is used in all transformation experiments. A binary plasmid vector comprising the expression cassette described above is introduced into *Agrobacterium* strain EHA 105 via freeze-thawing as described by Holsters et al. (1978) *Mol. Gen.*

*Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 g/L yeast extract, 10 g/L Bactopeptone, and 5 g/L NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 g/L $NH_4Cl$, and 0.3 g/L $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/L cefotaxime and 50 mg/L kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/L cefotaxime for a second 3-day phytohormone treatment. Leaf samples from green, kanamycin-resistant shoots are assayed for the presence of NPTII by ELISA and for the presence of transgene expression by assaying for the activity of the cystatin sequences.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of To plants (parental generation) maturing in the greenhouse are identified by NPTII ELISA and/or by the analysis of the activity of the cystatin sequences in the leaf extracts while transgenic seeds harvested from NPTII-positive To plants are identified by the analysis of the activity the cystatin sequences in small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 mL of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/L adenine sulfate, 3% sucrose, 0.5 mg/L 6-BAP, 0.25 mg/L IAA, 0.1 mg/L GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µL absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/L yeast extract, 10 g/L Bactopeptone, and 5 g/L NaCl, pH 7.0) in the presence of 50 µg/L kanamycin is resuspended in an inoculation medium (12.5 mM 2-mM 2-(N-morpholino) ethanesulfonic acid, MES, 1 g/L $NH_4Cl$ and 0.3 g/L $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/mL cefotaxime). The plantlets are cultured on the medium for about two weeks under 16-hour day and 26° C. incubation conditions.

Explants (around 2 cm long) from two weeks of culture in 374C medium are screened for cystatin activity using assays known in the art. After positive (i.e., for cystatin expression) explants are identified, those shoots that fail to exhibit cystatin activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for defense-inducible expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 mL of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

EXAMPLE 6

Transformation of BL21 Star Cells and Cystatin Expression and Purification

Strain Transformation

One µL samples of mini-prep DNA were incubated on ice with 20 µL of BL21 Star cells (Invitrogen) for 30 minutes.

The DNA/cell mixtures were then heated at 42° C. for 45 sec, then iced for 2 min. 200 μL of SOC were added to each tube, and these mixtures were then incubated at 37° C. for 1 hour. 50 μL samples were spread out on LB broth plates containing 100 mg/L carbenicillin and 0.1M $MgSO_4$ to incubate overnight at 37° C.

Protein Expression

Bacteria samples in duplicate were selected from the plates, and these were incubated overnight in 2.0 mL of 2xYT media containing 100 μg/mL carbenicillin. The incubations took place in a 48 well, pyramid bottom plate (Innovative Microplate) at 37° C. on a shaker (225 rpm).

The next day, the OD readings for the wells were obtained after diluting 10 μL bacterial samples with 90 μL of water in a standard 96-well, flat bottomed microtiter plate, with the absorbance read at 600 nm. Based on these values, the cultures were diluted with fresh 2xYT (+carb.) to the two target induction $OD_{600}$ values of 0.1 and 0.6, to a final volume of 2 mL. Each target OD value was diluted in quadruplicate to account for two isopropyl-beta-D-thiogalactopyranoside (IPTG) induction values each and two incubation temperatures each. When the plates were ready, the wells were induced with IPTG at concentrations of either 0.05 mM or 1.0 mM. The plates were then incubated overnight on shakers (225 rpm) at temperatures of either 16° C. or 30° C. After approximately 20 hours of incubation, the OD values for all the wells were obtained as described supra. The cells were then harvested by centrifuging the plates at 1700 rpm for 10 minutes. The supernatants were discarded and the pelleted cells frozen at −20° C. until purification could take place.

Protein Purification

The cells were allowed to thaw for several minutes, then 200 μL of B-PerII protein extraction reagent (Pierce) containing 0.2 units of benzonase (Novagen) were added to each well, and the solution was pipetted repeatedly to resuspend the pellet. The cells were incubated for 10 min in the B-PerII solution.

25–30 μm MBPP 800 μL purification filter plates (Whatman) were prepared by adding 200 μL of 50% slurry of glutathione Sepharose 4B resin (Amersham) for GST-tagged proteins, or TALON resin (Clontech) for HIS-tagged proteins into each well. The plates were centrifuged briefly to remove excess buffer. The lysates were transferred directly from the growth plate to the plates with the resins, and the solutions were pipetted up and down several times to mix them well. The plates were then centrifuged at 760 rpm for 5 min, and the flow-through was discarded. The resins with the bound proteins were washed twice with 200 μL of buffer A (50 mM Tris, pH 8.0, 200 mM NaCl, 10% glycerol), and each time the plates were centrifuged at 760 rpm for 5 min and the wash was discarded. Standard 96 well plates were placed underneath the Whatman filter plates, and the proteins were eluted by adding and mixing 100 μL of buffer A containing either 20 mM reduced glutathione (Sigma) for GST tags, or 500 mM imidazole (Sigma) for HIS tags. The plates were centrifuged at 1000 rpm for 5 min, and the purified proteins were collected in the standard 96 well plates placed underneath.

Bradford reactions were performed to determine the protein concentrations for all the samples. These values were used to establish normalization plates for the cystatin assays where equal volumes contained equal amounts of protein. However, when the protein concentration was too low for a given sample, 20 μL were used directly in the cystatin assay to come as close as possible to the target amount of 6 μg of protein.

EXAMPLE 7

Anti-Fungal and Anti-Bacterial Assays

The anti-fungal and anti-bacterial activity of the cystatin polypeptides of the invention can be tested using a variety of assays.

BL21 cells were transformed with cystatin genes using the Lambda CE6 Induction Kit (Stratagene) according to the manufacturer's protocol. The induced BL21 cells were grown and harvested, and then resuspended in the binding buffer from a His-Bind Kit (Novagen). The suspended cells were sonicated to release the expressed protein from the cells. The crude protein extract was denatured by dissolving it into a 6 M urea solution for 1 hour on ice in order to allow the His-tag to efficiently bind to the resin. The denatured cystatins were then purified by His-Bind Resin Chromatography according to the manufacturer's protocol, except that 6M Urea was added to the binding, washing and elution buffers.

The purified proteins were renatured by dialysis using 1xPBS buffer with gradually decreased concentration of urea (5M, 4M, 3M, 1.5M, and 0.75M). The dialyses were performed with each concentration of urea for one hour and then with 1xPBS buffer without urea overnight at 4° C. Bradford reactions were performed to determine the protein concentrations for all the samples. The isolated polypeptide was then tested for activity.

Anti-Fungal Assays:

*Fusadum verticillioides* (strain M033) was grown on ½× potato dextrose agar plates: (For each liter, 12 grams Difco Potato Dextrose Broth (#0549-17-9) and 15 grams agar were suspended in $dH_2O$, final volume was raised to 1 liter and autoclaved at 121° C. for 20 minutes. Plates were poured in sterile hood.) Spores were collected from 10 day old to 3 week old culture plates of *Fusarium verticillioides* by rinsing a portion of the plate with potato dextrose broth (24 grams Difco Potato Dextrose Broth (#0549-17-9) per liter+ 0.08% tween-20). The collected spore solution was then vortexed and placed on ice. The spores were counted with a hemocytometer and used within 2 hours. 4× assay medium with spores was prepared by diluting the collected spores with potato dextrose broth+0.08% tween-20 to 16,000 spores per milliliter.

The two purified cystatins used in this assay were supplied in PBS buffer, which was prepared by diluting a 10× commercial stock buffer (10× phosphate buffered saline [137 mM NaCl, 2.7 mM KCl, 10 mM phosphate pH 7.3–7.5] EM Science Catalog #6505) with water. The protein concentration of each cystatin was measured using the Pierce BCA protein assay (BCA Protein Assay Reagent, Pierce catalog #23225; Smith, P. K., et al. (1985). Measurement of protein using bicinchoninic acid (*Anal. Biochem.* 150, 76–85.) calibrated against BSA. The purified GmCys-2 (SEQ ID NO: 30) protein was supplied at 5.7 mg/mL and the ZmCys-4 (SEQ ID NO: 6) protein was supplied at 3.2 mg/mL.

For an assay, 25 μL of the 4× assay medium with spores was diluted to 1× with 75 μL test sample/water. Assays were conducted in 96 well microtiter plates.

Plates were covered and incubated at 28° in the dark for 24–48 h. Growth was evaluated visually using an inverted microscope, and a scale of 0–4 was used to rate the effect of added peptide.

Antifungal activity was rated as follows:
0=no observable inhibition relative to water control
1=slight inhibition
2=strong inhibition, contained growth (fuzzy balls)
3=strong inhibition, very little branching
4=complete inhibition of germination PBS buffer was tested at an equivalent dilution and no effect was observed (score=0) for all control samples.

TABLE 13

Anti-Fusarium activity of maize cystatin
Zm-Cys4 and soybean cystatin Gm-Cys2.

| ZmCys-4 (SEQ ID NO: 6) | | GmCys-2 (SEQ ID NO: 30) | | |
|---|---|---|---|---|
| Concentration | Score | Concentration | Score | |
| (µg/mL) | 26 hours | (µg/mL) | 24 hours | 48 hours |
| 400 | 3.5 | 570 | 4 | 3.5 |
| 200 | 3.5 | 280 | 4 | 0 |
| 100 | 3.5 | 140 | 3 | 0 |
| 50 | 3 | 71 | 2 | 0 |
| 25 | 2 | 35 | 1 | 0 |
| 12.5 | 1 | 18 | 0 | 0 |
| 6 | 1 | 9 | 0 | 0 |
| 3 | 1 | 4 | 0 | 0 |

The results shown in Table 13, above, are a clear indication that both ZmCys4 (SEQ ID NO: 6) and GmCys-2 (SEQ ID NO: 30) have a significant anti-fungal activity towards *F. verticillioides*.

Anti-bacterial Assays. Cultures are grown to midlog phase (*E. coli* in LB broth and *C. nebraskense* in NBY) and are then harvested by centrifugation (2000×g for 10 min). Cells are washed with 10 mM sodium phosphate buffer, pH 5.8 (*C. nebraskense*) or pH 6.5 (*E. coli*) by centrifugation and then colony forming units are estimated spectrophotometrically at 600 nm with previously established colony forming unit-optical density relationships used as a reference.

Assays for bactericidal activity are performed by incubating $10^5$ bacterial colony forming units in 90 µL with 10 mL of peptide (or water for control). After 60 min at 37° C. (*E. coli*) or 25° C. (*C. nebraskense*), four serial, 10-fold dilutions are made in sterile phosphate buffer. Aliquots of 100 µL are plated on LB or NBY plates, using 1 or 2 plates/dilution. Resulting colonies are counted, and the effect of the peptide is expressed as percent of initial colony count (Selsted et al. (1984) *Infect. Immun.* 45:150–154).

Assays for bacteriostatic activity are performed by incubating $10^5$ bacteria with MBP-1 in 200 µL of dilute medium (1 part NBY broth to 4 parts 10 mM sodium phosphate, pH 5.8) in microtiter plate wells. Plates are covered, sealed, and incubated at 28° C. Growth is monitored spectrophotometrically at 600 nm. After 41 h controls will have grown sufficiently (optical density>0.20) to measure effect of peptide as percent of control.

EXAMPLE 8

Proteinase Inhibition Assays Cystatin Assay

The measurement of inhibition activity of cystatins toward papain was based on the method by Kouzuma et al. (1996) (*J. Biochem.* 119: 1106–1113) (see FIG. 1). The assay was performed in a 96 well plate. Twenty µL of a cystatin solution containing either 6 µg or 0.06 µg of cystatin protein were incubated with 20 µL of papain solution (0.1 mg/mL papain (Calbiochem) stock in 100 mM phosphate buffer, pH 6.5, 0.3 M KCl, 0.1 mM EDTA, and 1 mM freshly added DTT) at 37° C. for 15 min. 200 µL of filtered substrate solution (504 µM L-pyroglutamyl-L-phenylalanyl-L-leucine p-nitroanilide (Pyr-Phe-Leu-pNA; Sigma, P3169) with 10% DMSO (Sigma) in the same buffer as above) were then added to the reaction mix and the plate incubated at 37° C. for one hour. Formation of p-nitroaniline was measured by measuring absorbance at 420 nm. Further 37° C. incubation took place with 420 nm readings being taken at desired time intervals. The reaction was stopped by the addition of 30 µL of 30% acetic acid without significantly affecting the absorbance values. Cysteine proteinase inhibitory activity was indicated by smaller absorbance values for the 6 µg protein wells versus the 0.06 µg wells for each cystatin. Negative controls consisted of buffer without cystatin protein. Positive controls consisted of previously tested cystatins.

TABLE 14

Impact of N-terminal tag and induction conditions on cystatin activity.

| | | Cystatin activity | | |
|---|---|---|---|---|
| Gene | SEQ ID NO: | GST-tagged | His-tagged | Conditions for highest activity |
| GmCys2 | 29 | low/medium | Low | GST: 16 C His: 25 C, OD 0.8 |
| GmCys4 | 33 | not detected | not detected | |
| GmCys5 | 35 | low/medium | not detected | GST: 30 C, 0.05 mM IPTG, OD 0.1 |
| GmCys7 | 39 | low | not detected | GST: 30 C, 0.05 mM IPTG, OD 0.1 |
| GmCys9 | 43 | high | High | GST: 30 C, 0.05 mM IPTG, OD 0.1 His: 16 C, 1 mM IPTG, OD 0.6 |
| OsCys4 | 51 | not detected | not detected | |
| OsCys6 | 55 | high | High | GST: 30 C, 1 mM IPTG, OD 0.6 His: 16 C, 0.05 mM IPTG, OD 0.6 |
| TaCys8 | 67 | low/medium (transient) | low/medium (transient) | GST: 30 C His: 30 C |
| ZmCys4 | 5 | high | High | GST: 25 C HIS: 30 C |
| ZmCys6 | 9 | not detected | not detected | |
| ZmCys7 | 11 | high | Low | GST: 30 C His: 30 C, OD 0.6 |
| ZmCys8 | 13 | not detected | not detected | |
| ZmCys10 | 17 | not detected | not detected | |
| ZmCys11 | 19 | not detected | very low | His: 16 C, 0.05 mM IPTG, OD 0.1 |
| ZmCys12 | 21 | low | Low | GST: 30 C, 0.05 mM IPTG, OD 0.1 His: 30 C, 1 mM IPTG, OD 0.6 |
| ZmCys13 | 23 | high | High | GST: 30 C His: 16 C, OD 0.6 |
| ZmCys14 | 25 | low/medium | low/medium | GST: 30 C His: 30 C |

Table 14, above, is a summary of the cystatin activity detected in the tested genes of the present invention.

Detailed data for the assay results on each of the above cystatins is presented in tables 15 through 60.

Some of the identified cystatins did not show any proteinase inhibitor activity in the conditions of the assay as conducted above. There can be numerous reasons for these results. As is well known in the art, certain microorganisms perform better than others for expression of a given protein. Often it is difficult to predict which one will work best. The cystatins of the present invention have been expressed in BL21 Star cells (Invitrogen). Other bacterial lines or expression systems may be more effective for a selection of the genes. Furthermore, the cystatin proteins were expressed with a N-terminal His- or GST-tag to facilitate cystatin purification from the bacterial culture. It is possible that the BL21 bacteria were unable to express sufficient amounts of correctly folded protein or, that for unknown reasons, recovery of certain cystatin proteins from the bacterial culture was low. It is also possible that correct folding and cystatin activity are impacted by the presence of the GST or His tag. See results given in Table 14. A C-terminal tag may be more effective for certain cystatins. A preferred method for expression of these proteins in plants would be to express the cystatins without a tag. Untagged cystatins can be expected to have improved activity compared to tagged cystatins. It is also possible that certain cystatins have a pH optimum that is distinct from pH 6.5 at which papain inhibition was measured. Another possibility is that while certain cystatins appear to be inactive as inhibitors of papain the expressed proteins inhibit other proteinases.

TABLE 15

Cystatin Activity Results
GST fusion tagged protein, first replicate
GmCys4 (SEQ ID NO: 34)

| | | | | | | Cystatin Assay 9/26 First Replicate | | | | | |
| | | | | | | 1 hour | | | Overnight | | |
| Cell Type | Temp ° C. | IPTG (mM) | OD600 | Final OD | Bradford (ug/uL) | 6000 ng | 60 ng | Δ | 6000 ng | 60 ng | Δ |
|---|---|---|---|---|---|---|---|---|---|---|---|
| BL21 | 16 | 0.05 | 0.1 | 2.404 | 0.082 | 0.281 | 0.206 | −0.08 | 0.556 | 0.537 | −0.02 |
| | 16 | 1.0 | 0.1 | 2.312 | 0.048 | 0.258 | 0.207 | −0.05 | 0.552 | 0.553 | 0.00 |
| | 16 | 0.05 | 0.6 | 3.654 | 0.079 | 0.276 | 0.205 | −0.07 | 0.550 | 0.541 | −0.01 |
| | 16 | 1.0 | 0.6 | 3.747 | 0.039 | 0.260 | 0.209 | −0.05 | 0.557 | 0.552 | −0.01 |
| | 30 | 0.05 | 0.1 | 5.419 | 0.194 | 0.303 | 0.247 | −0.06 | 0.545 | 0.552 | 0.01 |
| | 30 | 1.0 | 0.1 | 6.305 | 0.161 | 0.293 | 0.240 | −0.05 | 0.548 | 0.556 | 0.01 |
| | 30 | 0.05 | 0.6 | 6.259 | 0.179 | 0.305 | 0.241 | −0.06 | 0.551 | 0.554 | 0.00 |
| | 30 | 1.0 | 0.6 | 6.259 | 0.150 | 0.302 | 0.245 | −0.06 | 0.552 | 0.555 | 0.00 |
| BL21 Star | 16 | 0.05 | 0.1 | 0.882 | 0.021 | 0.229 | 0.204 | −0.03 | 0.562 | 0.552 | −0.01 |
| | 16 | 1.0 | 0.1 | 0.882 | 0.026 | 0.237 | 0.206 | −0.03 | 0.551 | 0.550 | 0.00 |
| | 16 | 0.05 | 0.6 | 1.712 | 0.064 | 0.262 | 0.214 | −0.05 | 0.547 | 0.552 | 0.01 |
| | 16 | 1.0 | 0.6 | 1.389 | 0.046 | 0.255 | 0.219 | −0.04 | 0.549 | 0.555 | 0.01 |
| | 30 | 0.05 | 0.1 | 4.025 | 0.096 | 0.242 | 0.226 | −0.02 | 0.544 | 0.554 | 0.01 |
| | 30 | 1.0 | 0.1 | 4.303 | 0.154 | 0.269 | 0.221 | −0.05 | 0.542 | 0.556 | 0.01 |
| | 30 | 0.05 | 0.6 | 4.675 | 0.154 | 0.261 | 0.224 | −0.04 | 0.551 | 0.547 | 0.00 |
| | 30 | 1.0 | 0.6 | 5.047 | 0.110 | 0.202 | 0.224 | 0.02 | 0.547 | 0.550 | 0.00 |

TABLE 16

Cystatin Activity Results
GST fusion tagged protein, second replicate
GmCys4 (SEQ ID NO: 34)

| | | | | | | Cystatin Assay 9/26 Second Replicate | | | | | |
| | | | | | | 1 hour | | | Overnight | | |
| Cell Type | Temp ° C. | IPTG (Mm) | OD600 | Final OD | Bradford (ug/uL) | 6000 ng | 60 ng | Δ | 6000 ng | 60 ng | Δ |
|---|---|---|---|---|---|---|---|---|---|---|---|
| BL21 | 16 | 0.05 | 0.1 | 2.543 | 0.095 | 0.292 | 0.246 | −0.05 | 0.549 | 0.564 | 0.01 |
| | 16 | 1.0 | 0.1 | 2.404 | 0.077 | 0.302 | 0.250 | −0.05 | 0.554 | 0.564 | 0.01 |
| | 16 | 0.05 | 0.6 | 3.191 | 0.064 | 0.288 | 0.230 | −0.06 | 0.551 | 0.556 | 0.01 |
| | 16 | 1.0 | 0.6 | 3.283 | 0.066 | 0.313 | 0.224 | −0.09 | 0.549 | 0.549 | 0.00 |
| | 30 | 0.05 | 0.1 | 5.233 | 0.119 | 0.296 | 0.247 | −0.05 | 0.549 | 0.552 | 0.00 |
| | 30 | 1.0 | 0.1 | 5.746 | 0.165 | 0.295 | 0.251 | −0.04 | 0.543 | 0.552 | 0.01 |
| | 30 | 0.05 | 0.6 | 6.119 | 0.182 | 0.311 | 0.259 | −0.05 | 0.557 | 0.553 | 0.00 |
| | 30 | 1.0 | 0.6 | 6.445 | 0.152 | 0.303 | 0.251 | −0.05 | 0.557 | 0.552 | −0.01 |
| BL21 Star | 16 | 0.05 | 0.1 | 0.928 | 0.023 | 0.254 | 0.222 | −0.03 | 0.568 | 0.551 | −0.02 |
| | 16 | 1.0 | 0.1 | 0.882 | 0.019 | 0.245 | 0.228 | −0.02 | 0.561 | 0.554 | −0.01 |
| | 16 | 0.05 | 0.6 | 1.758 | 0.064 | 0.285 | 0.221 | −0.06 | 0.546 | 0.545 | 0.00 |
| | 16 | 1.0 | 0.6 | 1.620 | 0.05 | 0.283 | 0.226 | −0.06 | 0.544 | 0.549 | 0.01 |
| | 30 | 0.05 | 0.1 | 4.350 | 0.125 | 0.259 | 0.234 | −0.03 | 0.545 | 0.550 | 0.01 |

TABLE 16-continued

Cystatin Activity Results
GST fusion tagged protein, second replicate
GmCys4 (SEQ ID NO: 34)

| Cell Type | Temp °C. | IPTG (Mm) | OD600 | Final OD | Bradford (ug/uL) | \multicolumn{3}{c}{Cystatin Assay 9/26 Second Replicate} | | | | | |
|---|---|---|---|---|---|---|---|---|---|---|---|
| | | | | | | \multicolumn{3}{c}{1 hour} | \multicolumn{3}{c}{Overnight} |
| | | | | | | 6000 ng | 60 ng | Δ | 6000 ng | 60 ng | Δ |
| | 30 | 1.0 | 0.1 | 4.396 | 0.152 | 0.272 | 0.235 | −0.04 | 0.543 | 0.556 | 0.01 |
| | 30 | 0.05 | 0.6 | 5.419 | 0.1 | 0.278 | 0.242 | −0.04 | 0.546 | 0.544 | 0.00 |
| | 30 | 1.0 | 0.6 | 5.419 | 0.137 | 0.273 | 0.240 | −0.03 | 0.525 | 0.538 | 0.01 |

15

TABLE 17

Cystatin Activity Results
His fusion tagged protein, first replicate
GmCys4 (SEQ ID NO:34)

| Cell Type | Temp °C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 2.404 | 0.233 | 0.254 | 0.205 | −0.05 | 0.543 | 0.554 | 0.01 |
| | 16 | 1.0 | 0.1 | 1.896 | 0.228 | 0.247 | 0.202 | −0.05 | 0.536 | 0.549 | 0.01 |
| | 16 | 0.05 | 0.6 | 3.422 | 0.347 | 0.273 | 0.197 | −0.08 | 0.535 | 0.544 | 0.01 |
| | 16 | 1.0 | 0.6 | 2.543 | 0.302 | 0.273 | 0.202 | −0.07 | 0.542 | 0.543 | 0.00 |
| | 30 | 0.05 | 0.1 | 6.212 | 0.457 | 0.270 | 0.229 | −0.04 | 0.541 | 0.552 | 0.01 |
| | 30 | 1.0 | 0.1 | 5.187 | 0.410 | 0.267 | 0.223 | −0.04 | 0.542 | 0.548 | 0.01 |
| | 30 | 0.05 | 0.6 | 5.839 | 0.570 | 0.275 | 0.225 | −0.05 | 0.536 | 0.550 | 0.01 |
| | 30 | 1.0 | 0.6 | 5.559 | 0.463 | 0.266 | 0.215 | −0.05 | 0.533 | 0.547 | 0.01 |
| BL21 Star | 16 | 0.05 | 0.1 | 1.389 | 0.084 | 0.271 | 0.206 | −0.07 | 0.543 | 0.547 | 0.00 |
| | 16 | 1.0 | 0.1 | 1.389 | 0.079 | 0.271 | 0.218 | −0.05 | 0.542 | 0.544 | 0.00 |
| | 16 | 0.05 | 0.6 | 2.867 | 0.302 | 0.273 | 0.206 | −0.07 | 0.538 | 0.540 | 0.00 |
| | 16 | 1.0 | 0.6 | 2.219 | 0.246 | 0.280 | 0.200 | −0.08 | 0.534 | 0.540 | 0.01 |
| | 30 | 0.05 | 0.1 | 5.001 | 0.435 | 0.269 | 0.226 | −0.04 | 0.527 | 0.552 | 0.03 |
| | 30 | 1.0 | 0.1 | 5.187 | 0.456 | 0.267 | 0.229 | −0.04 | 0.521 | 0.549 | 0.03 |
| | 30 | 0.05 | 0.6 | 4.629 | 0.412 | 0.282 | 0.219 | −0.06 | 0.545 | 0.546 | 0.00 |
| | 30 | 1.0 | 0.6 | 4.861 | 0.456 | 0.275 | 0.216 | −0.06 | 0.535 | 0.544 | 0.01 |

TABLE 18

Cystatin Activity Results
His fusion tagged protein, second replicate
GmCys4 (SEQ ID NO: 34)

| Cell Type | Temp °C. | IPTG (Mm) | OD600 | Final OD | Bradford (ug/uL) | Cystatin Assay 9/26 Second Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 2.219 | 0.255 | 0.289 | 0.223 | −0.07 | 0.539 | 0.547 | 0.01 |
| | 16 | 1.0 | 0.1 | 1.989 | 0.261 | 0.291 | 0.225 | −0.07 | 0.543 | 0.553 | 0.01 |
| | 16 | 0.05 | 0.6 | 2.867 | 0.3 | 0.298 | 0.221 | −0.08 | 0.538 | 0.547 | 0.01 |
| | 16 | 1.0 | 0.6 | 2.635 | 0.282 | 0.284 | 0.213 | −0.07 | 0.536 | 0.540 | 0.00 |
| | 30 | 0.05 | 0.1 | 5.746 | 0.528 | 0.282 | 0.232 | −0.05 | 0.539 | 0.544 | 0.01 |
| | 30 | 1.0 | 0.1 | 4.954 | 0.312 | 0.274 | 0.231 | −0.04 | 0.543 | 0.551 | 0.01 |
| | 30 | 0.05 | 0.6 | 5.932 | 0.534 | 0.282 | 0.243 | −0.04 | 0.531 | 0.548 | 0.02 |
| | 30 | 1.0 | 0.6 | 5.606 | 0.44 | 0.278 | 0.239 | −0.04 | 0.537 | 0.542 | 0.01 |
| BL21 Star | 16 | 0.05 | 0.1 | 1.297 | 0.086 | 0.294 | 0.226 | −0.07 | 0.546 | 0.544 | 0.00 |
| | 16 | 1.0 | 0.1 | 1.389 | 0.084 | 0.291 | 0.223 | −0.07 | 0.544 | 0.549 | 0.01 |
| | 16 | 0.05 | 0.6 | 2.728 | 0.016 | 0.221 | 0.215 | −0.01 | 0.550 | 0.543 | −0.01 |
| | 16 | 1.0 | 0.6 | 2.497 | 0.212 | 0.289 | 0.214 | −0.08 | 0.538 | 0.537 | 0.00 |
| | 30 | 0.05 | 0.1 | 5.094 | 0.471 | 0.277 | 0.209 | −0.07 | 0.540 | 0.541 | 0.00 |

TABLE 18-continued

Cystatin Activity Results
His fusion tagged protein, second replicate
GmCys4 (SEQ ID NO: 34)

| | | | | | Cystatin Assay 9/26 Second Replicate | | | | | |
|---|---|---|---|---|---|---|---|---|---|---|
| | | | | | 1 hour | | | Overnight | | |
| Cell | Temp | IPTG | | | Bradford | | | | | |
| Type | ° C. | (Mm) | OD600 | Final OD | (ug/uL) | 6000 ng | 60 ng | Δ | 6000 ng | 60 ng | Δ |
| | 30 | 1.0 | 0.1 | 5.140 | 0.515 | 0.281 | 0.235 | −0.05 | 0.533 | 0.546 | 0.01 |
| | 30 | 0.05 | 0.6 | 4.303 | 0.463 | 0.280 | 0.239 | −0.04 | 0.528 | 0.546 | 0.02 |
| | 30 | 1.0 | 0.6 | 4.629 | 0.377 | 0.286 | 0.231 | −0.06 | 0.530 | 0.529 | 0.00 |

15

TABLE 19

Cystatin Activity Results
GST fusion tagged protein, first replicate
GmCys2 (SEQ ID NO: 30)

| | | | | | | Cystatin Assay 6/12 | | | |
|---|---|---|---|---|---|---|---|---|---|
| | | | | | | Overnight | | | |
| Cell | Temp | IPTG | | | Bradford | | | | |
| Type | ° C. | (Mm) | OD600 | Final OD | (ug/uL) | 600 ng | 60 ng | 6 ng | Δ |
| BL21 | 16 | 0.5 | 0.1 | 4.559 | 0.089 | 0.270 | 0.232 | 0.233 | −0.038 |
| | 16 | 0.5 | 0.8 | 6.894 | 0.129 | 0.258 | 0.230 | 0.224 | −0.031 |
| | 16 | 0.05 | 0.1 | 7.694 | 0.150 | 0.275 | 0.229 | 0.240 | −0.040 |
| | 16 | 0.05 | 0.8 | 11.171 | 0.143 | 0.263 | 0.229 | 0.220 | −0.038 |
| | 25 | 0.5 | 0.1 | 3.140 | 0.000 | 0.237 | 0.206 | 0.201 | −0.034 |
| | 25 | 0.5 | 0.8 | 3.186 | 0.004 | 0.233 | 0.211 | 0.197 | −0.029 |
| | 25 | 0.05 | 0.1 | 4.285 | 0.062 | 0.245 | 0.216 | 0.214 | −0.030 |
| | 25 | 0.05 | 0.8 | 4.461 | 0.067 | 0.244 | 0.211 | 0.206 | −0.036 |
| BL21 Star | 16 | 0.5 | 0.1 | 1.906 | 0.134 | 0.258 | 0.222 | 0.223 | −0.036 |
| | 16 | 0.5 | 0.8 | 5.131 | 0.171 | 0.216 | 0.224 | 0.219 | 0.006 |
| | 16 | 0.05 | 0.1 | 1.726 | 0.024 | 0.241 | 0.223 | 0.221 | −0.019 |
| | 16 | 0.05 | 0.8 | 4.415 | 0.159 | 0.201 | 0.219 | 0.218 | 0.017 |
| | 25 | 0.5 | 0.1 | 3.547 | 0.212 | 0.210 | 0.195 | 0.193 | −0.016 |
| | 25 | 0.5 | 0.8 | 4.248 | 0.276 | 0.209 | 0.188 | 0.194 | −0.018 |
| | 25 | 0.05 | 0.1 | 3.241 | 0.259 | 0.215 | 0.199 | 0.195 | −0.019 |
| | 25 | 0.05 | 0.8 | 3.714 | 0.524 | 0.204 | 0.194 | 0.189 | −0.012 |

TABLE 20

Cystatin Activity Results
GST fusion tagged protein, second replicate
GmCys2 (SEQ ID NO: 30)

| | | | | | | Cystatin Assay 7/24 | | | |
|---|---|---|---|---|---|---|---|---|---|
| | | | | | | Overnight | | | |
| Cell | Temp | IPTG | | | Bradford | | | | |
| Type | ° C. | (Mm) | OD600 | Final OD | (ug/uL) | 600 ng | 60 ng | 6 ng | Δ |
| BL21 | 16 | 0.5 | 0.1 | 5.331 | 0.058 | 0.243 | 0.200 | 0.186 | −0.049 |
| | 16 | 0.5 | 0.8 | 7.142 | 0.081 | 0.240 | 0.200 | 0.198 | −0.041 |
| | 16 | 0.05 | 0.1 | 7.769 | 0.082 | 0.239 | 0.200 | 0.193 | −0.043 |
| | 16 | 0.05 | 0.8 | 10.354 | 2.948 | 0.254 | 0.201 | 0.203 | −0.052 |
| | 25 | 0.5 | 0.1 | 2.894 | 0.000 | 0.253 | 0.204 | 0.191 | −0.055 |
| | 25 | 0.5 | 0.8 | 3.010 | 0.009 | 0.243 | 0.196 | 0.185 | −0.052 |
| | 25 | 0.05 | 0.1 | 3.686 | 0.048 | 0.250 | 0.208 | 0.211 | −0.040 |
| | 25 | 0.05 | 0.8 | 4.294 | 0.052 | 0.244 | 0.197 | 0.198 | −0.046 |
| BL21 Star | 16 | 0.5 | 0.1 | 3.269 | 0.135 | 0.226 | 0.181 | 0.186 | −0.042 |
| | 16 | 0.5 | 0.8 | 6.576 | 0.119 | 0.211 | 0.190 | 0.191 | −0.020 |
| | 16 | 0.05 | 0.1 | 2.899 | 0.155 | 0.215 | 0.188 | 0.185 | −0.028 |
| | 16 | 0.05 | 0.8 | 5.401 | 0.097 | 0.178 | 0.186 | 0.187 | 0.008 |
| | 25 | 0.5 | 0.1 | 3.862 | 0.542 | 0.232 | 0.185 | 0.183 | −0.048 |

TABLE 20-continued

Cystatin Activity Results
GST fusion tagged protein, second replicate
GmCys2 (SEQ ID NO: 30)

| Cell Type | Temp °C. | IPTG (Mm) | OD600 | Final OD | Bradford (ug/uL) | Cystatin Assay 7/24 Overnight | | | |
|---|---|---|---|---|---|---|---|---|---|
| | | | | | | 600 ng | 60 ng | 6 ng | Δ |
| | 25 | 0.5 | 0.8 | 3.802 | 0.246 | 0.221 | 0.186 | 0.180 | −0.038 |
| | 25 | 0.05 | 0.1 | 3.492 | 0.302 | 0.231 | 0.186 | 0.190 | −0.043 |
| | 25 | 0.05 | 0.8 | 3.329 | 0.669 | 0.215 | 0.192 | 0.195 | −0.022 |

TABLE 21

Cystatin Activity Results
His fusion tagged protein, first replicate
GmCys2 (SEQ ID NO: 30)

| Cell Type | Temp °C. | IPTG (Mm) | OD600 | Final OD | Bradford (ug/uL) | Cystatin Assay 6/12 Overnight | | | |
|---|---|---|---|---|---|---|---|---|---|
| | | | | | | 600 ng | 60 ng | 6 ng | Δ |
| BL21 | 16 | 0.5 | 0.1 | 5.312 | 0.351 | 0.256 | 0.227 | 0.225 | −0.030 |
| | 16 | 0.5 | 0.8 | 7.076 | 0.456 | 0.297 | 0.295 | 0.285 | −0.007 |
| | 16 | 0.05 | 0.1 | 7.324 | 0.410 | 0.260 | 0.224 | 0.228 | −0.033 |
| | 16 | 0.05 | 0.8 | 10.935 | 0.578 | 0.294 | 0.290 | 0.296 | −0.001 |
| | 25 | 0.5 | 0.1 | 3.241 | 0.280 | 0.235 | 0.198 | 0.210 | −0.031 |
| | 25 | 0.5 | 0.8 | 3.468 | 0.203 | 0.258 | 0.208 | 0.216 | −0.046 |
| | 25 | 0.05 | 0.1 | 4.498 | 0.300 | 0.238 | 0.244 | 0.215 | −0.008 |
| | 25 | 0.05 | 0.8 | 4.215 | 0.345 | 0.259 | 0.227 | 0.222 | −0.035 |
| BL21 Star | 16 | 0.5 | 0.1 | 5.760 | 0.342 | 0.263 | 0.220 | 0.225 | −0.041 |
| | 16 | 0.5 | 0.8 | 7.058 | 0.456 | 0.283 | 0.294 | 0.290 | 0.009 |
| | 16 | 0.05 | 0.1 | 4.698 | 0.295 | 0.259 | 0.224 | 0.219 | −0.037 |
| | 16 | 0.05 | 0.8 | 5.690 | 0.453 | 0.285 | 0.288 | 0.294 | 0.005 |
| | 25 | 0.5 | 0.1 | 4.016 | 0.337 | 0.215 | 0.192 | 0.194 | −0.022 |
| | 25 | 0.5 | 0.8 | 3.714 | 0.353 | 0.243 | 0.216 | 0.210 | −0.030 |
| | 25 | 0.05 | 0.1 | 3.492 | 0.383 | 0.224 | 0.199 | 0.197 | −0.026 |
| | 25 | 0.05 | 0.8 | 2.941 | 0.410 | 0.249 | 0.216 | 0.212 | −0.035 |

TABLE 22

Cystatin Activity Results
His fusion tagged protein, second replicate
GmCys2 (SEQ ID NO: 30)

| Cell Type | Temp °C. | IPTG (Mm) | OD600 | Final OD | Bradford (ug/uL) | Cystatin Assay 7/24 Overnight | | | |
|---|---|---|---|---|---|---|---|---|---|
| | | | | | | 600 ng | 60 ng | 6 ng | Δ |
| BL21 | 16 | 0.5 | 0.1 | 5.131 | 0.245 | 0.234 | 0.188 | 0.206 | −0.037 |
| | 16 | 0.5 | 0.8 | 6.049 | 0.421 | 0.254 | 0.205 | 0.201 | −0.051 |
| | 16 | 0.05 | 0.1 | 7.268 | 0.306 | 0.244 | 0.200 | 0.203 | −0.042 |
| | 16 | 0.05 | 0.8 | 8.599 | 0.559 | 0.245 | 0.213 | 0.538 | 0.130 |
| | 25 | 0.5 | 0.1 | 2.728 | 0.204 | 0.234 | 0.197 | 0.241 | −0.015 |
| | 25 | 0.5 | 0.8 | 2.880 | 0.290 | 0.266 | 0.219 | 0.206 | −0.053 |
| | 25 | 0.05 | 0.1 | 3.473 | 0.300 | 0.223 | 0.240 | 0.217 | 0.006 |
| | 25 | 0.05 | 0.8 | 3.825 | 0.352 | 0.251 | 0.207 | 0.202 | −0.046 |
| BL21 Star | 16 | 0.5 | 0.1 | 4.991 | 0.302 | 0.258 | 0.184 | 0.222 | −0.055 |
| | 16 | 0.5 | 0.8 | 6.553 | 0.434 | 0.245 | 0.208 | 0.194 | −0.044 |
| | 16 | 0.05 | 0.1 | 3.927 | 0.144 | 0.220 | 0.191 | 0.188 | −0.030 |
| | 16 | 0.05 | 0.8 | 5.014 | 0.458 | 0.245 | 0.201 | 0.203 | −0.043 |
| | 25 | 0.5 | 0.1 | 3.556 | 0.259 | 0.229 | 0.203 | 0.208 | −0.024 |
| | 25 | 0.5 | 0.8 | 3.427 | 0.219 | 0.247 | 0.213 | 0.207 | −0.038 |
| | 25 | 0.05 | 0.1 | 3.093 | 0.298 | 0.225 | 0.210 | 0.220 | −0.010 |
| | 25 | 0.05 | 0.8 | 3.019 | 0.259 | 0.271 | 0.189 | 0.214 | −0.069 |

TABLE 23

Cystatin Activity Results
GST fusion tagged protein, first replicate
OsCys4 (SEQ ID NO: 52)

| Cell Type | Temp °C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 2.312 | 0.073 | 0.275 | 0.203 | −0.07 | 0.554 | 0.536 | −0.02 |
| | 16 | 1.0 | 0.1 | 2.035 | 0.046 | 0.264 | 0.211 | −0.05 | 0.553 | 0.550 | 0.00 |
| | 16 | 0.05 | 0.6 | 3.839 | 0.073 | 0.282 | 0.204 | −0.08 | 0.559 | 0.539 | −0.02 |
| | 16 | 1.0 | 0.6 | 3.515 | 0.059 | 0.271 | 0.187 | −0.08 | 0.549 | 0.540 | −0.01 |
| | 30 | 0.05 | 0.1 | 6.352 | 0.171 | 0.304 | 0.242 | −0.06 | 0.543 | 0.546 | 0.00 |
| | 30 | 1.0 | 0.1 | 5.746 | 0.156 | 0.296 | 0.235 | −0.06 | 0.540 | 0.548 | 0.01 |
| | 30 | 0.05 | 0.6 | 5.932 | 0.100 | 0.292 | 0.235 | −0.06 | 0.550 | 0.552 | 0.00 |
| | 30 | 1.0 | 0.6 | 6.305 | 0.110 | 0.285 | 0.233 | −0.05 | 0.542 | 0.554 | 0.01 |
| BL21 Star | 16 | 0.05 | 0.1 | 1.067 | 0.019 | 0.232 | 0.194 | −0.04 | 0.566 | 0.552 | −0.01 |
| | 16 | 1.0 | 0.1 | 1.021 | 0.017 | 0.239 | 0.195 | −0.04 | 0.558 | 0.547 | −0.01 |
| | 16 | 0.05 | 0.6 | 1.896 | 0.070 | 0.263 | 0.198 | −0.07 | 0.541 | 0.546 | 0.01 |
| | 16 | 1.0 | 0.6 | 1.989 | 0.075 | 0.269 | 0.191 | −0.08 | 0.542 | 0.545 | 0.00 |
| | 30 | 0.05 | 0.1 | 4.489 | 0.182 | 0.275 | 0.224 | −0.05 | 0.539 | 0.545 | 0.01 |
| | 30 | 1.0 | 0.1 | 4.954 | 0.123 | 0.205 | 0.220 | 0.02 | 0.539 | 0.551 | 0.01 |
| | 30 | 0.05 | 0.6 | 4.582 | 0.158 | 0.265 | 0.217 | −0.05 | 0.536 | 0.549 | 0.01 |
| | 30 | 1.0 | 0.6 | 5.094 | 0.150 | 0.232 | 0.219 | −0.01 | 0.552 | 0.545 | −0.01 |

TABLE 24

Cystatin Activity Results
GST fusion tagged protein, second replicate
OsCys4 (SEQ ID NO: 52)

| Cell Type | Temp °C. | IPTG (Mm) | OD600 | Final OD | Bradford (ug/uL) | Cystatin Assay 9/26 Second Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 2.035 | 0.075 | 0.291 | 0.214 | −0.08 | 0.552 | 0.540 | −0.01 |
| | 16 | 1.0 | 0.1 | 2.173 | 0.062 | 0.297 | 0.210 | −0.09 | 0.554 | 0.543 | −0.01 |
| | 16 | 0.05 | 0.6 | 3.654 | 0.098 | 0.297 | 0.222 | −0.08 | 0.551 | 0.545 | −0.01 |
| | 16 | 1.0 | 0.6 | 3.144 | 0.068 | 0.303 | 0.228 | −0.08 | 0.548 | 0.557 | 0.01 |
| | 30 | 0.05 | 0.1 | 6.072 | 0.228 | 0.296 | 0.244 | −0.05 | 0.542 | 0.545 | 0.00 |
| | 30 | 1.0 | 0.1 | 6.025 | 0.154 | 0.285 | 0.240 | −0.05 | 0.535 | 0.551 | 0.02 |
| | 30 | 0.05 | 0.6 | 6.679 | 0.085 | 0.280 | 0.241 | −0.04 | 0.549 | 0.547 | 0.00 |
| | 30 | 1.0 | 0.6 | 6.119 | 0.182 | 0.294 | 0.245 | −0.05 | 0.542 | 0.554 | 0.01 |
| BL21 Star | 16 | 0.05 | 0.1 | 0.975 | 0.023 | 0.252 | 0.220 | −0.03 | 0.562 | 0.549 | −0.01 |
| | 16 | 1.0 | 0.1 | 0.975 | 0.025 | 0.262 | 0.230 | −0.03 | 0.559 | 0.554 | −0.01 |
| | 16 | 0.05 | 0.6 | 1.804 | 0.062 | 0.294 | 0.225 | −0.07 | 0.548 | 0.558 | 0.01 |
| | 16 | 1.0 | 0.6 | 1.850 | 0.077 | 0.295 | 0.230 | −0.07 | 0.544 | 0.562 | 0.02 |
| | 30 | 0.05 | 0.1 | 4.350 | 0.217 | 0.256 | 0.238 | −0.02 | 0.530 | 0.550 | 0.02 |
| | 30 | 1.0 | 0.1 | 4.954 | 0.282 | 0.266 | 0.233 | −0.03 | 0.535 | 0.546 | 0.01 |
| | 30 | 0.05 | 0.6 | 5.513 | 0.266 | 0.243 | 0.238 | −0.01 | 0.537 | 0.553 | 0.02 |
| | 30 | 1.0 | 0.6 | 5.419 | 0.163 | 0.275 | 0.236 | −0.04 | 0.541 | 0.548 | 0.01 |

TABLE 25

Cystatin Activity Results
His fusion tagged protein, first replicate
OsCys4 (SEQ ID NO: 52)

|  |  |  |  |  |  | Cystatin Assay 9/26 First Replicate | | | | | |
|---|---|---|---|---|---|---|---|---|---|---|---|
|  |  |  |  |  | Bradford | 1 hour | | | Overnight | | |
| Cell | Temp | IPTG |  |  |  |  |  |  |  |  |  |
| Type | ° C. | (Mm) | OD600 | Final OD | (ug/uL) | 6000 ng | 60 ng | Δ | 6000 ng | 60 ng | Δ |
| BL21 | 16 | 0.05 | 0.1 | 2.219 | 0.194 | 0.257 | 0.197 | −0.06 | 0.542 | 0.540 | 0.00 |
|  | 16 | 1.0 | 0.1 | 1.942 | 0.212 | 0.263 | 0.193 | −0.07 | 0.538 | 0.544 | 0.01 |
|  | 16 | 0.05 | 0.6 | 3.283 | 0.304 | 0.275 | 0.186 | −0.09 | 0.533 | 0.542 | 0.01 |
|  | 16 | 1.0 | 0.6 | 2.728 | 0.313 | 0.262 | 0.186 | −0.08 | 0.537 | 0.542 | 0.01 |
|  | 30 | 0.05 | 0.1 | 6.072 | 0.459 | 0.279 | 0.218 | −0.06 | 0.535 | 0.543 | 0.01 |
|  | 30 | 1.0 | 0.1 | 5.466 | 0.391 | 0.278 | 0.210 | −0.07 | 0.532 | 0.542 | 0.01 |
|  | 30 | 0.05 | 0.6 | 5.979 | 0.448 | 0.273 | 0.219 | −0.05 | 0.530 | 0.542 | 0.01 |
|  | 30 | 1.0 | 0.6 | 5.559 | 0.438 | 0.266 | 0.228 | −0.04 | 0.522 | 0.558 | 0.04 |
| BL21 Star | 16 | 0.05 | 0.1 | 1.389 | 0.095 | 0.272 | 0.198 | −0.07 | 0.543 | 0.547 | 0.00 |
|  | 16 | 1.0 | 0.1 | 1.343 | 0.100 | 0.281 | 0.215 | −0.07 | 0.541 | 0.543 | 0.00 |
|  | 16 | 0.05 | 0.6 | 3.329 | 0.295 | 0.260 | 0.190 | −0.07 | 0.534 | 0.536 | 0.00 |
|  | 16 | 1.0 | 0.6 | 2.820 | 0.270 | 0.265 | 0.196 | −0.07 | 0.534 | 0.541 | 0.01 |
|  | 30 | 0.05 | 0.1 | 5.326 | 0.433 | 0.279 | 0.200 | −0.08 | 0.534 | 0.534 | 0.00 |
|  | 30 | 1.0 | 0.1 | 6.072 | 0.459 | 0.278 | 0.203 | −0.08 | 0.528 | 0.537 | 0.01 |
|  | 30 | 0.05 | 0.6 | 5.280 | 0.415 | 0.260 | 0.216 | −0.04 | 0.533 | 0.542 | 0.01 |
|  | 30 | 1.0 | 0.6 | 4.954 | 0.423 | 0.271 | 0.218 | −0.05 | 0.539 | 0.538 | 0.00 |

TABLE 26

Cystatin Activity Results
His fusion tagged protein, second replicate
OsCys4 (SEQ ID NO: 52)

|  |  |  |  |  |  | Cystatin Assay 9/26 Second Replicate | | | | | |
|---|---|---|---|---|---|---|---|---|---|---|---|
|  |  |  |  |  | Bradford | 1 hour | | | Overnight | | |
| Cell | Temp | IPTG |  |  |  |  |  |  |  |  |  |
| Type | ° C. | (Mm) | OD600 | Final OD | (ug/uL) | 6000 ng | 60 ng | Δ | 6000 ng | 60 ng | Δ |
| BL21 | 16 | 0.05 | 0.1 | 1.989 | 0.217 | 0.291 | 0.224 | −0.07 | 0.544 | 0.552 | 0.01 |
|  | 16 | 1.0 | 0.1 | 2.035 | 0.237 | 0.284 | 0.219 | −0.07 | 0.543 | 0.548 | 0.01 |
|  | 16 | 0.05 | 0.6 | 2.820 | 0.304 | 0.297 | 0.222 | −0.08 | 0.545 | 0.549 | 0.00 |
|  | 16 | 1.0 | 0.6 | 2.867 | 0.288 | 0.279 | 0.225 | −0.05 | 0.543 | 0.547 | 0.00 |
|  | 30 | 0.05 | 0.1 | 5.606 | 0.463 | 0.277 | 0.232 | −0.05 | 0.531 | 0.542 | 0.01 |
|  | 30 | 1.0 | 0.1 | 5.280 | 0.412 | 0.269 | 0.231 | −0.04 | 0.529 | 0.545 | 0.02 |
|  | 30 | 0.05 | 0.6 | 5.885 | 0.505 | 0.276 | 0.231 | −0.05 | 0.537 | 0.547 | 0.01 |
|  | 30 | 1.0 | 0.6 | 5.466 | 0.49 | 0.275 | 0.231 | −0.04 | 0.538 | 0.549 | 0.01 |
| BL21 Star | 16 | 0.05 | 0.1 | 1.435 | 0.1 | 0.291 | 0.221 | −0.07 | 0.541 | 0.548 | 0.01 |
|  | 16 | 1.0 | 0.1 | 1.389 | 0.088 | 0.289 | 0.207 | −0.08 | 0.539 | 0.536 | 0.00 |
|  | 16 | 0.05 | 0.6 | 2.682 | 0.205 | 0.279 | 0.228 | −0.05 | 0.543 | 0.561 | 0.02 |
|  | 16 | 1.0 | 0.6 | 2.312 | 0.156 | 0.297 | 0.229 | −0.07 | 0.539 | 0.550 | 0.01 |
|  | 30 | 0.05 | 0.1 | 5.140 | 0.517 | 0.267 | 0.237 | −0.03 | 0.521 | 0.544 | 0.02 |
|  | 30 | 1.0 | 0.1 | 5.326 | 0.509 | 0.274 | 0.236 | −0.04 | 0.523 | 0.540 | 0.02 |
|  | 30 | 0.05 | 0.6 | 5.792 | 0.469 | 0.223 | 0.235 | 0.01 | 0.546 | 0.547 | 0.00 |
|  | 30 | 1.0 | 0.6 | 5.140 | 0.45 | 0.276 | 0.223 | −0.05 | 0.529 | 0.534 | 0.01 |

TABLE 27

Cystatin Activity Results
GST fusion tagged protein, first replicate
ZmCys4 (SEQ ID NO: 6)

| Cell Type | Temp ° C. | IPTG (mM) | OD600 | Final OD | Bradford (ug/uL) | Cystatin Assay 6/12 Overnight | | | |
|---|---|---|---|---|---|---|---|---|---|
| | | | | | | 600 ng | 60 ng | 6 ng | Δ |
| BL21 | 16 | 0.5 | 0.1 | 5.298 | 0.061 | 0.272 | 0.238 | 0.236 | −0.035 |
| | 16 | 0.5 | 0.8 | 6.749 | 0.097 | 0.229 | 0.231 | 0.223 | −0.002 |
| | 16 | 0.05 | 0.1 | 8.848 | 0.093 | 0.277 | 0.246 | 0.244 | −0.032 |
| | 16 | 0.05 | 0.8 | 12.435 | 0.137 | 0.270 | 0.247 | 0.233 | −0.030 |
| | 25 | 0.5 | 0.1 | 3.038 | 0.830 | 0.234 | 0.206 | 0.207 | −0.027 |
| | 25 | 0.5 | 0.8 | 3.237 | 0.145 | 0.222 | 0.206 | 0.189 | −0.025 |
| | 25 | 0.05 | 0.1 | 5.452 | 0.188 | 0.240 | 0.226 | 0.221 | −0.017 |
| | 25 | 0.05 | 0.8 | 4.577 | 0.241 | 0.226 | 0.208 | 0.195 | −0.025 |
| BL21 Star | 16 | 0.5 | 0.1 | 1.550 | 0.124 | 0.233 | 0.231 | 0.229 | −0.003 |
| | 16 | 0.5 | 0.8 | 3.552 | 0.364 | 0.188 | 0.237 | 0.222 | 0.042 |
| | 16 | 0.05 | 0.1 | 1.906 | 0.088 | 0.215 | 0.218 | 0.212 | 0.000 |
| | 16 | 0.05 | 0.8 | 2.991 | 0.588 | 0.223 | 0.227 | 0.222 | 0.002 |
| | 25 | 0.5 | 0.1 | 3.575 | 0.112 | 0.184 | 0.198 | 0.196 | 0.013 |
| | 25 | 0.5 | 0.8 | 3.830 | 0.354 | 0.169 | 0.200 | 0.197 | 0.029 |
| | 25 | 0.05 | 0.1 | 3.459 | 0.150 | 0.141 | 0.235 | 0.202 | 0.077 |
| | 25 | 0.05 | 0.8 | 3.839 | 0.353 | 0.116 | 0.209 | 0.190 | 0.084 |

TABLE 28

Cystatin Activity Results
GST fusion tagged protein, second replicate
ZmCys4 (SEQ ID NO: 6)

| Cell Type | Temp ° C. | IPTG (mM) | OD600 | Final OD | Bradford (ug/uL) | Cystatin Assay 7/24 Overnight | | | |
|---|---|---|---|---|---|---|---|---|---|
| | | | | | | 600 ng | 60 ng | 6 ng | Δ |
| BL21 | 16 | 0.5 | 0.1 | 5.243 | 0.195 | 0.198 | 0.202 | 0.200 | 0.003 |
| | 16 | 0.5 | 0.8 | 7.029 | 0.112 | 0.194 | 0.187 | 0.321 | 0.060 |
| | 16 | 0.05 | 0.1 | 8.322 | 0.153 | 0.247 | 0.217 | 0.204 | −0.037 |
| | 16 | 0.05 | 0.8 | 11.639 | 0.170 | 0.244 | 0.252 | 0.224 | −0.006 |
| | 25 | 0.5 | 0.1 | 2.982 | 0.094 | 0.239 | 0.195 | 0.222 | −0.031 |
| | 25 | 0.5 | 0.8 | 2.968 | 0.082 | 0.234 | 0.195 | 0.199 | −0.036 |
| | 25 | 0.05 | 0.1 | 4.601 | 0.272 | 0.240 | 0.211 | 0.203 | −0.033 |
| | 25 | 0.05 | 0.8 | 4.294 | 0.167 | 0.236 | 0.210 | 0.201 | −0.030 |
| BL21 Star | 16 | 0.5 | 0.1 | 1.744 | 0.082 | 0.162 | 0.198 | 0.200 | 0.037 |
| | 16 | 0.5 | 0.8 | 4.275 | 0.319 | 0.127 | 0.205 | 0.206 | 0.078 |
| | 16 | 0.05 | 0.1 | 2.002 | 0.154 | 0.165 | 0.214 | 0.191 | 0.038 |
| | 16 | 0.05 | 0.8 | 4.164 | 0.414 | 0.124 | 0.200 | 0.218 | 0.085 |
| | 25 | 0.5 | 0.1 | 3.167 | 0.812 | 0.216 | 0.192 | 0.190 | −0.025 |
| | 25 | 0.5 | 0.8 | 3.965 | 0.237 | 0.092 | 0.208 | 0.191 | 0.107 |
| | 25 | 0.05 | 0.1 | 3.140 | 0.725 | 0.116 | 0.203 | 0.194 | 0.082 |
| | 25 | 0.05 | 0.8 | 3.478 | 0.273 | 0.097 | 0.191 | 0.194 | 0.095 |

TABLE 29

Cystatin Activity Results
His fusion tagged protein, first replicate
ZmCys4 (SEQ ID NO: 6)

| Cell Type | Temp ° C. | IPTG (mM) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.850 | 0.226 | 0.274 | 0.193 | −0.08 | 0.540 | 0.537 | 0.00 |
| | 16 | 1.0 | 0.1 | 1.804 | 0.211 | 0.268 | 0.192 | −0.08 | 0.539 | 0.534 | −0.01 |

TABLE 29-continued

Cystatin Activity Results
His fusion tagged protein, first replicate
ZmCys4 (SEQ ID NO: 6)

| Cell Type | Temp ° C. | IPTG (mM) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| | 16 | 0.05 | 0.6 | 2.913 | 0.338 | 0.270 | 0.185 | −0.09 | 0.540 | 0.538 | 0.00 |
| | 16 | 1.0 | 0.6 | 2.358 | 0.325 | 0.260 | 0.198 | −0.06 | 0.536 | 0.532 | 0.00 |
| | 30 | 0.05 | 0.1 | 5.326 | 0.490 | 0.295 | 0.248 | −0.05 | 0.524 | 0.526 | 0.00 |
| | 30 | 1.0 | 0.1 | 5.419 | 0.478 | 0.291 | 0.258 | −0.03 | 0.518 | 0.538 | 0.02 |
| | 30 | 0.05 | 0.6 | 5.513 | 0.455 | 0.303 | 0.268 | −0.04 | 0.529 | 0.537 | 0.01 |
| | 30 | 1.0 | 0.6 | 5.140 | 0.490 | 0.303 | 0.273 | −0.03 | 0.536 | 0.538 | 0.00 |
| BL21 Star | 16 | 0.05 | 0.1 | 1.297 | 0.045 | 0.082 | 0.194 | 0.11 | 0.402 | 0.535 | 0.13 |
| | 16 | 1.0 | 0.1 | 1.343 | 0.051 | 0.047 | 0.203 | 0.16 | 0.144 | 0.529 | 0.39 |
| | 16 | 0.05 | 0.6 | 2.358 | 0.213 | 0.045 | 0.205 | 0.16 | 0.123 | 0.539 | 0.42 |
| | 16 | 1.0 | 0.6 | 2.450 | 0.215 | 0.046 | 0.199 | 0.15 | 0.115 | 0.535 | 0.42 |
| | 30 | 0.05 | 0.1 | 5.094 | 0.467 | 0.053 | 0.265 | 0.21 | 0.120 | 0.538 | 0.42 |
| | 30 | 1.0 | 0.1 | 5.140 | 0.533 | 0.048 | 0.261 | 0.21 | 0.123 | 0.531 | 0.41 |
| | 30 | 0.05 | 0.6 | 4.768 | 0.400 | 0.265 | 0.278 | 0.01 | 0.545 | 0.535 | −0.01 |
| | 30 | 1.0 | 0.6 | 4.768 | 0.488 | 0.052 | 0.274 | 0.22 | 0.119 | 0.531 | 0.41 |

TABLE 30

Cystatin Activity Results
His fusion tagged protein, second replicate
ZmCys4 (SEQ ID NO: 6)

| Cell Type | Temp ° C. | IPTG (mM) | OD600 | Final OD | Bradford (ug/uL) | Cystatin Assay 9/26 Second Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.758 | 0.425 | 0.318 | 0.247 | −0.07 | 0.536 | 0.545 | 0.01 |
| | 16 | 1.0 | 0.1 | 1.712 | 0.453 | 0.313 | 0.233 | −0.08 | 0.537 | 0.539 | 0.00 |
| | 16 | 0.05 | 0.6 | 2.312 | 0.414 | 0.328 | 0.260 | −0.07 | 0.539 | 0.540 | 0.00 |
| | 16 | 1.0 | 0.6 | 2.219 | 0.348 | 0.325 | 0.258 | −0.07 | 0.543 | 0.546 | 0.00 |
| | 30 | 0.05 | 0.1 | 5.699 | 0.216 | 0.290 | 0.267 | −0.02 | 0.561 | 0.569 | 0.01 |
| | 30 | 1.0 | 0.1 | 5.699 | 0.222 | 0.292 | 0.263 | −0.03 | 0.559 | 0.566 | 0.01 |
| | 30 | 0.05 | 0.6 | 5.466 | 0.293 | 0.297 | — | — | 0.521 | — | — |
| | 30 | 1.0 | 0.6 | 5.979 | 0.316 | 0.294 | — | — | 0.530 | — | — |
| BL21 Star | 16 | 0.05 | 0.1 | 1.297 | 0.427 | 0.265 | 0.234 | −0.03 | 0.549 | 0.547 | 0.00 |
| | 16 | 1.0 | 0.1 | 1.251 | 0.446 | 0.235 | 0.232 | 0.00 | 0.536 | 0.536 | 0.00 |
| | 16 | 0.05 | 0.6 | 2.404 | 0.427 | 0.079 | 0.233 | 0.15 | 0.305 | 0.541 | 0.24 |
| | 16 | 1.0 | 0.6 | 2.589 | 0.453 | 0.063 | 0.222 | 0.16 | 0.243 | 0.542 | 0.30 |
| | 30 | 0.05 | 0.1 | 4.629 | 0.083 | 0.095 | 0.260 | 0.17 | 0.371 | 0.557 | 0.19 |
| | 30 | 1.0 | 0.1 | 4.118 | 0.109 | 0.102 | 0.269 | 0.17 | 0.426 | 0.558 | 0.13 |
| | 30 | 0.05 | 0.6 | 4.582 | 0.175 | 0.067 | — | — | 0.150 | — | — |
| | 30 | 1.0 | 0.6 | 5.280 | 0.354 | 0.068 | — | — | 0.272 | — | — |

TABLE 31

Cystatin Activity Results
GST fusion tagged protein, first replicate
ZmCys6 (SEQ ID NO: 10)

| Cell Type | Temp ° C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 2.358 | 0.093 | 0.293 | 0.211 | −0.08 | 0.553 | 0.544 | −0.01 |
| | 16 | 1.0 | 0.1 | 2.219 | 0.060 | 0.286 | 0.221 | −0.07 | 0.552 | 0.561 | 0.01 |

TABLE 31-continued

Cystatin Activity Results
GST fusion tagged protein, first replicate
ZmCys6 (SEQ ID NO: 10)

| Cell Type | Temp °C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| | 16 | 0.05 | 0.6 | 3.237 | 0.103 | 0.292 | 0.220 | −0.07 | 0.549 | 0.554 | 0.01 |
| | 16 | 1.0 | 0.6 | 2.589 | 0.072 | 0.291 | 0.223 | −0.07 | 0.558 | 0.557 | 0.00 |
| | 30 | 0.05 | 0.1 | 5.606 | 0.142 | 0.298 | 0.247 | −0.05 | 0.552 | 0.549 | 0.00 |
| | 30 | 1.0 | 0.1 | 6.165 | 0.197 | 0.289 | 0.248 | −0.04 | 0.539 | 0.554 | 0.02 |
| | 30 | 0.05 | 0.6 | 5.746 | 0.166 | 0.296 | 0.256 | −0.04 | 0.547 | 0.552 | 0.01 |
| | 30 | 1.0 | 0.6 | 6.445 | 0.170 | 0.305 | 0.262 | −0.04 | 0.549 | 0.558 | 0.01 |
| BL21 Star | 16 | 0.05 | 0.1 | 1.113 | 0.027 | 0.252 | 0.200 | −0.05 | 0.559 | 0.545 | −0.01 |
| | 16 | 1.0 | 0.1 | 0.975 | 0.037 | 0.268 | 0.210 | −0.06 | 0.549 | 0.549 | 0.00 |
| | 16 | 0.05 | 0.6 | 1.758 | 0.128 | 0.266 | 0.213 | −0.05 | 0.543 | 0.543 | 0.00 |
| | 16 | 1.0 | 0.6 | 1.758 | 0.170 | 0.279 | 0.214 | −0.07 | 0.540 | 0.544 | 0.00 |
| | 30 | 0.05 | 0.1 | 4.396 | 0.632 | 0.266 | 0.226 | −0.04 | 0.537 | 0.552 | 0.02 |
| | 30 | 1.0 | 0.1 | 4.257 | 0.516 | 0.269 | 0.231 | −0.04 | 0.536 | 0.550 | 0.01 |
| | 30 | 0.05 | 0.6 | 4.954 | 0.676 | 0.274 | 0.241 | −0.03 | 0.544 | 0.551 | 0.01 |
| | 30 | 1.0 | 0.6 | 4.536 | 0.710 | 0.268 | 0.237 | −0.03 | 0.542 | 0.553 | 0.01 |

TABLE 32

Cystatin Activity Results
GST fusion tagged protein, second replicate
ZmCys6 (SEQ ID NO: 10)

| Cell Type | Temp° C. | IPTG (Mm) | OD600 | Final OD | Bradford (ug/uL) | Cystatin Assay 9/26 Second Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.896 | 0.068 | 0.252 | 0.213 | −0.04 | 0.548 | 0.548 | 0.00 |
| | 16 | 1.0 | 0.1 | 1.896 | 0.072 | 0.271 | 0.222 | −0.05 | 0.555 | 0.550 | −0.01 |
| | 16 | 0.05 | 0.6 | 2.635 | 0.116 | 0.291 | 0.212 | −0.08 | 0.549 | 0.545 | 0.00 |
| | 16 | 1.0 | 0.6 | 2.266 | 0.076 | 0.291 | 0.232 | −0.06 | 0.550 | 0.549 | 0.00 |
| | 30 | 0.05 | 0.1 | 5.932 | 0.174 | 0.335 | 0.274 | −0.06 | 0.540 | 0.542 | 0.00 |
| | 30 | 1.0 | 0.1 | 6.212 | 0.178 | 0.350 | 0.307 | −0.04 | 0.544 | 0.546 | 0.00 |
| | 30 | 0.05 | 0.6 | 5.746 | 0.145 | 0.337 | 0.283 | −0.05 | 0.553 | 0.540 | −0.01 |
| | 30 | 1.0 | 0.6 | 6.259 | 0.178 | 0.366 | 0.302 | −0.06 | 0.547 | 0.542 | −0.01 |
| BL21 Star | 16 | 0.05 | 0.1 | 0.836 | 0.024 | 0.233 | 0.207 | −0.03 | 0.566 | 0.550 | −0.02 |
| | 16 | 1.0 | 0.1 | 0.882 | 0.025 | 0.232 | 0.210 | −0.02 | 0.565 | 0.551 | −0.01 |
| | 16 | 0.05 | 0.6 | 1.389 | 0.153 | 0.265 | 0.201 | −0.06 | 0.543 | 0.535 | −0.01 |
| | 16 | 1.0 | 0.6 | 1.389 | 0.159 | 0.282 | 0.205 | −0.08 | 0.528 | 0.538 | 0.01 |
| | 30 | 0.05 | 0.1 | 5.001 | 0.657 | 0.355 | 0.312 | −0.04 | 0.545 | 0.543 | 0.00 |
| | 30 | 1.0 | 0.1 | 4.768 | 0.594 | 0.357 | 0.311 | −0.05 | 0.539 | 0.542 | 0.00 |
| | 30 | 0.05 | 0.6 | 4.489 | 0.63 | 0.375 | 0.297 | −0.08 | 0.539 | 0.532 | −0.01 |
| | 30 | 1.0 | 0.6 | 4.582 | 0.68 | 0.384 | 0.231 | −0.15 | 0.547 | 0.511 | −0.04 |

TABLE 33

Cystatin Activity Results
His fusion tagged protein, first replicate
ZmCys6 (SEQ ID NO: 10)

| Cell Type | Temp °C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.942 | 0.292 | 0.282 | 0.202 | −0.08 | 0.546 | 0.549 | 0.00 |
| | 16 | 1.0 | 0.1 | 2.035 | 0.238 | 0.266 | 0.199 | −0.07 | 0.537 | 0.542 | 0.01 |

TABLE 33-continued

Cystatin Activity Results
His fusion tagged protein, first replicate
ZmCys6 (SEQ ID NO: 10)

| Cell Type | Temp °C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| | 16 | 0.05 | 0.6 | 2.959 | 0.338 | 0.274 | 0.213 | −0.06 | 0.542 | 0.552 | 0.01 |
| | 16 | 1.0 | 0.6 | 2.913 | 0.300 | 0.284 | 0.197 | −0.09 | 0.544 | 0.538 | −0.01 |
| | 30 | 0.05 | 0.1 | 5.373 | 0.416 | 0.219 | 0.233 | 0.01 | 0.540 | 0.546 | 0.01 |
| | 30 | 1.0 | 0.1 | 4.954 | 0.452 | 0.263 | 0.231 | −0.03 | 0.533 | 0.548 | 0.02 |
| | 30 | 0.05 | 0.6 | 5.419 | 0.448 | 0.275 | 0.245 | −0.03 | 0.544 | 0.553 | 0.01 |
| | 30 | 1.0 | 0.6 | 5.373 | 0.459 | 0.275 | 0.236 | −0.04 | 0.542 | 0.553 | 0.01 |
| BL21 Star | 16 | 0.05 | 0.1 | 1.297 | 0.093 | 0.290 | 0.210 | −0.08 | 0.542 | 0.543 | 0.00 |
| | 16 | 1.0 | 0.1 | 1.343 | 0.091 | 0.287 | 0.218 | −0.07 | 0.542 | 0.552 | 0.01 |
| | 16 | 0.05 | 0.6 | 2.266 | 0.284 | 0.264 | 0.206 | −0.06 | 0.536 | 0.542 | 0.01 |
| | 16 | 1.0 | 0.6 | 2.266 | 0.253 | 0.274 | 0.220 | −0.05 | 0.532 | 0.545 | 0.01 |
| | 30 | 0.05 | 0.1 | 4.675 | 0.463 | 0.214 | 0.228 | 0.01 | 0.548 | 0.550 | 0.00 |
| | 30 | 1.0 | 0.1 | 5.094 | 0.490 | 0.252 | 0.226 | −0.03 | 0.526 | 0.539 | 0.01 |
| | 30 | 0.05 | 0.6 | 4.814 | 0.402 | 0.263 | 0.230 | −0.03 | 0.538 | 0.546 | 0.01 |
| | 30 | 1.0 | 0.6 | 4.861 | 0.452 | 0.266 | 0.226 | −0.04 | 0.540 | 0.545 | 0.01 |

TABLE 34

Cystatin Activity Results
His fusion tagged protein, second replicate
ZmCys6 (SEQ ID NO: 10)

| Cell Type | Temp °C. | IPTG (Mm) | OD600 | Final OD | Bradford (ug/uL) | Cystatin Assay 9/26 Second Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.758 | 0.267 | 0.270 | 0.199 | −0.07 | 0.539 | 0.541 | 0.00 |
| | 16 | 1.0 | 0.1 | 1.666 | 0.25 | 0.271 | 0.196 | −0.08 | 0.544 | 0.541 | 0.00 |
| | 16 | 0.05 | 0.6 | 2.635 | 0.306 | 0.277 | 0.187 | −0.09 | 0.539 | 0.532 | −0.01 |
| | 16 | 1.0 | 0.6 | 2.497 | 0.286 | 0.276 | 0.190 | −0.09 | 0.532 | 0.528 | 0.00 |
| | 30 | 0.05 | 0.1 | 5.979 | 0.448 | 0.340 | 0.299 | −0.04 | 0.541 | 0.546 | 0.01 |
| | 30 | 1.0 | 0.1 | 5.979 | 0.414 | 0.349 | 0.303 | −0.05 | 0.536 | 0.542 | 0.01 |
| | 30 | 0.05 | 0.6 | 6.072 | 0.436 | 0.356 | 0.296 | −0.06 | 0.540 | 0.538 | 0.00 |
| | 30 | 1.0 | 0.6 | 6.072 | 0.431 | 0.366 | 0.303 | −0.06 | 0.533 | 0.536 | 0.00 |
| BL21 Star | 16 | 0.05 | 0.1 | 1.113 | 0.207 | 0.258 | 0.206 | −0.05 | 0.552 | 0.540 | −0.01 |
| | 16 | 1.0 | 0.1 | 1.159 | 0.132 | 0.267 | 0.220 | −0.05 | 0.543 | 0.546 | 0.00 |
| | 16 | 0.05 | 0.6 | 2.219 | 0.257 | 0.253 | 0.205 | −0.05 | 0.526 | 0.533 | 0.01 |
| | 16 | 1.0 | 0.6 | 2.081 | 0.186 | 0.284 | 0.219 | −0.07 | 0.531 | 0.534 | 0.00 |
| | 30 | 0.05 | 0.1 | 5.885 | 0.452 | 0.362 | 0.324 | −0.04 | 0.535 | 0.538 | 0.00 |
| | 30 | 1.0 | 0.1 | 6.259 | 0.471 | 0.341 | 0.284 | −0.06 | 0.530 | 0.533 | 0.00 |
| | 30 | 0.05 | 0.6 | 5.140 | 0.509 | 0.379 | 0.305 | −0.07 | 0.529 | 0.534 | 0.01 |
| | 30 | 1.0 | 0.6 | 5.652 | 0.476 | 0.345 | 0.269 | −0.08 | 0.528 | 0.524 | 0.00 |

TABLE 35

Cystatin Activity Results
GST fusion tagged protein, first replicate
ZmCys7 (SEQ ID NO: 12)

| Cell Type | Temp °C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 2.127 | 0.078 | 0.295 | 0.245 | −0.05 | 0.550 | 0.565 | 0.01 |
| | 16 | 1.0 | 0.1 | 2.127 | 0.072 | 0.291 | 0.224 | −0.07 | 0.557 | 0.555 | 0.00 |

TABLE 35-continued

Cystatin Activity Results
GST fusion tagged protein, first replicate
ZmCys7 (SEQ ID NO: 12)

| Cell Type | Temp ° C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| | 16 | 0.05 | 0.6 | 3.191 | 0.224 | 0.291 | 0.221 | −0.07 | 0.544 | 0.543 | 0.00 |
| | 16 | 1.0 | 0.6 | 2.959 | 0.261 | 0.281 | 0.225 | −0.06 | 0.544 | 0.547 | 0.00 |
| | 30 | 0.05 | 0.1 | 5.606 | 0.353 | 0.314 | 0.261 | −0.05 | 0.559 | 0.551 | −0.01 |
| | 30 | 1.0 | 0.1 | 6.025 | 0.370 | 0.320 | 0.266 | −0.05 | 0.554 | 0.553 | 0.00 |
| | 30 | 0.05 | 0.6 | 5.979 | 0.313 | 0.335 | 0.262 | −0.07 | 0.533 | 0.532 | 0.00 |
| | 30 | 1.0 | 0.6 | 6.445 | 0.277 | 0.328 | 0.268 | −0.06 | 0.529 | 0.537 | 0.01 |
| BL21 Star | 16 | 0.05 | 0.1 | 1.067 | 0.093 | 0.218 | 0.202 | −0.02 | 0.552 | 0.538 | −0.01 |
| | 16 | 1.0 | 0.1 | 0.975 | 0.097 | 0.173 | 0.209 | 0.04 | 0.525 | 0.540 | 0.02 |
| | 16 | 0.05 | 0.6 | 1.896 | 0.375 | 0.042 | 0.207 | 0.17 | 0.068 | 0.537 | 0.47 |
| | 16 | 1.0 | 0.6 | 1.758 | 0.373 | 0.040 | 0.208 | 0.17 | 0.065 | 0.542 | 0.48 |
| | 30 | 0.05 | 0.1 | 4.025 | 0.600 | 0.047 | 0.224 | 0.18 | 0.069 | 0.539 | 0.47 |
| | 30 | 1.0 | 0.1 | 4.536 | 0.621 | 0.045 | 0.219 | 0.17 | 0.064 | 0.532 | 0.47 |
| | 30 | 0.05 | 0.6 | 4.164 | 0.594 | 0.042 | 0.252 | 0.21 | 0.058 | 0.535 | 0.48 |
| | 30 | 1.0 | 0.6 | 4.350 | 0.602 | 0.042 | 0.259 | 0.22 | 0.057 | 0.545 | 0.49 |

TABLE 36

Cystatin Activity Results
GST fusion tagged protein, second replicate
ZmCys7 (SEQ ID NO: 12)

| Cell Type | Temp ° C. | IPTG (Mm) | OD600 | Final OD | Bradford (ug/uL) | Cystatin Assay 9/26 Second Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.942 | 0.19 | 0.308 | 0.251 | −0.06 | 0.548 | 0.536 | −0.01 |
| | 16 | 1.0 | 0.1 | 1.804 | 0.196 | 0.292 | 0.240 | −0.05 | 0.538 | 0.539 | 0.00 |
| | 16 | 0.05 | 0.6 | 2.774 | 0.167 | 0.321 | 0.248 | −0.07 | 0.544 | 0.536 | −0.01 |
| | 16 | 1.0 | 0.6 | 2.404 | 0.152 | 0.310 | 0.245 | −0.07 | 0.531 | 0.544 | 0.01 |
| | 30 | 0.05 | 0.1 | 6.072 | 0.054 | 0.327 | 0.262 | −0.07 | 0.534 | 0.556 | 0.02 |
| | 30 | 1.0 | 0.1 | 6.539 | 0.051 | 0.319 | 0.266 | −0.05 | 0.529 | 0.562 | 0.03 |
| | 30 | 0.05 | 0.6 | 5.932 | 0.075 | 0.329 | 0.273 | −0.06 | 0.567 | 0.561 | −0.01 |
| | 30 | 1.0 | 0.6 | 6.585 | 0.086 | 0.320 | 0.276 | −0.04 | 0.56 | 0.572 | 0.02 |
| BL21 Star | 16 | 0.05 | 0.1 | 0.928 | 0.713 | 0.235 | 0.210 | −0.03 | 0.551 | 0.532 | −0.02 |
| | 16 | 1.0 | 0.1 | 0.928 | 0.425 | 0.228 | 0.225 | 0.00 | 0.553 | 0.547 | −0.01 |
| | 16 | 0.05 | 0.6 | 1.666 | 0.785 | 0.149 | 0.227 | 0.08 | 0.489 | 0.543 | 0.05 |
| | 16 | 1.0 | 0.6 | 1.527 | 0.421 | 0.056 | 0.204 | 0.15 | 0.140 | 0.529 | 0.39 |
| | 30 | 0.05 | 0.1 | 4.257 | 0.019 | 0.043 | 0.244 | 0.20 | 0.061 | 0.545 | 0.48 |
| | 30 | 1.0 | 0.1 | 4.443 | 0.021 | 0.041 | 0.251 | 0.21 | 0.065 | 0.556 | 0.49 |
| | 30 | 0.05 | 0.6 | 4.489 | 0.077 | 0.044 | 0.246 | 0.20 | 0.060 | 0.562 | 0.50 |
| | 30 | 1.0 | 0.6 | 4.350 | 0.105 | 0.045 | 0.250 | 0.21 | 0.062 | 0.550 | 0.49 |

TABLE 37

Cystatin Activity Results
His fusion tagged protein, first replicate
ZmCys7 (SEQ ID NO: 12)

| Cell Type | Temp ° C. | IPTG (Mm) | OD600 | Final OD | Bradford (ug/uL) | Cystatin Assay 9/26 First Replicate | | | | | |
|---|---|---|---|---|---|---|---|---|---|---|---|
| | | | | | | 1 hour | | | Overnight | | |
| | | | | | | 6000 ng | 60 ng | Δ | 6000 ng | 60 ng | Δ |
| BL21 | 16 | 0.05 | 0.1 | 1.989 | 0.275 | 0.287 | 0.227 | −0.06 | 0.542 | 0.555 | 0.01 |
| | 16 | 1.0 | 0.1 | 1.850 | 0.244 | 0.282 | 0.194 | −0.09 | 0.545 | 0.529 | −0.02 |

TABLE 37-continued

Cystatin Activity Results
His fusion tagged protein, first replicate
ZmCys7 (SEQ ID NO: 12)

| | | | | | | Cystatin Assay 9/26 First Replicate | | | | | |
|---|---|---|---|---|---|---|---|---|---|---|---|
| Cell | Temp | IPTG | | | Bradford | 1 hour | | | Overnight | | |
| Type | ° C. | (Mm) | OD600 | Final OD | (ug/uL) | 6000 ng | 60 ng | Δ | 6000 ng | 60 ng | Δ |
| | 16 | 0.05 | 0.6 | 2.404 | 0.311 | 0.323 | 0.206 | −0.12 | 0.536 | 0.541 | 0.01 |
| | 16 | 1.0 | 0.6 | 2.266 | 0.280 | 0.271 | 0.187 | −0.08 | 0.531 | 0.531 | 0.00 |
| | 30 | 0.05 | 0.1 | 5.652 | 0.396 | 0.279 | 0.248 | −0.03 | 0.544 | 0.549 | 0.01 |
| | 30 | 1.0 | 0.1 | 5.326 | 0.461 | 0.265 | 0.236 | −0.03 | 0.539 | 0.539 | 0.00 |
| | 30 | 0.05 | 0.6 | 5.280 | 0.486 | 0.301 | 0.268 | −0.03 | 0.519 | 0.537 | 0.02 |
| | 30 | 1.0 | 0.6 | 5.187 | 0.448 | 0.304 | 0.262 | −0.04 | 0.523 | 0.534 | 0.01 |
| BL21 Star | 16 | 0.05 | 0.1 | 1.159 | 0.122 | 0.147 | 0.211 | 0.06 | 0.503 | 0.539 | 0.04 |
| | 16 | 1.0 | 0.1 | 1.251 | 0.112 | 0.220 | 0.211 | −0.01 | 0.540 | 0.535 | −0.01 |
| | 16 | 0.05 | 0.6 | 2.219 | 0.263 | 0.043 | 0.215 | 0.17 | 0.076 | 0.541 | 0.47 |
| | 16 | 1.0 | 0.6 | 2.266 | 0.358 | 0.058 | 0.203 | 0.15 | 0.148 | 0.520 | 0.37 |
| | 30 | 0.05 | 0.1 | 5.187 | 0.554 | 0.175 | 0.236 | 0.06 | 0.517 | 0.543 | 0.03 |
| | 30 | 1.0 | 0.1 | 5.094 | 0.537 | 0.212 | 0.230 | 0.02 | 0.521 | 0.535 | 0.01 |
| | 30 | 0.05 | 0.6 | 5.187 | 0.020 | 0.196 | 0.271 | 0.08 | 0.504 | 0.534 | 0.03 |
| | 30 | 1.0 | 0.6 | 4.768 | 0.520 | 0.234 | 0.265 | 0.03 | 0.506 | 0.535 | 0.03 |

TABLE 38

Cystatin Activity Results
His fusion tagged protein, second replicate
ZmCys7 (SEQ ID NO: 12)

| | | | | | | Cystatin Assay 9/26 Second Replicate | | | | | |
|---|---|---|---|---|---|---|---|---|---|---|---|
| Cell | Temp | IPTG | | | Bradford | 1 hour | | | Overnight | | |
| Type | ° C. | (Mm) | OD600 | Final OD | (ug/uL) | 6000 ng | 60 ng | Δ | 6000 ng | 60 ng | Δ |
| BL21 | 16 | 0.05 | 0.1 | 1.804 | 0.482 | 0.286 | 0.222 | −0.06 | 0.529 | 0.529 | 0.00 |
| | 16 | 1.0 | 0.1 | 1.804 | 0.453 | 0.295 | 0.212 | −0.08 | 0.532 | 0.527 | −0.01 |
| | 16 | 0.05 | 0.6 | 2.266 | 0.463 | 0.291 | 0.220 | −0.07 | 0.532 | 0.533 | 0.00 |
| | 16 | 1.0 | 0.6 | 2.358 | 0.491 | 0.288 | 0.222 | −0.07 | 0.527 | 0.537 | 0.01 |
| | 30 | 0.05 | 0.1 | 5.606 | 0.237 | 0.298 | 0.263 | −0.04 | 0.530 | 0.562 | 0.03 |
| | 30 | 1.0 | 0.1 | 5.094 | 0.224 | 0.290 | 0.255 | −0.04 | 0.530 | 0.540 | 0.01 |
| | 30 | 0.05 | 0.6 | 5.513 | 0.32 | 0.301 | 0.264 | −0.04 | 0.558 | 0.565 | 0.01 |
| | 30 | 1.0 | 0.6 | 5.513 | 0.337 | 0.295 | 0.266 | −0.03 | 0.554 | 0.534 | −0.02 |
| BL21 Star | 16 | 0.05 | 0.1 | 1.021 | 0.47 | 0.214 | 0.227 | 0.01 | 0.549 | 0.540 | −0.01 |
| | 16 | 1.0 | 0.1 | 1.113 | 0.485 | 0.238 | 0.224 | −0.01 | 0.544 | 0.540 | 0.00 |
| | 16 | 0.05 | 0.6 | 2.127 | 0.431 | 0.051 | 0.220 | 0.17 | 0.110 | 0.539 | 0.43 |
| | 16 | 1.0 | 0.6 | 1.989 | 0.395 | 0.088 | 0.219 | 0.13 | 0.325 | 0.535 | 0.21 |
| | 30 | 0.05 | 0.1 | 5.280 | 0.036 | 0.173 | 0.258 | 0.09 | 0.504 | 0.548 | 0.04 |
| | 30 | 1.0 | 0.1 | 5.140 | 0.049 | 0.230 | 0.262 | 0.03 | 0.515 | 0.553 | 0.04 |
| | 30 | 0.05 | 0.6 | 5.373 | 0.164 | 0.193 | 0.265 | 0.07 | 0.535 | 0.552 | 0.02 |
| | 30 | 1.0 | 0.6 | 5.187 | 0.203 | 0.208 | 0.268 | 0.06 | 0.533 | 0.549 | 0.02 |

TABLE 39

Cystatin Activity Results
GST fusion tagged protein, first and second replicates
OsCys6 (SEQ ID NO: 56)

| | | | | | | 1 hour | | | Overnight | | |
|---|---|---|---|---|---|---|---|---|---|---|---|
| Cell | Temp | IPTG | | | Bradford | | | | | | |
| Type | ° C. | (Mm) | OD600 | Final OD | (ug/uL) | 6000 ng | 60 ng | Δ | 6000 ng | 60 ng | Δ |
| | | | | | | Cystatin Assay 10/22 First Replicate | | | | | |
| BL21 Star | 16 | 0.05 | 0.1 | 1.758 | −0.018 | 0.651 | 0.482 | −0.169 | 1.235 | 1.4 | 0.165 |
| | 16 | 1.0 | 0.1 | 1.067 | −0.025 | 0.638 | 0.49 | −0.148 | 1.286 | 1.382 | 0.096 |

TABLE 39-continued

Cystatin Activity Results
GST fusion tagged protein, first and second replicates
OsCys6 (SEQ ID NO: 56)

| Cell Type | Temp ° C. | IPTG (Mm) | OD600 | Final OD | Bradford (ug/uL) | 1 hour | | | Overnight | | |
|---|---|---|---|---|---|---|---|---|---|---|---|
| | | | | | | 6000 ng | 60 ng | Δ | 6000 ng | 60 ng | Δ |
| | 16 | 0.05 | 0.6 | 2.45 | 0.058 | 0.701 | 0.477 | −0.224 | 1.222 | 1.333 | 0.111 |
| | 16 | 1.0 | 0.6 | 1.758 | 0.015 | 0.657 | 0.427 | −0.230 | 1.239 | 1.103 | −0.136 |
| | 30 | 0.05 | 0.1 | 5.094 | 0.313 | 0.057 | 0.494 | 0.437 | 0.14 | 1.037 | 0.897 |
| | 30 | 1.0 | 0.1 | 3.052 | 0.196 | 0.051 | 0.489 | 0.438 | 0.126 | 1.204 | 1.078 |
| | 30 | 0.05 | 0.6 | 2.682 | 0.276 | 0.06 | 0.457 | 0.397 | 0.117 | 1.002 | 0.885 |
| | 30 | 1.0 | 0.6 | 2.589 | 0.191 | 0.053 | 0.486 | 0.433 | 0.12 | 1.402 | 1.282 |
| | | | | | | Cystatin Assay 10/22 Second Replicate | | | | | |
| BL21 Star | 16 | 0.05 | 0.1 | 1.573 | −0.016 | 0.501 | 0.38 | −0.121 | 1.231 | 1.36 | 0.129 |
| | 16 | 1.0 | 0.1 | 1.021 | −0.025 | 0.447 | 0.361 | −0.086 | 1.269 | 1.176 | −0.093 |
| | 16 | 0.05 | 0.6 | 2.035 | 0.076 | 0.525 | 0.406 | −0.119 | 1.386 | 1.689 | 0.303 |
| | 16 | 1.0 | 0.6 | 1.85 | −0.034 | 0.477 | 0.367 | −0.110 | 1.456 | 1.325 | −0.131 |
| | 30 | 0.05 | 0.1 | 3.237 | 0.287 | 0.061 | 0.453 | 0.392 | 0.129 | 1.198 | 1.069 |
| | 30 | 1.0 | 0.1 | 3.283 | 0.142 | 0.077 | 0.426 | 0.349 | 0.288 | 1.39 | 1.102 |
| | 30 | 0.05 | 0.6 | 3.607 | 0.268 | 0.06 | 0.462 | 0.402 | 0.116 | 1.242 | 1.126 |
| | 30 | 1.0 | 0.6 | 3.283 | −0.004 | 0.415 | 0.385 | −0.030 | 1.114 | 1.188 | 0.074 |

TABLE 40

Cystatin Activity Results
His fusion tagged protein, first and second replicates
OsCys6 (SEQ ID NO: 56)

| Cell Type | Temp ° C. | IPTG (Mm) | OD600 | Final OD | Bradford (ug/uL) | 1 hour | | | Overnight | | |
|---|---|---|---|---|---|---|---|---|---|---|---|
| | | | | | | 6000 ng | 60 ng | Δ | 6000 ng | 60 ng | Δ |
| | | | | | | Cystatin Assay 10/22 First Replicate | | | | | |
| BL21 Star | 16 | 0.05 | 0.1 | 1.113 | 0.004 | 0.429 | 0.389 | −0.040 | 1.107 | 1.284 | 0.177 |
| | 16 | 1.0 | 0.1 | 1.251 | 0.024 | 0.297 | 0.38 | 0.083 | 1.291 | 1.32 | 0.029 |
| | 16 | 0.05 | 0.6 | 2.173 | 0.265 | 0.056 | 0.389 | 0.333 | 0.111 | 1.148 | 1.037 |
| | 16 | 1.0 | 0.6 | 2.358 | −0.034 | 0.359 | 0.378 | 0.019 | 1.18 | 1.293 | 0.113 |
| | 30 | 0.05 | 0.1 | 4.675 | 0.462 | 0.567 | 0.453 | −0.114 | 1.123 | 1.294 | 0.171 |
| | 30 | 1.0 | 0.1 | 4.629 | 0.429 | 0.599 | 0.459 | −0.140 | 1.346 | 1.45 | 0.104 |
| | 30 | 0.05 | 0.6 | 6.305 | 0.374 | 0.585 | 0.455 | −0.130 | 1.321 | 1.282 | −0.039 |
| | 30 | 1.0 | 0.6 | 3.932 | 0.368 | 0.559 | 0.447 | −0.112 | 1.484 | 1.359 | −0.125 |
| | | | | | | Cystatin Assay 10/22 Second Replicate | | | | | |
| BL21 Star | 16 | 0.05 | 0.1 | 1.021 | −0.01 | 0.479 | 0.427 | −0.052 | 1.252 | 1.597 | 0.345 |
| | 16 | 1.0 | 0.1 | 1.159 | −0.013 | 0.405 | 0.368 | −0.037 | 1.187 | 1.311 | 0.124 |
| | 16 | 0.05 | 0.6 | 1.896 | 0.21 | 0.056 | 0.424 | 0.368 | 0.116 | 1.326 | 1.210 |
| | 16 | 1.0 | 0.6 | 2.035 | 0.216 | 0.07 | 0.384 | 0.314 | 0.126 | 1.392 | 1.266 |
| | 30 | 0.05 | 0.1 | 3.654 | 0.394 | 0.609 | 0.499 | −0.110 | 1.22 | 1.291 | 0.071 |
| | 30 | 1.0 | 0.1 | 3.607 | 0.286 | 0.599 | 0.503 | −0.096 | 1.314 | 1.409 | 0.095 |
| | 30 | 0.05 | 0.6 | 3.468 | 0.292 | 0.599 | 0.51 | −0.089 | 1.693 | 1.392 | −0.301 |
| | 30 | 1.0 | 0.6 | 3.329 | 0.347 | 0.522 | 0.495 | −0.027 | 1.321 | 1.721 | 0.400 |

TABLE 41

Cystatin Activity Results
GST fusion tagged protein, first and second replicates
GmCys5 (SEQ ID NO: 36)

| Cell Type | Temp ° C. | IPTG (mM) | OD600 | Final OD | Bradford (ug/uL) | 1 hour | | | Overnight | | |
|---|---|---|---|---|---|---|---|---|---|---|---|
| | | | | | | 6000 ng | 60 ng | Δ | 6000 ng | 60 ng | Δ |
| | | | | | | Cystatin Assay 10/22 First Replicate | | | | | |
| BL21 Star | 16 | 0.05 | 0.1 | 1.758 | −0.013 | 0.654 | 0.423 | −0.231 | 1.163 | 1.368 | 0.205 |
| | 16 | 1.0 | 0.1 | 1.343 | −0.016 | 0.608 | 0.468 | −0.140 | 1.241 | 1.252 | 0.011 |
| | 16 | 0.05 | 0.6 | 1.896 | 0.04 | 0.662 | 0.454 | −0.208 | 1.244 | 1.304 | 0.060 |
| | 16 | 1.0 | 0.6 | 1.804 | 0.085 | 0.656 | 0.438 | −0.218 | 1.176 | 1.309 | 0.133 |
| | 30 | 0.05 | 0.1 | 2.959 | 0.174 | 0.288 | 0.494 | 0.206 | 1.195 | 1.382 | 0.187 |
| | 30 | 1.0 | 0.1 | 2.867 | 0.134 | 0.359 | 0.491 | 0.132 | 0.985 | 1.17 | 0.185 |
| | 30 | 0.05 | 0.6 | 3.422 | 0.147 | 0.299 | 0.492 | 0.193 | 1.309 | 1.434 | 0.125 |
| | 30 | 1.0 | 0.6 | 3.747 | 0.119 | 0.362 | 0.446 | 0.084 | 1.126 | 0.993 | −0.133 |
| | | | | | | Cystatin Assay 10/22 Second Replicate | | | | | |
| | 16 | 0.05 | 0.1 | 1.021 | 0.004 | 0.463 | 0.347 | −0.116 | 1.185 | 1.256 | 0.071 |
| | 16 | 1.0 | 0.1 | 1.389 | −0.002 | 0.496 | 0.342 | −0.154 | 1.48 | 1.099 | −0.381 |
| | 16 | 0.05 | 0.6 | 2.127 | 0.036 | 0.479 | 0.351 | −0.128 | 1.17 | 1.417 | 0.247 |
| | 16 | 1.0 | 0.6 | 2.081 | 0.044 | 0.486 | 0.35 | −0.136 | 1.067 | 1.248 | 0.181 |
| | 30 | 0.05 | 0.1 | 3.237 | 0.187 | 0.114 | 0.425 | 0.311 | 0.731 | 1.534 | 0.803 |
| | 30 | 1.0 | 0.1 | 3.052 | 0.162 | 0.126 | 0.38 | 0.254 | 0.717 | 1.194 | 0.477 |
| | 30 | 0.05 | 0.6 | 3.515 | 0.113 | 0.206 | 0.428 | 0.222 | 1.214 | 1.437 | 0.223 |
| | 30 | 1.0 | 0.6 | 2.635 | 0.091 | 0.182 | 0.392 | 0.210 | 1.063 | 1.279 | 0.216 |

TABLE 42

Cystatin Activity Results
His fusion tagged protein, first and second replicates
GmCys5 (SEQ ID NO: 36)

| Cell Type | Temp ° C. | IPTG (Mm) | OD600 | Final OD | Bradford (ug/uL) | 1 hour | | | Overnight | | |
|---|---|---|---|---|---|---|---|---|---|---|---|
| | | | | | | 6000 ng | 60 ng | Δ | 6000 ng | 60 ng | Δ |
| | | | | | | Cystatin Assay 10/22 First Replicate | | | | | |
| BL21 Star | 16 | 0.05 | 0.1 | 1.251 | −0.006 | 0.451 | 0.362 | −0.089 | 1.166 | 1.283 | 0.117 |
| | 16 | 1.0 | 0.1 | 2.219 | −0.015 | 0.442 | 0.356 | −0.086 | 1.19 | 1.143 | −0.047 |
| | 16 | 0.05 | 0.6 | 2.404 | 0.218 | 0.266 | 0.374 | 0.108 | 1.118 | 1.124 | 0.006 |
| | 16 | 1.0 | 0.6 | 2.543 | 0.193 | 0.238 | 0.357 | 0.119 | 1.336 | 1.344 | 0.008 |
| | 30 | 0.05 | 0.1 | 3.561 | 0.345 | 0.586 | 0.431 | −0.155 | 1.355 | 1.374 | 0.019 |
| | 30 | 1.0 | 0.1 | 5.932 | 0.38 | 0.569 | 0.435 | −0.134 | 1.339 | 1.308 | −0.031 |
| | 30 | 0.05 | 0.6 | 4.303 | 0.386 | 0.576 | 0.435 | −0.141 | 1.29 | 1.521 | 0.231 |
| | 30 | 1.0 | 0.6 | 4.303 | 0.372 | 0.555 | 0.388 | −0.167 | 1.06 | 1.048 | −0.012 |
| | | | | | | Cystatin Assay 10/22 Second Replicate | | | | | |
| BL21 Star | 16 | 0.05 | 0.1 | 1.113 | −0.021 | 0.465 | 0.364 | −0.101 | 1.273 | 1.347 | 0.074 |
| | 16 | 1.0 | 0.1 | 1.021 | −0.023 | 0.467 | 0.359 | −0.108 | 1.232 | 1.176 | −0.056 |
| | 16 | 0.05 | 0.6 | 2.312 | 0.165 | 0.306 | 0.38 | 0.074 | 1.323 | 1.369 | 0.046 |
| | 16 | 1.0 | 0.6 | 2.173 | 0.206 | 0.202 | 0.388 | 0.186 | 0.973 | 1.686 | 0.713 |
| | 30 | 0.05 | 0.1 | 3.468 | 0.284 | 0.581 | 0.478 | −0.103 | 1.223 | 1.173 | −0.050 |
| | 30 | 1.0 | 0.1 | 3.376 | 0.286 | 0.593 | 0.422 | −0.171 | 1.541 | 1.766 | 0.225 |
| | 30 | 0.05 | 0.6 | 3.098 | 0.276 | 0.61 | 0.49 | −0.120 | 1.265 | 1.205 | −0.060 |
| | 30 | 1.0 | 0.6 | 2.867 | 0.255 | 0.594 | 0.445 | −0.149 | 1.784 | 1.802 | 0.018 |

TABLE 43

Cystatin Activity Results
GST fusion tagged protein, first and second replicates
GmCys7 (SEQ ID NO: 40)

| Cell Type | Temp °C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.435 | −0.013 | 0.609 | 0.452 | −0.157 | 1.179 | 1.263 | 0.084 |
| | 16 | 1.0 | 0.1 | 1.113 | −0.02 | 0.562 | 0.433 | −0.129 | 1.155 | 1.184 | 0.029 |
| | 16 | 0.05 | 0.6 | 1.573 | 0.067 | 0.556 | 0.361 | −0.195 | 1.187 | 1.191 | 0.004 |
| | 16 | 1.0 | 0.6 | 1.573 | 0.053 | 0.52 | 0.376 | −0.144 | 1.171 | 1.231 | 0.060 |
| | 30 | 0.05 | 0.1 | 3.515 | 0.274 | 0.246 | 0.501 | 0.255 | 1.164 | 1.217 | 0.053 |
| | 30 | 1.0 | 0.1 | 2.867 | 0.17 | 0.336 | 0.45 | 0.114 | 1.295 | 1.061 | −0.234 |
| | 30 | 0.05 | 0.6 | 3.422 | 0.225 | 0.216 | 0.461 | 0.245 | 1.05 | 1.126 | 0.076 |
| | 30 | 1.0 | 0.6 | 2.82 | 0.179 | 0.258 | 0.446 | 0.188 | 1.156 | 1.069 | −0.087 |
| | | | | | | Cystatin Assay 10/22 Second Replicate | | | | | |
| BL21 Star | 16 | 0.05 | 0.1 | 0.975 | −0.019 | 0.525 | 0.404 | −0.121 | 1.204 | 1.393 | 0.189 |
| | 16 | 1.0 | 0.1 | 1.389 | −0.034 | 0.492 | 0.366 | −0.126 | 1.343 | 1.333 | −0.010 |
| | 16 | 0.05 | 0.6 | 1.666 | 0.054 | 0.512 | 0.402 | −0.110 | 1.298 | 1.29 | −0.008 |
| | 16 | 1.0 | 0.6 | 1.573 | 0.024 | 0.486 | 0.374 | −0.112 | 1.333 | 1.285 | −0.048 |
| | 30 | 0.05 | 0.1 | 3.654 | 0.216 | 0.212 | 0.482 | 0.270 | 1.115 | 1.348 | 0.233 |
| | 30 | 1.0 | 0.1 | 3.098 | 0.104 | 0.3 | 0.475 | 0.175 | 1.222 | 1.297 | 0.075 |
| | 30 | 0.05 | 0.6 | 3.191 | 0.245 | 0.236 | 0.445 | 0.209 | 1.244 | 1.262 | 0.018 |
| | 30 | 1.0 | 0.6 | 2.82 | 0.145 | 0.322 | 0.462 | 0.140 | 1.185 | 1.326 | 0.141 |

TABLE 44

Cystatin Activity Results
His fusion tagged protein, first and second replicates
GmCys7 (SEQ ID NO: 40)

| Cell Type | Temp °C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.113 | 0 | 0.486 | 0.403 | −0.083 | 1.134 | 1.185 | 0.051 |
| | 16 | 1.0 | 0.1 | 1.159 | −0.017 | 0.423 | 0.374 | −0.049 | 1.051 | 1.178 | 0.127 |
| | 16 | 0.05 | 0.6 | 2.266 | 0.12 | 0.387 | 0.397 | 0.010 | 1.075 | 1.144 | 0.069 |
| | 16 | 1.0 | 0.6 | 2.404 | 0.094 | 0.289 | 0.367 | 0.078 | 1.858 | 1.2 | −0.658 |
| | 30 | 0.05 | 0.1 | 3.886 | 0.429 | 0.475 | 0.515 | 0.040 | 1.277 | 1.771 | 0.494 |
| | 30 | 1.0 | 0.1 | 3.515 | 0.411 | 0.471 | 0.479 | 0.008 | 1.318 | 1.317 | −0.001 |
| | 30 | 0.05 | 0.6 | 3.747 | 0.405 | 0.478 | 0.456 | −0.022 | 1.499 | 1.364 | −0.135 |
| | 30 | 1.0 | 0.6 | 4.21 | 0.386 | 0.443 | 0.479 | 0.036 | 1.475 | 1.615 | 0.140 |
| | | | | | | Cystatin Assay 10/22 Second Replicate | | | | | |
| BL21 Star | 16 | 0.05 | 0.1 | 0.975 | 0 | 0.571 | 0.473 | −0.098 | 1.236 | 1.18 | −0.056 |
| | 16 | 1.0 | 0.1 | 1.159 | −0.011 | 0.54 | 0.438 | −0.102 | 1.259 | 1.11 | −0.149 |
| | 16 | 0.05 | 0.6 | 1.942 | 0.087 | 0.453 | 0.429 | −0.024 | 1.035 | 1.078 | 0.043 |
| | 16 | 1.0 | 0.6 | 1.942 | 0.067 | 0.345 | 0.446 | 0.101 | 1.033 | 1.178 | 0.145 |
| | 30 | 0.05 | 0.1 | 3.283 | 0.322 | 0.641 | 0.539 | −0.102 | 1.249 | 1.331 | 0.082 |
| | 30 | 1.0 | 0.1 | 3.376 | 0.308 | 0.622 | 0.54 | −0.082 | 1.345 | 1.453 | 0.108 |
| | 30 | 0.05 | 0.6 | 3.329 | 0.285 | 0.579 | 0.552 | −0.027 | 1.263 | 1.36 | 0.097 |
| | 30 | 1.0 | 0.6 | 3.329 | 0.302 | 0.605 | 0.503 | −0.102 | 1.551 | 1.294 | −0.257 |

TABLE 45

Cystatin Activity Results
GST fusion tagged protein, first and second replicates
GmCys9 (SEQ ID NO: 44)

| Cell Type | Temp ° C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.021 | −0.016 | 0.591 | 0.434 | −0.157 | 1.131 | 1.066 | −0.065 |
| | 16 | 1.0 | 0.1 | 1.067 | −0.018 | 0.586 | 0.45 | −0.136 | 1.069 | 1.173 | 0.104 |
| | 16 | 0.05 | 0.6 | 3.237 | 0.056 | 0.541 | 0.454 | −0.087 | 1.178 | 1.196 | 0.018 |
| | 16 | 1.0 | 0.6 | 2.127 | 0.053 | 0.543 | 0.452 | −0.091 | 1.111 | 1.256 | 0.145 |
| | 30 | 0.05 | 0.1 | 3.144 | 0.187 | 0.066 | 0.501 | 0.435 | 0.194 | 1.236 | 1.042 |
| | 30 | 1.0 | 0.1 | 3.191 | −0.002 | 0.44 | 0.471 | 0.031 | 1.267 | 1.162 | −0.105 |
| | 30 | 0.05 | 0.6 | 3.607 | 0.153 | 0.09 | 0.554 | 0.464 | 0.371 | 1.364 | 0.993 |
| | 30 | 1.0 | 0.6 | 2.728 | 0.094 | 0.217 | 0.481 | 0.264 | 1.007 | 1.203 | 0.196 |
| | | | | | | Cystatin Assay 10/22 Second Replicate | | | | | |
| BL21 Star | 16 | 0.05 | 0.1 | 1.343 | −0.007 | 0.477 | 0.371 | −0.106 | 1.416 | 1.062 | −0.354 |
| | 16 | 1.0 | 0.1 | 1.113 | −0.013 | 0.444 | 0.362 | −0.082 | 1.286 | 1.167 | −0.119 |
| | 16 | 0.05 | 0.6 | 1.989 | 0.033 | 0.501 | 0.405 | −0.096 | 1.036 | 1.251 | 0.215 |
| | 16 | 1.0 | 0.6 | 2.035 | 0.011 | 0.471 | 0.403 | −0.068 | 1.222 | 1.511 | 0.289 |
| | 30 | 0.05 | 0.1 | 3.747 | 0.238 | 0.063 | 0.455 | 0.392 | 0.145 | 1.119 | 0.974 |
| | 30 | 1.0 | 0.1 | 5.094 | 0.134 | 0.123 | 0.458 | 0.335 | 0.725 | 1.233 | 0.508 |
| | 30 | 0.05 | 0.6 | 3.376 | 0.151 | 0.131 | 0.496 | 0.365 | 0.73 | 1.314 | 0.584 |
| | 30 | 1.0 | 0.6 | 3.005 | 0.085 | 0.236 | 0.456 | 0.220 | 1.048 | 1.32 | 0.272 |

TABLE 46

Cystatin Activity Results
His fusion tagged protein, first and second replicates
GmCys9 (SEQ ID NO: 44)

| Cell Type | Temp ° C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.113 | 0.007 | 0.476 | 0.402 | −0.074 | 1.148 | 1.388 | 0.240 |
| | 16 | 1.0 | 0.1 | 1.113 | 0 | 0.295 | 0.393 | 0.098 | 1.246 | 1.421 | 0.175 |
| | 16 | 0.05 | 0.6 | 2.45 | 0.206 | 0.056 | 0.405 | 0.349 | 0.137 | 1.084 | 0.947 |
| | 16 | 1.0 | 0.6 | 2.312 | 0.201 | 0.059 | 0.404 | 0.345 | 0.114 | 1.286 | 1.172 |
| | 30 | 0.05 | 0.1 | 5.047 | 0.417 | 0.497 | 0.469 | −0.028 | 1.369 | 1.199 | −0.170 |
| | 30 | 1.0 | 0.1 | 3.839 | 0.392 | 0.558 | 0.474 | −0.084 | 1.263 | 1.429 | 0.166 |
| | 30 | 0.05 | 0.6 | 4.443 | 0.382 | 0.423 | 0.489 | 0.066 | 1.115 | 1.221 | 0.106 |
| | 30 | 1.0 | 0.6 | 3.839 | 0.321 | 0.432 | 0.496 | 0.064 | 0.937 | 1.26 | 0.323 |
| | | | | | | Cystatin Assay 10/22 Second Replicate | | | | | |
| BL21 Star | 16 | 0.05 | 0.1 | 1.297 | 0.014 | 0.613 | 0.495 | −0.118 | 1.303 | 1.166 | −0.137 |
| | 16 | 1.0 | 0.1 | 1.067 | 0.012 | 0.381 | 0.513 | 0.132 | 1.081 | 1.422 | 0.341 |
| | 16 | 0.05 | 0.6 | 1.942 | 0.236 | 0.08 | 0.477 | 0.397 | 0.33 | 1.115 | 0.785 |
| | 16 | 1.0 | 0.6 | 2.081 | 0.259 | 0.054 | 0.474 | 0.420 | 0.114 | 1.228 | 1.114 |
| | 30 | 0.05 | 0.1 | 3.561 | 0.397 | 0.292 | 0.53 | 0.238 | 1.077 | 1.269 | 0.192 |
| | 30 | 1.0 | 0.1 | 3.376 | 0.304 | 0.48 | 0.501 | 0.021 | 1.195 | 1.305 | 0.110 |
| | 30 | 0.05 | 0.6 | 3.144 | 0.257 | 0.364 | 0.511 | 0.147 | 1.372 | 1.222 | −0.150 |
| | 30 | 1.0 | 0.6 | 3.191 | 0.332 | 0.383 | 0.491 | 0.108 | 1.291 | 1.293 | 0.002 |

TABLE 47

Cystatin Activity Results
GST fusion tagged protein, first and second replicates
TaCys8 (SEQ ID NO: 68)

| Cell Type | Temp °C. | IPTG (Mm) | OD600 | Final OD | Bradford(ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.481 | −0.007 | 0.608 | 0.392 | −0.216 | 1.323 | 1.516 | 0.193 |
| | 16 | 1.0 | 0.1 | 1.021 | −0.007 | 0.587 | 0.428 | −0.159 | 1.272 | 1.198 | −0.074 |
| | 16 | 0.05 | 0.6 | 2.173 | 0.076 | 0.546 | 0.417 | −0.129 | 0.95 | 1.197 | 0.247 |
| | 16 | 1.0 | 0.6 | 1.896 | 0.04 | 0.537 | 0.433 | −0.104 | 1.338 | 1.188 | −0.150 |
| | 30 | 0.05 | 0.1 | 3.005 | 0.208 | 0.121 | 0.471 | 0.350 | 0.879 | 1.15 | 0.271 |
| | 30 | 1.0 | 0.1 | 2.774 | 0.166 | 0.191 | 0.444 | 0.253 | 1.025 | 1.156 | 0.131 |
| | 30 | 0.05 | 0.6 | 4.536 | 0.183 | 0.134 | 0.46 | 0.326 | 0.985 | 1.058 | 0.073 |
| | 30 | 1.0 | 0.6 | 2.913 | 0.159 | 0.142 | 0.448 | 0.306 | 0.838 | 1.037 | 0.199 |
| | | | | | | Cystatin Assay 10/22 Second Replicate | | | | | |
| BL21 Star | 16 | 0.05 | 0.1 | 1.343 | −0.002 | 0.45 | 0.34 | −0.110 | 1.227 | 1.191 | −0.036 |
| | 16 | 1.0 | 0.1 | 1.62 | 0.002 | 0.398 | 0.357 | −0.041 | 1.092 | 1.304 | 0.212 |
| | 16 | 0.05 | 0.6 | 2.035 | 0.031 | 0.4 | 0.352 | −0.048 | 1.118 | 1.364 | 0.246 |
| | 16 | 1.0 | 0.6 | 2.081 | 0.024 | 0.336 | 0.358 | 0.022 | 1.091 | 1.19 | 0.099 |
| | 30 | 0.05 | 0.1 | 3.515 | 0.272 | 0.095 | 0.406 | 0.311 | 0.753 | 1.103 | 0.350 |
| | 30 | 1.0 | 0.1 | 2.774 | 0.164 | 0.116 | 0.392 | 0.276 | 0.916 | 1.159 | 0.243 |
| | 30 | 0.05 | 0.6 | 3.468 | 0.191 | 0.117 | 0.433 | 0.316 | 0.818 | 1.184 | 0.366 |
| | 30 | 1.0 | 0.6 | 2.728 | 0.189 | 0.111 | 0.416 | 0.305 | 0.76 | 1.099 | 0.339 |

TABLE 48

Cystatin Activity Results
His fusion tagged protein, first and second replicates
TaCys8 (SEQ ID NO: 68)

| Cell Type | Temp °C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.389 | −0.006 | 0.484 | 0.387 | −0.097 | 1.28 | 1.614 | 0.334 |
| | 16 | 1.0 | 0.1 | 1.113 | −0.008 | 0.417 | 0.354 | −0.063 | 1.163 | 1.451 | 0.288 |
| | 16 | 0.05 | 0.6 | 2.266 | 0.158 | 0.38 | 0.414 | 0.034 | 1.21 | 1.428 | 0.218 |
| | 16 | 1.0 | 0.6 | 2.404 | 0.152 | 0.357 | 0.406 | 0.049 | 1.307 | 1.227 | −0.080 |
| | 30 | 0.05 | 0.1 | 3.839 | 0.517 | 0.093 | 0.438 | 0.345 | 0.796 | 1.514 | 0.718 |
| | 30 | 1.0 | 0.1 | 3.839 | 0.53 | 0.097 | 0.416 | 0.319 | 0.78 | 1.245 | 0.465 |
| | 30 | 0.05 | 0.6 | 4.814 | 0.462 | 0.099 | 0.455 | 0.356 | 0.678 | 1.101 | 0.423 |
| | 30 | 1.0 | 0.6 | 3.839 | 0.415 | 0.092 | 0.422 | 0.330 | 0.676 | 0.99 | 0.314 |
| | | | | | | Cystatin Assay 10/22 Second Replicate | | | | | |
| BL21 Star | 16 | 0.05 | 0.1 | 1.205 | 0 | 0.636 | 0.498 | −0.138 | 1.461 | 1.677 | 0.216 |
| | 16 | 1.0 | 0.1 | 0.975 | 0 | 0.63 | 0.494 | −0.136 | 1.463 | 1.354 | −0.109 |
| | 16 | 0.05 | 0.6 | 2.127 | 0.197 | 0.339 | 0.455 | 0.116 | 0.98 | 1.102 | 0.122 |
| | 16 | 1.0 | 0.6 | 2.035 | 0.22 | 0.261 | 0.447 | 0.186 | 1.035 | 1.056 | 0.021 |
| | 30 | 0.05 | 0.1 | 3.839 | 0.277 | 0.386 | 0.503 | 0.117 | 1.165 | 1.225 | 0.060 |
| | 30 | 1.0 | 0.1 | 3.191 | 0.306 | 0.425 | 0.498 | 0.073 | 1.169 | 1.406 | 0.237 |
| | 30 | 0.05 | 0.6 | 3.7 | 0.297 | 0.223 | 0.479 | 0.256 | 1.097 | 1.226 | 0.129 |
| | 30 | 1.0 | 0.6 | 3.191 | 0.304 | 0.216 | 0.488 | 0.272 | 1.062 | 1.071 | 0.009 |

TABLE 49

Cystatin Activity Results
GST fusion tagged protein, first and second replicates
ZmCys8 (SEQ ID NO: 14)

| Cell Type | Temp ° C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.666 | −0.009 | 0.606 | 0.425 | −0.181 | 1.435 | 1.288 | −0.147 |
| | 16 | 1.0 | 0.1 | 0.882 | −0.011 | 0.581 | 0.437 | −0.144 | 1.283 | 1.369 | 0.086 |
| | 16 | 0.05 | 0.6 | 1.758 | 0.047 | 0.526 | 0.351 | −0.175 | 1.027 | 1.126 | 0.099 |
| | 16 | 1.0 | 0.6 | 1.758 | 0.067 | 0.541 | 0.368 | −0.173 | 1.168 | 1.156 | −0.012 |
| | 30 | 0.05 | 0.1 | 2.589 | 0.213 | 0.484 | 0.464 | −0.020 | 0.914 | 1.219 | 0.305 |
| | 30 | 1.0 | 0.1 | 2.635 | 0.174 | 0.508 | 0.444 | −0.064 | 0.951 | 1.116 | 0.165 |
| | 30 | 0.05 | 0.6 | 2.173 | 0.189 | 0.463 | 0.416 | −0.047 | 1.069 | 0.968 | −0.101 |
| | 30 | 1.0 | 0.6 | 2.173 | 0.138 | 0.523 | 0.434 | −0.089 | 1.349 | 1.404 | 0.055 |
| | | | | | | Cystatin Assay 10/22 Second Replicate | | | | | |
| BL21 Star | 16 | 0.05 | 0.1 | 1.159 | −0.017 | 0.49 | 0.348 | −0.142 | 1.326 | 1.308 | −0.018 |
| | 16 | 1.0 | 0.1 | 1.251 | −0.013 | 0.495 | 0.37 | −0.125 | 1.411 | 1.256 | −0.155 |
| | 16 | 0.05 | 0.6 | 1.297 | 0.052 | 0.512 | 0.364 | −0.148 | 1.306 | 1.447 | 0.141 |
| | 16 | 1.0 | 0.6 | 1.297 | 0.062 | 0.51 | 0.369 | −0.141 | 1.365 | 1.387 | 0.022 |
| | 30 | 0.05 | 0.1 | 2.682 | 0.173 | 0.469 | 0.426 | −0.043 | 1.212 | 1.153 | −0.059 |
| | 30 | 1.0 | 0.1 | 2.543 | 0.149 | 0.544 | 0.447 | −0.097 | 1.349 | 1.282 | −0.067 |
| | 30 | 0.05 | 0.6 | 2.543 | 0.165 | 0.481 | 0.426 | −0.055 | 1.146 | 1.359 | 0.213 |
| | 30 | 1.0 | 0.6 | 2.173 | 0.118 | 0.541 | 0.422 | −0.119 | 1.57 | 1.603 | 0.033 |

TABLE 50

Cystatin Activity Results
His fusion tagged protein, first and second replicates
ZmCys8 (SEQ ID NO: 14)

| Cell Type | Temp ° C. | IPTG (Mm) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.527 | −0.013 | 0.464 | 0.382 | −0.082 | 1.168 | 1.229 | 0.061 |
| | 16 | 1.0 | 0.1 | 1.343 | −0.021 | 0.413 | 0.368 | −0.045 | 1.028 | 1.08 | 0.052 |
| | 16 | 0.05 | 0.6 | 2.543 | 0.099 | 0.487 | 0.368 | −0.119 | 1.117 | 1.147 | 0.030 |
| | 16 | 1.0 | 0.6 | 2.358 | 0.064 | 0.486 | 0.366 | −0.120 | 1.311 | 1.355 | 0.044 |
| | 30 | 0.05 | 0.1 | 4.025 | 0.403 | 0.557 | 0.464 | −0.093 | 1.346 | 1.576 | 0.230 |
| | 30 | 1.0 | 0.1 | 5.28 | 0.446 | 0.548 | 0.445 | −0.103 | 1.337 | 1.448 | 0.111 |
| | 30 | 0.05 | 0.6 | 4.071 | 0.353 | 0.517 | 0.466 | −0.051 | 1.199 | 1.389 | 0.190 |
| | 30 | 1.0 | 0.6 | 3.376 | 0.308 | 0.491 | 0.438 | −0.053 | 1.062 | 1.665 | 0.603 |
| | | | | | | Cystatin Assay 10/22 Second Replicate | | | | | |
| BL21 Star | 16 | 0.05 | 0.1 | 0.975 | −0.013 | 0.522 | 0.436 | −0.086 | 1.283 | 1.163 | −0.120 |
| | 16 | 1.0 | 0.1 | 0.975 | −0.013 | 0.53 | 0.421 | −0.109 | 1.314 | 1.256 | −0.058 |
| | 16 | 0.05 | 0.6 | 1.942 | 0.161 | 0.527 | 0.427 | −0.100 | 1.148 | 1.055 | −0.093 |
| | 16 | 1.0 | 0.6 | 1.804 | 0.095 | 0.505 | 0.417 | −0.088 | 1.071 | 1.075 | 0.004 |
| | 30 | 0.05 | 0.1 | 3.144 | 0.257 | 0.646 | 0.554 | −0.092 | 1.176 | 1.318 | 0.142 |
| | 30 | 1.0 | 0.1 | 3.515 | 0.332 | 0.675 | 0.509 | −0.166 | 1.541 | 1.5 | −0.041 |
| | 30 | 0.05 | 0.6 | 2.774 | 0.214 | 0.661 | 0.505 | −0.156 | 1.396 | 1.296 | −0.100 |
| | 30 | 1.0 | 0.6 | 2.543 | 0.234 | 0.678 | 0.505 | −0.173 | 1.532 | 1.418 | −0.114 |

TABLE 51

Cystatin Activity Results
GST fusion tagged protein, first and second replicates
ZmCys10 (SEQ ID NO: 18)

| Cell Type | Temp °C. | IPTG (mM) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | Cystatin Assay 10/22 First Replicate | | | | | | |
| BL21 Star | 16 | 0.05 | 0.1 | 2.127 | −0.027 | 0.581 | 0.463 | −0.118 | 1.184 | 1.334 | 0.150 |
| | 16 | 1.0 | 0.1 | 1.481 | −0.011 | 0.632 | 0.478 | −0.154 | 1.324 | 1.385 | 0.061 |
| | 16 | 0.05 | 0.6 | 2.127 | 0.056 | 0.612 | 0.457 | −0.155 | 1.252 | 1.243 | −0.009 |
| | 16 | 1.0 | 0.6 | 2.219 | 0.047 | 0.668 | 0.464 | −0.204 | 1.208 | 1.353 | 0.145 |
| | 30 | 0.05 | 0.1 | 4.35 | 0.1 | 0.622 | 0.482 | −0.140 | 1.158 | 1.187 | 0.029 |
| | 30 | 1.0 | 0.1 | 4.443 | 0.106 | 0.629 | 0.483 | −0.146 | 1.122 | 1.151 | 0.029 |
| | 30 | 0.05 | 0.6 | 3.7 | 0.072 | 0.592 | 0.466 | −0.126 | 1.23 | 1.146 | −0.084 |
| | 30 | 1.0 | 0.6 | 2.635 | 0.068 | 0.617 | 0.477 | −0.140 | 1.29 | 1.268 | −0.022 |
| | | | | | Cystatin Assay 10/22 Second Replicate | | | | | | |
| BL21 Star | 16 | 0.05 | 0.1 | 1.021 | −0.018 | 0.446 | 0.341 | −0.105 | 1.12 | 1.218 | 0.098 |
| | 16 | 1.0 | 0.1 | 1.113 | −0.009 | 0.473 | 0.352 | −0.121 | 1.217 | 1.172 | −0.045 |
| | 16 | 0.05 | 0.6 | 2.266 | 0.009 | 0.459 | 0.334 | −0.125 | 1.494 | 1.18 | −0.314 |
| | 16 | 1.0 | 0.6 | 2.127 | 0.038 | 0.486 | 0.358 | −0.128 | 1.229 | 1.161 | −0.068 |
| | 30 | 0.05 | 0.1 | 2.728 | 0.074 | 0.547 | 0.412 | −0.135 | 1.193 | 1.136 | −0.057 |
| | 30 | 1.0 | 0.1 | 2.959 | 0.083 | 0.512 | 0.403 | −0.109 | 1.094 | 1.178 | 0.084 |
| | 30 | 0.05 | 0.6 | 2.173 | 0.047 | 0.528 | 0.424 | −0.104 | 1.122 | 1.315 | 0.193 |
| | 30 | 1.0 | 0.6 | 2.358 | 0.045 | 0.564 | 0.425 | −0.139 | 1.594 | 1.58 | −0.014 |

TABLE 52

Cystatin Activity Results
His fusion tagged protein, first and second replicates
ZmCys10 (SEQ ID NO: 18)

| Cell Type | Temp °C. | IPTG (mM) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | Cystatin Assay 10/22 First Replicate | | | | | | |
| BL21 Star | 16 | 0.05 | 0.1 | 1.62 | 0.002 | 0.481 | 0.357 | −0.124 | 1.291 | 1.21 | −0.081 |
| | 16 | 1.0 | 0.1 | 1.113 | 0.011 | 0.468 | 0.336 | −0.132 | 1.161 | 1.278 | 0.117 |
| | 16 | 0.05 | 0.6 | 2.497 | 0.214 | 0.499 | 0.365 | −0.134 | 1.192 | 1.136 | −0.056 |
| | 16 | 1.0 | 0.6 | 2.266 | 0.214 | 0.495 | 0.36 | −0.135 | 1.175 | 1.211 | 0.036 |
| | 30 | 0.05 | 0.1 | 4.722 | 0.446 | 0.56 | 0.415 | −0.145 | 1.233 | 1.295 | 0.062 |
| | 30 | 1.0 | 0.1 | 3.654 | 0.339 | 0.58 | 0.387 | −0.193 | 1.2 | 1.276 | 0.076 |
| | 30 | 0.05 | 0.6 | 5.001 | 0.339 | 0.543 | 0.418 | −0.125 | 1.14 | 1.254 | 0.114 |
| | 30 | 1.0 | 0.6 | 4.118 | 0.38 | 0.576 | 0.39 | −0.186 | 1.291 | 1.29 | −0.001 |
| | | | | | Cystatin Assay 10/22 Second Replicate | | | | | | |
| BL21 Star | 16 | 0.05 | 0.1 | 1.021 | −0.008 | 0.491 | 0.356 | −0.135 | 1.137 | 1.392 | 0.255 |
| | 16 | 1.0 | 0.1 | 1.021 | −0.004 | 0.434 | 0.353 | −0.081 | 1.163 | 1.474 | 0.311 |
| | 16 | 0.05 | 0.6 | 1.896 | 0.287 | 0.54 | 0.386 | −0.154 | 1.48 | 1.423 | −0.057 |
| | 16 | 1.0 | 0.6 | 2.173 | 0.227 | 0.51 | 0.362 | −0.148 | 1.242 | 1.362 | 0.120 |
| | 30 | 0.05 | 0.1 | 3.468 | 0.31 | 0.597 | 0.472 | −0.125 | 1.308 | 1.232 | −0.076 |
| | 30 | 1.0 | 0.1 | 3.329 | 0.325 | 0.559 | 0.469 | −0.090 | 1.042 | 1.169 | 0.127 |
| | 30 | 0.05 | 0.6 | 2.959 | 0.272 | 0.632 | 0.485 | −0.147 | 1.597 | 1.161 | −0.436 |
| | 30 | 1.0 | 0.6 | 3.098 | 0.308 | 0.577 | 0.484 | −0.093 | 1.119 | 1.107 | −0.012 |

TABLE 53

Cystatin Activity Results
GST fusion tagged protein, first and second replicates
ZmCys11 (SEQ ID NO: 20)

| Cell Type | Temp °C. | IPTG (mM) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.942 | −0.016 | 0.598 | 0.443 | −0.155 | 1.414 | 1.123 | −0.291 |
| | 16 | 1.0 | 0.1 | 2.081 | −0.042 | 0.581 | 0.456 | −0.125 | 1.247 | 1.244 | −0.003 |
| | 16 | 0.05 | 0.6 | 3.283 | 0.053 | 0.603 | 0.427 | −0.176 | 1.136 | 1.193 | 0.057 |
| | 16 | 1.0 | 0.6 | 2.589 | 0.091 | 0.621 | 0.45 | −0.171 | 1.125 | 1.282 | 0.157 |
| | 30 | 0.05 | 0.1 | 3.7 | 0.104 | 0.554 | 0.434 | −0.120 | 1.192 | 1.171 | −0.021 |
| | 30 | 1.0 | 0.1 | 4.025 | 0.085 | 0.557 | 0.454 | −0.103 | 1.001 | 1.202 | 0.201 |
| | 30 | 0.05 | 0.6 | 3.098 | 0.074 | 0.485 | 0.446 | −0.039 | 0.964 | 1.082 | 0.118 |
| | 30 | 1.0 | 0.6 | 2.913 | 0.089 | 0.529 | 0.46 | −0.069 | 1.013 | 1.1 | 0.087 |
| | | | | | | Cystatin Assay 10/22 Second Replicate | | | | | |
| BL21 Star | 16 | 0.05 | 0.1 | 1.067 | −0.013 | 0.438 | 0.335 | −0.103 | 1.093 | 1.296 | 0.203 |
| | 16 | 1.0 | 0.1 | 1.067 | 0.011 | 0.455 | 0.338 | −0.117 | 1.167 | 1.015 | −0.152 |
| | 16 | 0.05 | 0.6 | 2.404 | 0.082 | 0.461 | 0.331 | −0.130 | 0.946 | 1.235 | 0.289 |
| | 16 | 1.0 | 0.6 | 2.404 | 0.013 | 0.46 | 0.358 | −0.102 | 1.106 | 1.1 | −0.006 |
| | 30 | 0.05 | 0.1 | 3.237 | 0.079 | 0.509 | 0.401 | −0.108 | 1.149 | 1.099 | −0.050 |
| | 30 | 1.0 | 0.1 | 3.793 | 0.07 | 0.506 | 0.404 | −0.102 | 1.082 | 1.01 | −0.072 |
| | 30 | 0.05 | 0.6 | 2.867 | 0.068 | 0.5 | 0.44 | −0.060 | 1.264 | 1.201 | −0.063 |
| | 30 | 1.0 | 0.6 | 3.747 | 0.072 | 0.433 | 0.442 | 0.009 | 1.293 | 1.236 | −0.057 |

TABLE 54

Cystatin Activity Results
His fusion tagged protein, first and second replicates
ZmCys11 (SEQ ID NO: 20)

| Cell Type | Temp °C. | IPTG (mM) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.712 | 0.024 | 0.467 | 0.372 | −0.095 | 1.176 | 1.526 | 0.350 |
| | 16 | 1.0 | 0.1 | 1.159 | 0.404 | 0.456 | 0.364 | −0.092 | 1.088 | 1.235 | 0.147 |
| | 16 | 0.05 | 0.6 | 2.682 | 0.265 | 0.492 | 0.431 | −0.061 | 1.122 | 1.418 | 0.296 |
| | 16 | 1.0 | 0.6 | 2.312 | 0.319 | 0.479 | 0.454 | −0.025 | 1.04 | 1.543 | 0.503 |
| | 30 | 0.05 | 0.1 | 4.768 | 0.433 | 0.514 | 0.439 | −0.075 | 1.308 | 1.335 | 0.027 |
| | 30 | 1.0 | 0.1 | 3.468 | 0.356 | 0.527 | 0.435 | −0.092 | 1.453 | 1.511 | 0.058 |
| | 30 | 0.05 | 0.6 | 3.839 | 0.339 | 0.525 | 0.461 | −0.064 | 1.228 | 1.229 | 0.001 |
| | 30 | 1.0 | 0.6 | 3.283 | 0.272 | 0.523 | 0.454 | −0.069 | 1.337 | 1.172 | −0.165 |
| | | | | | | Cystatin Assay 10/22 Second Replicate | | | | | |
| BL21 Star | 16 | 0.05 | 0.1 | 1.021 | 0.032 | 0.518 | 0.48 | −0.038 | 1.326 | 1.467 | 0.141 |
| | 16 | 1.0 | 0.1 | 1.067 | 0.026 | 0.64 | 0.491 | −0.149 | 1.298 | 1.255 | −0.043 |
| | 16 | 0.05 | 0.6 | 1.989 | 0.344 | 0.519 | 0.431 | −0.088 | 1.041 | 1.007 | −0.034 |
| | 16 | 1.0 | 0.6 | 1.989 | 0.336 | 0.656 | 0.507 | −0.149 | 1.222 | 1.288 | 0.066 |
| | 30 | 0.05 | 0.1 | 3.237 | 0.314 | 0.599 | 0.493 | −0.106 | 1.147 | 1.117 | −0.030 |
| | 30 | 1.0 | 0.1 | 2.913 | 0.318 | 0.646 | 0.501 | −0.145 | 1.453 | 1.682 | 0.229 |
| | 30 | 0.05 | 0.6 | 3.237 | 0.275 | 0.599 | 0.49 | −0.109 | 1.262 | 1.523 | 0.261 |
| | 30 | 1.0 | 0.6 | 3.561 | 0.269 | 0.621 | 0.483 | −0.138 | 1.33 | 1.337 | 0.007 |

TABLE 55

Cystatin Activity Results
GST fusion tagged protein, first and second replicates
ZmCys12 (SEQ ID NO: 22)

| Cell Type | Temp °C. | IPTG (mM) | OD600 | Final OD | Bradford (ug/uL) | 1 hour | | | Overnight | | |
|---|---|---|---|---|---|---|---|---|---|---|---|
| | | | | | | 6000 ng | 60 ng | Δ | 6000 ng | 60 ng | Δ |
| | | | | | Cystatin Assay 10/22 First Replicate | | | | | | |
| BL21 Star | 16 | 0.05 | 0.1 | 0.882 | −0.02 | 0.552 | 0.428 | −0.124 | 1.307 | 1.093 | −0.214 |
| | 16 | 1.0 | 0.1 | 1.021 | −0.007 | 0.561 | 0.434 | −0.127 | 1.609 | 1.369 | −0.240 |
| | 16 | 0.05 | 0.6 | 1.573 | 0.04 | 0.505 | 0.359 | −0.146 | 1.18 | 1.41 | 0.230 |
| | 16 | 1.0 | 0.6 | 1.942 | 0.071 | 0.491 | 0.355 | −0.136 | 1.171 | 1.108 | −0.063 |
| | 30 | 0.05 | 0.1 | 4.814 | 0.198 | 0.165 | 0.455 | 0.290 | 0.881 | 1.121 | 0.240 |
| | 30 | 1.0 | 0.1 | 3.793 | 0.136 | 0.435 | 0.458 | 0.023 | 1.069 | 1.252 | 0.183 |
| | 30 | 0.05 | 0.6 | 2.173 | 0.234 | 0.257 | 0.415 | 0.158 | 0.994 | 1.083 | 0.089 |
| | 30 | 1.0 | 0.6 | 3.283 | 0.213 | 0.211 | 0.405 | 0.194 | 0.934 | 1.406 | 0.472 |
| | | | | | Cystatin Assay 10/22 Second Replicate | | | | | | |
| BL21 Star | 16 | 0.05 | 0.1 | 1.067 | −0.013 | 0.511 | 0.375 | −0.136 | 1.372 | 1.221 | −0.151 |
| | 16 | 1.0 | 0.1 | 0.882 | −0.015 | 0.491 | 0.347 | −0.144 | 1.234 | 1.209 | −0.025 |
| | 16 | 0.05 | 0.6 | 1.527 | 0.041 | 0.477 | 0.367 | −0.110 | 1.309 | 1.418 | 0.109 |
| | 16 | 1.0 | 0.6 | 2.404 | 0.037 | 0.468 | 0.348 | −0.120 | 1.246 | 1.229 | −0.017 |
| | 30 | 0.05 | 0.1 | 2.635 | 0.165 | 0.219 | 0.436 | 0.217 | 1.26 | 1.424 | 0.164 |
| | 30 | 1.0 | 0.1 | 3.144 | 0.132 | 0.417 | 0.462 | 0.045 | 1.773 | 1.297 | −0.476 |
| | 30 | 0.05 | 0.6 | 3.654 | 0.12 | 0.322 | 0.414 | 0.092 | 1.559 | 1.443 | −0.116 |
| | 30 | 1.0 | 0.6 | 3.607 | 0.106 | 0.389 | 0.437 | 0.048 | 1.27 | 1.249 | −0.021 |

TABLE 56

Cystatin Activity Results
His fusion tagged protein, first and second replicates
ZmCys12 (SEQ ID NO: 22)

| Cell Type | Temp °C. | IPTG (mM) | OD600 | Final OD | Bradford (ug/uL) | 1 hour | | | Overnight | | |
|---|---|---|---|---|---|---|---|---|---|---|---|
| | | | | | | 6000 ng | 60 ng | Δ | 6000 ng | 60 ng | Δ |
| | | | | | Cystatin Assay 10/22 First Replicate | | | | | | |
| BL21 Star | 16 | 0.05 | 0.1 | 1.297 | −0.025 | 0.508 | 0.364 | −0.144 | 1.289 | 1.036 | −0.253 |
| | 16 | 1.0 | 0.1 | 1.067 | −0.015 | 0.538 | 0.375 | −0.163 | 1.589 | 1.006 | −0.583 |
| | 16 | 0.05 | 0.6 | 2.035 | 0.186 | 0.49 | 0.365 | −0.125 | 1.376 | 1.348 | −0.028 |
| | 16 | 1.0 | 0.6 | 2.219 | 0.154 | 0.47 | 0.377 | −0.093 | 1.276 | 1.171 | −0.105 |
| | 30 | 0.05 | 0.1 | 3.932 | 0.425 | 0.423 | 0.47 | 0.047 | 1.345 | 1.489 | 0.144 |
| | 30 | 1.0 | 0.1 | 3.561 | 0.411 | 0.491 | 0.432 | −0.059 | 1.141 | 1.016 | −0.125 |
| | 30 | 0.05 | 0.6 | 3.839 | 0.513 | 0.321 | 0.458 | 0.137 | 1.676 | 1.602 | −0.074 |
| | 30 | 1.0 | 0.6 | 3.747 | 0.38 | 0.396 | 0.456 | 0.060 | 1.118 | 1.771 | 0.653 |
| | | | | | Cystatin Assay 10/22 Second Replicate | | | | | | |
| BL21 Star | 16 | 0.05 | 0.1 | 0.882 | 0.01 | 0.533 | 0.418 | −0.115 | 1.266 | 1.19 | −0.076 |
| | 16 | 1.0 | 0.1 | 1.021 | 0.01 | 0.553 | 0.435 | −0.118 | 1.328 | 1.209 | −0.119 |
| | 16 | 0.05 | 0.6 | 1.666 | 0.324 | 0.33 | 0.442 | 0.112 | 1.202 | 1.172 | −0.030 |
| | 16 | 1.0 | 0.6 | 1.85 | 0.273 | 0.344 | 0.438 | 0.094 | 1.1 | 1.188 | 0.088 |
| | 30 | 0.05 | 0.1 | 2.497 | 0.299 | 0.136 | 0.493 | 0.357 | 1.092 | 1.511 | 0.419 |
| | 30 | 1.0 | 0.1 | 2.728 | 0.359 | 0.263 | 0.482 | 0.219 | 1.251 | 1.224 | −0.027 |
| | 30 | 0.05 | 0.6 | 3.376 | 0.365 | 0.2 | 0.518 | 0.318 | 1.117 | 1.177 | 0.060 |
| | 30 | 1.0 | 0.6 | 2.589 | 0.336 | 0.15 | 0.453 | 0.303 | 0.962 | 1.2 | 0.238 |

TABLE 57

Cystatin Activity Results
GST fusion tagged protein, first and second replicates
ZmCys13 (SEQ ID NO: 24)

| Cell Type | Temp ° C. | IPTG (mM) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 2.82 | 0 | 0.701 | 0.5 | −0.201 | 1.364 | 1.272 | −0.092 |
| | 16 | 1.0 | 0.1 | 1.62 | −0.011 | 0.66 | 0.512 | −0.148 | 1.244 | 1.55 | 0.306 |
| | 16 | 0.05 | 0.6 | 3.191 | 0.071 | 0.672 | 0.478 | −0.194 | 1.303 | 1.18 | −0.123 |
| | 16 | 1.0 | 0.6 | 3.005 | 0.047 | 0.654 | 0.489 | −0.165 | 1.286 | 1.261 | −0.025 |
| | 30 | 0.05 | 0.1 | 4.025 | 0.387 | 0.056 | 0.473 | 0.417 | 0.135 | 1.148 | 1.013 |
| | 30 | 1.0 | 0.1 | 2.82 | 0.257 | 0.055 | 0.486 | 0.431 | 0.158 | 1.344 | 1.186 |
| | 30 | 0.05 | 0.6 | 4.35 | 0.347 | 0.053 | 0.472 | 0.419 | 0.126 | 1.727 | 1.601 |
| | 30 | 1.0 | 0.6 | 2.45 | 0.291 | 0.051 | 0.432 | 0.381 | 0.133 | 0.99 | 0.857 |
| | | | | | | Cystatin Assay 10/22 Second Replicate | | | | | |
| BL21 Star | 16 | 0.05 | 0.1 | 1.527 | 0.011 | 0.473 | 0.36 | −0.113 | 1.096 | 1.082 | −0.014 |
| | 16 | 1.0 | 0.1 | 1.343 | 0.015 | 0.622 | 0.47 | −0.152 | 1.004 | 1.124 | 0.120 |
| | 16 | 0.05 | 0.6 | 2.219 | 0.089 | 0.478 | 0.365 | −0.113 | 1.07 | 1.225 | 0.155 |
| | 16 | 1.0 | 0.6 | 2.312 | 0.091 | 0.641 | 0.492 | −0.149 | 1.158 | 1.236 | 0.078 |
| | 30 | 0.05 | 0.1 | 3.283 | 0.357 | 0.053 | 0.371 | 0.318 | 0.132 | 0.989 | 0.857 |
| | 30 | 1.0 | 0.1 | 3.932 | 0.249 | 0.056 | 0.406 | 0.350 | 0.142 | 1.265 | 1.123 |
| | 30 | 0.05 | 0.6 | 2.82 | 0.349 | 0.05 | 0.397 | 0.347 | 0.113 | 1.207 | 1.094 |
| | 30 | 1.0 | 0.6 | 4.443 | 0.323 | 0.054 | 0.42 | 0.366 | 0.121 | 1.324 | 1.203 |

TABLE 58

Cystatin Activity Results
His fusion tagged protein, first and second replicates
ZmCys13 (SEQ ID NO: 24)

| Cell Type | Temp ° C. | IPTG (mM) | OD600 | Final OD | Bradford (ug/uL) | 1 hour 6000 ng | 60 ng | Δ | Overnight 6000 ng | 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.343 | 0.019 | 0.417 | 0.386 | −0.031 | 1.141 | 1.314 | 0.173 |
| | 16 | 1.0 | 0.1 | 1.804 | 0.022 | 0.429 | 0.396 | −0.033 | 1.205 | 1.318 | 0.113 |
| | 16 | 0.05 | 0.6 | 2.82 | 0.276 | 0.066 | 0.409 | 0.343 | 0.232 | 1.148 | 0.916 |
| | 16 | 1.0 | 0.6 | 3.005 | 0.231 | 0.068 | 0.4 | 0.332 | 0.239 | 1.155 | 0.916 |
| | 30 | 0.05 | 0.1 | 5.14 | 0.411 | 0.459 | 0.412 | −0.047 | 1.052 | 1.256 | 0.204 |
| | 30 | 1.0 | 0.1 | 3.561 | 0.376 | 0.463 | 0.44 | −0.023 | 1.205 | 1.383 | 0.178 |
| | 30 | 0.05 | 0.6 | 5.233 | 0.362 | 0.129 | 0.448 | 0.319 | 0.917 | 1.397 | 0.480 |
| | 30 | 1.0 | 0.6 | 3.422 | 0.358 | 0.132 | 0.433 | 0.301 | 0.895 | 1.308 | 0.413 |
| | | | | | | Cystatin Assay 10/22 Second Replicate | | | | | |
| BL21 Star | 16 | 0.05 | 0.1 | 1.666 | 0.004 | 0.504 | 0.448 | −0.056 | 1.094 | 1.401 | 0.307 |
| | 16 | 1.0 | 0.1 | 1.205 | −0.013 | 0.424 | 0.385 | −0.039 | 1.182 | 1.215 | 0.033 |
| | 16 | 0.05 | 0.6 | 2.543 | 0.291 | 0.064 | 0.475 | 0.411 | 0.241 | 1.301 | 1.060 |
| | 16 | 1.0 | 0.6 | 2.404 | 0.178 | 0.059 | 0.409 | 0.350 | 0.26 | 1.592 | 1.332 |
| | 30 | 0.05 | 0.1 | 3.376 | 0.368 | 0.446 | 0.45 | 0.004 | 1.052 | 1.036 | −0.016 |
| | 30 | 1.0 | 0.1 | 4.396 | 0.394 | 0.457 | 0.415 | −0.042 | 0.915 | 0.932 | 0.017 |
| | 30 | 0.05 | 0.6 | 4.164 | 0.364 | 0.174 | 0.474 | 0.300 | 0.8 | 1.355 | 0.555 |
| | 30 | 1.0 | 0.6 | 4.396 | 0.315 | 0.181 | 0.464 | 0.283 | 1.06 | 1.272 | 0.212 |

TABLE 59

Cystatin Activity Results
GST fusion tagged protein, first and second replicates
ZmCys14 (SEQ ID NO: 26)

| Cell Type | Temp °C. | IPTG (mM) | OD600 | Final OD | Bradford (ug/uL) | 1 hour 6000 ng | 1 hour 60 ng | Δ | Overnight 6000 ng | Overnight 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.113 | −0.018 | 0.604 | 0.477 | −0.127 | 1.298 | 1.255 | −0.043 |
| | 16 | 1.0 | 0.1 | 1.343 | −0.016 | 0.643 | 0.493 | −0.150 | 1.39 | 1.257 | −0.133 |
| | 16 | 0.05 | 0.6 | 2.45 | 0.056 | 0.476 | 0.456 | −0.020 | 1.185 | 1.314 | 0.129 |
| | 16 | 1.0 | 0.6 | 3.052 | 0.051 | 0.488 | 0.436 | −0.052 | 1.025 | 1.012 | −0.013 |
| | 30 | 0.05 | 0.1 | 3.654 | 0.245 | 0.082 | 0.459 | 0.377 | 0.836 | 1.257 | 0.421 |
| | 30 | 1.0 | 0.1 | 3.283 | 0.204 | 0.08 | 0.484 | 0.404 | 0.813 | 1.27 | 0.457 |
| | 30 | 0.05 | 0.6 | 5.326 | 0.264 | 0.062 | 0.436 | 0.374 | 0.592 | 1.122 | 0.530 |
| | 30 | 1.0 | 0.6 | 3.747 | 0.251 | 0.064 | 0.416 | 0.352 | 0.538 | 0.923 | 0.385 |
| | | | | | | Cystatin Assay 10/22 Second Replicate | | | | | |
| BL21 Star | 16 | 0.05 | 0.1 | 1.989 | 0.002 | 0.426 | 0.348 | −0.078 | 1.043 | 1.017 | −0.026 |
| | 16 | 1.0 | 0.1 | 1.113 | −0.002 | 0.587 | 0.46 | −0.127 | 1.215 | 1.019 | −0.196 |
| | 16 | 0.05 | 0.6 | 1.942 | 0.053 | 0.377 | 0.354 | −0.023 | 1.092 | 0.95 | −0.142 |
| | 16 | 1.0 | 0.6 | 2.913 | 0.022 | 0.526 | 0.488 | −0.038 | 0.943 | 1.159 | 0.216 |
| | 30 | 0.05 | 0.1 | 3.144 | 0.289 | 0.061 | 0.374 | 0.313 | 0.532 | 0.949 | 0.417 |
| | 30 | 1.0 | 0.1 | 3.329 | 0.221 | 0.07 | 0.414 | 0.344 | 0.647 | 1.23 | 0.583 |
| | 30 | 0.05 | 0.6 | 4.768 | 0.274 | 0.059 | 0.43 | 0.371 | 0.512 | 1.246 | 0.734 |
| | 30 | 1.0 | 0.6 | 2.959 | 0.221 | 0.085 | 0.455 | 0.370 | 0.716 | 1.224 | 0.508 |

TABLE 60

Cystatin Activity Results
His fusion tagged protein, first and second replicates
ZmCys14 (SEQ ID NO: 26)

| Cell Type | Temp °C. | IPTG (Mm) | OD600 | Final OD | Bradford (ug/uL) | 1 hour 6000 ng | 1 hour 60 ng | Δ | Overnight 6000 ng | Overnight 60 ng | Δ |
|---|---|---|---|---|---|---|---|---|---|---|---|
| | | | | | | Cystatin Assay 10/22 First Replicate | | | | | |
| BL21 Star | 16 | 0.05 | 0.1 | 1.251 | 0.032 | 0.372 | 0.408 | 0.036 | 1.206 | 1.292 | 0.086 |
| | 16 | 1.0 | 0.1 | 1.251 | 0.017 | 0.41 | 0.396 | −0.014 | 1.249 | 1.293 | 0.044 |
| | 16 | 0.05 | 0.6 | 2.497 | 0.265 | 0.13 | 0.539 | 0.409 | 0.764 | 1.31 | 0.546 |
| | 16 | 1.0 | 0.6 | 3.191 | 0.235 | 0.093 | 0.477 | 0.384 | 0.705 | 1.498 | 0.793 |
| | 30 | 0.05 | 0.1 | 3.515 | 0.481 | 0.065 | 0.453 | 0.388 | 0.602 | 1.365 | 0.763 |
| | 30 | 1.0 | 0.1 | 3.932 | 0.481 | 0.078 | 0.465 | 0.387 | 0.672 | 1.29 | 0.618 |
| | 30 | 0.05 | 0.6 | 5.047 | 0.394 | 0.069 | 0.454 | 0.385 | 0.504 | 1.465 | 0.961 |
| | 30 | 1.0 | 0.6 | 5.513 | 0.472 | 0.062 | 0.449 | 0.387 | 0.517 | 1.373 | 0.856 |
| | | | | | | Cystatin Assay 10/22 Second Replicate | | | | | |
| BL21 Star | 16 | 0.05 | 0.1 | 1.021 | 0.022 | 0.518 | 0.541 | 0.023 | 1.22 | 1.407 | 0.187 |
| | 16 | 1.0 | 0.1 | 1.021 | 0.02 | 0.489 | 0.589 | 0.100 | 1.147 | 1.308 | 0.161 |
| | 16 | 0.05 | 0.6 | 2.035 | 0.306 | 0.092 | 0.499 | 0.407 | 0.785 | 1.188 | 0.403 |
| | 16 | 1.0 | 0.6 | 2.081 | 0.273 | 0.081 | 0.475 | 0.394 | 0.636 | 1.037 | 0.401 |
| | 30 | 0.05 | 0.1 | 3.607 | 0.324 | 0.17 | 0.489 | 0.319 | 0.881 | 1.484 | 0.603 |
| | 30 | 1.0 | 0.1 | 3.561 | 0.359 | 0.181 | 0.496 | 0.315 | 0.941 | 1.592 | 0.651 |
| | 30 | 0.05 | 0.6 | 3.515 | 0.365 | 0.065 | 0.462 | 0.397 | 0.566 | 1.169 | 0.603 |
| | 30 | 1.0 | 0.6 | 3.237 | 0.355 | 0.076 | 0.485 | 0.409 | 0.64 | 1.223 | 0.583 |

EXAMPLE 9

Microinjection Assay for Anti-Nematodal Activity of Cystatins

Two of the cystatin genes of the present invention, ZmCys4 (SEQ ID NO: 5) and GmCys2 (SEQ ID NO: 29), were expressed in, and their encoded proteins purified from *E. coli* as set forth in Example 7. A control expression vector was also prepared which contained no cystatin gene. The purified cystatins and control were injected into sugar beet nematode-induced syncytia in *Arabidopsis* roots one week after inoculation, as per the methods outlined in Bockenhoff and Grundler ((1994), Parasitology. 109: 249–255), hereby incorporated by reference. Fluorescent dye was used to monitor the growth of the nematodes following injection, as per Bockenhoff and Grundler (1994). The anti-nematodal activity of the cystatins was measured by comparing the nematode growth and development 10 days following injection, and comparing it with the control. Results of the experiment are presented in Table 61, below.

TABLE 61

Effect of Two Cystatins on Nematode Development

| Protein Injected | Lethality (%) |
|---|---|
| Control | 30 |
| Zm-Cys4 (SEQ ID NO: 6) | 50 |
| Gm-Cys2 (SEQ ID NO: 30) | 58 |

These results show that both Zm-Cys4 and Gm-Cys2 had significant inhibitory effects on the growth and development of sugar beet nematode juveniles in *Arabidopsis*. Sugar beet nematode is a genetically close relative of soybean cyst nematode. It has been reported that there is a high cysteine proteinase activity in SCN intestines (Lilley, C. J. et al. (1996) 113: 415–424). These data indicate that both Zm-Cys4 and Gm-Cys2 confer resistance to nematodes by inhibiting SCN growth and development in roots.

EXAMPLE 10

Use of *C. elegans* as a Model to Analyze Cystatin Anti-Nematodal Activity

*C. elegans* populations are cultured on NGM agar carrying a lawn of *E. coli* OP50 cells as described by Wood ((1988) The nematode *C. elegans*, Cold Spring Harbor, N.Y. Cold Spring Harbor Laboratory Press). After populations are maintained for five days, agar plugs are removed to fresh plates. Cystatins are added to the medium to a final concentration of 2.5 mg/L just prior to pouring. In order to study the effect of the cystatins on egg laying, hermaphrodite nematodes are taken from their normal growth media and transferred individually to fresh plates containing the cystatin(s) to be used for testing. Egg laying is carefully monitored.

Half of the eggs laid on each plate are removed to fresh plates containing media not supplemented with the cystatin(s) being tested. Development of the hatched larvae is monitored.

Alternately, groups of larvae hatched on normal media can be transferred to plates containing the cystatin(s) to be tested at time points corresponding to larval stages L1, L2, L3 and L4. The larvae for each stage should be removed, respectively, 6, 12, 24, and 30 hours post hatching. Development of the various larval stages on the supplemented media is monitored.

All publications and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

TABLE 62

Multiple Alignment of All Cystatin Sequences

```
Plurality: 2.00  Threshold: 4  AveWeight 1.00
AveMatch 2.78  AvMisMatch -2.25
Symbol comparison table: blosum62.cmp CompCheck: 1102

GapWeight: 8
GapLengthWeight: 2

Pileup  MSF: 314  Type: P  May 13, 2003  15:11  Check: 6646 . . .

//

1                                                  50
    gm-cys6   ~~~~~~~~~~ ~~~~~~~~~~ ~~~~~~~~~~ ~~~~~~~~~~ ~~~~~~~~~~     (SEQ ID NO:38)

gm-cys8   ~~~~~~~~~~ ~~~~~~~~~~ ~~~~~~~~~~ ~~~~~~~~~~ ~~~~~~~~~~     (SEQ ID NO:42)

ta-cys8   ~~~~~~~~~~ ~~~~~~~~~~ ~~~~~~~~~~ ~~~~~~~MAR  VIGASGACAL    (SEQ ID NO:68)

ta-cys9   ~~~~~~~~~~ ~~~~~~~~~~ ~~~~~~~~~~ ~~~~~~~MAR  LVGAAGACAL    (SEQ ID NO:70)

ZmCys14   ~~~~~~~~~~ ~~~~~~~~~~ ~~~~~~~~~~ ~~~~~~~MAR  ...ALGACVL    (SEQ ID NO:26)

os-cys5   ~~~~~~~~~~ ~~~~~~~~~~ ~~~~~~~~~~ ~~~~~~~~~~ ~~~~~~~~~M     (SEQ ID NO:54)

ZmCys3    ~~~~~~~~~~ ~~~~~~~~~~ ~~~~~~~~~~ ~~~~~~~~~~ ~~~~~~~MRK     (SEQ ID NO:4)

ZmCys4    ~~~~~~~~~~ ~~~~~~~~~~ ~~~~~~~~~~ ~~~~~~~~~~ ~~~~~~~MRK     (SEQ ID NO:6)

ta-cys13  ~~~~~~~~~~ ~~~~~~~~~~ ~~~~~~~~~~ ~~~~~~~~~~ ~~~~~~~~~~     (SEQ ID NO:76)

ZmCys1    ~~~~~~~~~~ ~~~~~~~~~~ ~~~~~~~~~~ ~~~~~~~~~~ ~~~~~~~MRK     (SEQ ID NO:2)

os-cys1   ~~~~~~~~~~ ~~~~~~~~~~ ~~~~~~~~~~ ~~~~~~~~~~ ~~~~~~~~~~     (SEQ ID NO:46)

ta-cys1   ~~~~~~~~~~ ~~~~~~~~~~ ~~~~~~~~~~ ~~~~~~~~~~ ~MEMWKYRVV     (SEQ ID NO:58)
```

TABLE 62-continued

Multiple Alignment of All Cystatin Sequences

```
ta-cys2   ~~~~~~~~~~  ~~~~~~~~~~  ~~~~~~~~~~  ~~~~~~~~~~  ~~~~~~~~~~   (SEQ ID NO:60)

ta-cys4   ~~~~~~~~~~  ~~~~~~~~~~  ~~~~~~~~~~  ~~~~~~~~~~  ~~~~~~~~~~   (SEQ ID NO:64)

ta-cys6   ~~~~~~~~~~  ~~~~~~~~~~  ~~~~~~~~~~  ~~~~~~~~~~  ~~~~~~~~~~   (SEQ ID NO:66)

os-cys3   ~~~~~~~~~~  ~~~~~~~~~~  ~~~~~~~~~~  ~~~~~~~~~~  ~~~~~~~~~~   (SEQ ID NO:50)

ZmCys8    ~~~~~~~~~~  ~~~~~~~~~~  ~~~~~~~~~~  ~~~~~~~~~~  ~~~~~~~~~~   (SEQ ID NO:14)

ZmCys12   ~~~~~~~~~~  ~~~~~~~~~~  ~~~~~~~~~~  ~~~~~~~~~~  MRVAAT...R   (SEQ ID NO:22)

ZmCys5    ~~~~~~~~~~  ~~~~~~~~~~  ~~~~~~~~~~  ~~~~~~~~~~  MRVAAT...R   (SEQ ID NO:8)

os-cys2   ~~~~~~~~~~  ~~~~~~~~~~  ~~~~~~~~~~  ~~~~~~~~~~  MRVAATTRPA   (SEQ ID NO:48)

ta-cys10  ~~~~~~~~~~  ~~~~~~~~~~  ~~~~~~~~~~  ~~~~~~~~~~  MRVAATRPAS   (SEQ ID NO:72)

gm-cys2   ~~~~~~~~~~  ~~~~~~~~~~  ~~~~~~~~~~  ~~~~~~~~~~  ~~~~~~~~~~   (SEQ ID NO:30)

gm-cys7   ~~~~~~~~~~  ~~~~~~~~~~  ~~~~~~~~~~  ~~~~~~~~~~  ~~~~~~~~~~   (SEQ ID NO:40)

gm-cys1   ~~~~~~~~~~  ~~~~~~~~~~  ~~~~~~~~~~  ~~~~~~~~~~  MRALTSSSST   (SEQ ID NO:28)

gm-cys3   ~~~~~~~~~~  ~~~~~~~~~~  ~~~~~~~~~~  ~~~~~~~~~~  ~~~~~~~~~~   (SEQ ID NO:32)

gm-cys4   ~~~~~~~~~~  ~~~~~~~~~~  ~~~~~~~~~~  ~~~~~~~~~~  ~~~~~~~~~~   (SEQ ID NO:34)

ZmCys10   ~~~~~~~~~~  ~~~~~~~~~~  ~~~~~~~~~~  ~~~~~~~~~~  ~~~~~~~~~~   (SEQ ID NO:18)

ZmCys6    ~~~~~~~~~~  ~~~~~~~~~~  ~~~~~~~~~~  ~~~~~~~~~~  ~~~~~~~~~~   (SEQ ID NO:10)

os-cys4   ~~~~~~~~~~  ~~~~~~~~~~  ~~~~~~~~~~  ~~~~~~~~~M  LRRRGFCCCS   (SEQ ID NO:52)

ta-cys11  ~~~~~~~~~~  ~~~~~~~~~~  ~~~~~~~~~~  ~~~~~~~~~~  ~~MVRRCGCS   (SEQ ID NO:74)

gm-cys5   ~~~~~~~~~~  ~~~~~~~~~~  ~~~~~~~~~~  ~~~~~~~~~~  ~~~~~~~~~~   (SEQ ID NO:36)

gm-cys9   ~~~~~~~~~~  ~~~~~~~~~~  ~~~~~~~~~~  ~~~~~~~~~~  ~~~~~~~~~~   (SEQ ID NO:44)

ZmCys7    ~~~~~~~~~~  ~~~~~~~~~~  ~~~~~~~~~~  ~~~~~~~~~~  ~~~~~~~~~~   (SEQ ID NO:12)

os-cys6   ~~~~~~~~~~  ~~~~~~~~~~  ~~~~~~~~~~  ~~~~~~~~~~  ~~~~~~~~~~   (SEQ ID NO:56)

ZmCys9    ~~~~~~~~~~  ~~~~~~~~~~  ~~~~~~~~~~  ~~~~~~~~~~  ~~~~~~~~~~   (SEQ ID NO:16)

ZmCys13   ~~~~~~~~~~  ~~~~~~~~~~  ~~~~~~~~~~  ~~~~~~~~~~  ~~~~~~~~~M   (SEQ ID NO:24)

ta-cys3   ~~~~~~~~~~  ~~~~~~~~~~  ~~~~~~~~~~  ~~~~~~~~~~  ~~~~~~~~~M   (SEQ ID NO:62)

ZmCys11   MAFLSTNALM  SVPITAAAAP  RHRRSLVVVR  AAAVKSNEHL  QEEQASVADG   (SEQ ID NO:20)

51                                          100
gm-cys6   ~~~~~~~~~~  ~~~~~~~~~~  ~~~~~~~~~~  ~~~~~~MVGG  KTEVP.DVRT gm-cys8   ~~~~~~~~~~  ~~~~MAVALT  ILVTLLSVLS  SASCARMVGG  KTEIP.EVRK ta-cys8   LVVLLVACA.  ASAARTE...  .PGAA.RQLW  ED..GRKVGG  RTEVR.DVES ta-cys9   LVILLMACA.  ASAARSE...  .PGAA.RQLW  DD..GRKVGG  RTEVT.DVEG ZmCys14   LAVLLGALAP  AAAARAHDDQ  GSGAGIRQPS  GEYRGRKVGA  RTEVR.DVEG os-cys5   ATSPMLFLVS  LLLVLVAAAT  GDEASPSNAA  APAAPVLVGG  RTEIR.DVGS ZmCys3    HRIVSLVAAL  LILLAL.AVS  STRNAQEDSM  ADNTGTLAGG  IKDVP.GNEN ZmCys4    HRIVSLVAAL  LILLAL.AVS  STRNAQEDSM  ADNTGTLAGG  IKDVP.GNEN ta-cys13  ~~~~SLVAAL  LILLAL.AVS  STRNAQEDSM  ADNTGTLAGG  IKDVP.GNEN ZmCys1    HRIVSLVAAL  LVLLALAAVS  STRSAQKESV  ADNAGMLAGG  IKDVP.ANEN os-cys1   ~~~~~~~~~~  ~~~~~~~~~~  ~~~~~~~~~M  SSDGGPVLGG  VEPV..GNEN ta-cys1   GSVAALLLLL  AIVVPFTQTQ  TQSARDKAAM  AEDAGPLVGG  ISDSPMGQEN
```

TABLE 62-continued

Multiple Alignment of All Cystatin Sequences

```
ta-cys2    ~~~~~~~~LL  AIVVPFTQTR  TQSARDKAAM  AEDAGPLVGG  IKDSPMGQEN ta-cys4    ~~~~~~~~~~  ~~~~~~~~~~  ~MAEAAQGGG  LRGRGALLGG  VQDAPAGREN ta-cys6    ~~~~~~~~~~  ~~~~~~~~~~  ~MAEAAQGGG  LRGRGVLLGG  VQDAPAGREN os-cys3    ~~~~~~~~~~  ~~~~~~~~~~  ~MAEEAQ...  .QPRGVKVGG  IHDAPAGREN ZmCys8     ~~~~~~~~~~  ~~~~~~~~~~  ~~~~MAEVHN  ERPVG.MVGD  VRDAPVGREN ZmCys12    AAAAAHPPSA  FLLLLLLLGC  ASL.AIGGA.  .AMAGHVLGG  VKENP.AAAN ZmCys5     AAAAAHPPSA  FLLLLLLLGC  ASL.AIGGA.  .AMAGHVLGG  VKENP.AAAN os-cys2    SSSAAAPLPL  FLLLAVAAAA  AALFLVGSAS  LAMAGHVLGG  AHDAP.SAAN ta-cys10   SAPVA..LLA  ALALLFLVGS  ASL.AIG...  .AMASHVLGG  KSENP.DAAN gm-cys2    ~~~~~~~~~~  ~~~~~~~~~~  ~~~~~~~~~~  ~~~~MAALGG  NRDVT.GSQN gm-cys7    ~~~~~~~~~~  ~~~~~~~~~~  ~~~~~~~~~~  ~~~~MAALGG  NRDVA.GSQN gm-cys1    FIPKRYSFFF  FLSILFALRS  SSGGCSEYHH  HHAPMATIGG  LRDSQ.GSQN gm-cys3    ~~~~~~~~~~  ~~~~~~~~~~  ~~~~~~~~~~  ~~~~MAALGG  FTDIT.GAQN gm-cys4    ~~~~~~~~~~  ~~~~~~~~~~  ~~~~~~~~~~  ~~~~~~~~~~  ~~~MP.TLGA ZmCys10    ~~~MMPRRAL  LFAAVLLAAS  A.AAVSGFHL  GGDESGLVRG  VL.AALRER.

ZmCys6     ~~MTMPRRAL  LFAAVLLAAS  A.AAVSGFHL  AGDESGLVRG  VL.TAVRERA os-cys4    GAPAAAAAAL  LLLAV..AAA  A.PRAAGFHL  GGDESVLVRG  ML.AAIR.RE ta-cys11   GAMLLA....  LSLAVLLAAS  AVPGAAGFHL  GGDESGLVRG  ML.AAVRER.

gm-cys5    ~~~~~~~~~~  ~~MRHHCL.L  LVSLVLVSYA  AR.SESALGG  WS..PIKDVN gm-cys9    ~~~~~~~~~~  ~~MKQKCLVV  LVFVVLLACA  VGWDEGIPGG  WN..PIKNIN ZmCys7     ~~~~~~~~MS  ARALLLTTAT  LLLLVAAAR.  ..AGQPLAGG  WS..PIRNVS os-cys6    ~~~MARIPLL  LALLLAVSAA  AAAQVGGNR.  ..GHGPLVGG  WS..PITDVG ZmCys9     ~~~MATHRHC  LPLLLLVAAA  LAAVPARAAL  GGGRGPLLGG  WN..PIPDVS ZmCys13    AMTMTLGSML  IAAAAVVGLC  SVAPAASARE  EPLQPQIVGG  WK..PIKNVN ta-cys3    RTSSFLLIIV  VAFLYAIGSP  AIGCGERMGN  QLWNTAIENG  WE..PIGNIN ZmCys11    ARGRRRAMVL  LAATAAVTGS  SVAICRSARA  AGV.TTLSGQ  YV..KIENVK
```

```
               101                                                    150
gm-cys6    NREVQELGRF  AVEEYNRGLK  Q.WKN....N  GSEQLNFSEV  VEAQQQVVSG gm-cys8    NRQVQELGRF  AVEEYNLGLK  L.LKNNNVDN  GREQLNFSAV  VEAQQQVVSG ta-cys8    DREVQELGRY  SVEEHNRRRE  EGCEGGGGVC  GR..LEFARV  VSAQRQVVSG ta-cys9    DREVQELGRY  SVEEHNRRRE  EGCEGGGGVC  GR..LEFARV  VSAQRQVVSG ZmCys14    DGEVQELGRF  SVAEYNRQLR  EG..GGGG..  GR..LEFGRV  VAAQRQVVSG os-cys5    NKAVQSLGRF  AVAEHNRRLR  HGGSGGPADP  VPVKLAFARV  VEAQKQVVSD ZmCys3     DLHLQELARF  AVDEHN...K  KA........  .NALLGFEKL  VKAKTQVVAG ZmCys4     DLHLQELARF  AVDEHN...K  KA........  .NALLGFEKL  VKAKTQVVAG ta-cys13   DLHLQELARF  AVDEHN...K  KA........  .NALLGFEKL  VKAKTQVVAG ZmCys1     DLQLQELARF  AVNEHN...Q  KA........  .NALLGFEKL  VKAKTQVVAG os-cys1    DLHLVDLARF  AVTEHN...K  KA........  .NSLLEFEKL  VSVKQQVVAG ta-cys1    DLDVIALARF  AVSEHN...N  KA........  .NALLEFENV  VKVKKQTVAG
```

TABLE 62-continued

Multiple Alignment of All Cystatin Sequences

```
ta-cys2   DLDVIALARF  AVSEHN...N  KA........  .NALLEFENV  VKLKKQTVAG ta-cys4   DLETIELARF  AVAEHN...T  KA........  .NALLEFERL  VKVRQQVVAG ta-cys6   DLATIELARF  AVAEHN...T  KA........  .NALLEFERL  VKVRQQVVAG os-cys3   DLTTVELARF  AVAEHN...S  KA........  .NAMLELERV  VKVRQQVVGG ZmCys8    DLEAIELARF  AVAEHN...S  KT........  .NAMLEFERL  VKVRHQVVAG ZmCys12   SAESDGLGRF  AVDEHN...R  RE........  .NALLEFVRV  VEAKEQVVAG ZmCys5    SAESDGLGRF  AVDEHN...R  RE........  .NALLEFVRV  VEAKEQVVAG os-cys2   SVETDALARF  AVDEHN...K  RE........  .NALLEFVRV  VEAKEQVVAG ta-cys10  SLETDGLARF  AVDEHN...K  RE........  .NALLEFVRV  VEAKEQTVAG gm-cys2   SVEIDALARF  AVEEHN...K  KQ........  .NALLEFEKV  VTAKQQVVSG gm-cys7   SLEIDGLARF  AVEEHN...K  KQ........  .NALLEFEKV  VSAKQQVVSG gm-cys1   SVQTEALARF  AVDEHN...K  KQ........  .NSLLEFSRV  VRTQEQVVAG gm-cys3   SIDIENLARF  AVDEHN...K  KE........  .NAVLEFVRV  ISAKKQVVSG gm-cys4   GGEIDHLARF  AVEEQN...K  RE........  .NANLEFVGV  IRAKQQVVEG ZmCys10   .AEAEDAARF  AVAHYN...K  NQ........  .GAALEFTRV  LKSKRQVVTG ZmCys6    EAEAEDAARF  AVAYHN...R  NQ........  .GAALEFTRV  LKSKRQVVTG os-cys4   QAEAEDAARF  AVAEYN...K  NQ........  .GAELEFARI  VKAKRQVVTG ta-cys11  .AXAXDAARF  XVAEHN...R  XQ........  .GSALEFTRV  VNAKXQVVAG gm-cys5   DSHVAEIANY  ALSEYD...K  RS........  .GAKLTLVKV  VKGETQVVSG gm-cys9   DPHVTEIANF  AVTEYD...K  QS........  .GEKLKLVKV  IKGDLQVVAG ZmCys7    DPHIQELGGW  AVTEHV...R  RA........  .NDGLRFGEV  TGGEEQVVSG os-cys6   DPHIQELGGW  AVERHA...S  LS........  .SDGLRFRRV  TSGEQQVVSG ZmCys9    DSHIQELGGW  ALGQA.KHQK  LA........  .ADGLRFRRV  VRGEQQVVSG ZmCys13   DPHVQEIGRW  AVSEHI...K  TA........  .NDGLGFGRV  VSGEEQIVAG ta-cys3   DQHIQELGRW  AVLEFGKHVN  CV........  ....LKFNKV  VSGRQQLVSG ZmCys11   DPYVQGVGEW  AVKEHN...R  QT........  .GESLQFAEV  VSGMEQVVAG 151                                            200
gm-cys6   MKYYLKISAT  HKG.......  .VHKMFTSVV  VVKPWLHS..  KQLLHFAPAA gm-cys8   MKYYLKISAT  HNG.......  .VHEMFNSVV  VVKPWLHS..  KQLLHFAPAS ta-cys8   IKYYLRVAAA  EENGAGSNVV  SDGRVFDAVV  VVKPWLQS..  RALVRFAPAD ta-cys9   IKYYLRVAAA  EEGGAGSNGV  TDGRVFDAVV  VVKPWLQS..  RALIRFAPAD ZmCys14   LKYYLRVVAV  EEGGAGNGG.  ..ERVFDAVV  VVKPWLDS..  RTLLTFAPAA os-cys5   VAYYLKVAAS  ARDPRGGAAA  GGDRVFDAVV  VVKAWLKS..  KELVSFTPAS ZmCys3    TMYYLTIEVK  D..GEVK...  ...KLYEAKV  WEKPWEN..F  KELQEFKPVE ZmCys4    TMYYLTIEVK  D..GEVK...  ...KLYEAKV  WEKPWEN..F  KELQEFKPVE ta-cys13  TMYYLTIEVK  D..GEVK...  ...KLYEAKV  WEKPWEN..F  KELQEFKPVE ZmCys1    TMYYLTIEVK  D..GEVN...  ...KLYEAKV  WEKPWEN..F  KQLQEFKPVE os-cys1   TLYYFTIEVK  E..GDAK...  ...KLYEAKV  WEKPWMD..F  KELQEFKPVD ta-cys1   TMHYITIRVT  E..GGAK...  ...KLYEAKV  WEKPWEN..F  KKLEEFKLVE
```

TABLE 62-continued

Multiple Alignment of All Cystatin Sequences

| | | | | |
|---|---|---|---|---|
| ta-cys2 | TMHYITIRVT | E..GGAK... | ...KLYEAKV | WEKPWEN..F | KQLQEFKPVE |
| ta-cys4 | CMHYFTIEVK | E.GGA.K... | ...KLYEAKV | WEKAWEN..F | KQLQDFKPAA |
| ta-cys6 | CMHYFTIEVK | E.GGA.K... | ...KLYEAKV | WEKAWEN..F | KQLQDFKPAA |
| os-cys3 | FMHYLTVEVK | EPGGA.N... | ...KLYEAKV | WERAWEN..F | KQLQDFKPLD |
| ZmCys8 | TLHHFTVEVK | EAGGGEK... | ...KLYEAKV | WEKAWEN..F | KQLQSFELVG |
| ZmCys12 | TLHHLTLEAV | E..AGRK... | ...KLYEAKV | WVKPWLD..F | KELQEFSHKG |
| ZmCys5 | TLHHLTLEAV | E..AGRK... | ...KLYEAKV | WVKPWLD..F | KELQEFSHKG |
| os-cys2 | TLHHLTLEAL | E..AGRK... | ...KVYEAKV | WVKPWLD..F | KELQEFRNTG |
| ta-cys10 | TVHHLTLEAL | E..AGRK... | ...KLYEAKV | WVKPWLD..F | KELQEFRHTG |
| gm-cys2 | TLYTITLEAK | D..GGQK... | ...KVYEAKV | WEKSWLN..F | KEVQEFKLVG |
| gm-cys7 | TLYTITLEAK | D..GGQK... | ...KVYEAKV | WEKAWLN..F | KEVQEFKLVG |
| gm-cys1 | TLHHLTLEAI | E..AGEK... | ...KLYEAKV | WVKPWLN..F | KELQEFKPAG |
| gm-cys3 | TLYYITLEAN | D..GVTK... | ...KVYETKV | LEKPWLN..I | KEVQEFKPIT |
| gm-cys4 | FIYYITLEAK | D..GETK... | ...NVYETKV | WVRSWLN..S | KEVLEFKPIS |
| ZmCys10 | TLHDLILEAA | D..AGKK... | ...SVYRAKV | WVKSWED..F | KSVVEFRLVG |
| ZmCys6 | TLHDLILEAA | D..AGKK... | ...SLYRAKV | WVKPWED..F | KSVVEFRLAG |
| os-cys4 | TLHDLMLEVV | D..SGKK... | ...SLYSAKV | WVKPWLD..F | KAVVEFRHVG |
| ta-cys11 | TLHDLMVEVV | D..SGXK... | ....ICTTQS | LGEAWQN..F | XAVVEFRHAG |
| gm-cys5 | TNYRLVLKAK | D.GSATA... | ...S.YEAIV | WEKPWL..HF | MNLTSFKPLH |
| gm-cys9 | LNYRLSLTAS | D.SN...... | ...N.YQAIV | YEKAWAREHY | RNLTSFTPLH |
| ZmCys7 | MNYKLVLDAT | DADGKVA... | ...A.YGAFV | YEQSWTNT.. | RELVSFAPAS |
| os-cys6 | MNYRLVVSAS | DPAGATA... | ...S.YVAVV | YEQSWTNT.. | RQLTSFKPAA |
| ZmCys9 | MNYRLYVDAA | DPAGRTV... | ...P.YVAVV | YEQVWTAP.. | ...ASSPPST |
| ZmCys13 | KNYRLRIQAT | KVGGQKA... | ...M.YRAVV | YEQL.TNT.. | RQLLSFDPAN |
| ta-cys3 | MNYELIIEAS | DIGGKED... | ...K.YKAEV | YEQTWTHK.. | RQLLSFAKVK |
| ZmCys11 | TNYKLNLATK | DP...TS... | ...S.YQAVV | FDPLPNSSKN | RQLMSFKSI~ |

| | 201 | | | | 250 |
|---|---|---|---|---|---|
| gm-cys6 | PSSKDF~~~~ | ~~~~~~~~~ | ~~~~~~~~~ | ~~~~~~~~~ | ~~~~~~~~~ |
| gm-cys8 | SSTTTTNNNM | HPIVRKDN~~ | ~~~~~~~~~ | ~~~~~~~~~ | ~~~~~~~~~ |
| ta-cys8 | AK~~~~~~~ | ~~~~~~~~~ | ~~~~~~~~~ | ~~~~~~~~~ | ~~~~~~~~~ |
| ta-cys9 | AK~~~~~~~ | ~~~~~~~~~ | ~~~~~~~~~ | ~~~~~~~~~ | ~~~~~~~~~ |
| ZmCys14 | AK~~~~~~~ | ~~~~~~~~~ | ~~~~~~~~~ | ~~~~~~~~~ | ~~~~~~~~~ |
| os-cys5 | STK~~~~~~ | ~~~~~~~~~ | ~~~~~~~~~ | ~~~~~~~~~ | ~~~~~~~~~ |
| ZmCys3 | EGASA~~~~~ | ~~~~~~~~~ | ~~~~~~~~~ | ~~~~~~~~~ | ~~~~~~~~~ |
| ZmCys4 | EGASA~~~~~ | ~~~~~~~~~ | ~~~~~~~~~ | ~~~~~~~~~ | ~~~~~~~~~ |
| ta-cys13 | EGASA~~~~~ | ~~~~~~~~~ | ~~~~~~~~~ | ~~~~~~~~~ | ~~~~~~~~~ |
| ZmCys1 | EGASA~~~~~ | ~~~~~~~~~ | ~~~~~~~~~ | ~~~~~~~~~ | ~~~~~~~~~ |
| os-cys1 | ASANA~~~~~ | ~~~~~~~~~ | ~~~~~~~~~ | ~~~~~~~~~ | ~~~~~~~~~ |
| ta-cys1 | DVPSA~~~~~ | ~~~~~~~~~ | ~~~~~~~~~ | ~~~~~~~~~ | ~~~~~~~~~ |

TABLE 62-continued

Multiple Alignment of All Cystatin Sequences

| | | | | | |
|---|---|---|---|---|---|
| ta-cys2 | DAAIA~~~~~ | ~~~~~~~~~~ | ~~~~~~~~~~ | ~~~~~~~~~~ | ~~~~~~~~~~ |
| ta-cys4 | ~~~~~~~~~~ | ~~~~~~~~~~ | ~~~~~~~~~~ | ~~~~~~~~~~ | ~~~~~~~~~~ |
| ta-cys6 | ~~~~~~~~~~ | ~~~~~~~~~~ | ~~~~~~~~~~ | ~~~~~~~~~~ | ~~~~~~~~~~ |
| os-cys3 | DATA~~~~~~ | ~~~~~~~~~~ | ~~~~~~~~~~ | ~~~~~~~~~~ | ~~~~~~~~~~ |
| ZmCys8 | DAAVA~~~~~ | ~~~~~~~~~~ | ~~~~~~~~~~ | ~~~~~~~~~~ | ~~~~~~~~~~ |
| ZmCys12 | DATAFTNADL | GAKQGGHEPG | WREVPVEDPV | VKDAAHHAVK | SIQERSNSLF |
| ZmCys5 | DATAFTNADL | GAKQGGHEPG | WREVPVEDPV | VKDAAHHAVK | SIQERSNSLF |
| os-cys2 | DATTFTNADL | GAKKGGHEPG | WRDVPVHDPV | VKDAADHAVK | SIQQRSNSLF |
| ta-cys10 | D~~~~~~~~~ | ~~~~~~~~~~ | ~~~~~~~~~~ | ~~~~~~~~~~ | ~~~~~~~~~~ |
| gm-cys2 | DAPA~~~~~~ | ~~~~~~~~~~ | ~~~~~~~~~~ | ~~~~~~~~~~ | ~~~~~~~~~~ |
| gm-cys7 | DAPA~~~~~~ | ~~~~~~~~~~ | ~~~~~~~~~~ | ~~~~~~~~~~ | ~~~~~~~~~~ |
| gm-cys1 | DVPSFTSADL | GVKKDGHQPG | WQSVPTHDPQ | VQDAANHAIK | TIQQRSNSLV |
| gm-cys3 | VAVNPLSVTV | ~~~~~~~~~~ | ~~~~~~~~~~ | ~~~~~~~~~~ | ~~~~~~~~~~ |
| gm-cys4 | INPLSVSV~~ | ~~~~~~~~~~ | ~~~~~~~~~~ | ~~~~~~~~~~ | ~~~~~~~~~~ |
| ZmCys10 | DSESEPEPSV | ASDVSSGQAI | AKLSLEADIV | QEEARLHTIE | NDGLSGDFTS |
| ZmCys6 | DSESEPEPSV | ASDEGSGQGV | AKLSLEADII | HEEAHLHTIE | NDGLSSDFAS |
| os-cys4 | DSQS..QSAT | AADDNAGQDT | AD.....PTV | ASRNDLHNTE | NNKVSVVLST |
| ta-cys11 | TXSXLPLLYG | RXGKLPQASL | KXHAXRXQHX | NTXSVTHLSR | KHXVWCXYIX |
| gm-cys5 | ~~~~~~~~~~ | ~~~~~~~~~~ | ~~~~~~~~~~ | ~~~~~~~~~~ | ~~~~~~~~~~ |
| gm-cys9 | A~~~~~~~~~ | ~~~~~~~~~~ | ~~~~~~~~~~ | ~~~~~~~~~~ | ~~~~~~~~~~ |
| ZmCys7 | ~~~~~~~~~~ | ~~~~~~~~~~ | ~~~~~~~~~~ | ~~~~~~~~~~ | ~~~~~~~~~~ |
| os-cys6 | AH~~~~~~~~ | ~~~~~~~~~~ | ~~~~~~~~~~ | ~~~~~~~~~~ | ~~~~~~~~~~ |
| ZmCys9 | RCPAPTETIR | TRVGRSDVLR | QLRVELILLL | FLLL~~~~~~ | ~~~~~~~~~~ |
| ZmCys13 | ~~~~~~~~~~ | ~~~~~~~~~~ | ~~~~~~~~~~ | ~~~~~~~~~~ | ~~~~~~~~~~ |
| ta-cys3 | ~~~~~~~~~~ | ~~~~~~~~~~ | ~~~~~~~~~~ | ~~~~~~~~~~ | ~~~~~~~~~~ |
| ZmCys11 | ~~~~~~~~~~ | ~~~~~~~~~~ | ~~~~~~~~~~ | ~~~~~~~~~~ | ~~~~~~~~~~ |
| | 251 | | | | 300 |
| gm-cys6 | ~~~~~~~~~~ | ~~~~~~~~~~ | ~~~~~~~~~~ | ~~~~~~~~~~ | ~~~~~~~~~~ |
| gm-cys8 | ~~~~~~~~~~ | ~~~~~~~~~~ | ~~~~~~~~~~ | ~~~~~~~~~~ | ~~~~~~~~~~ |
| ta-cys8 | ~~~~~~~~~~ | ~~~~~~~~~~ | ~~~~~~~~~~ | ~~~~~~~~~~ | ~~~~~~~~~~ |
| ta-cys9 | ~~~~~~~~~~ | ~~~~~~~~~~ | ~~~~~~~~~~ | ~~~~~~~~~~ | ~~~~~~~~~~ |
| ZmCys14 | ~~~~~~~~~~ | ~~~~~~~~~~ | ~~~~~~~~~~ | ~~~~~~~~~~ | ~~~~~~~~~~ |
| os-cys5 | ~~~~~~~~~~ | ~~~~~~~~~~ | ~~~~~~~~~~ | ~~~~~~~~~~ | ~~~~~~~~~~ |
| ZmCys3 | ~~~~~~~~~~ | ~~~~~~~~~~ | ~~~~~~~~~~ | ~~~~~~~~~~ | ~~~~~~~~~~ |
| ZmCys4 | ~~~~~~~~~~ | ~~~~~~~~~~ | ~~~~~~~~~~ | ~~~~~~~~~~ | ~~~~~~~~~~ |
| ta-cys13 | ~~~~~~~~~~ | ~~~~~~~~~~ | ~~~~~~~~~~ | ~~~~~~~~~~ | ~~~~~~~~~~ |
| ZmCys1 | ~~~~~~~~~~ | ~~~~~~~~~~ | ~~~~~~~~~~ | ~~~~~~~~~~ | ~~~~~~~~~~ |
| os-cys1 | ~~~~~~~~~~ | ~~~~~~~~~~ | ~~~~~~~~~~ | ~~~~~~~~~~ | ~~~~~~~~~~ |
| ta-cys1 | ~~~~~~~~~~ | ~~~~~~~~~~ | ~~~~~~~~~~ | ~~~~~~~~~~ | ~~~~~~~~~~ |

TABLE 62-continued

Multiple Alignment of All Cystatin Sequences

```
ta-cys2   ~~~~~~~~~~  ~~~~~~~~~~  ~~~~~~~~~~  ~~~~~~~~~~  ~~~~~~~~~~
ta-cys4   ~~~~~~~~~~  ~~~~~~~~~~  ~~~~~~~~~~  ~~~~~~~~~~  ~~~~~~~~~~
ta-cys6   ~~~~~~~~~~  ~~~~~~~~~~  ~~~~~~~~~~  ~~~~~~~~~~  ~~~~~~~~~~
os-cys3   ~~~~~~~~~~  ~~~~~~~~~~  ~~~~~~~~~~  ~~~~~~~~~~  ~~~~~~~~~~
ZmCys8    ~~~~~~~~~~  ~~~~~~~~~~  ~~~~~~~~~~  ~~~~~~~~~~  ~~~~~~~~~~
ZmCys12   PYELLEILRA  HAQVVEDFAK  FDILMKLKRG  SKEEKIKAEV  HKSLEGAFVL
ZmCys5    PYELLEILRA  HAQVVEDFAK  FDILMKLKRG  SKEEKIKAEV  HKSLEGAFVL
os-cys2   PYELLEIVRA  KAEVVEDFAK  FDILMKLKRG  NKEEKFKAEV  HKNLEGAFVL
ta-cys10  ~~~~~~~~~~  ~~~~~~~~~~  ~~~~~~~~~~  ~~~~~~~~~~  ~~~~~~~~~~
gm-cys2   ~~~~~~~~~~  ~~~~~~~~~~  ~~~~~~~~~~  ~~~~~~~~~~  ~~~~~~~~~~
gm-cys7   ~~~~~~~~~~  ~~~~~~~~~~  ~~~~~~~~~~  ~~~~~~~~~~  ~~~~~~~~~~
gm-cys1   PYELHEVADA  KAEVIDDFAK  FNLLLKVKRG  QKEEKFKVEV  HKNNQGGFHL
gm-cys3   ~~~~~~~~~~  ~~~~~~~~~~  ~~~~~~~~~~  ~~~~~~~~~~  ~~~~~~~~~~
gm-cys4   ~~~~~~~~~~  ~~~~~~~~~~  ~~~~~~~~~~  ~~~~~~~~~~  ~~~~~~~~~~
ZmCys10   SSS~~~~~~~  ~~~~~~~~~~  ~~~~~~~~~~  ~~~~~~~~~~  ~~~~~~~~~~
ZmCys6    SA~~~~~~~~  ~~~~~~~~~~  ~~~~~~~~~~  ~~~~~~~~~~  ~~~~~~~~~~
os-cys4   FSQTYSV~~~  ~~~~~~~~~~  ~~~~~~~~~~  ~~~~~~~~~~  ~~~~~~~~~~
ta-cys11  LQLXXE~~~~  ~~~~~~~~~~  ~~~~~~~~~~  ~~~~~~~~~~  ~~~~~~~~~~
gm-cys5   ~~~~~~~~~~  ~~~~~~~~~~  ~~~~~~~~~~  ~~~~~~~~~~  ~~~~~~~~~~
gm-cys9   ~~~~~~~~~~  ~~~~~~~~~~  ~~~~~~~~~~  ~~~~~~~~~~  ~~~~~~~~~~
ZmCys7    ~~~~~~~~~~  ~~~~~~~~~~  ~~~~~~~~~~  ~~~~~~~~~~  ~~~~~~~~~~
os-cys6   ~~~~~~~~~~  ~~~~~~~~~~  ~~~~~~~~~~  ~~~~~~~~~~  ~~~~~~~~~~
ZmCys9    ~~~~~~~~~~  ~~~~~~~~~~  ~~~~~~~~~~  ~~~~~~~~~~  ~~~~~~~~~~
ZmCys13   ~~~~~~~~~~  ~~~~~~~~~~  ~~~~~~~~~~  ~~~~~~~~~~  ~~~~~~~~~~
ta-cys3   ~~~~~~~~~~  ~~~~~~~~~~  ~~~~~~~~~~  ~~~~~~~~~~  ~~~~~~~~~~
ZmCys11   ~~~~~~~~~~  ~~~~~~~~~~  ~~~~~~~~~~  ~~~~~~~~~~  ~~~~~~~~~~

301         314
gm-cys6   ~~~~~~~~~~  ~~~~
gm-cys8   ~~~~~~~~~~  ~~~~
ta-cys8   ~~~~~~~~~~  ~~~~
ta-cys9   ~~~~~~~~~~  ~~~~
ZmCys14   ~~~~~~~~~~  ~~~~
os-cys5   ~~~~~~~~~~  ~~~~
ZmCys3    ~~~~~~~~~~  ~~~~
ZmCys4    ~~~~~~~~~~  ~~~~
ta-cys13  ~~~~~~~~~~  ~~~~
ZmCys1    ~~~~~~~~~~  ~~~~
os-cys1   ~~~~~~~~~~  ~~~~
ta-cys1   ~~~~~~~~~~  ~~~~
```

TABLE 62-continued

Multiple Alignment of All Cystatin Sequences

| | | |
|---|---|---|
| ta-cys2 | ~~~~~~~~~~ | ~~~~ |
| ta-cys4 | ~~~~~~~~~~ | ~~~~ |
| ta-cys6 | ~~~~~~~~~~ | ~~~~ |
| os-cys3 | ~~~~~~~~~~ | ~~~~ |
| ZmCys8 | ~~~~~~~~~~ | ~~~~ |
| ZmCys12 | NQHQPAEHDE | SSSQ |
| ZmCys5 | NQHQPAEHDE | SSSQ |
| os-cys2 | NQMQ.QEHDE | SSSQ |
| ta-cys10 | ~~~~~~~~~~ | ~~~~ |
| gm-cys2 | ~~~~~~~~~~ | ~~~~ |
| gm-cys7 | ~~~~~~~~~~ | ~~~~ |
| gm-cys1 | NQMEQDHS~~ | ~~~~ |
| gm-cys3 | ~~~~~~~~~~ | ~~~~ |
| gm-cys4 | ~~~~~~~~~~ | ~~~~ |
| ZmCys10 | ~~~~~~~~~~ | ~~~~ |
| ZmCys6 | ~~~~~~~~~~ | ~~~~ |
| os-cys4 | ~~~~~~~~~~ | ~~~~ |
| ta-cys11 | ~~~~~~~~~~ | ~~~~ |
| gm-cys5 | ~~~~~~~~~~ | ~~~~ |
| gm-cys9 | ~~~~~~~~~~ | ~~~~ |
| ZmCys7 | ~~~~~~~~~~ | ~~~~ |
| os-cys6 | ~~~~~~~~~~ | ~~~~ |
| ZmCys9 | ~~~~~~~~~~ | ~~~~ |
| ZmCys13 | ~~~~~~~~~~ | ~~~~ |
| ta-cys3 | ~~~~~~~~~~ | ~~~~ |
| ZmCys11 | ~~~~~~~~~~ | ~~~~ |

What is claimed is:

1. An isolated polynucleotide comprising a nucleic acid sequence selected from the group consisting of:
    (a) a nucleic acid sequence set forth in SEQ ID NO: 11;
    (b) a nucleotide sequence that encodes a polypeptide having the amino acid sequence set forth in SEQ ID NO: 12;
    (c) a nucleic acid sequence having at least 95% sequence identity over the entire length of SEQ ID NO: 11 as determined by the GAP algorithm under default parameters, wherein said nucleic acid sequence encodes a polypeptide with cysteine proteinase inhibitor activity;
    (d) a nucleic acid sequence that encodes a polypeptide with cysteine proteinase inhibitor activity, wherein said polypeptide has at least 95% sequence identity to SEQ ID NO: 12; and
    (e) a nucleic acid sequence that comprises the full length complement of any one of (a) to (d).

2. The isolated polynucleotide of claim 1, wherein said polynucleotide is optimized for expression in a plant.

3. A DNA construct comprising the isolated polynucleotide of claim 1, wherein said polynucleotide is operably linked to a promoter that drives expression in a host cell.

4. The DNA construct of claim 3, wherein said polynucleotide is operably linked in an antisense orientation to said promoter.

5. An expression cassette comprising the DNA construct of claim 3.

6. A host cell having stably incorporated into its genome at least one DNA construct of claim 3.

7. The host cell of claim 6, wherein said host cell is a plant cell.

8. A transgenic plant having stably incorporated into its genome the DNA construct of claim 3.

9. The transgenic plant according to claim 8, wherein said plant is a monocot.

10. The transgenic plant according to claim 8, wherein said plant is a dicot.

11. The transgenic plant according to claim 8, wherein said plant is selected from the group consisting of: corn, soybean, wheat, rice, alfalfa, barley, millet, sunflower, sorghum, canola and cotton.

12. Transformed seed of the transgenic plant of claim 8, wherein said transformed seed comprises the DNA construct of claim 3.

13. A method for enhancing the disease resistance of a plant comprising:
    (a) introducing into a plant cell at least one DNA construct comprising a polynucleotide operably linked to a promoter that drives expression of a cysteine proteinase inhibitor polypeptide in plant cells, wherein said polynucleotide comprises a nucleotide sequence selected from the group consisting of:
        (i) a nucleic acid sequence set forth in SEQ ID NO: 11;
        (ii) a nucleic acid sequence that encodes a polypeptide having the amino acid sequence set forth in SEQ ID NO: 12;
        (iii) a nucleic acid sequence having at least 95% sequence identity over the entire length of SEQ ID NO: 11 as determined by the GAP algorithm under default parameters, wherein said nucleic acid sequence encodes a polypeptide with cysteine proteinase inhibitor activity;
        (iv) a nucleic acid sequence that encodes a polypeptide with cysteine proteinase inhibitor activity, wherein said polypeptide has at least 95% sequence identity to SEQ ID NO: 12; and
        (v) a nucleotide sequence that comprises the full length complement of any one of (i) through (iv);
    (b) growing the plant cell under plant growing conditions to produce a regenerated plant; and
    (c) inducing expression of said polynucleotide for a time sufficient to enhance the disease resistance of said plant.

14. The method of claim 13, wherein said promoter is selected from the group consisting of:
    (a) a strong constitutive promoter;
    (b) a tissue-specific promoter;
    (c) a temporally-defined promoter; and
    (d) an inducible promoter.

15. The method of claim 13, wherein said plant expresses a polypeptide having pesticidal activity against fungal pathogens.

16. The method of claim 15, wherein said fungus is *Fusarium* ssp.

17. The method of claim 13, wherein said plant expresses a polypeptide having pesticidal activity against insects.

18. The method of claim 13, wherein said plant expresses a polypeptide having pesticidal activity against nematodes.

19. The method of claim 18, wherein said nematode is a Soybean Cyst Nematode.

* * * * *

SEQUENCE LISTING

<160> NUMBER OF SEQ ID NOS: 195

<210> SEQ ID NO 1
<211> LENGTH: 786
<212> TYPE: DNA
<213> ORGANISM: Zea mays
<220> FEATURE:
<221> NAME/KEY: CDS
<222> LOCATION: (106)...(513)

<400> SEQUENCE: 1
cacgccgcca caacaatatc gcattgacac atcgttcatc ggatccagtc ttctcccggc    60

```
atctcctccg gctataaatt tccggcccca attcacccaa tccag atg cgc aaa cat    117
                                                  Met Arg Lys His
                                                    1 cga atc gtc tcg cta gtg gct gcc cta ctc gtg ctg ctt gcc ctc gcc    165
Arg Ile Val Ser Leu Val Ala Ala Leu Leu Val Leu Leu Ala Leu Ala
  5              10                  15                  20 gcc gtt tcc tcc acg cgc agc gca caa aag gag tcc gtg gct gac aac    213
Ala Val Ser Ser Thr Arg Ser Ala Gln Lys Glu Ser Val Ala Asp Asn
             25                  30                  35 gcc ggg atg ttg gca ggc ggc atc aag gac gtg ccg gcg aac gag aac    261
Ala Gly Met Leu Ala Gly Gly Ile Lys Asp Val Pro Ala Asn Glu Asn
         40                  45                  50 gac ctc cag ctc cag gag ctc gcg cgc ttc gcc gtc aat gag cac aac    309
Asp Leu Gln Leu Gln Glu Leu Ala Arg Phe Ala Val Asn Glu His Asn
     55                  60                  65 caa aag gcc aat gct ctt ctg ggg ttc gag aag ctt gtg aag gcc aag    357
Gln Lys Ala Asn Ala Leu Leu Gly Phe Glu Lys Leu Val Lys Ala Lys
 70                  75                  80 aca caa gtg gtt gct ggc acg atg tac tat ctc act att gaa gtg aag    405
Thr Gln Val Val Ala Gly Thr Met Tyr Tyr Leu Thr Ile Glu Val Lys
 85                  90                  95                 100 gat ggc gaa gtc aat aag ctc tat gaa gct aag gtc tgg gag aag cca    453
Asp Gly Glu Val Asn Lys Leu Tyr Glu Ala Lys Val Trp Glu Lys Pro
                105                 110                 115 tgg gag aac ttc aag cag ctg cag gaa ttc aag cct gtt gaa gag ggt    501
Trp Glu Asn Phe Lys Gln Leu Gln Glu Phe Lys Pro Val Glu Glu Gly
                120                 125                 130 gct agc gcc taa ggatctgtcg tctccctgtg caatttgctg cctgaagcgc        553
Ala Ser Ala *
        135 aaaactaagt tgcagaataa ggagctgctt cggaacatgc cagagcatgc accctcgcgt   613 attttcataa aatcagtgct cttaatgtaa tatcttgaat tgccgtgcca tgtgtaataa   673 gtaatatcat gaataacagt tgctattatg ggttctaaat gtgtattaac agccatccat   733 ggcagagttc tcatattaaa aaaaaaaaaa aaaaaaaaa aaaaaaaaaa aaa          786
```

<210> SEQ ID NO 2
<211> LENGTH: 135
<212> TYPE: PRT
<213> ORGANISM: Zea mays
<220> FEATURE:
<221> NAME/KEY: DOMAIN
<222> LOCATION: (59)...(68)
<223> OTHER INFORMATION: N-terminal alpha-1 helix domain
<220> FEATURE:
<221> NAME/KEY: DOMAIN
<222> LOCATION: (86)...(96)
<223> OTHER INFORMATION: First hairpin loop domain
<220> FEATURE:
<221> NAME/KEY: DOMAIN
<222> LOCATION: (109)...(117)
<223> OTHER INFORMATION: Second hairpin loop domain

<400> SEQUENCE: 2

Met Arg Lys His Arg Ile Val Ser Leu Val Ala Ala Leu Leu Val Leu
 1               5                  10                  15

Leu Ala Leu Ala Ala Val Ser Ser Thr Arg Ser Ala Gln Lys Glu Ser
                20                  25                  30

Val Ala Asp Asn Ala Gly Met Leu Ala Gly Gly Ile Lys Asp Val Pro
             35                  40                  45

Ala Asn Glu Asn Asp Leu Gln Leu Gln Glu Leu Ala Arg Phe Ala Val

```
                      50                  55                  60
Asn Glu His Asn Gln Lys Ala Asn Ala Leu Leu Gly Phe Glu Lys Leu
 65                  70                  75                  80

Val Lys Ala Lys Thr Gln Val Val Ala Gly Thr Met Tyr Tyr Leu Thr
                     85                  90                  95

Ile Glu Val Lys Asp Gly Glu Val Asn Lys Leu Tyr Glu Ala Lys Val
                100                 105                 110

Trp Glu Lys Pro Trp Glu Asn Phe Lys Gln Leu Gln Glu Phe Lys Pro
            115                 120                 125

Val Glu Glu Gly Ala Ser Ala
            130             135

<210> SEQ ID NO 3
<211> LENGTH: 915
<212> TYPE: DNA
<213> ORGANISM: Zea mays
<220> FEATURE:
<221> NAME/KEY: CDS
<222> LOCATION: (112)...(516)

<400> SEQUENCE: 3
ctccgcccgc cacaacaata tcgcattgac agatcgttca tcgtagcctc ctccagtcgt      60
ctcccgggat cttctccggc tataaatttc cgccccaatt ccccaatcca g atg cgc     117
                                                         Met Arg
                                                           1 aaa cat cga atc gtc tcg ctc gtg gct gcc ctg ctc ata ctg ctt gcc      165
Lys His Arg Ile Val Ser Leu Val Ala Ala Leu Leu Ile Leu Leu Ala
          5                  10                  15 ctc gcc gta tcg tcc acc cgc aac gca cag gag gat tcc atg gcc gac      213
Leu Ala Val Ser Ser Thr Arg Asn Ala Gln Glu Asp Ser Met Ala Asp
 20                  25                  30 aac acc ggg acg ttg gcg ggc ggc atc aag gac gtg ccg ggg aac gag      261
Asn Thr Gly Thr Leu Ala Gly Gly Ile Lys Asp Val Pro Gly Asn Glu
 35                  40                  45                  50 aac gac ctt cac ctc cag gaa ctc gcc cgc ttc gcc gtc gat gag cac      309
Asn Asp Leu His Leu Gln Glu Leu Ala Arg Phe Ala Val Asp Glu His
             55                  60                  65 aac aag aag gcc aat gct ctt ctg ggg ttc gag aag ctt gtg aag gcc      357
Asn Lys Lys Ala Asn Ala Leu Leu Gly Phe Glu Lys Leu Val Lys Ala
         70                  75                  80 aag aca caa gtg gtt gct ggc acg atg tac tat ctc act att gaa gtg      405
Lys Thr Gln Val Val Ala Gly Thr Met Tyr Tyr Leu Thr Ile Glu Val
             85                  90                  95 aag gat ggc gaa gtg aag aag ctc tac gaa gct aag gtc tgg gag aag      453
Lys Asp Gly Glu Val Lys Lys Leu Tyr Glu Ala Lys Val Trp Glu Lys
            100                 105                 110 cca tgg gag aac ttc aag gag ctg cag gaa ttc aag cct gtt gaa gag      501
Pro Trp Glu Asn Phe Lys Glu Leu Gln Glu Phe Lys Pro Val Glu Glu
115                 120                 125                 130 ggt gct agc gcc taa ggatctctcc ttctccatgt gcgagcctga agctcaaagc      556
Gly Ala Ser Ala * aaagttgcag aataaggagc cacctcccaa catgctagac catgctccct tgtgtaattt      616
cataagacta caacccttttt agggcttgtt cgtttgtgtc tgtgtctaag ggaattgaag      676
gtgattaaat ttccttctat acaaatagag gggctttaat ccactccaat acttttcaat      736
ccacgcctaa ccgaacaagc ccttaatatg atatcttaga ttgccgtacc tgtgtaatat      796
catgaataaa atttgctatt atggattcta aggtttatga actaccatac atggcagaat      856
```

-continued cctcatgtta ctttgctgaa atctttgttg gaagttggaa cgtaaaaaaa aaaaaaaaa    915

<210> SEQ ID NO 4
<211> LENGTH: 134
<212> TYPE: PRT
<213> ORGANISM: Zea mays
<220> FEATURE:
<221> NAME/KEY: DOMAIN
<222> LOCATION: (58)...(67)
<223> OTHER INFORMATION: N-terminal alpha-1 helix domain
<220> FEATURE:
<221> NAME/KEY: DOMAIN
<222> LOCATION: (85)...(95)
<223> OTHER INFORMATION: First hairpin loop domain
<220> FEATURE:
<221> NAME/KEY: DOMAIN
<222> LOCATION: (108)...(116)
<223> OTHER INFORMATION: Second hairpin loop domain

<400> SEQUENCE: 4

Met Arg Lys His Arg Ile Val Ser Leu Val Ala Ala Leu Leu Ile Leu
 1               5                  10                  15

Leu Ala Leu Ala Val Ser Ser Thr Arg Asn Ala Gln Glu Asp Ser Met
            20                  25                  30

Ala Asp Asn Thr Gly Thr Leu Ala Gly Gly Ile Lys Asp Val Pro Gly
        35                  40                  45

Asn Glu Asn Asp Leu His Leu Gln Glu Leu Ala Arg Phe Ala Val Asp
    50                  55                  60

Glu His Asn Lys Lys Ala Asn Ala Leu Leu Gly Phe Glu Lys Leu Val
65                  70                  75                  80

Lys Ala Lys Thr Gln Val Val Ala Gly Thr Met Tyr Tyr Leu Thr Ile
                85                  90                  95

Glu Val Lys Asp Gly Glu Val Lys Lys Leu Tyr Glu Ala Lys Val Trp
            100                 105                 110

Glu Lys Pro Trp Glu Asn Phe Lys Glu Leu Gln Glu Phe Lys Pro Val
        115                 120                 125

Glu Glu Gly Ala Ser Ala
    130

<210> SEQ ID NO 5
<211> LENGTH: 915
<212> TYPE: DNA
<213> ORGANISM: Zea mays
<220> FEATURE:
<221> NAME/KEY: CDS
<222> LOCATION: (112)...(516)

<400> SEQUENCE: 5
ctccgcccgc cacaacaata tcgcattgac agatcgttca tcgtagcctc ctccagtcgt    60
ctcccgggat cttctccggc tataaatttc cgccccaatt ccccaatcca g atg cgc    117
                                                        Met Arg
                                                          1 aaa cat cga atc gtc tcg ctc gtg gct gcc ctg ctc ata ctg ctt gcc    165
Lys His Arg Ile Val Ser Leu Val Ala Ala Leu Leu Ile Leu Leu Ala
      5                  10                  15 ctc gcc gta tcg tcc acc cgc aac gca cag gag gat tcc atg gcc gac    213
Leu Ala Val Ser Ser Thr Arg Asn Ala Gln Glu Asp Ser Met Ala Asp
 20                  25                  30 aac acc ggg acg ttg gcg ggc ggc atc aag gac gtg ccg ggg aac gag    261
Asn Thr Gly Thr Leu Ala Gly Gly Ile Lys Asp Val Pro Gly Asn Glu
         35                  40                  45                  50 aac gac ctt cac ctc cag gaa ctc gcc cgc ttc gcc gtc gat gag cac    309

-continued

| | | |
|---|---|---|
| Asn Asp Leu His Leu Gln Glu Leu Ala Arg Phe Ala Val Asp Glu His<br>  55                  60                  65 | | |
| aac aag aag gcc aat gct ctt ctg ggg ttc gag aag ctt gtg aag gcc<br>Asn Lys Lys Ala Asn Ala Leu Leu Gly Phe Glu Lys Leu Val Lys Ala<br>            70                  75                  80 | 357 | |
| aag aca caa gtg gtt gct ggc acg atg tac tat ctc act att gaa gtg<br>Lys Thr Gln Val Val Ala Gly Thr Met Tyr Tyr Leu Thr Ile Glu Val<br>        85                  90                  95 | 405 | |
| aag gat ggc gaa gtg aag aag ctc tac gaa gct aag gtc tgg gag aag<br>Lys Asp Gly Glu Val Lys Lys Leu Tyr Glu Ala Lys Val Trp Glu Lys<br>    100                 105                 110 | 453 | |
| cca tgg gag aac ttc aag gag ctg cag gaa ttc aag cct gtt gaa gag<br>Pro Trp Glu Asn Phe Lys Glu Leu Gln Glu Phe Lys Pro Val Glu Glu<br>115                 120                 125                 130 | 501 | |
| ggt gct agc gcc taa ggatctctcc ttctccatgt gcgagcctga agctcaaagc<br>Gly Ala Ser Ala * | 556 | |
| aaagttgcag aataaggagc cacctcccaa catgctagac catgctccct tgtgtaattt | 616 | |
| cataagacta caacccttttt agggcttgtt cgtttgtgtc tgtgtctaag ggaattgaag | 676 | |
| gtgattaaat ttccttctat acaaatagag gggctttaat ccactccaat acttttcaat | 736 | |
| ccacgcctaa ccgaacaagc ccttaatatg atatcttaga ttgccgtacc tgtgtaatat | 796 | |
| catgaataaa atttgctatt atggattcta aggtttatga actaccatac atggcagaat | 856 | |
| cctcatgtta ctttgctgaa atctttgttg gaagttggaa cgtaaaaaaa aaaaaaaaa | 915 | |

<210> SEQ ID NO 6
<211> LENGTH: 134
<212> TYPE: PRT
<213> ORGANISM: Zea mays
<220> FEATURE:
<221> NAME/KEY: DOMAIN
<222> LOCATION: (58)...(67)
<223> OTHER INFORMATION: N-terminal alpha-1 helix domain
<220> FEATURE:
<221> NAME/KEY: DOMAIN
<222> LOCATION: (85)...(95)
<223> OTHER INFORMATION: First hairpin loop domain
<220> FEATURE:
<221> NAME/KEY: DOMAIN
<222> LOCATION: (108)...(116)
<223> OTHER INFORMATION: Second hairpin loop domain

<400> SEQUENCE: 6

Met Arg Lys His Arg Ile Val Ser Leu Val Ala Ala Leu Leu Ile Leu
 1               5                  10                  15

Leu Ala Leu Ala Val Ser Ser Thr Arg Asn Ala Gln Glu Asp Ser Met
            20                  25                  30

Ala Asp Asn Thr Gly Thr Leu Ala Gly Gly Ile Lys Asp Val Pro Gly
        35                  40                  45

Asn Glu Asn Asp Leu His Leu Gln Glu Leu Ala Arg Phe Ala Val Asp
    50                  55                  60

Glu His Asn Lys Lys Ala Asn Ala Leu Leu Gly Phe Glu Lys Leu Val
65                  70                  75                  80

Lys Ala Lys Thr Gln Val Val Ala Gly Thr Met Tyr Tyr Leu Thr Ile
                85                  90                  95

Glu Val Lys Asp Gly Glu Val Lys Lys Leu Tyr Glu Ala Lys Val Trp
            100                 105                 110

Glu Lys Pro Trp Glu Asn Phe Lys Glu Leu Gln Glu Phe Lys Pro Val
        115                 120                 125

Glu Glu Gly Ala Ser Ala
    130

<210> SEQ ID NO 7
<211> LENGTH: 1102
<212> TYPE: DNA
<213> ORGANISM: Zea mays
<220> FEATURE:
<221> NAME/KEY: CDS
<222> LOCATION: (69)...(806)

<400> SEQUENCE: 7

| | | |
|---|---|---|
| cgagcaaagc aaagccaaag caatctcaag tgaatcaaac cgccagtcct cctccccact | 60 |
| accagagc atg cgc gtt gcc gcg acc cga gcc gcc gcc gcc gct cac cct<br>         Met Arg Val Ala Ala Thr Arg Ala Ala Ala Ala Ala His Pro<br>          1             5                   10 | 110 |
| ccg agc gcc ttc ctg ctc ctc ctg tta ctc ctc ggt tgc gcg tcc ctc<br>Pro Ser Ala Phe Leu Leu Leu Leu Leu Leu Leu Gly Cys Ala Ser Leu<br> 15               20                25              30 | 158 |
| gcg atc gga gga gca gcc atg gcc ggc cac gtc ctc ggc ggc gtg aag<br>Ala Ile Gly Gly Ala Ala Met Ala Gly His Val Leu Gly Gly Val Lys<br>                 35                40              45 | 206 |
| gag aac cca gcc gcg gcc aac agc gcc gag tcc gac ggg ctc ggc cgc<br>Glu Asn Pro Ala Ala Asn Ser Ala Glu Ser Asp Gly Leu Gly Arg<br>        50                55              60 | 254 |
| ttc gcc gtc gat gag cac aac agg cgc gag aac gcg ctg ctg gag ttc<br>Phe Ala Val Asp Glu His Asn Arg Arg Glu Asn Ala Leu Leu Glu Phe<br>              65                70              75 | 302 |
| gtg cgc gtg gtg gag gcc aag gag cag gtg gtg gcc ggc acg ctg cac<br>Val Arg Val Val Glu Ala Lys Glu Gln Val Val Ala Gly Thr Leu His<br> 80               85                90 | 350 |
| cac ctc acg ctc gag gcc gtc gag gcc ggg agg aag aag ctc tac gag<br>His Leu Thr Leu Glu Ala Val Glu Ala Gly Arg Lys Lys Leu Tyr Glu<br> 95               100             105            110 | 398 |
| gcc aag gtc tgg gtc aag cca tgg ctc gac ttc aag gag ctc cag gaa<br>Ala Lys Val Trp Val Lys Pro Trp Leu Asp Phe Lys Glu Leu Gln Glu<br>               115             120            125 | 446 |
| ttc agc cac aag ggg gac gcc acc gcc ttc acc aac gcc gac ctc ggc<br>Phe Ser His Lys Gly Asp Ala Thr Ala Phe Thr Asn Ala Asp Leu Gly<br>            130              135            140 | 494 |
| gcc aag caa ggt gga cat gag cct ggt tgg cgt gag gtt cca gta gag<br>Ala Lys Gln Gly Gly His Glu Pro Gly Trp Arg Glu Val Pro Val Glu<br>145              150              155 | 542 |
| gat cct gtg gtc aaa gat gct gca cac cat gct gtg aaa tcg atc caa<br>Asp Pro Val Val Lys Asp Ala Ala His His Ala Val Lys Ser Ile Gln<br>   160               165              170 | 590 |
| gag agg tcc aac tcc ctg ttt ccc tac gaa ctt ctc gag atc ctt cgt<br>Glu Arg Ser Asn Ser Leu Phe Pro Tyr Glu Leu Leu Glu Ile Leu Arg<br>175              180              185            190 | 638 |
| gcc cat gca cag gtt gtg gaa gac ttt gca aaa ttt gac att ctg atg<br>Ala His Ala Gln Val Val Glu Asp Phe Ala Lys Phe Asp Ile Leu Met<br>            195              200            205 | 686 |
| aaa ctg aag aga ggc agc aag gag gag aag atc aaa gcc gag gtc cat<br>Lys Leu Lys Arg Gly Ser Lys Glu Glu Lys Ile Lys Ala Glu Val His<br>            210              215            220 | 734 |
| aag agc ctg gaa ggg gcc ttt gtg cta aac cag cat cag ccg gcg gag<br>Lys Ser Leu Glu Gly Ala Phe Val Leu Asn Gln His Gln Pro Ala Glu<br>   225               230              235 | 782 |
| cat gat gag tcg agc agc cag tga actgacgtaa ctgtgtgagc tgtagtagta<br>His Asp Glu Ser Ser Ser Gln *<br>240              245 | 836 |

-continued

```
acgtacttcg tgttacgtag aagaataagg agaaaacgac caatccggtt ttatctggat      896
gtcatgtatg gtcgacggtc gttgctggct tggcttccga acgcagcagg catactggtg      956
ctggaagacg gtacctgctg tcgcacttgc cgttataata ggcattggaa cttgtcgatt     1016
tcgggagctg atctgtttgt accgtattgt ttatttataa tatgatggat cgtatgttgt     1076
ttaaaaaaaa aaaaaaaaaa aaaaaa                                          1102
```

<210> SEQ ID NO 8
<211> LENGTH: 245
<212> TYPE: PRT
<213> ORGANISM: Zea mays
<220> FEATURE:
<221> NAME/KEY: DOMAIN
<222> LOCATION: (60)...(69)
<223> OTHER INFORMATION: N-terminal alpha-1 helix domain
<220> FEATURE:
<221> NAME/KEY: DOMAIN
<222> LOCATION: (87)...(97)
<223> OTHER INFORMATION: First hairpin loop domain
<220> FEATURE:
<221> NAME/KEY: DOMAIN
<222> LOCATION: (110)...(118)
<223> OTHER INFORMATION: Second hairpin loop domain

<400> SEQUENCE: 8

```
Met Arg Val Ala Ala Thr Arg Ala Ala Ala Ala His Pro Pro Ser
 1               5                  10                  15

Ala Phe Leu Leu Leu Leu Leu Leu Gly Cys Ala Ser Leu Ala Ile
            20                  25                  30

Gly Gly Ala Ala Met Ala Gly His Val Leu Gly Gly Val Lys Glu Asn
        35                  40                  45

Pro Ala Ala Ala Asn Ser Ala Glu Ser Asp Gly Leu Gly Arg Phe Ala
    50                  55                  60

Val Asp Glu His Asn Arg Arg Glu Asn Ala Leu Leu Glu Phe Val Arg
65                  70                  75                  80

Val Val Glu Ala Lys Glu Gln Val Val Ala Gly Thr Leu His His Leu
                85                  90                  95

Thr Leu Glu Ala Val Glu Ala Gly Arg Lys Lys Leu Tyr Glu Ala Lys
            100                 105                 110

Val Trp Val Lys Pro Trp Leu Asp Phe Lys Glu Leu Gln Glu Phe Ser
        115                 120                 125

His Lys Gly Asp Ala Thr Ala Phe Thr Asn Ala Asp Leu Gly Ala Lys
    130                 135                 140

Gln Gly Gly His Glu Pro Gly Trp Arg Glu Val Pro Val Glu Asp Pro
145                 150                 155                 160

Val Val Lys Asp Ala Ala His His Ala Val Lys Ser Ile Gln Glu Arg
                165                 170                 175

Ser Asn Ser Leu Phe Pro Tyr Glu Leu Leu Glu Ile Leu Arg Ala His
            180                 185                 190

Ala Gln Val Val Glu Asp Phe Ala Lys Phe Asp Ile Leu Met Lys Leu
        195                 200                 205

Lys Arg Gly Ser Lys Glu Lys Ile Lys Ala Glu Val His Lys Ser
    210                 215                 220

Leu Glu Gly Ala Phe Val Leu Asn Gln His Gln Pro Ala Glu His Asp
225                 230                 235                 240

Glu Ser Ser Ser Gln
                245
```

```
<210> SEQ ID NO 9
<211> LENGTH: 944
<212> TYPE: DNA
<213> ORGANISM: Zea mays
<220> FEATURE:
<221> NAME/KEY: CDS
<222> LOCATION: (114)...(644)

<400> SEQUENCE: 9
cgtctgcgca gagcagccaa gcgccacacg ccgacgcgaa ccaaccaggc aaccagatgg      60
tagtaggtta gctaagctcg ggatcggagg agaggtgccc cgcgaccctg acg atg       116
                                                          Met
                                                           1 acg atg cct cgc cgc gcc ctt ctc ttc gcc gcg gtg ctc ctc gcg gcc      164
Thr Met Pro Arg Arg Ala Leu Leu Phe Ala Ala Val Leu Leu Ala Ala
          5                  10                  15 tcc gcc gcc gcg gtc tcc ggg ttc cac ctc gcc ggg gac gag agc ggc      212
Ser Ala Ala Ala Val Ser Gly Phe His Leu Ala Gly Asp Glu Ser Gly
         20                  25                  30 ctc gtg agg ggc gtg ctc aca gcg gtc cgc gag cgg gcc gag gcc gag      260
Leu Val Arg Gly Val Leu Thr Ala Val Arg Glu Arg Ala Glu Ala Glu
 35                  40                  45 gcc gag gac gcc gcg cgc ttc gcc gtc gcc tac cac aac agg aac cag      308
Ala Glu Asp Ala Ala Arg Phe Ala Val Ala Tyr His Asn Arg Asn Gln
 50                  55                  60                  65 ggt gct gct ttg gag ttc act agg gtg ctc aaa tcg aag cgg cag gtt      356
Gly Ala Ala Leu Glu Phe Thr Arg Val Leu Lys Ser Lys Arg Gln Val
                 70                  75                  80 gtg acc ggg acc ctg cat gac ctg ata ctg gag gca gct gat gct gga      404
Val Thr Gly Thr Leu His Asp Leu Ile Leu Glu Ala Ala Asp Ala Gly
             85                  90                  95 aaa aag agt ctg tac aga gca aaa gtc tgg gtg aag ccg tgg gag gat      452
Lys Lys Ser Leu Tyr Arg Ala Lys Val Trp Val Lys Pro Trp Glu Asp
        100                 105                 110 ttc aag tcc gtt gtc gag ttt cgc ctt gct gga gac tct gaa tct gaa      500
Phe Lys Ser Val Val Glu Phe Arg Leu Ala Gly Asp Ser Glu Ser Glu
    115                 120                 125 ccc gag cct tct gtt gct tct gat gaa ggc tct ggg caa gga gtt gcc      548
Pro Glu Pro Ser Val Ala Ser Asp Glu Gly Ser Gly Gln Gly Val Ala
130                 135                 140                 145 aag ctc tct ctt gaa gca gac atc ata cac gaa gag gct cac ctg cac      596
Lys Leu Ser Leu Glu Ala Asp Ile Ile His Glu Glu Ala His Leu His
                150                 155                 160 acc att gag aat gat gga ctt tcc agc gat ttc gca tca tcc gct tag      644
Thr Ile Glu Asn Asp Gly Leu Ser Ser Asp Phe Ala Ser Ser Ala *
            165                 170                 175 acatacttgg tgtgactagg attccaggca aggatggaaa gcgtgaaagt ttaaaatgaa      704
ggtttaggta tttagaattc taatagtagg ttgctgtcaa gctgaaatgc tttgcctcta      764
tcggaatatg tatgttttgt ttggaacgta ggagcataga actgtatatt tcggtatttc      824
acaccgttca tttccatgtc tgtatataag actatctcca gccatattct cccatatata      884
tttcactacc tatactttt attatatttt acatttttac tacaaaaaaa aaaaaaaaaa      944

<210> SEQ ID NO 10
<211> LENGTH: 176
<212> TYPE: PRT
<213> ORGANISM: Zea mays
<220> FEATURE:
<221> NAME/KEY: DOMAIN
<222> LOCATION: (53)...(62)
<223> OTHER INFORMATION: N-terminal alpha-1 helix domain
```

```
<220> FEATURE:
<221> NAME/KEY: DOMAIN
<222> LOCATION: (80)...(90)
<223> OTHER INFORMATION: First hairpin loop domain
<220> FEATURE:
<221> NAME/KEY: DOMAIN
<222> LOCATION: (103)...(111)
<223> OTHER INFORMATION: Second hairpin loop domain

<400> SEQUENCE: 10
```

| Met | Thr | Met | Pro | Arg | Arg | Ala | Leu | Leu | Phe | Ala | Ala | Val | Leu | Leu | Ala |
|---|---|---|---|---|---|---|---|---|---|---|---|---|---|---|---|
| 1 | | | | 5 | | | | | 10 | | | | | 15 | |

| Ala | Ser | Ala | Ala | Ala | Val | Ser | Gly | Phe | His | Leu | Ala | Gly | Asp | Glu | Ser |
|---|---|---|---|---|---|---|---|---|---|---|---|---|---|---|---|
| | | | 20 | | | | | 25 | | | | | 30 | | |

| Gly | Leu | Val | Arg | Gly | Val | Leu | Thr | Ala | Val | Arg | Glu | Arg | Ala | Glu | Ala |
|---|---|---|---|---|---|---|---|---|---|---|---|---|---|---|---|
| | | | 35 | | | | | 40 | | | | | 45 | | |

| Glu | Ala | Glu | Asp | Ala | Ala | Arg | Phe | Ala | Val | Ala | Tyr | His | Asn | Arg | Asn |
|---|---|---|---|---|---|---|---|---|---|---|---|---|---|---|---|
| | 50 | | | | | 55 | | | | | 60 | | | | |

| Gln | Gly | Ala | Ala | Leu | Glu | Phe | Thr | Arg | Val | Leu | Lys | Ser | Lys | Arg | Gln |
|---|---|---|---|---|---|---|---|---|---|---|---|---|---|---|---|
| 65 | | | | | 70 | | | | | 75 | | | | | 80 |

| Val | Val | Thr | Gly | Thr | Leu | His | Asp | Leu | Ile | Leu | Glu | Ala | Ala | Asp | Ala |
|---|---|---|---|---|---|---|---|---|---|---|---|---|---|---|---|
| | | | | 85 | | | | | 90 | | | | | 95 | |

| Gly | Lys | Lys | Ser | Leu | Tyr | Arg | Ala | Lys | Val | Trp | Val | Lys | Pro | Trp | Glu |
|---|---|---|---|---|---|---|---|---|---|---|---|---|---|---|---|
| | | | 100 | | | | | 105 | | | | | 110 | | |

| Asp | Phe | Lys | Ser | Val | Val | Glu | Phe | Arg | Leu | Ala | Gly | Asp | Ser | Glu | Ser |
|---|---|---|---|---|---|---|---|---|---|---|---|---|---|---|---|
| | | | 115 | | | | | 120 | | | | | 125 | | |

| Glu | Pro | Glu | Pro | Ser | Val | Ala | Ser | Asp | Glu | Gly | Ser | Gly | Gln | Gly | Val |
|---|---|---|---|---|---|---|---|---|---|---|---|---|---|---|---|
| | 130 | | | | | 135 | | | | | 140 | | | | |

| Ala | Lys | Leu | Ser | Leu | Glu | Ala | Asp | Ile | Ile | His | Glu | Glu | Ala | His | Leu |
|---|---|---|---|---|---|---|---|---|---|---|---|---|---|---|---|
| 145 | | | | | 150 | | | | | 155 | | | | | 160 |

| His | Thr | Ile | Glu | Asn | Asp | Gly | Leu | Ser | Ser | Asp | Phe | Ala | Ser | Ala |
|---|---|---|---|---|---|---|---|---|---|---|---|---|---|---|
| | | | | 165 | | | | | 170 | | | | | 175 |

```
<210> SEQ ID NO 11
<211> LENGTH: 688
<212> TYPE: DNA
<213> ORGANISM: Zea mays
<220> FEATURE:
<221> NAME/KEY: CDS
<222> LOCATION: (66)...(416)

<400> SEQUENCE: 11
ctccttcccg cacgtcagac gtcgtcacac acaatctagc gcgtacgtac gtcccaaacc      60
```

| aaacc atg | tcc | gcg | aga | gct | ctt | ctc | ctg | acg | acc | gcg | acg | ctg | ctc | ctg | 110 |
|---|---|---|---|---|---|---|---|---|---|---|---|---|---|---|---|
| Met | Ser | Ala | Arg | Ala | Leu | Leu | Leu | Thr | Thr | Ala | Thr | Leu | Leu | Leu | |
| 1 | | | | 5 | | | | | 10 | | | | | 15 | |

| ctc | gtc | gcc | gct | gcg | cgt | gcg | ggg | cag | ccg | ctc | gcc | ggc | ggg | tgg | agc | 158 |
|---|---|---|---|---|---|---|---|---|---|---|---|---|---|---|---|---|
| Leu | Val | Ala | Ala | Ala | Arg | Ala | Gly | Gln | Pro | Leu | Ala | Gly | Gly | Trp | Ser | |
| | | | 20 | | | | | 25 | | | | | 30 | | | |

| ccg | atc | agg | aac | gtc | agc | gac | ccg | cac | atc | cag | gag | ctc | ggc | ggc | tgg | 206 |
|---|---|---|---|---|---|---|---|---|---|---|---|---|---|---|---|---|
| Pro | Ile | Arg | Asn | Val | Ser | Asp | Pro | His | Ile | Gln | Glu | Leu | Gly | Gly | Trp | |
| | | 35 | | | | | 40 | | | | | 45 | | | | |

| gcg | gtg | acg | gag | cac | gtc | agg | cgg | gcc | aac | gac | ggg | ctg | cgg | ttc | ggc | 254 |
|---|---|---|---|---|---|---|---|---|---|---|---|---|---|---|---|---|
| Ala | Val | Thr | Glu | His | Val | Arg | Arg | Ala | Asn | Asp | Gly | Leu | Arg | Phe | Gly | |
| | 50 | | | | | 55 | | | | | 60 | | | | | |

| gag | gtg | acg | ggc | ggc | gag | gag | cag | gtg | gtg | tcc | ggg | atg | aac | tac | aag | 302 |
|---|---|---|---|---|---|---|---|---|---|---|---|---|---|---|---|---|
| Glu | Val | Thr | Gly | Gly | Glu | Glu | Gln | Val | Val | Ser | Gly | Met | Asn | Tyr | Lys | |
| 65 | | | | | 70 | | | | | 75 | | | | | | |

| ctc | gtc | ctc | gac | gcc | acg | gac | gcc | gac | ggc | aag | gtc | gcg | gcg | tac | ggg | 350 |
|---|---|---|---|---|---|---|---|---|---|---|---|---|---|---|---|---|
| Leu | Val | Leu | Asp | Ala | Thr | Asp | Ala | Asp | Gly | Lys | Val | Ala | Ala | Tyr | Gly | |

-continued

```
         80                  85                  90                  95
gcc ttc gtg tac gag cag tcg tgg acc aac acc cgc gag ctc gtg tcc        398
Ala Phe Val Tyr Glu Gln Ser Trp Thr Asn Thr Arg Glu Leu Val Ser
             100                 105                 110 ttc gcg ccg gcc agc tga cgaccagctg gacgtaatta atcagcggcg              446
Phe Ala Pro Ala Ser *
         115 ccgcaatgtg tctttggagt aacgtgtcat taagcaaaat acaattacca tagtactaca     506 ctaggacctc gtatcatgaa gacatactct tgtgatcttg tcacggactc acgggtcctc     566 acttaataag ccgtcttggc attatctgta ctgctatatc aacagatcat tactgttttt    626 ctcgattgca atccccttt ttttcaaggg tggcgtattt tttcccaaaa aaaaaaaaa       686 aa                                                                    688
```

<210> SEQ ID NO 12
<211> LENGTH: 116
<212> TYPE: PRT
<213> ORGANISM: Zea mays
<220> FEATURE:
<221> NAME/KEY: DOMAIN
<222> LOCATION: (44)...(53)
<223> OTHER INFORMATION: N-terminal alpha-1 helix domain
<220> FEATURE:
<221> NAME/KEY: DOMAIN
<222> LOCATION: (71)...(81)
<223> OTHER INFORMATION: First hairpin loop domain
<220> FEATURE:
<221> NAME/KEY: DOMAIN
<222> LOCATION: (95)...(103)
<223> OTHER INFORMATION: Second hairpin loop domain

<400> SEQUENCE: 12

Met Ser Ala Arg Ala Leu Leu Leu Thr Thr Ala Thr Leu Leu Leu Leu
1               5                   10                  15

Val Ala Ala Arg Ala Gly Gln Pro Leu Ala Gly Gly Trp Ser Pro
            20                  25                  30

Ile Arg Asn Val Ser Asp Pro His Ile Gln Glu Leu Gly Gly Trp Ala
        35                  40                  45

Val Thr Glu His Val Arg Arg Ala Asn Asp Gly Leu Arg Phe Gly Glu
    50                  55                  60

Val Thr Gly Gly Glu Gln Val Val Ser Gly Met Asn Tyr Lys Leu
65                  70                  75                  80

Val Leu Asp Ala Thr Asp Ala Asp Gly Lys Val Ala Ala Tyr Gly Ala
                85                  90                  95

Phe Val Tyr Glu Gln Ser Trp Thr Asn Thr Arg Glu Leu Val Ser Phe
            100                 105                 110

Ala Pro Ala Ser
        115

<210> SEQ ID NO 13
<211> LENGTH: 622
<212> TYPE: DNA
<213> ORGANISM: Zea mays
<220> FEATURE:
<221> NAME/KEY: CDS
<222> LOCATION: (83)...(415)

<400> SEQUENCE: 13

```
tccgtctcgt ctctcctctc ctctcctttt tcccctccc tgcacagcgc cgctcaccgt      60
caccggacca cagcagcgat cg atg gct gag gta cac aat gag cgg ccc gtg     112
                        Met Ala Glu Val His Asn Glu Arg Pro Val
```

-continued

```
        1               5                    10
ggg atg gtg ggc gac gtc cgg gac gca ccg gtg ggc cgc gag aac gac        160
Gly Met Val Gly Asp Val Arg Asp Ala Pro Val Gly Arg Glu Asn Asp
         15                  20                  25 ctc gag gcc atc gag ctc gcg cgc ttc gcg gtc gcc gag cac aac agc        208
Leu Glu Ala Ile Glu Leu Ala Arg Phe Ala Val Ala Glu His Asn Ser
             30                  35                  40 aag acc aac gcg atg ctg gaa ttc gag agg ctg gtg aag gtg agg cac        256
Lys Thr Asn Ala Met Leu Glu Phe Glu Arg Leu Val Lys Val Arg His
                 45                  50                  55 cag gtc gtg gcc ggg acc ctg cac cac ttc acc gtc gag gtg aag gag        304
Gln Val Val Ala Gly Thr Leu His His Phe Thr Val Glu Val Lys Glu
     60                  65                  70 gcc ggc ggc ggc gaa aag aag ctg tac gag gcc aag gtg tgg gag aag        352
Ala Gly Gly Gly Glu Lys Lys Leu Tyr Glu Ala Lys Val Trp Glu Lys
 75                  80                  85                  90 gcg tgg gag aac ttc aag cag ctg cag agc ttc gag ctc gtc gga gac        400
Ala Trp Glu Asn Phe Lys Gln Leu Gln Ser Phe Glu Leu Val Gly Asp
                         95                 100                 105 gcc gcg gtc gcc tga ggcgcacagg cttttcgctg gaggctggag cacaacaatg        455
Ala Ala Val Ala *
         110 aaagaattta actgtcatcc cactggaaaa gtatgatata atgaataaac cagcgtctta     515 cccacatgta ttgtacccta atgagatatt tgaccactgt aatagaatga gatgtgctaa     575 ggaatctgaa agccttcttg cttttgttg ccaaaaaaaa aaaaaaa                    622
```

<210> SEQ ID NO 14
<211> LENGTH: 110
<212> TYPE: PRT
<213> ORGANISM: Zea mays
<220> FEATURE:
<221> NAME/KEY: DOMAIN
<222> LOCATION: (32)...(41)
<223> OTHER INFORMATION: N-terminal alpha-1 helix domain
<220> FEATURE:
<221> NAME/KEY: DOMAIN
<222> LOCATION: (59)...(69)
<223> OTHER INFORMATION: First hairpin loop domain
<220> FEATURE:
<221> NAME/KEY: DOMAIN
<222> LOCATION: (84)...(92)
<223> OTHER INFORMATION: Second hairpin loop domain

<400> SEQUENCE: 14

Met Ala Glu Val His Asn Glu Arg Pro Val Gly Met Val Gly Asp Val
 1               5                  10                  15

Arg Asp Ala Pro Val Gly Arg Glu Asn Asp Leu Glu Ala Ile Glu Leu
             20                  25                  30

Ala Arg Phe Ala Val Ala Glu His Asn Ser Lys Thr Asn Ala Met Leu
         35                  40                  45

Glu Phe Glu Arg Leu Val Lys Val Arg His Gln Val Val Ala Gly Thr
     50                  55                  60

Leu His His Phe Thr Val Glu Val Lys Glu Ala Gly Gly Gly Glu Lys
 65                  70                  75                  80

Lys Leu Tyr Glu Ala Lys Val Trp Glu Lys Ala Trp Glu Asn Phe Lys
                 85                  90                  95

Gln Leu Gln Ser Phe Glu Leu Val Gly Asp Ala Ala Val Ala
            100                 105                 110

<210> SEQ ID NO 15

```
-continued

<211> LENGTH: 802
<212> TYPE: DNA
<213> ORGANISM: Zea mays
<220> FEATURE:
<221> NAME/KEY: CDS
<222> LOCATION: (61)...(534)

<400> SEQUENCE: 15
aggaaacagt cacgtctccc agatctaact gccccctcgac tcacgaatcc caaagcctcc      60 atg gcg acg cac cgg cac tgc ctc cca ctc ctc ctc ctc gtg gcc gcc      108
Met Ala Thr His Arg His Cys Leu Pro Leu Leu Leu Leu Val Ala Ala
 1               5                  10                  15 gcc ctc gcc gcc gtc cct gct cgc gcg gcg ctg ggc ggc ggg cgc ggc      156
Ala Leu Ala Ala Val Pro Ala Arg Ala Ala Leu Gly Gly Gly Arg Gly
             20                  25                  30 ccg ctg ctg ggc ggg tgg aac ccg atc cct gac gtg agc gac tcg cac      204
Pro Leu Leu Gly Gly Trp Asn Pro Ile Pro Asp Val Ser Asp Ser His
         35                  40                  45 atc cag gag cta ggc ggg tgg gcg ctg ggg cag gcg aag cac cag aag      252
Ile Gln Glu Leu Gly Gly Trp Ala Leu Gly Gln Ala Lys His Gln Lys
     50                  55                  60 ctg gcc gcc gac ggg ctg cgg ttc cgc gcc gtg gtg cgc ggc gag cag      300
Leu Ala Ala Asp Gly Leu Arg Phe Arg Arg Val Val Arg Gly Glu Gln
 65                  70                  75                  80 cag gtc gtg tcc ggg atg aac tac cgc ctc tac gtc gac gcc gcc gac      348
Gln Val Val Ser Gly Met Asn Tyr Arg Leu Tyr Val Asp Ala Ala Asp
                 85                  90                  95 ccc gcc ggc cgc acc gtg ccc tac gtc gcc gtc gtg tac gag cag gtc      396
Pro Ala Gly Arg Thr Val Pro Tyr Val Ala Val Val Tyr Glu Gln Val
            100                 105                 110 tgg acc gca ccc gcc agc tcg cct cct tca acc cgg tgc ccc gcg ccc      444
Trp Thr Ala Pro Ala Ser Ser Pro Pro Ser Thr Arg Cys Pro Ala Pro
        115                 120                 125 act gaa acc ata cgc aca cgg gtg ggc cga agc gac gtt ctc cgt caa      492
Thr Glu Thr Ile Arg Thr Arg Val Gly Arg Ser Asp Val Leu Arg Gln
    130                 135                 140 tta cgt gtc gag cta atc tta tta ttg ttt cta tta tta taa              534
Leu Arg Val Glu Leu Ile Leu Leu Leu Phe Leu Leu Leu  *
145                 150                 155 taatgcttct ccctgttcct atggacctat agtagtatac tagtatgttg cgagggagcg      594
agtagaccgt gtgtttcgct atcgtgggac tagaataagc catgtcaatg aacatgagcc      654
gaatagaggc tacgtactgt tattgtatca gtactagtac catatatata tatgggcgca      714
ctacagtctg tgatgtaatg gattgtgcta gtatttgact cttgcttttg tacagaatta      774
ttattattta aaaaaaaaaa aaaaaaaa                                         802

<210> SEQ ID NO 16
<211> LENGTH: 157
<212> TYPE: PRT
<213> ORGANISM: Zea mays
<220> FEATURE:
<221> NAME/KEY: DOMAIN
<222> LOCATION: (35)...(44)
<223> OTHER INFORMATION: N-terminal alpha-1 helix domain
<220> FEATURE:
<221> NAME/KEY: DOMAIN
<222> LOCATION: (81)...(91)
<223> OTHER INFORMATION: First hairpin loop domain
<220> FEATURE:
<221> NAME/KEY: DOMAIN
<222> LOCATION: (105)...(113)
<223> OTHER INFORMATION: Second hairpin loop domain
```

-continued

```
<400> SEQUENCE: 16

Met Ala Thr His Arg His Cys Leu Pro Leu Leu Leu Val Ala Ala
1               5                   10                  15

Ala Leu Ala Ala Val Pro Ala Arg Ala Ala Leu Gly Gly Arg Gly
            20                  25                  30

Pro Leu Leu Gly Gly Trp Asn Pro Ile Pro Asp Val Ser Asp Ser His
            35                  40                  45

Ile Gln Glu Leu Gly Gly Trp Ala Leu Gly Gln Ala Lys His Gln Lys
    50                  55                  60

Leu Ala Ala Asp Gly Leu Arg Phe Arg Arg Val Val Arg Gly Glu Gln
65                  70                  75                  80

Gln Val Val Ser Gly Met Asn Tyr Arg Leu Tyr Val Asp Ala Ala Asp
                85                  90                  95

Pro Ala Gly Arg Thr Val Pro Tyr Val Ala Val Tyr Glu Gln Val
                100                 105                 110

Trp Thr Ala Pro Ala Ser Ser Pro Ser Thr Arg Cys Pro Ala Pro
            115                 120                 125

Thr Glu Thr Ile Arg Thr Arg Val Gly Arg Ser Asp Val Leu Arg Gln
130                 135                 140

Leu Arg Val Glu Leu Ile Leu Leu Phe Leu Leu Leu
145                 150                 155

<210> SEQ ID NO 17
<211> LENGTH: 871
<212> TYPE: DNA
<213> ORGANISM: Zea mays
<220> FEATURE:
<221> NAME/KEY: CDS
<222> LOCATION: (109)...(633)

<400> SEQUENCE: 17
gcaaaaagag cgaacacgag cacgaacaca agcgcagagc agccaagcgc cacacacacg      60
ccgacgcgaa ccaaccaacc agctggtagt aggttcgccg cgctgacg atg atg cct     117
                                                    Met Met Pro
                                                    1 cgc cgc gcc ctt ctc ttc gcc gcg gtg ctc ctc gcg gcc tcc gcc gcc     165
Arg Arg Ala Leu Leu Phe Ala Ala Val Leu Leu Ala Ala Ser Ala Ala
    5                   10                  15 gcg gtc tcc ggg ttc cac ctg gga ggg gac gag agc ggt ctc gtg agg     213
Ala Val Ser Gly Phe His Leu Gly Gly Asp Glu Ser Gly Leu Val Arg
20                  25                  30                  35 ggt gtg ctc gcc gcg ctc cgc gag cga gcc gag gcc gag gac gcc gct     261
Gly Val Leu Ala Ala Leu Arg Glu Arg Ala Glu Ala Glu Asp Ala Ala
                40                  45                  50 cgc ttc gcc gtc gcc cac tac aac aag aac cag ggc gcc gct ttg gag     309
Arg Phe Ala Val Ala His Tyr Asn Lys Asn Gln Gly Ala Ala Leu Glu
            55                  60                  65 ttt act agg gtg ctc aaa tcc aag cgg cag gtg gtg acc ggg acc ctg     357
Phe Thr Arg Val Leu Lys Ser Lys Arg Gln Val Val Thr Gly Thr Leu
        70                  75                  80 cat gac ctg ata ctg gag gca gct gat gct gga aaa aag agt gtg tac     405
His Asp Leu Ile Leu Glu Ala Ala Asp Ala Gly Lys Lys Ser Val Tyr
    85                  90                  95 aga gca aag gtt tgg gtg aag tcg tgg gaa gat ttc aag tct gtc gtc     453
Arg Ala Lys Val Trp Val Lys Ser Trp Glu Asp Phe Lys Ser Val Val
100                 105                 110                 115 gag ttt cgc ctt gtt gga gac tct gaa tct gaa ccc gag cct tct gtt     501
Glu Phe Arg Leu Val Gly Asp Ser Glu Ser Glu Pro Glu Pro Ser Val
```

```
                 120                125                130
gct tct gat gtt agc tct ggg caa gca att gcc aag ctc tct ctt gaa      549
Ala Ser Asp Val Ser Ser Gly Gln Ala Ile Ala Lys Leu Ser Leu Glu
            135                140                145 gca gat att gta caa gaa gag gct cgc ctg cac acc att gag aat gat      597
Ala Asp Ile Val Gln Glu Glu Ala Arg Leu His Thr Ile Glu Asn Asp
        150                155                160 gga ctt tct ggc gat ttc aca tca tca tca tct tag gattccaggc           643
Gly Leu Ser Gly Asp Phe Thr Ser Ser Ser Ser  *
    165                170 aaggatggaa agcgtaaagg tttaaaatga agatttaggt atttagggtt ctacatagta    703
tgtcaagctg aaatgctttg ccttgtttct tggcatatgt atgtgtcgtt tcaaacgtgg    763
gagcatagaa ctgtatattt cggtatttca cactgttcat ttccatgtct gtattcttct   823
ggctatatat atatattttg atcctcaagt aaaaaaaaaa aaaaaaaa                 871
```

<210> SEQ ID NO 18
<211> LENGTH: 174
<212> TYPE: PRT
<213> ORGANISM: Zea mays
<220> FEATURE:
<221> NAME/KEY: DOMAIN
<222> LOCATION: (50)...(59)
<223> OTHER INFORMATION: N-terminal alpha-1 helix domain
<220> FEATURE:
<221> NAME/KEY: DOMAIN
<222> LOCATION: (77)...(87)
<223> OTHER INFORMATION: First hairpin loop domain
<220> FEATURE:
<221> NAME/KEY: DOMAIN
<222> LOCATION: (100)...(108)
<223> OTHER INFORMATION: Second hairpin loop domain

<400> SEQUENCE: 18

```
Met Met Pro Arg Arg Ala Leu Leu Phe Ala Ala Val Leu Leu Ala Ala
 1               5                  10                  15

Ser Ala Ala Ala Val Ser Gly Phe His Leu Gly Gly Asp Glu Ser Gly
                20                  25                  30

Leu Val Arg Gly Val Leu Ala Ala Leu Arg Glu Arg Ala Glu Ala Glu
            35                  40                  45

Asp Ala Ala Arg Phe Ala Val Ala His Tyr Asn Lys Asn Gln Gly Ala
        50                  55                  60

Ala Leu Glu Phe Thr Arg Val Leu Lys Ser Lys Arg Gln Val Val Thr
 65                  70                  75                  80

Gly Thr Leu His Asp Leu Ile Leu Glu Ala Ala Asp Ala Gly Lys Lys
                85                  90                  95

Ser Val Tyr Arg Ala Lys Val Trp Val Lys Ser Trp Glu Asp Phe Lys
            100                 105                 110

Ser Val Val Glu Phe Arg Leu Val Gly Asp Ser Glu Ser Glu Pro Glu
        115                 120                 125

Pro Ser Val Ala Ser Asp Val Ser Ser Gly Gln Ala Ile Ala Lys Leu
    130                 135                 140

Ser Leu Glu Ala Asp Ile Val Gln Glu Glu Ala Arg Leu His Thr Ile
145                 150                 155                 160

Glu Asn Asp Gly Leu Ser Gly Asp Phe Thr Ser Ser Ser Ser
                165                 170
```

<210> SEQ ID NO 19
<211> LENGTH: 716
<212> TYPE: DNA

-continued

```
<213> ORGANISM: Zea mays
<220> FEATURE:
<221> NAME/KEY: CDS
<222> LOCATION: (54)...(578)

<400> SEQUENCE: 19
caagccagca gcacaagaac cagagtccat agacatccat caagccaaga aga atg          56
                                                            Met
                                                            1 gca ttc ctc agc acg aac gcg ttg atg agc gtc ccc atc acg gcg gca        104
Ala Phe Leu Ser Thr Asn Ala Leu Met Ser Val Pro Ile Thr Ala Ala
          5                  10                  15 gcc gct cct cgc cac cgc cgc agc ttg gtc gtg gta agg gcc gcg gcc        152
Ala Ala Pro Arg His Arg Arg Ser Leu Val Val Val Arg Ala Ala Ala
             20                  25                  30 gtc aaa tct aac gag cac ctg cag gaa gag caa gca tcc gtg gcc gac        200
Val Lys Ser Asn Glu His Leu Gln Glu Glu Gln Ala Ser Val Ala Asp
 35                  40                  45 gga gct cgt ggg cgt cgc cga gcc atg gtg ttg ttg gcc gcc acc gct        248
Gly Ala Arg Gly Arg Arg Arg Ala Met Val Leu Leu Ala Ala Thr Ala
 50                  55                  60                  65 gct gtc act gga tca tcc gta gcc atc tgc agg tct gct aga gct gca        296
Ala Val Thr Gly Ser Ser Val Ala Ile Cys Arg Ser Ala Arg Ala Ala
                 70                  75                  80 ggt gtc acc acg ctg agc gga cag tat gtc aaa ata gag aac gtc aag        344
Gly Val Thr Thr Leu Ser Gly Gln Tyr Val Lys Ile Glu Asn Val Lys
             85                  90                  95 gac cca tat gtc cag ggt gtc ggc gaa tgg gct gtc aag gag cac aac        392
Asp Pro Tyr Val Gln Gly Val Gly Glu Trp Ala Val Lys Glu His Asn
        100                 105                 110 agg cag act ggt gag agc ttg cag ttc gcc gag gtg gtc agt ggc atg        440
Arg Gln Thr Gly Glu Ser Leu Gln Phe Ala Glu Val Val Ser Gly Met
115                 120                 125 gaa cag gtg gtc gcc ggc acc aac tac aag ctc aac ctc gca acc aaa        488
Glu Gln Val Val Ala Gly Thr Asn Tyr Lys Leu Asn Leu Ala Thr Lys
130                 135                 140                 145 gat cca acg tcg tct tac caa gca gtt gtg ttt gat ccg ttg cca aac        536
Asp Pro Thr Ser Ser Tyr Gln Ala Val Val Phe Asp Pro Leu Pro Asn
                150                 155                 160 tcc agc aaa aat cgc cag ctc atg tcc ttc aag tct att tga               578
Ser Ser Lys Asn Arg Gln Leu Met Ser Phe Lys Ser Ile *
                165                 170 tctctctctc tcacgcctgc gtgggttgca gaataaatgt gtggccttgt atttgtgatg      638
aggaaataat aatggaataa atgtgtggcc ttgtatttgt caaaaaaaaa aaaaaaaaaa      698
aaaaaaaaaa aaaaaaaa                                                    716

<210> SEQ ID NO 20
<211> LENGTH: 174
<212> TYPE: PRT
<213> ORGANISM: Zea mays
<220> FEATURE:
<221> NAME/KEY: DOMAIN
<222> LOCATION: (104)...(113)
<223> OTHER INFORMATION: N-terminal alpha-1 helix domain
<220> FEATURE:
<221> NAME/KEY: DOMAIN
<222> LOCATION: (131)...(141)
<223> OTHER INFORMATION: First hairpin loop domain
<220> FEATURE:
<221> NAME/KEY: DOMAIN
<222> LOCATION: (152)...(160)
<223> OTHER INFORMATION: Second hairpin loop domain
```

-continued

```
<400> SEQUENCE: 20

Met Ala Phe Leu Ser Thr Asn Ala Leu Met Ser Val Pro Ile Thr Ala
 1               5                  10                  15

Ala Ala Ala Pro Arg His Arg Arg Ser Leu Val Val Arg Ala Ala
             20                  25                  30

Ala Val Lys Ser Asn Glu His Leu Gln Glu Glu Gln Ala Ser Val Ala
         35                  40                  45

Asp Gly Ala Arg Gly Arg Arg Ala Met Val Leu Leu Ala Ala Thr
     50                  55                  60

Ala Ala Val Thr Gly Ser Ser Val Ala Ile Cys Arg Ser Ala Arg Ala
65                  70                  75                  80

Ala Gly Val Thr Thr Leu Ser Gly Gln Tyr Val Lys Ile Glu Asn Val
                 85                  90                  95

Lys Asp Pro Tyr Val Gln Gly Val Gly Glu Trp Ala Val Lys Glu His
            100                 105                 110

Asn Arg Gln Thr Gly Glu Ser Leu Gln Phe Ala Glu Val Val Ser Gly
            115                 120                 125

Met Glu Gln Val Val Ala Gly Thr Asn Tyr Lys Leu Asn Leu Ala Thr
130                 135                 140

Lys Asp Pro Thr Ser Ser Tyr Gln Ala Val Val Phe Asp Pro Leu Pro
145                 150                 155                 160

Asn Ser Ser Lys Asn Arg Gln Leu Met Ser Phe Lys Ser Ile
                165                 170

<210> SEQ ID NO 21
<211> LENGTH: 1102
<212> TYPE: DNA
<213> ORGANISM: Zea mays
<220> FEATURE:
<221> NAME/KEY: CDS
<222> LOCATION: (76)...(813)

<400> SEQUENCE: 21
agcaaagcaa agccaaagca atctcaagtg aatcaaaccg ccagacttcg cagtcctcct      60
ccccactacc agagc atg cgc gtt gcc gcg acc cga gcc gcc gcc gcc gct     111
                Met Arg Val Ala Ala Thr Arg Ala Ala Ala Ala Ala
                 1               5                  10 cac cct ccg agc gcc ttc ctg ctc ctc ctg tta ctc ctc ggt tgc gcg     159
His Pro Pro Ser Ala Phe Leu Leu Leu Leu Leu Leu Leu Gly Cys Ala
            15                  20                  25 tcc ctc gcg atc gga gga gca gcc atg gcc ggc cac gtc ctc ggc ggc     207
Ser Leu Ala Ile Gly Gly Ala Ala Met Ala Gly His Val Leu Gly Gly
         30                  35                  40 gtg aag gag aac cca gcc gcg gcc aac agc gcc gag tcc gac ggg ctc     255
Val Lys Glu Asn Pro Ala Ala Ala Asn Ser Ala Glu Ser Asp Gly Leu
 45                  50                  55                  60 ggc cgc ttc gcc gtc gat gag cac aac agg cgc gag aac gcg ctg ctg     303
Gly Arg Phe Ala Val Asp Glu His Asn Arg Arg Glu Asn Ala Leu Leu
                 65                  70                  75 gag ttc gtg cgc gtg gtg gag gcc aag gag cag gtg gtg gcc ggc acg     351
Glu Phe Val Arg Val Val Glu Ala Lys Glu Gln Val Val Ala Gly Thr
             80                  85                  90 ctg cac cac ctc acg ctc gag gcc gtc gag gcc ggg agg aag aag ctc     399
Leu His His Leu Thr Leu Glu Ala Val Glu Ala Gly Arg Lys Lys Leu
         95                 100                 105 tac gag gcc aag gtc tgg gtc aag cca tgg ctc gac ttc aag gag ctc     447
Tyr Glu Ala Lys Val Trp Val Lys Pro Trp Leu Asp Phe Lys Glu Leu
    110                 115                 120
```

```
cag gaa ttc agc cac aag ggg gac gcc acc gcc ttc acc aac gcc gac     495
Gln Glu Phe Ser His Lys Gly Asp Ala Thr Ala Phe Thr Asn Ala Asp
125                 130                 135                 140 ctc ggc gcc aag caa ggt gga cat gag cct ggt tgg cgt gag gtt cca     543
Leu Gly Ala Lys Gln Gly Gly His Glu Pro Gly Trp Arg Glu Val Pro
            145                 150                 155 gta gag gat cct gtg gtc aaa gat gct gca cac cat gct gtg aaa tcg     591
Val Glu Asp Pro Val Val Lys Asp Ala Ala His His Ala Val Lys Ser
160                 165                 170 atc caa gag agg tcc aac tcc ctg ttt ccc tac gaa ctt ctc gag atc     639
Ile Gln Glu Arg Ser Asn Ser Leu Phe Pro Tyr Glu Leu Leu Glu Ile
        175                 180                 185 ctt cgt gcc cat gca cag gtt gtg gaa gac ttt gca aaa ttt gac att     687
Leu Arg Ala His Ala Gln Val Val Glu Asp Phe Ala Lys Phe Asp Ile
        190                 195                 200 ctg atg aaa ctg aag aga ggc agc aag gag gag aag atc aaa gcc gag     735
Leu Met Lys Leu Lys Arg Gly Ser Lys Glu Glu Lys Ile Lys Ala Glu
205                 210                 215                 220 gtc cat aag agc ctg gaa ggg gcc ttt gtg cta aac cag cat cag ccg     783
Val His Lys Ser Leu Glu Gly Ala Phe Val Leu Asn Gln His Gln Pro
                225                 230                 235 gcg gag cat gat gag tcg agc agc cag tga actgacgtaa ctgtgtgagc       833
Ala Glu His Asp Glu Ser Ser Ser Gln *
            240                 245 tgtagtagta acgtacttcg tgttacgtag aagaataagg agaaaacgac caatccggtt    893
ttatctggat gtcatgtatg gtcgacggtc gttgctggct tggcttccga acgcagcagg    953
catactggtg ctggaagacg gtacctgctg tcgcacttgc cgttataata ggcattggaa   1013
cttgtcgatt tcgggagctg atctgtttgt accgtattgt ttatttataa tatgatggat   1073
cgtatgttga taaaaaaaaa aaaaaaaaa                                     1102

<210> SEQ ID NO 22
<211> LENGTH: 245
<212> TYPE: PRT
<213> ORGANISM: Zea mays
<220> FEATURE:
<221> NAME/KEY: DOMAIN
<222> LOCATION: (60)...(69)
<223> OTHER INFORMATION: N-terminal alpha-1 helix domain
<220> FEATURE:
<221> NAME/KEY: DOMAIN
<222> LOCATION: (87)...(97)
<223> OTHER INFORMATION: First hairpin loop domain
<220> FEATURE:
<221> NAME/KEY: DOMAIN
<222> LOCATION: (110)...(118)
<223> OTHER INFORMATION: Second hairpin loop domain

<400> SEQUENCE: 22

Met Arg Val Ala Ala Thr Arg Ala Ala Ala Ala His Pro Pro Ser
 1               5                  10                  15

Ala Phe Leu Leu Leu Leu Leu Leu Gly Cys Ala Ser Leu Ala Ile
            20                  25                  30

Gly Gly Ala Ala Met Ala Gly His Val Leu Gly Gly Val Lys Glu Asn
            35                  40                  45

Pro Ala Ala Ala Asn Ser Ala Glu Ser Asp Gly Leu Gly Arg Phe Ala
        50                  55                  60

Val Asp Glu His Asn Arg Arg Glu Asn Ala Leu Leu Glu Phe Val Arg
65                  70                  75                  80

Val Val Glu Ala Lys Glu Gln Val Val Ala Gly Thr Leu His His Leu
```

```
                    85                  90                  95
Thr Leu Glu Ala Val Glu Ala Gly Arg Lys Lys Leu Tyr Glu Ala Lys
            100                 105                 110

Val Trp Val Lys Pro Trp Leu Asp Phe Lys Glu Leu Gln Glu Phe Ser
        115                 120                 125

His Lys Gly Asp Ala Thr Ala Phe Thr Asn Ala Asp Leu Gly Ala Lys
    130                 135                 140

Gln Gly Gly His Glu Pro Gly Trp Arg Glu Val Pro Val Glu Asp Pro
145                 150                 155                 160

Val Val Lys Asp Ala Ala His His Ala Val Lys Ser Ile Gln Glu Arg
            165                 170                 175

Ser Asn Ser Leu Phe Pro Tyr Glu Leu Leu Glu Ile Leu Arg Ala His
        180                 185                 190

Ala Gln Val Val Glu Asp Phe Ala Lys Phe Asp Ile Leu Met Lys Leu
    195                 200                 205

Lys Arg Gly Ser Lys Glu Lys Ile Lys Ala Glu Val His Lys Ser
210                 215                 220

Leu Glu Gly Ala Phe Val Leu Asn Gln His Gln Pro Ala Glu His Asp
225                 230                 235                 240

Glu Ser Ser Ser Gln
                245

<210> SEQ ID NO 23
<211> LENGTH: 761
<212> TYPE: DNA
<213> ORGANISM: Zea mays
<220> FEATURE:
<221> NAME/KEY: CDS
<222> LOCATION: (61)...(444)

<400> SEQUENCE: 23
ggcctattct ccattgtgga accaacaaat ctccaagctc tcccaattta gaaacgagag      60 atg gcc atg acg atg acc ctc ggt tcc atg ctc atc gcc gcc gcc gca     108
Met Ala Met Thr Met Thr Leu Gly Ser Met Leu Ile Ala Ala Ala Ala
  1               5                  10                  15 gtt gtc ggc ctg tgc tcc gtc gct ccc gct gca tca gcg cgc gag gag     156
Val Val Gly Leu Cys Ser Val Ala Pro Ala Ala Ser Ala Arg Glu Glu
             20                  25                  30 cca cta cag ccg cag atc gtc ggc ggg tgg aaa ccg atc aag aac gtg     204
Pro Leu Gln Pro Gln Ile Val Gly Gly Trp Lys Pro Ile Lys Asn Val
         35                  40                  45 aac gac ccc cac gtc caa gag atc ggc cgg tgg gcg gtt tcg gag cac     252
Asn Asp Pro His Val Gln Glu Ile Gly Arg Trp Ala Val Ser Glu His
     50                  55                  60 atc aag acg gcc aac gac ggg ctg ggc ttc ggc agg gtg gtg agc ggc     300
Ile Lys Thr Ala Asn Asp Gly Leu Gly Phe Gly Arg Val Val Ser Gly
 65                  70                  75                  80 gag gag cag atc gtc gcc ggg aaa aac tac agg ctg cgc att caa gcg     348
Glu Glu Gln Ile Val Ala Gly Lys Asn Tyr Arg Leu Arg Ile Gln Ala
                 85                  90                  95 acg aag gtc ggc ggg cag aag gcg atg tac cgt gcg gtg gtg tac gag     396
Thr Lys Val Gly Gly Gln Lys Ala Met Tyr Arg Ala Val Val Tyr Glu
            100                 105                 110 cag ctt acc aac aca agg cag ctc cta tcg ttt gat ccg gcg aac tga    444
Gln Leu Thr Asn Thr Arg Gln Leu Leu Ser Phe Asp Pro Ala Asn  *
        115                 120                 125 tctaattatg gcgtcgctgg acaacaacgg ttcgagtcgc cttctaggat ttcagattaa     504
```

-continued

```
aattctgcaa gtaccgcgtg taacaaacca actgatgtgt tgccctagtc atatcgtgga    564
attagaataa gatccagcct atctttatct gtttttaatg ttaaaaggaa ataatgaact    624
cagagtcgag ataaaattat cctcccaaaa aaaaaaaaaa aaaaaaaaaa aaaaaaaaaa    684
aaaaaaaaaa aaaaaaaaaa aaaaaaaaaa aaaaaaaaaa aaaaaaaaaa aaaaaaaaaa    744
aaaaaaaaaa aaaaaa                                                    761
```

<210> SEQ ID NO 24
<211> LENGTH: 127
<212> TYPE: PRT
<213> ORGANISM: Zea mays
<220> FEATURE:
<221> NAME/KEY: DOMAIN
<222> LOCATION: (56)...(65)
<223> OTHER INFORMATION: N-terminal alpha-1 helix domain
<220> FEATURE:
<221> NAME/KEY: DOMAIN
<222> LOCATION: (83)...(93)
<223> OTHER INFORMATION: First hairpin loop domain
<220> FEATURE:
<221> NAME/KEY: DOMAIN
<222> LOCATION: (107)...(115)
<223> OTHER INFORMATION: Second hairpin loop domain

<400> SEQUENCE: 24

```
Met Ala Met Thr Met Thr Leu Gly Ser Met Leu Ile Ala Ala Ala
 1               5                  10                  15

Val Val Gly Leu Cys Ser Val Ala Pro Ala Ala Ser Ala Arg Glu Glu
                20                  25                  30

Pro Leu Gln Pro Gln Ile Val Gly Gly Trp Lys Pro Ile Lys Asn Val
            35                  40                  45

Asn Asp Pro His Val Gln Glu Ile Gly Arg Trp Ala Val Ser Glu His
        50                  55                  60

Ile Lys Thr Ala Asn Asp Gly Leu Gly Phe Gly Arg Val Val Ser Gly
65                  70                  75                  80

Glu Glu Gln Ile Val Ala Gly Lys Asn Tyr Arg Leu Arg Ile Gln Ala
                85                  90                  95

Thr Lys Val Gly Gly Gln Lys Ala Met Tyr Arg Ala Val Val Tyr Glu
            100                 105                 110

Gln Leu Thr Asn Thr Arg Gln Leu Leu Ser Phe Asp Pro Ala Asn
        115                 120                 125
```

<210> SEQ ID NO 25
<211> LENGTH: 749
<212> TYPE: DNA
<213> ORGANISM: Zea mays
<220> FEATURE:
<221> NAME/KEY: CDS
<222> LOCATION: (75)...(527)

<400> SEQUENCE: 25

```
acactgacac acacaccacc accacggcac cgctagtgag aagcggagcg ggaggacacg    60
cggcgcggac tgcg atg gct cgt gcg ctc ggc gct tgc gtg ctg ctc gcc   110
              Met Ala Arg Ala Leu Gly Ala Cys Val Leu Leu Ala
                1               5                  10 gtc ctg ctc ggt gcc ctg gcg ccg gcg gcg gcc gcg cgc gcc cac gac   158
Val Leu Leu Gly Ala Leu Ala Pro Ala Ala Ala Ala Arg Ala His Asp
            15                  20                  25 gac cag ggc agc ggg gcc ggc ata cgg cag ccg agc ggc gag tac cgc   206
Asp Gln Gly Ser Gly Ala Gly Ile Arg Gln Pro Ser Gly Glu Tyr Arg
        30                  35                  40
```

|  |  |
|---|---|
| ggg agg aag gtg ggg gcc agg acg gag gtg cgg gac gtg gag ggc gac<br>Gly Arg Lys Val Gly Ala Arg Thr Glu Val Arg Asp Val Glu Gly Asp<br>    45                  50                    55                  60 | 254 |
| ggc gag gtg cag gag ctc ggc cgg ttc tcc gtc gcc gag tac aac cgg<br>Gly Glu Val Gln Glu Leu Gly Arg Phe Ser Val Ala Glu Tyr Asn Arg<br>                  65                    70                    75 | 302 |
| cag ctc cga gaa ggt ggc ggc ggc ggc agg ctc gag ttc ggc agg<br>Gln Leu Arg Glu Gly Gly Gly Gly Gly Arg Leu Glu Phe Gly Arg<br>              80                    85                    90 | 350 |
| gtg gtg gcg gcg cag cgg cag gtg gtg tcg ggg ctc aag tac tac ctc<br>Val Val Ala Ala Gln Arg Gln Val Val Ser Gly Leu Lys Tyr Tyr Leu<br>                95                   100                 105 | 398 |
| cgc gtc gtg gcc gtg gag gag ggc ggc gcg ggg aac ggc ggc gag cgc<br>Arg Val Val Ala Val Glu Glu Gly Gly Ala Gly Asn Gly Gly Glu Arg<br>        110                    115                 120 | 446 |
| gtg ttc gac gcc gtc gtc gtc gtc aag ccc tgg ctc gac tcg cgc acc<br>Val Phe Asp Ala Val Val Val Val Lys Pro Trp Leu Asp Ser Arg Thr<br>125                 130                 135               140 | 494 |
| ctg ctc acg ttc gcg ccg gcg gcc gcc aag taa gcgcggcgct accgccggtg<br>Leu Leu Thr Phe Ala Pro Ala Ala Ala Lys *<br>               145                 150 | 547 |
| tagacgtcta gtgtagtatc tctggtctgc ccttctcgga gaccatggac gctgaataaa | 607 |
| gtcttgtgtg ttttgtataa gcgaagcgta ctagagagtg aagatggacg aactctgcgc | 667 |
| tgccgcgcgc agatcgatgt tttttttttc aaaggctgtt gcacaaatag aggagacgag | 727 |
| agtctgagac tgagagagaa ta | 749 |

<210> SEQ ID NO 26
<211> LENGTH: 150
<212> TYPE: PRT
<213> ORGANISM: Zea mays
<220> FEATURE:
<221> NAME/KEY: DOMAIN
<222> LOCATION: (66)...(75)
<223> OTHER INFORMATION: N-terminal alpha-1 helix domain
<220> FEATURE:
<221> NAME/KEY: DOMAIN
<222> LOCATION: (99)...(109)
<223> OTHER INFORMATION: First hairpin loop domain
<220> FEATURE:
<221> NAME/KEY: DOMAIN
<222> LOCATION: (127)...(135)
<223> OTHER INFORMATION: Second hairpin loop domain
<400> SEQUENCE: 26

Met Ala Arg Ala Leu Gly Ala Cys Val Leu Leu Ala Val Leu Leu Gly
1               5                   10                  15

Ala Leu Ala Pro Ala Ala Ala Ala Arg Ala His Asp Asp Gln Gly Ser
            20                  25                  30

Gly Ala Gly Ile Arg Gln Pro Ser Gly Glu Tyr Arg Gly Arg Lys Val
        35                  40                  45

Gly Ala Arg Thr Glu Val Arg Asp Val Glu Gly Asp Gly Glu Val Gln
    50                  55                  60

Glu Leu Gly Arg Phe Ser Val Ala Glu Tyr Asn Arg Gln Leu Arg Glu
65                  70                  75                  80

Gly Gly Gly Gly Gly Arg Leu Glu Phe Gly Arg Val Val Ala Ala
                85                  90                  95

Gln Arg Gln Val Val Ser Gly Leu Lys Tyr Tyr Leu Arg Val Val Ala
            100                 105                 110

Val Glu Glu Gly Gly Ala Gly Asn Gly Gly Glu Arg Val Phe Asp Ala
        115                 120                 125

```
Val Val Val Lys Pro Trp Leu Asp Ser Arg Thr Leu Leu Thr Phe
    130             135                 140

Ala Pro Ala Ala Lys
145             150

<210> SEQ ID NO 27
<211> LENGTH: 1140
<212> TYPE: DNA
<213> ORGANISM: Glycine max
<220> FEATURE:
<221> NAME/KEY: CDS
<222> LOCATION: (65)...(802)

<400> SEQUENCE: 27
ccaaacaaac aaataaagca aaaggccttt ttattccaaa gcaaggaagg aagaaataaa      60 ccga atg aga gca tta acc tct tct tct tcc act ttc att cca aag cgt     109
     Met Arg Ala Leu Thr Ser Ser Ser Ser Thr Phe Ile Pro Lys Arg
      1               5                  10                  15 tat tcc ttc ttc ttc ttc ctc tcc att ctc ttc gct ctt cga tcc tcg     157
Tyr Ser Phe Phe Phe Phe Leu Ser Ile Leu Phe Ala Leu Arg Ser Ser
                 20                  25                  30 tcc ggg ggc tgc tcc gaa tac cac cac cac cac gcg ccg atg gcc acg     205
Ser Gly Gly Cys Ser Glu Tyr His His His His Ala Pro Met Ala Thr
             35                  40                  45 ata gga ggc tta cgc gac tcc caa ggc tct cag aac agc gtc caa acc     253
Ile Gly Gly Leu Arg Asp Ser Gln Gly Ser Gln Asn Ser Val Gln Thr
         50                  55                  60 gag gcc ctc gct cga ttc gcc gtc gat gaa cac aac aag aag cag aat     301
Glu Ala Leu Ala Arg Phe Ala Val Asp Glu His Asn Lys Lys Gln Asn
     65                  70                  75 tca ctt ctg gag ttt tct agg gtg gtg agg aca cag gaa cag gtt gtt     349
Ser Leu Leu Glu Phe Ser Arg Val Val Arg Thr Gln Glu Gln Val Val
 80                  85                  90                  95 gcg gga acc ctg cat cac ctt act ctc gaa gct att gag gca ggt gag     397
Ala Gly Thr Leu His His Leu Thr Leu Glu Ala Ile Glu Ala Gly Glu
                100                 105                 110 aag aag ctc tat gaa gcc aag gtg tgg gtg aaa cca tgg ttg aat ttc     445
Lys Lys Leu Tyr Glu Ala Lys Val Trp Val Lys Pro Trp Leu Asn Phe
            115                 120                 125 aaa gaa ctc caa gag ttc aag cct gct ggt gat gta cca tca ttt acc     493
Lys Glu Leu Gln Glu Phe Lys Pro Ala Gly Asp Val Pro Ser Phe Thr
        130                 135                 140 tct gct gat ctt ggt gtc aaa aag gat ggt cac caa cct gga tgg caa     541
Ser Ala Asp Leu Gly Val Lys Lys Asp Gly His Gln Pro Gly Trp Gln
145                 150                 155 tct gtg cca aca cat gac cct caa gtt cag gat gca gca aat cat gcg     589
Ser Val Pro Thr His Asp Pro Gln Val Gln Asp Ala Ala Asn His Ala
160                 165                 170                 175 atc aag act atc cag caa agg tct aat tca cta gta ccc tat gag ctt     637
Ile Lys Thr Ile Gln Gln Arg Ser Asn Ser Leu Val Pro Tyr Glu Leu
                180                 185                 190 cat gag gtt gct gat gca aag gct gag gtc att gat gac ttt gcc aag     685
His Glu Val Ala Asp Ala Lys Ala Glu Val Ile Asp Asp Phe Ala Lys
            195                 200                 205 ttt aat ctg ctt ctc aaa gtc aag agg gga cag aag gaa gag aag ttc     733
Phe Asn Leu Leu Leu Lys Val Lys Arg Gly Gln Lys Glu Glu Lys Phe
        210                 215                 220 aag gta gag gta cat aag aat aac caa ggt ggg ttc cat cta aat cag     781
Lys Val Glu Val His Lys Asn Asn Gln Gly Gly Phe His Leu Asn Gln
225                 230                 235
```

```
atg gaa caa gat cat tcc taa ttctgatcgg aagtttggcc acgctagcag      832
Met Glu Gln Asp His Ser  *
240                 245 tataggcctg ggtggcacct aaaatatacc ttttttttc agtggggtgt atgaatctta   892
ttatctatgc tatacataat tatatactaa tcgggtattg ttcttatctc tgtctcagca   952
agtatgttag tgcttacccc tttctctaag ccttggcaga taagttttcc tatgtgtatt  1012
ggctttatta actgggaagc taccaagtta cattagtacc tttgtaacgt aaatatttac  1072
ttaacataaa aatgtggatg ttgaccattt gcatttaaaa aaaaaaaaaa aaaaaaaaa   1132 aaaaaaaa                                                          1140
```

<210> SEQ ID NO 28
<211> LENGTH: 245
<212> TYPE: PRT
<213> ORGANISM: Glycine max
<220> FEATURE:
<221> NAME/KEY: DOMAIN
<222> LOCATION: (66)...(75)
<223> OTHER INFORMATION: N-terminal alpha-1 helix domain
<220> FEATURE:
<221> NAME/KEY: DOMAIN
<222> LOCATION: (93)...(103)
<223> OTHER INFORMATION: First hairpin loop domain
<220> FEATURE:
<221> NAME/KEY: DOMAIN
<222> LOCATION: (116)...(124)
<223> OTHER INFORMATION: Second hairpin loop domain

<400> SEQUENCE: 28

```
Met Arg Ala Leu Thr Ser Ser Ser Thr Phe Ile Pro Lys Arg Tyr
 1               5                  10                  15

Ser Phe Phe Phe Phe Leu Ser Ile Leu Phe Ala Leu Arg Ser Ser Ser
                20                  25                  30

Gly Gly Cys Ser Glu Tyr His His His Ala Pro Met Ala Thr Ile
            35                  40                  45

Gly Gly Leu Arg Asp Ser Gln Gly Ser Gln Asn Ser Val Gln Thr Glu
        50                  55                  60

Ala Leu Ala Arg Phe Ala Val Asp Glu His Asn Lys Lys Gln Asn Ser
65                  70                  75                  80

Leu Leu Glu Phe Ser Arg Val Val Arg Thr Gln Glu Gln Val Val Ala
                85                  90                  95

Gly Thr Leu His His Leu Thr Leu Glu Ala Ile Glu Ala Gly Glu Lys
            100                 105                 110

Lys Leu Tyr Glu Ala Lys Val Trp Val Lys Pro Trp Leu Asn Phe Lys
        115                 120                 125

Glu Leu Gln Glu Phe Lys Pro Ala Gly Asp Val Pro Ser Phe Thr Ser
    130                 135                 140

Ala Asp Leu Gly Val Lys Lys Asp Gly His Gln Pro Gly Trp Gln Ser
145                 150                 155                 160

Val Pro Thr His Asp Pro Gln Val Gln Asp Ala Ala Asn His Ala Ile
                165                 170                 175

Lys Thr Ile Gln Gln Arg Ser Asn Ser Leu Val Pro Tyr Glu Leu His
            180                 185                 190

Glu Val Ala Asp Ala Lys Ala Glu Val Ile Asp Asp Phe Ala Lys Phe
        195                 200                 205

Asn Leu Leu Leu Lys Val Lys Arg Gly Gln Lys Glu Glu Lys Phe Lys
    210                 215                 220
```

```
Val Glu Val His Lys Asn Asn Gln Gly Gly Phe His Leu Asn Gln Met
225                 230                 235                 240

Glu Gln Asp His Ser
            245

<210> SEQ ID NO 29
<211> LENGTH: 552
<212> TYPE: DNA
<213> ORGANISM: Glycine max
<220> FEATURE:
<221> NAME/KEY: CDS
<222> LOCATION: (9)...(302)

<400> SEQUENCE: 29 gagagaga atg gca gca ctt ggt ggg aat cgt gat gtg aca gga agc cag      50
         Met Ala Ala Leu Gly Gly Asn Arg Asp Val Thr Gly Ser Gln
           1               5                  10 aac agc gtt gag atc gat gct cta gct cgc ttt gct gtt gaa gaa cac      98
Asn Ser Val Glu Ile Asp Ala Leu Ala Arg Phe Ala Val Glu Glu His
 15              20                  25                  30 aac aaa aaa cag aat gcc ctt ttg gag ttt gaa aag gtg gta act gcg     146
Asn Lys Lys Gln Asn Ala Leu Leu Glu Phe Glu Lys Val Val Thr Ala
             35                  40                  45 aaa cag caa gtg gtt tct ggt acc ttg tac acc atc act ttg gag gca     194
Lys Gln Gln Val Val Ser Gly Thr Leu Tyr Thr Ile Thr Leu Glu Ala
         50                  55                  60 aaa gat ggt ggg caa aag aag gtt tat gaa gcc aaa gtt tgg gag aag     242
Lys Asp Gly Gly Gln Lys Lys Val Tyr Glu Ala Lys Val Trp Glu Lys
     65                  70                  75 tca tgg ttg aac ttc aag gag gtg caa gag ttc aag ctt gtt gga gat     290
Ser Trp Leu Asn Phe Lys Glu Val Gln Glu Phe Lys Leu Val Gly Asp
 80                  85                  90 gca cct gca tag tctagtgctt aattaggttg ctgaagagtg aagaatgaga         342
Ala Pro Ala  *
 95 cagcctggtt cgaaggggaa aagcctaagg atatatcaaa ggatcctata tgtataaaat   402 aaatgttgct ttttaccctt cggtattgat atctgaagtc taatttgaca tcctatatat   462 gaatatatga tctatgtgtt tctttctctc aaaaaaaaaa aaaaaaaaaa aaaaaaaaaa   522 aaaaaaaaaa aaaaaaaaaa aaaaaaaaaa                                    552

<210> SEQ ID NO 30
<211> LENGTH: 97
<212> TYPE: PRT
<213> ORGANISM: Glycine max
<220> FEATURE:
<221> NAME/KEY: DOMAIN
<222> LOCATION: (22)...(31)
<223> OTHER INFORMATION: N-terminal alpha-1 helix domain
<220> FEATURE:
<221> NAME/KEY: DOMAIN
<222> LOCATION: (49)...(59)
<223> OTHER INFORMATION: First hairpin loop domain
<220> FEATURE:
<221> NAME/KEY: DOMAIN
<222> LOCATION: (72)...(80)
<223> OTHER INFORMATION: Second hairpin loop domain

<400> SEQUENCE: 30

Met Ala Ala Leu Gly Gly Asn Arg Asp Val Thr Gly Ser Gln Asn Ser
  1               5                  10                  15

Val Glu Ile Asp Ala Leu Ala Arg Phe Ala Val Glu Glu His Asn Lys
             20                  25                  30
```

-continued

```
Lys Gln Asn Ala Leu Leu Glu Phe Glu Lys Val Val Thr Ala Lys Gln
         35                  40                  45
Gln Val Val Ser Gly Thr Leu Tyr Thr Ile Thr Leu Glu Ala Lys Asp
 50                  55                  60
Gly Gly Gln Lys Lys Val Tyr Glu Ala Lys Val Trp Glu Lys Ser Trp
 65                  70                  75                  80
Leu Asn Phe Lys Glu Val Gln Glu Phe Lys Leu Val Gly Asp Ala Pro
                 85                  90                  95
Ala
```

<210> SEQ ID NO 31
<211> LENGTH: 484
<212> TYPE: DNA
<213> ORGANISM: Glycine max
<220> FEATURE:
<221> NAME/KEY: CDS
<222> LOCATION: (32)...(343)

<400> SEQUENCE: 31

```
gaaagaagat caaaagaaaa aagagaaaca a atg gca gca ctg ggt ggc ttt       52
                                   Met Ala Ala Leu Gly Gly Phe
                                     1               5 acc gac atc acc gga gca cag aac agc atc gat atc gaa aat ctc gct    100
Thr Asp Ile Thr Gly Ala Gln Asn Ser Ile Asp Ile Glu Asn Leu Ala
         10                  15                  20 cgc ttt gct gtt gat gaa cac aac aaa aaa gag aat gca gtt ctg gag    148
Arg Phe Ala Val Asp Glu His Asn Lys Lys Glu Asn Ala Val Leu Glu
     25                  30                  35 ttt gtg agg gtg att agt gca aag aaa caa gtg gtt tct ggc acc ttg    196
Phe Val Arg Val Ile Ser Ala Lys Lys Gln Val Val Ser Gly Thr Leu
 40                  45                  50                  55 tac tat atc act ttg gag gca aat gat ggt gtg acg aaa aag gtt tat    244
Tyr Tyr Ile Thr Leu Glu Ala Asn Asp Gly Val Thr Lys Lys Val Tyr
                 60                  65                  70 gaa act aag gtg ttg gag aaa cca tgg ttg aac atc aag gag gtt cag    292
Glu Thr Lys Val Leu Glu Lys Pro Trp Leu Asn Ile Lys Glu Val Gln
             75                  80                  85 gaa ttc aag ccc atc act gtt gct gtt aat cct ctt tcg gtg acg gtc    340
Glu Phe Lys Pro Ile Thr Val Ala Val Asn Pro Leu Ser Val Thr Val
         90                  95                 100 tag cacatagcta ggttatggaa gtgactagct tggccgcaag agtaataata          393
 * tgtatgaact gaataaatgt acctattaac tctacaaacg gtgtggggtt gtgcatgttt   453
gccatcctat atatttcagt ataaatattg c                                  484
```

<210> SEQ ID NO 32
<211> LENGTH: 103
<212> TYPE: PRT
<213> ORGANISM: Glycine max
<220> FEATURE:
<221> NAME/KEY: DOMAIN
<222> LOCATION: (22)...(31)
<223> OTHER INFORMATION: N-terminal alpha-1 helix domain
<220> FEATURE:
<221> NAME/KEY: DOMAIN
<222> LOCATION: (49)...(59)
<223> OTHER INFORMATION: First hairpin loop domain
<220> FEATURE:
<221> NAME/KEY: DOMAIN
<222> LOCATION: (72)...(80)
<223> OTHER INFORMATION: Second hairpin loop domain

<400> SEQUENCE: 32

-continued

```
Met Ala Ala Leu Gly Gly Phe Thr Asp Ile Thr Gly Ala Gln Asn Ser
 1               5                  10                  15

Ile Asp Ile Glu Asn Leu Ala Arg Phe Ala Val Asp Glu His Asn Lys
            20                  25                  30

Lys Glu Asn Ala Val Leu Glu Phe Val Arg Val Ile Ser Ala Lys Lys
        35                  40                  45

Gln Val Val Ser Gly Thr Leu Tyr Tyr Ile Thr Leu Glu Ala Asn Asp
    50                  55                  60

Gly Val Thr Lys Lys Val Tyr Glu Thr Lys Val Leu Glu Lys Pro Trp
65                  70                  75                  80

Leu Asn Ile Lys Glu Val Gln Glu Phe Lys Pro Ile Thr Val Ala Val
                85                  90                  95

Asn Pro Leu Ser Val Thr Val
            100
```

```
<210> SEQ ID NO 33
<211> LENGTH: 814
<212> TYPE: DNA
<213> ORGANISM: Glycine max
<220> FEATURE:
<221> NAME/KEY: CDS
<222> LOCATION: (292)...(570)

<400> SEQUENCE: 33
```

| | |
|---|---|
| ctcgtgccga attcggcacg agcagaaaca aaagtggcag tattaggtgg catcaccgaa | 60 |
| gtgcagggag ctgccaacag cgtcgagatc aacaatctcg ctcgctttgc tgtagaggaa | 120 |
| caaaacaaaa gagagaattc agttctggag tttgtgaggg tgattagtgc acagcagcaa | 180 |
| gtggtttctg gagtgaatta ctacataaca ttggaagcaa agatggtga gattaaaaat | 240 |
| gagtataaag cgaaggtttg ggagagggaa tcccaagagt tgctagaatt c atg cca | 297 |
| | Met Pro |
| | 1 |

```
aca tta ggt gca gga ggc gag atc gac cat ctc gct cgc ttt gct gta    345
Thr Leu Gly Ala Gly Gly Glu Ile Asp His Leu Ala Arg Phe Ala Val
        5                  10                  15 gag gaa caa aac aaa aga gag aat gca aat ctg gag ttt gtg ggg gtg    393
Glu Glu Gln Asn Lys Arg Glu Asn Ala Asn Leu Glu Phe Val Gly Val
    20                  25                  30 att agg gca aag cag cag gtg gtg gaa ggg ttc ata tac tac atc act    441
Ile Arg Ala Lys Gln Gln Val Val Glu Gly Phe Ile Tyr Tyr Ile Thr
35                  40                  45                  50 ttg gaa gca aaa gat ggt gaa acc aaa aat gtg tat gaa acg aag gtg    489
Leu Glu Ala Lys Asp Gly Glu Thr Lys Asn Val Tyr Glu Thr Lys Val
                55                  60                  65 tgg gtg aga tca tgg ttg aac tcc aag gag gtc ctc gaa ttc aag ccc    537
Trp Val Arg Ser Trp Leu Asn Ser Lys Glu Val Leu Glu Phe Lys Pro
            70                  75                  80 atc agt att aat cct ctt tcg gtg tcg gtc tag tctttataag gttacagaaa    590
Ile Ser Ile Asn Pro Leu Ser Val Ser Val *
                85                  90
```

| | |
|---|---|
| taaatggtcg caagctgaaa gttgtactaa aatttatttt ttataaaaaa atcgaaggta | 650 |
| gtattaaata tgttatatgt atgtattgtg cggaataaat gcagccacgt actatatata | 710 |
| atggtacata cggtgtaggg ctgtacaagt tgggcatcct atttcaatat taacgaccac | 770 |
| taataaatat taccattgga gttaaaaaaa aaaaaaaaaa aaaa | 814 |

```
<210> SEQ ID NO 34
```

```
<211> LENGTH: 92
<212> TYPE: PRT
<213> ORGANISM: Glycine max
<220> FEATURE:
<221> NAME/KEY: DOMAIN
<222> LOCATION: (13)...(22)
<223> OTHER INFORMATION: N-terminal alpha-1 helix domain
<220> FEATURE:
<221> NAME/KEY: DOMAIN
<222> LOCATION: (40)...(50)
<223> OTHER INFORMATION: First hairpin loop domain
<220> FEATURE:
<221> NAME/KEY: DOMAIN
<222> LOCATION: (63)...(71)
<223> OTHER INFORMATION: Second hairpin loop domain

<400> SEQUENCE: 34

Met Pro Thr Leu Gly Ala Gly Gly Glu Ile Asp His Leu Ala Arg Phe
 1               5                  10                  15

Ala Val Glu Glu Gln Asn Lys Arg Glu Asn Ala Asn Leu Glu Phe Val
            20                  25                  30

Gly Val Ile Arg Ala Lys Gln Gln Val Val Glu Gly Phe Ile Tyr Tyr
        35                  40                  45

Ile Thr Leu Glu Ala Lys Asp Gly Glu Thr Lys Asn Val Tyr Glu Thr
    50                  55                  60

Lys Val Trp Val Arg Ser Trp Leu Asn Ser Lys Glu Val Leu Glu Phe
65                  70                  75                  80

Lys Pro Ile Ser Ile Asn Pro Leu Ser Val Ser Val
                85                  90

<210> SEQ ID NO 35
<211> LENGTH: 504
<212> TYPE: DNA
<213> ORGANISM: Glycine max
<220> FEATURE:
<221> NAME/KEY: CDS
<222> LOCATION: (9)...(347)

<400> SEQUENCE: 35 gtttgaca atg aga cat cac tgc ctc ctt ctg gtc tcc ctg gtg ttg gtc      50
         Met Arg His His Cys Leu Leu Leu Val Ser Leu Val Leu Val
          1               5                  10 tcc tac gct gcc cgg tcg gaa tca gcg ctg ggc ggc tgg agc ccc atc       98
Ser Tyr Ala Ala Arg Ser Glu Ser Ala Leu Gly Gly Trp Ser Pro Ile
 15                  20                  25                  30 aag gac gta aac gac agc cac gtg gcg gag atc gcc aac tac gcg ctg      146
Lys Asp Val Asn Asp Ser His Val Ala Glu Ile Ala Asn Tyr Ala Leu
                 35                  40                  45 agc gag tac gac aag cgt tct ggg gcc aag ctc acc ctt gtc aag gtc      194
Ser Glu Tyr Asp Lys Arg Ser Gly Ala Lys Leu Thr Leu Val Lys Val
             50                  55                  60 gtc aag ggc gag act cag gtc gtt tcc ggc acc aac tac cgt ctc gtc      242
Val Lys Gly Glu Thr Gln Val Val Ser Gly Thr Asn Tyr Arg Leu Val
         65                  70                  75 ctc aaa gcc aag gat gga tcc gcc acg gcc agt tac gaa gcc atc gtc      290
Leu Lys Ala Lys Asp Gly Ser Ala Thr Ala Ser Tyr Glu Ala Ile Val
     80                  85                  90 tgg gag aag cct tgg ctc cat ttc atg aat ctc act tcc ttc aaa ccc      338
Trp Glu Lys Pro Trp Leu His Phe Met Asn Leu Thr Ser Phe Lys Pro
 95                 100                 105                 110 ctt cat taa tcttagatcc atactttttct tcactttctc tcttatcata              387
Leu His * tttcatgtgt tagctattct gttttttctca ataaggttcc tgtcatgtgc taattaatct   447
```

```
caaattgtat gttggattaa aaaaaaaaaa aaaaaaaaaa aaaaaaaaaa aaaaaaa        504

<210> SEQ ID NO 36
<211> LENGTH: 112
<212> TYPE: PRT
<213> ORGANISM: Glycine max
<220> FEATURE:
<221> NAME/KEY: DOMAIN
<222> LOCATION: (41)...(50)
<223> OTHER INFORMATION: N-terminal alpha-1 helix domain
<220> FEATURE:
<221> NAME/KEY: DOMAIN
<222> LOCATION: (68)...(78)
<223> OTHER INFORMATION: First hairpin loop domain
<220> FEATURE:
<221> NAME/KEY: DOMAIN
<222> LOCATION: (91)...(99)
<223> OTHER INFORMATION: Second hairpin loop domain

<400> SEQUENCE: 36

Met Arg His His Cys Leu Leu Leu Val Ser Leu Val Leu Val Ser Tyr
 1               5                  10                  15

Ala Ala Arg Ser Glu Ser Ala Leu Gly Gly Trp Ser Pro Ile Lys Asp
            20                  25                  30

Val Asn Asp Ser His Val Ala Glu Ile Ala Asn Tyr Ala Leu Ser Glu
        35                  40                  45

Tyr Asp Lys Arg Ser Gly Ala Lys Leu Thr Leu Val Lys Val Val Lys
    50                  55                  60

Gly Glu Thr Gln Val Val Ser Gly Thr Asn Tyr Arg Leu Val Leu Lys
65                  70                  75                  80

Ala Lys Asp Gly Ser Ala Thr Ala Ser Tyr Glu Ala Ile Val Trp Glu
                85                  90                  95

Lys Pro Trp Leu His Phe Met Asn Leu Thr Ser Phe Lys Pro Leu His
            100                 105                 110

<210> SEQ ID NO 37
<211> LENGTH: 708
<212> TYPE: DNA
<213> ORGANISM: Glycine max
<220> FEATURE:
<221> NAME/KEY: CDS
<222> LOCATION: (134)...(448)

<400> SEQUENCE: 37
ttactactta atttccactt ctaattaaca aagttaagca agcattgact tggtacctat        60
aagtagtaat ggctgtggct ttgacgattg tgttgagttg ctctcggttc tctcttctgc       120
atcttgtgca cga atg gtg ggg ggg aag acg gag gtc ccc gac gtg aga          169
            Met Val Gly Gly Lys Thr Glu Val Pro Asp Val Arg
             1               5                  10 aca aac agg gaa gtg caa gag ctt gga agg ttc gcg gtg gag gag tac         217
Thr Asn Arg Glu Val Gln Glu Leu Gly Arg Phe Ala Val Glu Glu Tyr
             15                  20                  25 aac cgc ggt ttg aaa cag tgg aag aac aat ggg agt gaa cag ttg aac         265
Asn Arg Gly Leu Lys Gln Trp Lys Asn Asn Gly Ser Glu Gln Leu Asn
         30                  35                  40 ttt tcg gag gtg gtg gag gcg cag caa caa gtg gtg tca gga atg aag         313
Phe Ser Glu Val Val Glu Ala Gln Gln Gln Val Val Ser Gly Met Lys
     45                  50                  55                  60 tac tac ttg aag atc tca gct act cat aaa ggg gtt cac aaa atg ttc         361
Tyr Tyr Leu Lys Ile Ser Ala Thr His Lys Gly Val His Lys Met Phe
                 65                  70                  75
```

```
acc tct gtt gtg gtg gtc aag cca tgg ctt cat tcc aag caa ctc ctt      409
Thr Ser Val Val Val Val Lys Pro Trp Leu His Ser Lys Gln Leu Leu
            80                  85                  90 cat ttt gcg cct gca gca cca tcc agt aaa gat ttt tga gatgcatgca       458
His Phe Ala Pro Ala Ala Pro Ser Ser Lys Asp Phe *
        95                 100 tgctagctat ttggagctaa ttaattatat aataattaat aaccatggcg gtatttgtaa    518
ttgcaagtga gcttttgat tttcttctac taaagttttc ctctactttt tgtaatgggt     578
atatctgtgg gcagaacaac aaaaatcaac tacgagttga aatcttactt accagccata    638
tgtaccaaag aaagtgaata ataactatat atatgctata gttttgttct aaaaaaaaaa    698
aaaaaaaaaa                                                           708

<210> SEQ ID NO 38
<211> LENGTH: 104
<212> TYPE: PRT
<213> ORGANISM: Glycine max
<220> FEATURE:
<221> NAME/KEY: DOMAIN
<222> LOCATION: (20)...(29)
<223> OTHER INFORMATION: N-terminal alpha-1 helix domain
<220> FEATURE:
<221> NAME/KEY: DOMAIN
<222> LOCATION: (54)...(64)
<223> OTHER INFORMATION: First hairpin loop domain
<220> FEATURE:
<221> NAME/KEY: DOMAIN
<222> LOCATION: (77)...(85)
<223> OTHER INFORMATION: Second hairpin loop domain

<400> SEQUENCE: 38

Met Val Gly Gly Lys Thr Glu Val Pro Asp Val Arg Thr Asn Arg Glu
 1               5                  10                  15

Val Gln Glu Leu Gly Arg Phe Ala Val Glu Glu Tyr Asn Arg Gly Leu
            20                  25                  30

Lys Gln Trp Lys Asn Asn Gly Ser Glu Gln Leu Asn Phe Ser Glu Val
        35                  40                  45

Val Glu Ala Gln Gln Val Val Ser Gly Met Lys Tyr Tyr Leu Lys
    50                  55                  60

Ile Ser Ala Thr His Lys Gly Val His Lys Met Phe Thr Ser Val Val
65                  70                  75                  80

Val Val Lys Pro Trp Leu His Ser Lys Gln Leu Leu His Phe Ala Pro
                85                  90                  95

Ala Ala Pro Ser Ser Lys Asp Phe
            100

<210> SEQ ID NO 39
<211> LENGTH: 505
<212> TYPE: DNA
<213> ORGANISM: Glycine max
<220> FEATURE:
<221> NAME/KEY: CDS
<222> LOCATION: (19)...(312)

<400> SEQUENCE: 39
gcgagagaga gagagaga atg gca gca ctt ggt ggc aat cgt gat gtg gca       51
                    Met Ala Ala Leu Gly Gly Asn Arg Asp Val Ala
                     1               5                  10 gga agc cag aac agc ctt gag atc gat ggt tta gct cgc ttt gct gtt       99
Gly Ser Gln Asn Ser Leu Glu Ile Asp Gly Leu Ala Arg Phe Ala Val
            15                  20                  25 gaa gaa cac aac aaa aaa cag aat gcc ctt ttg gag ttt gaa aag gta      147
```

```
                         gta agt gca aaa cag caa gtg gtt tct ggt acc ttg tac acc atc act    195
                         Val Ser Ala Lys Gln Gln Val Val Ser Gly Thr Leu Tyr Thr Ile Thr
                          45                  50                  55 ttg gag gca aaa gat ggt ggg caa aag aag gtt tat gaa gcc aaa gtt    243
                         Leu Glu Ala Lys Asp Gly Gly Gln Lys Lys Val Tyr Glu Ala Lys Val
                          60                  65                  70                  75 tgg gag aag gca tgg ttg aac ttc aag gag gtg caa gag ttc aag ctt    291
                         Trp Glu Lys Ala Trp Leu Asn Phe Lys Glu Val Gln Glu Phe Lys Leu
                                          80                  85                  90 gtt gga gat gca cct gca tag tctagtgctt aattaggttg cagaagagtg         342
                         Val Gly Asp Ala Pro Ala *
                                          95 aagagtgaga cagcctggct cgaaggggaa agcctaagga tatatcaaag catgctatat    402 gtataaaata aatgtagctt ttctaccttc ggtattgata tttgaaatcg tgatttggca    462 tcttatatat gatctctgtg tttgtctaaa aaaaaaaaa aaa                       505
```

Glu Glu His Asn Lys Lys Gln Asn Ala Leu Leu Glu Phe Glu Lys Val
         30                  35                  40

<210> SEQ ID NO 40
<211> LENGTH: 97
<212> TYPE: PRT
<213> ORGANISM: Glycine max
<220> FEATURE:
<221> NAME/KEY: DOMAIN
<222> LOCATION: (22)...(31)
<223> OTHER INFORMATION: N-terminal alpha-1 helix domain
<220> FEATURE:
<221> NAME/KEY: DOMAIN
<222> LOCATION: (49)...(59)
<223> OTHER INFORMATION: First hairpin loop domain
<220> FEATURE:
<221> NAME/KEY: DOMAIN
<222> LOCATION: (72)...(80)
<223> OTHER INFORMATION: Second hairpin loop domain

<400> SEQUENCE: 40

Met Ala Ala Leu Gly Gly Asn Arg Asp Val Ala Gly Ser Gln Asn Ser
 1               5                  10                  15

Leu Glu Ile Asp Gly Leu Ala Arg Phe Ala Val Glu Glu His Asn Lys
             20                  25                  30

Lys Gln Asn Ala Leu Leu Glu Phe Glu Lys Val Val Ser Ala Lys Gln
         35                  40                  45

Gln Val Val Ser Gly Thr Leu Tyr Thr Ile Thr Leu Glu Ala Lys Asp
     50                  55                  60

Gly Gly Gln Lys Lys Val Tyr Glu Ala Lys Val Trp Glu Lys Ala Trp
 65                  70                  75                  80

Leu Asn Phe Lys Glu Val Gln Glu Phe Lys Leu Val Gly Asp Ala Pro
                 85                  90                  95

Ala

<210> SEQ ID NO 41
<211> LENGTH: 573
<212> TYPE: DNA
<213> ORGANISM: Glycine max
<220> FEATURE:
<221> NAME/KEY: CDS
<222> LOCATION: (81)...(509)

<400> SEQUENCE: 41
gcttaatgct taatttctac tttctacttc tagctaacaa agttaagtaa actttcgctt     60
cagtacttta tatatatata atg gct gtg gct ttg acg att ctg gtg acc ctt    113

|  |  |  |  |  |  |  |  |  |  |  |  |  |  |  |
|---|---|---|---|---|---|---|---|---|---|---|---|---|---|---|
|  |  | Met | Ala | Val | Ala | Leu | Thr | Ile | Leu | Val | Thr | Leu |  |  |
|  |  | 1 |  |  |  | 5 |  |  |  |  | 10 |  |  |  |

| ctt | tcg | gtt | ctc | tct | tct | gca | tcg | tgt | gca | cga | atg | gtt | ggg | ggg | aag | 161 |
|---|---|---|---|---|---|---|---|---|---|---|---|---|---|---|---|---|
| Leu | Ser | Val | Leu | Ser | Ser | Ala | Ser | Cys | Ala | Arg | Met | Val | Gly | Gly | Lys |  |
|  |  |  | 15 |  |  |  |  | 20 |  |  |  |  | 25 |  |  |  |

| acg | gag | atc | cct | gaa | gtg | aga | aaa | aac | agg | caa | gtg | caa | gag | ctt | gga | 209 |
|---|---|---|---|---|---|---|---|---|---|---|---|---|---|---|---|---|
| Thr | Glu | Ile | Pro | Glu | Val | Arg | Lys | Asn | Arg | Gln | Val | Gln | Glu | Leu | Gly |  |
|  |  | 30 |  |  |  |  | 35 |  |  |  |  | 40 |  |  |  |  |

| agg | ttc | gcg | gtg | gag | gag | tat | aac | ctt | ggt | tta | aag | ctg | ttg | aag | aac | 257 |
|---|---|---|---|---|---|---|---|---|---|---|---|---|---|---|---|---|
| Arg | Phe | Ala | Val | Glu | Glu | Tyr | Asn | Leu | Gly | Leu | Lys | Leu | Leu | Lys | Asn |  |
|  | 45 |  |  |  |  | 50 |  |  |  |  | 55 |  |  |  |  |  |

| aac | aac | gtc | gac | aat | ggg | aga | gaa | cag | ttg | aac | ttt | tca | gcg | gtg | gtg | 305 |
|---|---|---|---|---|---|---|---|---|---|---|---|---|---|---|---|---|
| Asn | Asn | Val | Asp | Asn | Gly | Arg | Glu | Gln | Leu | Asn | Phe | Ser | Ala | Val | Val |  |
| 60 |  |  |  |  | 65 |  |  |  |  | 70 |  |  |  |  | 75 |  |

| gag | gcg | cag | caa | caa | gtg | gtg | tca | ggg | atg | aag | tac | tac | ttg | aag | atc | 353 |
|---|---|---|---|---|---|---|---|---|---|---|---|---|---|---|---|---|
| Glu | Ala | Gln | Gln | Gln | Val | Val | Ser | Gly | Met | Lys | Tyr | Tyr | Leu | Lys | Ile |  |
|  |  |  |  | 80 |  |  |  |  | 85 |  |  |  |  | 90 |  |  |

| tct | gct | act | cat | aat | ggt | gtt | cac | gaa | atg | ttc | aac | tct | gtg | gtg | gtg | 401 |
|---|---|---|---|---|---|---|---|---|---|---|---|---|---|---|---|---|
| Ser | Ala | Thr | His | Asn | Gly | Val | His | Glu | Met | Phe | Asn | Ser | Val | Val | Val |  |
|  |  |  | 95 |  |  |  |  | 100 |  |  |  |  | 105 |  |  |  |

| gtc | aag | cca | tgg | ctt | cat | tcc | aag | cag | ctc | ctc | cat | ttt | gcg | cct | gca | 449 |
|---|---|---|---|---|---|---|---|---|---|---|---|---|---|---|---|---|
| Val | Lys | Pro | Trp | Leu | His | Ser | Lys | Gln | Leu | Leu | His | Phe | Ala | Pro | Ala |  |
|  |  | 110 |  |  |  |  | 115 |  |  |  |  | 120 |  |  |  |  |

| tca | tca | tcc | acc | acc | acc | aac | aac | aac | atg | cat | cca | ata | gta | cgt | 497 |
|---|---|---|---|---|---|---|---|---|---|---|---|---|---|---|---|
| Ser | Ser | Ser | Thr | Thr | Thr | Thr | Asn | Asn | Asn | Met | His | Pro | Ile | Val | Arg |
|  | 125 |  |  |  |  | 130 |  |  |  |  | 135 |  |  |  |  |

| aaa | gat | aat | tga | gttgcatgcg | tacgtggctt | gctttaattt | ggagctaatt | 549 |
|---|---|---|---|---|---|---|---|---|
| Lys | Asp | Asn | * |  |  |  |  |  |
| 140 |  |  |  |  |  |  |  |  |

| atatgataat | aataaccata | ttaa | 573 |
|---|---|---|---|

<210> SEQ ID NO 42
<211> LENGTH: 142
<212> TYPE: PRT
<213> ORGANISM: Glycine max
<220> FEATURE:
<221> NAME/KEY: DOMAIN
<222> LOCATION: (42)...(51)
<223> OTHER INFORMATION: N-terminal alpha-1 helix domain
<220> FEATURE:
<221> NAME/KEY: DOMAIN
<222> LOCATION: (80)...(90)
<223> OTHER INFORMATION: First hairpin loop domain
<220> FEATURE:
<221> NAME/KEY: DOMAIN
<222> LOCATION: (103)...(111)
<223> OTHER INFORMATION: Second hairpin loop domain

<400> SEQUENCE: 42

| Met | Ala | Val | Ala | Leu | Thr | Ile | Leu | Val | Thr | Leu | Leu | Ser | Val | Leu | Ser |
|---|---|---|---|---|---|---|---|---|---|---|---|---|---|---|---|
| 1 |  |  |  | 5 |  |  |  |  | 10 |  |  |  |  | 15 |  |

| Ser | Ala | Ser | Cys | Ala | Arg | Met | Val | Gly | Gly | Lys | Thr | Glu | Ile | Pro | Glu |
|---|---|---|---|---|---|---|---|---|---|---|---|---|---|---|---|
|  |  |  | 20 |  |  |  |  | 25 |  |  |  |  | 30 |  |  |

| Val | Arg | Lys | Asn | Arg | Gln | Val | Gln | Glu | Leu | Gly | Arg | Phe | Ala | Val | Glu |
|---|---|---|---|---|---|---|---|---|---|---|---|---|---|---|---|
|  |  | 35 |  |  |  |  | 40 |  |  |  |  | 45 |  |  |  |

| Glu | Tyr | Asn | Leu | Gly | Leu | Lys | Leu | Leu | Lys | Asn | Asn | Asn | Val | Asp | Asn |
|---|---|---|---|---|---|---|---|---|---|---|---|---|---|---|---|
|  | 50 |  |  |  |  | 55 |  |  |  |  | 60 |  |  |  |  |

| Gly | Arg | Glu | Gln | Leu | Asn | Phe | Ser | Ala | Val | Val | Glu | Ala | Gln | Gln | Gln |
|---|---|---|---|---|---|---|---|---|---|---|---|---|---|---|---|
| 65 |  |  |  |  | 70 |  |  |  |  | 75 |  |  |  |  | 80 |

| Val | Val | Ser | Gly | Met | Lys | Tyr | Tyr | Leu | Lys | Ile | Ser | Ala | Thr | His | Asn |
|---|---|---|---|---|---|---|---|---|---|---|---|---|---|---|---|
|  |  |  | 85 |  |  |  |  | 90 |  |  |  |  | 95 |  |  |

```
Gly Val His Glu Met Phe Asn Ser Val Val Val Lys Pro Trp Leu
            100                 105                 110

His Ser Lys Gln Leu Leu His Phe Ala Pro Ala Ser Ser Thr Thr
        115                 120                 125

Thr Thr Asn Asn Asn Met His Pro Ile Val Arg Lys Asp Asn
        130                 135                 140

<210> SEQ ID NO 43
<211> LENGTH: 473
<212> TYPE: DNA
<213> ORGANISM: Glycine max
<220> FEATURE:
<221> NAME/KEY: CDS
<222> LOCATION: (21)...(365)

<400> SEQUENCE: 43
aaaaagacca gcggttgacg atg aaa cag aag tgt ctt gtt gtt ctg gtc ttt      53
                     Met Lys Gln Lys Cys Leu Val Val Leu Val Phe
                      1               5                  10 gtt gtt ctc ttg gct tgt gcg gtt ggt tgg gat gag ggt ata ccc ggc       101
Val Val Leu Leu Ala Cys Ala Val Gly Trp Asp Glu Gly Ile Pro Gly
             15                  20                  25 gga tgg aac ccc atc aag aac att aac gat cct cac gtg acg gag atc      149
Gly Trp Asn Pro Ile Lys Asn Ile Asn Asp Pro His Val Thr Glu Ile
         30                  35                  40 gcg aat ttc gcc gtg acg gaa tac gat aag caa tcc ggt gag aag cta      197
Ala Asn Phe Ala Val Thr Glu Tyr Asp Lys Gln Ser Gly Glu Lys Leu
     45                  50                  55 aag ttg gtg aag gtt atc aaa ggc gac ctt cag gta gta gca ggc ctc      245
Lys Leu Val Lys Val Ile Lys Gly Asp Leu Gln Val Val Ala Gly Leu
 60                  65                  70                  75 aac tac cgc ctc agc ctc acc gcc agc gac tcc aac aat tac caa gca      293
Asn Tyr Arg Leu Ser Leu Thr Ala Ser Asp Ser Asn Asn Tyr Gln Ala
                 80                  85                  90 att gtc tat gag aag gcg tgg gcc cgg gag cat tac aga aac ctt acc      341
Ile Val Tyr Glu Lys Ala Trp Ala Arg Glu His Tyr Arg Asn Leu Thr
             95                 100                 105 tcc ttt acc cct ctt cat gct taa cctcttttgt cttatcttct ctactgtatt    395
Ser Phe Thr Pro Leu His Ala  *
         110 attttaacca ataaaaaggt taagtgaatg agaatggcct ctttatctta aaaaaaaaaa    455 aaaaaaaaaa aaaaaaa                                                   473

<210> SEQ ID NO 44
<211> LENGTH: 114
<212> TYPE: PRT
<213> ORGANISM: Glycine max
<220> FEATURE:
<221> NAME/KEY: DOMAIN
<222> LOCATION: (43)...(52)
<223> OTHER INFORMATION: N-terminal alpha-1 helix domain
<220> FEATURE:
<221> NAME/KEY: DOMAIN
<222> LOCATION: (70)...(80)
<223> OTHER INFORMATION: First hairpin loop domain
<220> FEATURE:
<221> NAME/KEY: DOMAIN
<222> LOCATION: (90)...(98)
<223> OTHER INFORMATION: Second hairpin loop domain

<400> SEQUENCE: 44

Met Lys Gln Lys Cys Leu Val Val Leu Val Phe Val Val Leu Leu Ala
 1               5                  10                  15
```

```
                Cys Ala Val Gly Trp Asp Glu Gly Ile Pro Gly Gly Trp Asn Pro Ile
                         20                  25                  30

Lys Asn Ile Asn Asp Pro His Val Thr Glu Ile Ala Asn Phe Ala Val
                             35                  40                  45

Thr Glu Tyr Asp Lys Gln Ser Gly Glu Lys Leu Lys Leu Val Lys Val
                     50                  55                  60

Ile Lys Gly Asp Leu Gln Val Val Ala Gly Leu Asn Tyr Arg Leu Ser
                65                  70                  75                  80

Leu Thr Ala Ser Asp Ser Asn Asn Tyr Gln Ala Ile Val Tyr Glu Lys
                                 85                  90                  95

Ala Trp Ala Arg Glu His Tyr Arg Asn Leu Thr Ser Phe Thr Pro Leu
                            100                 105                 110

His Ala

<210> SEQ ID NO 45
<211> LENGTH: 797
<212> TYPE: DNA
<213> ORGANISM: Oryza sativa
<220> FEATURE:
<221> NAME/KEY: CDS
<222> LOCATION: (214)...(522)

<400> SEQUENCE: 45
gtcgcccatt ctacaccgtc tccatccatc tcatctcgtc gtcttccccc ccgcgagtcc       60
gcgacccccc gcgctataaa atccaaggcc gcgatcgaga tgcggaaata tcgagtcgcc      120
ggattggtag ccgccctgct cgtgctgcat tcgctagcca cgccgtccgc tcaggccgag      180
gcgcatcgcg caggggaga agggaggag aag atg tcg agc gac gga ggg ccg         234
                                  Met Ser Ser Asp Gly Gly Pro
                                   1               5 gtg ctt ggc ggc gtc gag ccg gtg ggg aac gag aac gac ctc cac ctc        282
Val Leu Gly Gly Val Glu Pro Val Gly Asn Glu Asn Asp Leu His Leu
         10                  15                  20 gtc gac ctc gcc cgc ttc gcc gtc acc gag cac aac aag aag gcc aat        330
Val Asp Leu Ala Arg Phe Ala Val Thr Glu His Asn Lys Lys Ala Asn
 25                  30                  35 tct ctg ctg gag ttc gag aag ctt gtg agt gtg aag cag caa gtt gtc        378
Ser Leu Leu Glu Phe Glu Lys Leu Val Ser Val Lys Gln Gln Val Val
 40                  45                  50                  55 gct ggc act ttg tac tat ttc aca att gag gtg aag gaa ggg gat gcc        426
Ala Gly Thr Leu Tyr Tyr Phe Thr Ile Glu Val Lys Glu Gly Asp Ala
             60                  65                  70 aag aag ctc tat gaa gct aag gtc tgg gag aaa cca tgg atg gac ttc        474
Lys Lys Leu Tyr Glu Ala Lys Val Trp Glu Lys Pro Trp Met Asp Phe
         75                  80                  85 aag gag ctc cag gag ttc aag cct gtc gat gcc agt gca aat gcc taa        522
Lys Glu Leu Gln Glu Phe Lys Pro Val Asp Ala Ser Ala Asn Ala  *
     90                  95                 100 ggcccatctc gtatcctatg tgtatcaagt tatcaagaag atggggaata atatggtgtg      582
gatatagcta ttggacatgt taattatcca catgataata tggcttggat ataaggatct      642
cacacgataa tatggcttgg atatatagct attaaagatt ttacctatgg catatttcaa      702
tgtgtattag tactaagtaa gaatgattgc aaggtgtatt aactacaaat attgcaataa      762
aagtccctgt tactacaaaa aaaaaaaaaa aaaaa                                 797

<210> SEQ ID NO 46
<211> LENGTH: 102
<212> TYPE: PRT
```

```
<213> ORGANISM: Oryza sativa
<220> FEATURE:
<221> NAME/KEY: DOMAIN
<222> LOCATION: (26)...(35)
<223> OTHER INFORMATION: N-terminal alpha-1 helix domain
<220> FEATURE:
<221> NAME/KEY: DOMAIN
<222> LOCATION: (53)...(63)
<223> OTHER INFORMATION: First hairpin loop domain
<220> FEATURE:
<221> NAME/KEY: DOMAIN
<222> LOCATION: (76)...(84)
<223> OTHER INFORMATION: Second hairpin loop domain

<400> SEQUENCE: 46

Met Ser Ser Asp Gly Gly Pro Val Leu Gly Val Glu Pro Val Gly
 1               5                  10                  15

Asn Glu Asn Asp Leu His Leu Val Asp Leu Ala Arg Phe Ala Val Thr
                20                  25                  30

Glu His Asn Lys Lys Ala Asn Ser Leu Leu Glu Phe Glu Lys Leu Val
            35                  40                  45

Ser Val Lys Gln Gln Val Val Ala Gly Thr Leu Tyr Tyr Phe Thr Ile
 50                  55                  60

Glu Val Lys Glu Gly Asp Ala Lys Lys Leu Tyr Glu Ala Lys Val Trp
 65                  70                  75                  80

Glu Lys Pro Trp Met Asp Phe Lys Glu Leu Gln Glu Phe Lys Pro Val
                85                  90                  95

Asp Ala Ser Ala Asn Ala
            100

<210> SEQ ID NO 47
<211> LENGTH: 1091
<212> TYPE: DNA
<213> ORGANISM: Oryza sativa
<220> FEATURE:
<221> NAME/KEY: CDS
<222> LOCATION: (92)...(844)

<400> SEQUENCE: 47
catatggcca tggaggccag tgcccgcacg aagcaaagaa gccgcaaccg caagccccaa      60
gagcgaaacc gtaacgaagg gaaagtttgg g atg cgc gtt gct gcg acg acg       112
                                   Met Arg Val Ala Ala Thr Thr
                                    1               5 cgg ccc gcc tcc tcc tcc gcc gcc gct ccg ctc ccc ctc ttc ctc ctc     160
Arg Pro Ala Ser Ser Ser Ala Ala Ala Pro Leu Pro Leu Phe Leu Leu
         10                  15                  20 ctc gcc gtc gcc gcc gcc gcc gcc gcc ctg ttc ctc gtc ggc tcc gcg     208
Leu Ala Val Ala Ala Ala Ala Ala Ala Leu Phe Leu Val Gly Ser Ala
     25                  30                  35 tcc ctc gcc atg gcc ggc cac gtc ctc ggc ggc gcg cac gac gcc ccc     256
Ser Leu Ala Met Ala Gly His Val Leu Gly Gly Ala His Asp Ala Pro
 40                  45                  50                  55 tcc gcc gcc aac agc gtc gag acc gac gcg ctc gcc cgc ttc gcc gtc     304
Ser Ala Ala Asn Ser Val Glu Thr Asp Ala Leu Ala Arg Phe Ala Val
                 60                  65                  70 gac gag cac aac aag cgc gag aac gcg ctg ctg gag ttc gtg cgg gtg     352
Asp Glu His Asn Lys Arg Glu Asn Ala Leu Leu Glu Phe Val Arg Val
             75                  80                  85 gtg gag gcg aag gag cag gtg gtg gcc ggc acg ctg cac cac ctc acg     400
Val Glu Ala Lys Glu Gln Val Val Ala Gly Thr Leu His His Leu Thr
         90                  95                 100 ctc gag gcc ctc gag gcg ggg agg aag aag gtg tac gag gcc aag gtc     448
```

```
Leu Glu Ala Leu Glu Ala Gly Arg Lys Lys Val Tyr Glu Ala Lys Val
    105                 110                 115 tgg gtc aag ccg tgg ctc gat ttc aag gag ctc cag gag ttc cgc aac      496
Trp Val Lys Pro Trp Leu Asp Phe Lys Glu Leu Gln Glu Phe Arg Asn
120                 125                 130                 135 act ggg gat gca acc acc ttc acc aac gcc gac ctc ggc gcc aag aaa      544
Thr Gly Asp Ala Thr Thr Phe Thr Asn Ala Asp Leu Gly Ala Lys Lys
                140                 145                 150 ggt gga cat gag cct ggg tgg cgt gat gtt cca gta cat gat cct gta      592
Gly Gly His Glu Pro Gly Trp Arg Asp Val Pro Val His Asp Pro Val
            155                 160                 165 gtc aaa gat gct gca gac cat gct gtg aaa tca atc cag cag agg tca      640
Val Lys Asp Ala Ala Asp His Ala Val Lys Ser Ile Gln Gln Arg Ser
        170                 175                 180 aac tcc ctg ttt cca tat gaa ctt ctc gag atc gtt cgt gca aag gca      688
Asn Ser Leu Phe Pro Tyr Glu Leu Leu Glu Ile Val Arg Ala Lys Ala
    185                 190                 195 gag gtt gtt gaa gac ttc gca aag ttt gac att ctg atg aaa ctt aag      736
Glu Val Val Glu Asp Phe Ala Lys Phe Asp Ile Leu Met Lys Leu Lys
200                 205                 210                 215 agg gga aac aag gag gag aag ttc aaa gcc gag gtc cac aag aac ctt      784
Arg Gly Asn Lys Glu Glu Lys Phe Lys Ala Glu Val His Lys Asn Leu
                220                 225                 230 gaa ggg gca ttt gta ctg aac cag atg caa caa gag cat gat gaa tcg      832
Glu Gly Ala Phe Val Leu Asn Gln Met Gln Gln Glu His Asp Glu Ser
            235                 240                 245 agc agc cag tga accttgccac attaagctgt agttatgtag tttgtgttca          884
Ser Ser Gln *
        250 ataagaaaac agtgaacatg cacccttccg tttctatcgg gacataggct ggaacttgtt    944 cctaacatcg atgaaaagaa gacactacac tatccttttg ttcctgttgc tcttagtgtg   1004 ataatacgat actggtcgtg taacttctca agggaaccgt gggtttatgc catacagctt   1064 gtgaatgtga aaaaaaaaa aaaaaaa                                        1091

<210> SEQ ID NO 48
<211> LENGTH: 250
<212> TYPE: PRT
<213> ORGANISM: Oryza sativa
<220> FEATURE:
<221> NAME/KEY: DOMAIN
<222> LOCATION: (66)...(76)
<223> OTHER INFORMATION: N-terminal alpha-1 helix domain
<220> FEATURE:
<221> NAME/KEY: DOMAIN
<222> LOCATION: (93)...(103)
<223> OTHER INFORMATION: First hairpin loop domain
<220> FEATURE:
<221> NAME/KEY: DOMAIN
<222> LOCATION: (116)...(124)
<223> OTHER INFORMATION: Second hairpin loop domain

<400> SEQUENCE: 48

Met Arg Val Ala Ala Thr Thr Arg Pro Ala Ser Ser Ala Ala Ala
1               5                   10                  15

Pro Leu Pro Leu Phe Leu Leu Ala Val Ala Ala Ala Ala Ala
            20                  25                  30

Leu Phe Leu Val Gly Ser Ala Ser Leu Ala Met Ala Gly His Val Leu
        35                  40                  45

Gly Gly Ala His Asp Ala Pro Ser Ala Ala Asn Ser Val Glu Thr Asp
    50                  55                  60
```

```
Ala Leu Ala Arg Phe Ala Val Asp Glu His Asn Lys Arg Glu Asn Ala
 65                  70                  75                  80

Leu Leu Glu Phe Val Arg Val Glu Ala Lys Glu Gln Val Val Ala
             85                  90                  95

Gly Thr Leu His His Leu Thr Leu Glu Ala Leu Glu Ala Gly Arg Lys
            100                 105                 110

Lys Val Tyr Glu Ala Lys Val Trp Val Lys Pro Trp Leu Asp Phe Lys
            115                 120                 125

Glu Leu Gln Glu Phe Arg Asn Thr Gly Asp Ala Thr Thr Phe Thr Asn
            130                 135                 140

Ala Asp Leu Gly Ala Lys Lys Gly Gly His Glu Pro Gly Trp Arg Asp
145                 150                 155                 160

Val Pro Val His Asp Pro Val Val Lys Asp Ala Asp His Ala Val
                165                 170                 175

Lys Ser Ile Gln Gln Arg Ser Asn Ser Leu Phe Pro Tyr Glu Leu Leu
            180                 185                 190

Glu Ile Val Arg Ala Lys Ala Glu Val Val Glu Asp Phe Ala Lys Phe
            195                 200                 205

Asp Ile Leu Met Lys Leu Lys Arg Gly Asn Lys Glu Lys Phe Lys
210                 215                 220

Ala Glu Val His Lys Asn Leu Glu Gly Ala Phe Val Leu Asn Gln Met
225                 230                 235                 240

Gln Gln Glu His Asp Glu Ser Ser Gln
                245                 250

<210> SEQ ID NO 49
<211> LENGTH: 744
<212> TYPE: DNA
<213> ORGANISM: Oryza sativa
<220> FEATURE:
<221> NAME/KEY: CDS
<222> LOCATION: (123)...(449)

<400> SEQUENCE: 49
atcactctct cttcgcggaa tcggtgttca ctacatctgc tgctgctggt cgtcgtcgtt      60
gtcctcgtct cgccgccgtt cccgttaccc tcttcttctc caccggtcgc ggctcgccgg     120 cg atg gcc gag gag gcg cag cag cca cgc ggc gtg aag gtg ggc ggc         167
   Met Ala Glu Glu Ala Gln Gln Pro Arg Gly Val Lys Val Gly Gly
    1               5                  10                  15 atc cac gac gcg ccg gcc ggg cgc gag aac gac ctc acc acc gtc gag        215
Ile His Asp Ala Pro Ala Gly Arg Glu Asn Asp Leu Thr Thr Val Glu
                20                  25                  30 ctc gcc cgg ttc gcc gtc gcc gag cac aac agc aag gcc aac gcg atg        263
Leu Ala Arg Phe Ala Val Ala Glu His Asn Ser Lys Ala Asn Ala Met
            35                  40                  45 ttg gag ttg gag agg gtg gtg aag gtg agg cag cag gtg gtg ggc ggg        311
Leu Glu Leu Glu Arg Val Val Lys Val Arg Gln Gln Val Val Gly Gly
        50                  55                  60 ttc atg cac tac ctc acc gtc gag gtg aag gaa ccc ggc ggc gcc aat        359
Phe Met His Tyr Leu Thr Val Glu Val Lys Glu Pro Gly Gly Ala Asn
65                  70                  75 aag ctg tac gag gcc aag gtg tgg gag agg gcg tgg gag aac ttc aag        407
Lys Leu Tyr Glu Ala Lys Val Trp Glu Arg Ala Trp Glu Asn Phe Lys
            80                  85                  90                  95 cag ctc cag gat ttc aag ccc ctc gac gac gcc acc gcc taa                449
Gln Leu Gln Asp Phe Lys Pro Leu Asp Asp Ala Thr Ala *
                100                 105
```

-continued

| | |
|---|---|
| acgtacatag atcatcgtcc ggctgctgaa tcatcggctt aaagcagagc catccagtga | 509 |
| tccaattatc tgctactaga acatgttact ggtcttgctg gaaggtgtaa tatgatgaat | 569 |
| aaaacctgct gctttgccgg gtcataaatg acatatcact tctgtatttc ctagtgcaat | 629 |
| acacaacatt ttcgcagtct ccttgtgttc ttggccatgg ccaagctttg cttgtaaatt | 689 |
| gtaataagtt ttcactttca cttttcacaa tttcatcaaa aaaaaaaaaa aaaaa | 744 |

```
<210> SEQ ID NO 50
<211> LENGTH: 108
<212> TYPE: PRT
<213> ORGANISM: Oryza sativa
<220> FEATURE:
<221> NAME/KEY: DOMAIN
<222> LOCATION: (32)...(41)
<223> OTHER INFORMATION: N-terminal alpha-1 helix domain
<220> FEATURE:
<221> NAME/KEY: DOMAIN
<222> LOCATION: (59)...(69)
<223> OTHER INFORMATION: First hairpin loop domain
<220> FEATURE:
<221> NAME/KEY: DOMAIN
<222> LOCATION: (83)...(91)
<223> OTHER INFORMATION: Second hairpin loop domain

<400> SEQUENCE: 50
```

Met Ala Glu Glu Ala Gln Gln Pro Arg Gly Val Lys Val Gly Gly Ile
1               5                   10                  15

His Asp Ala Pro Ala Gly Arg Glu Asn Asp Leu Thr Thr Val Glu Leu
                20                  25                  30

Ala Arg Phe Ala Val Ala Glu His Asn Ser Lys Ala Asn Ala Met Leu
            35                  40                  45

Glu Leu Glu Arg Val Val Lys Val Arg Gln Gln Val Val Gly Gly Phe
        50                  55                  60

Met His Tyr Leu Thr Val Glu Val Lys Glu Pro Gly Gly Ala Asn Lys
65                  70                  75                  80

Leu Tyr Glu Ala Lys Val Trp Glu Arg Ala Trp Glu Asn Phe Lys Gln
                85                  90                  95

Leu Gln Asp Phe Lys Pro Leu Asp Asp Ala Thr Ala
            100                 105

```
<210> SEQ ID NO 51
<211> LENGTH: 919
<212> TYPE: DNA
<213> ORGANISM: Oryza sativa
<220> FEATURE:
<221> NAME/KEY: CDS
<222> LOCATION: (69)...(623)

<400> SEQUENCE: 51
```
ccaaccggag aggaaaggaa agctcgggat cggagcagta gtagtactag gacgactcaa      60 cgacgacg atg ctt cgc cgc cgc ggc ttc tgc tgc tgc tcc ggc gca ccc      110
         Met Leu Arg Arg Arg Gly Phe Cys Cys Cys Ser Gly Ala Pro
         1               5                   10 gcc gcc gcc gcc gcc gcc ttg ctc cta ctg gcc gtg gcg gcg gcc gcc      158
Ala Ala Ala Ala Ala Ala Leu Leu Leu Leu Ala Val Ala Ala Ala Ala
15                  20                  25                  30 ccc cgc gcc gcc ggg ttc cac ctc ggg ggc gac gag agc gtc ctc gtg      206
Pro Arg Ala Ala Gly Phe His Leu Gly Gly Asp Glu Ser Val Leu Val
                35                  40                  45 cgg ggc atg ctc gcc gcg atc cgc cgc gag cag gcc gag gcg gag gac      254
Arg Gly Met Leu Ala Ala Ile Arg Arg Glu Gln Ala Glu Ala Glu Asp
            50                  55                  60

```
gcg gcg cgc ttc gcc gtc gcg gag tac aac aag aac cag ggt gct gaa    302
Ala Ala Arg Phe Ala Val Ala Glu Tyr Asn Lys Asn Gln Gly Ala Glu
            65                  70                  75 ttg gaa ttt gca cgg ata gtg aaa gcc aag cgt caa gtt gtg act ggt    350
Leu Glu Phe Ala Arg Ile Val Lys Ala Lys Arg Gln Val Val Thr Gly
 80                  85                  90 acc ttg cat gac ctg atg ttg gag gta gtt gat tct gga aag aaa agc    398
Thr Leu His Asp Leu Met Leu Glu Val Val Asp Ser Gly Lys Lys Ser
 95                 100                 105                 110 ctg tat agt gca aag gta tgg gtg aag ccg tgg cta gat ttt aag gca    446
Leu Tyr Ser Ala Lys Val Trp Val Lys Pro Trp Leu Asp Phe Lys Ala
                115                 120                 125 gtc gtc gag ttc cgt cac gtt ggg gac tcc cag tca cag tcg gcc act    494
Val Val Glu Phe Arg His Val Gly Asp Ser Gln Ser Gln Ser Ala Thr
                130                 135                 140 gct gct gat gat aac gct ggg caa gat act gct gat ccc act gtg gca    542
Ala Ala Asp Asp Asn Ala Gly Gln Asp Thr Ala Asp Pro Thr Val Ala
                145                 150                 155 tca agg aac gac ctg cac aac act gag aac aat aaa gtc tct gtt gtc    590
Ser Arg Asn Asp Leu His Asn Thr Glu Asn Asn Lys Val Ser Val Val
160                 165                 170 ctg tca acc ttt tct cag aca tac tcg gtg tga atctagctcc atggagagga  643
Leu Ser Thr Phe Ser Gln Thr Tyr Ser Val *
175                 180 tatggaagac ttgagcttct gagagctagc tgtcagtaat ttgtgaagta aagtagctgt  703
tatccttttg tgaagttttc cccactgtta tggaatgatg tctagatcgt aatatgccgt  763
tgagcagaca tgagtttgac atctggagtg tatatttgtt gctgcaaact gcaaagtgaa  823
cactcccatg tatattccat acctttcgtt cccatgcatg tatataaggc attactgcta  883
ccgttgtatg gtaaaaaaaa aaaaaaaaaa aaaaa                             919

<210> SEQ ID NO 52
<211> LENGTH: 184
<212> TYPE: PRT
<213> ORGANISM: Oryza sativa
<220> FEATURE:
<221> NAME/KEY: DOMAIN
<222> LOCATION: (63)...(72)
<223> OTHER INFORMATION: N-terminal alpha-1 helix domain
<220> FEATURE:
<221> NAME/KEY: DOMAIN
<222> LOCATION: (90)...(100)
<223> OTHER INFORMATION: First hairpin loop domain
<220> FEATURE:
<221> NAME/KEY: DOMAIN
<222> LOCATION: (113)...(121)
<223> OTHER INFORMATION: Second hairpin loop domain

<400> SEQUENCE: 52

Met Leu Arg Arg Gly Phe Cys Cys Cys Ser Gly Ala Pro Ala Ala
 1               5                  10                  15

Ala Ala Ala Ala Leu Leu Leu Ala Val Ala Ala Ala Pro Arg
                20                  25                  30

Ala Ala Gly Phe His Leu Gly Gly Asp Glu Ser Val Leu Val Arg Gly
                35                  40                  45

Met Leu Ala Ala Ile Arg Arg Glu Gln Ala Glu Ala Glu Asp Ala Ala
 50                  55                  60

Arg Phe Ala Val Ala Glu Tyr Asn Lys Asn Gln Gly Ala Glu Leu Glu
65                  70                  75                  80

Phe Ala Arg Ile Val Lys Ala Lys Arg Gln Val Val Thr Gly Thr Leu
```

```
                 85                  90                  95
His Asp Leu Met Leu Glu Val Val Asp Ser Gly Lys Lys Ser Leu Tyr
            100                 105                 110

Ser Ala Lys Val Trp Val Lys Pro Trp Leu Asp Phe Lys Ala Val Val
            115                 120                 125

Glu Phe Arg His Val Gly Asp Ser Gln Ser Gln Ser Ala Thr Ala Ala
            130                 135                 140

Asp Asp Asn Ala Gly Gln Asp Thr Ala Asp Pro Thr Val Ala Ser Arg
145                 150                 155                 160

Asn Asp Leu His Asn Thr Glu Asn Asn Lys Val Ser Val Leu Ser
                165                 170                 175

Thr Phe Ser Gln Thr Tyr Ser Val
            180

<210> SEQ ID NO 53
<211> LENGTH: 798
<212> TYPE: DNA
<213> ORGANISM: Oryza sativa
<220> FEATURE:
<221> NAME/KEY: CDS
<222> LOCATION: (6)...(461)

<400> SEQUENCE: 53 caaca atg gcc acc tct cct atg ctc ttc ctt gtc tcc ctc cta cta gta       50
      Met Ala Thr Ser Pro Met Leu Phe Leu Val Ser Leu Leu Leu Val
      1               5                  10                  15 cta gtc gcc gcc gcc act ggc gac gag gca tcg ccg tcg aac gcg gcg         98
Leu Val Ala Ala Ala Thr Gly Asp Glu Ala Ser Pro Ser Asn Ala Ala
            20                  25                  30 gcg ccg gcg gcg ccc gtg ctg gtc ggc ggg agg acg gag atc agg gac        146
Ala Pro Ala Ala Pro Val Leu Val Gly Gly Arg Thr Glu Ile Arg Asp
        35                  40                  45 gtg ggc agc aac aag gcg gtg cag tcg ctg ggc cgc ttc gcc gtc gcc        194
Val Gly Ser Asn Lys Ala Val Gln Ser Leu Gly Arg Phe Ala Val Ala
    50                  55                  60 gag cac aac cgc cgc ctc cgc cac ggc ggc tcc ggc ggc ccc gcc gac        242
Glu His Asn Arg Arg Leu Arg His Gly Gly Ser Gly Gly Pro Ala Asp
65                  70                  75 ccc gtc ccg gtg aag ctc gcg ttc gca cgc gtc gtg gag gcg cag aag        290
Pro Val Pro Val Lys Leu Ala Phe Ala Arg Val Val Glu Ala Gln Lys
80                  85                  90                  95 cag gtc gtc tcc gac gtg gcc tac tac ctc aag gtc gcc gcg agc gcg        338
Gln Val Val Ser Asp Val Ala Tyr Tyr Leu Lys Val Ala Ala Ser Ala
            100                 105                 110 agg gac ccc cgc ggc ggc gcc gcc gcc ggc ggt gac cgg gtg ttc gac        386
Arg Asp Pro Arg Gly Gly Ala Ala Ala Gly Gly Asp Arg Val Phe Asp
        115                 120                 125 gcc gtg gtg gtg gtg aag gcc tgg ctc aaa tcc aag gag ctc gtc tcc        434
Ala Val Val Val Val Lys Ala Trp Leu Lys Ser Lys Glu Leu Val Ser
    130                 135                 140 ttc acg cct gct tct tct acc aaa taa tcatgctcaa atatatgtat              481
Phe Thr Pro Ala Ser Ser Thr Lys *
145                 150 tagtttcact ctaattatat taattattac tagttggact ttactccctc cgtctaataa       541
aaaatcaacc ctagtacgga tgtaatacat tatagtacta cgaatcagac atccggtacc       601 atagttttt atggaacgga gatattagtt tttatgggga cggatggaat aattacgaag        661
catgtgcgtg cacaggctta tactcctcct tttggagtat atggcatatg catgtatggt       721
```

-continued

```
tttgtttggt tcctttggag ttttacatat cgataatcac atataaataa actcgtgtta      781
aaaaaaaaaa aaaaaaa                                                     798
```

<210> SEQ ID NO 54
<211> LENGTH: 151
<212> TYPE: PRT
<213> ORGANISM: Oryza sativa
<220> FEATURE:
<221> NAME/KEY: DOMAIN
<222> LOCATION: (57)...(66)
<223> OTHER INFORMATION: N-terminal alpha-1 helix domain
<220> FEATURE:
<221> NAME/KEY: DOMAIN
<222> LOCATION: (96)...(106)
<223> OTHER INFORMATION: First hairpin loop domain
<220> FEATURE:
<221> NAME/KEY: DOMAIN
<222> LOCATION: (127)...(135)
<223> OTHER INFORMATION: Second hairpin loop domain

<400> SEQUENCE: 54

```
Met Ala Thr Ser Pro Met Leu Phe Leu Val Ser Leu Leu Val Leu
 1               5                  10                  15

Val Ala Ala Ala Thr Gly Asp Glu Ala Ser Pro Ser Asn Ala Ala
                20                  25                  30

Pro Ala Ala Pro Val Leu Val Gly Gly Arg Thr Glu Ile Arg Asp Val
                35                  40                  45

Gly Ser Asn Lys Ala Val Gln Ser Leu Gly Arg Phe Ala Val Ala Glu
        50                  55                  60

His Asn Arg Arg Leu Arg His Gly Gly Ser Gly Gly Pro Ala Asp Pro
 65                 70                  75                  80

Val Pro Val Lys Leu Ala Phe Ala Arg Val Glu Ala Gln Lys Gln
                85                  90                  95

Val Val Ser Asp Val Ala Tyr Tyr Leu Lys Val Ala Ala Ser Ala Arg
               100                 105                 110

Asp Pro Arg Gly Gly Ala Ala Gly Gly Asp Arg Val Phe Asp Ala
           115                 120                 125

Val Val Val Val Lys Ala Trp Leu Lys Ser Lys Glu Leu Val Ser Phe
       130                 135                 140

Thr Pro Ala Ser Ser Thr Lys
145                 150
```

<210> SEQ ID NO 55
<211> LENGTH: 780
<212> TYPE: DNA
<213> ORGANISM: Oryza sativa
<220> FEATURE:
<221> NAME/KEY: CDS
<222> LOCATION: (117)...(488)

<400> SEQUENCE: 55

```
gcaattttag cccgtacccc cctgcatccc aagcgcccga aaccgcctct cccctacacc       60
aataccacca ccgcttcctt tccgatccga tcccttcccc tcgatcgacg gcggcc atg     119
                                                              Met
                                                               1 gcg aga atc ccg ctg ctg ctg gcc ctc ctg ctc gcc gtc tcc gcc gcc       167
Ala Arg Ile Pro Leu Leu Leu Ala Leu Leu Leu Ala Val Ser Ala Ala
         5                  10                  15 gcc gcc gcg cag gtc ggg ggt aac cgc ggc cat ggc ccg ctg gtg ggc       215
Ala Ala Ala Gln Val Gly Gly Asn Arg Gly His Gly Pro Leu Val Gly
     20                  25                  30
```

```
ggg tgg agc ccg atc acg gac gtg ggc gac ccc cac atc cag gag ctc       263
Gly Trp Ser Pro Ile Thr Asp Val Gly Asp Pro His Ile Gln Glu Leu
         35                  40                  45 ggc ggg tgg gcg gtg gag cgg cac gcc tcg ctc tcc agc gac ggg ctg       311
Gly Gly Trp Ala Val Glu Arg His Ala Ser Leu Ser Ser Asp Gly Leu
 50                  55                  60                  65 cgg ttc cgc cgc gtg acg agc ggc gag cag cag gtg gtc tcc ggg atg       359
Arg Phe Arg Arg Val Thr Ser Gly Glu Gln Gln Val Val Ser Gly Met
                 70                  75                  80 aac tac cgc ctc gtc gtc tcc gcg tca gat ccc gcg ggg gcc acc gcg       407
Asn Tyr Arg Leu Val Val Ser Ala Ser Asp Pro Ala Gly Ala Thr Ala
             85                  90                  95 tcc tac gtc gcc gtc gtg tac gag cag tcg tgg acc aac acc cgc cag       455
Ser Tyr Val Ala Val Val Tyr Glu Gln Ser Trp Thr Asn Thr Arg Gln
        100                 105                 110 ctc acc tcc ttc aag ccc gcc gcc gcg cac tga tccatccctc cctccagatc    508
Leu Thr Ser Phe Lys Pro Ala Ala Ala His  *
    115                 120 tatcttatct atgtctcttc tgctccatct cgatcagctg ttaaattttc cctgcctaat     568
ctctctctgt taatcacaca tctcatgtaa ttctcatgta tgatgagcac aagctaagta     628
cctgtacttg ttcggtctga gttgtgtccc cgtgtgtgcg gttcaatctt ttgcatgtaa     688
gacagcgagt ccacacttgt aatgaattag cgaataaaat ggtgggattg gaataatggt     748
gcccatctta attcaaaaaa aaaaaaaaaa aa                                   780

<210> SEQ ID NO 56
<211> LENGTH: 123
<212> TYPE: PRT
<213> ORGANISM: Oryza sativa
<220> FEATURE:
<221> NAME/KEY: DOMAIN
<222> LOCATION: (49)...(58)
<223> OTHER INFORMATION: N-terminal alpha-1 helix domain
<220> FEATURE:
<221> NAME/KEY: DOMAIN
<222> LOCATION: (76)...(86)
<223> OTHER INFORMATION: First hairpin loop domain
<220> FEATURE:
<221> NAME/KEY: DOMAIN
<222> LOCATION: (100)...(108)
<223> OTHER INFORMATION: Second hairpin loop domain

<400> SEQUENCE: 56

Met Ala Arg Ile Pro Leu Leu Ala Leu Leu Ala Val Ser Ala
 1               5                  10                  15

Ala Ala Ala Ala Gln Val Gly Gly Asn Arg Gly His Gly Pro Leu Val
                 20                  25                  30

Gly Gly Trp Ser Pro Ile Thr Asp Val Gly Asp Pro His Ile Gln Glu
         35                  40                  45

Leu Gly Gly Trp Ala Val Glu Arg His Ala Ser Leu Ser Ser Asp Gly
 50                  55                  60

Leu Arg Phe Arg Arg Val Thr Ser Gly Glu Gln Gln Val Val Ser Gly
 65                  70                  75                  80

Met Asn Tyr Arg Leu Val Val Ser Ala Ser Asp Pro Ala Gly Ala Thr
                 85                  90                  95

Ala Ser Tyr Val Ala Val Val Tyr Glu Gln Ser Trp Thr Asn Thr Arg
            100                 105                 110

Gln Leu Thr Ser Phe Lys Pro Ala Ala Ala His
        115                 120
```

-continued

```
<210> SEQ ID NO 57
<211> LENGTH: 626
<212> TYPE: DNA
<213> ORGANISM: Triticum aestivum
<220> FEATURE:
<221> NAME/KEY: CDS
<222> LOCATION: (72)...(500)

<400> SEQUENCE: 57
gctccgcccg gattgtatcc ctcctcccct gctctgccgc tgcagctata aatcccgacc      60
ccgatcgatc g atg gag atg tgg aaa tat cgg gtc gtg gga tcg gtt gct     110
            Met Glu Met Trp Lys Tyr Arg Val Val Gly Ser Val Ala
              1               5                  10 gcc ctc ctc ttg cta ctc gcc atc gtc gtg ccg ttt act cag acc cag      158
Ala Leu Leu Leu Leu Leu Ala Ile Val Val Pro Phe Thr Gln Thr Gln
         15                  20                  25 acg cag agc gca cgg gac aaa gct gcc atg gcg gaa gac gcg ggg ccg      206
Thr Gln Ser Ala Arg Asp Lys Ala Ala Met Ala Glu Asp Ala Gly Pro
 30                  35                  40                  45 ctg gtg gga ggc atc agt gac tcg ccg atg ggg caa gaa aac gac ctc      254
Leu Val Gly Gly Ile Ser Asp Ser Pro Met Gly Gln Glu Asn Asp Leu
                 50                  55                  60 gac gtc atc gcg ctc gcc cgc ttc gcc gtc tcc gag cac aac aac aag      302
Asp Val Ile Ala Leu Ala Arg Phe Ala Val Ser Glu His Asn Asn Lys
             65                  70                  75 gcc aat gcc ctg ctg gag ttc gag aat gtg gtg aag gtg aag aag caa      350
Ala Asn Ala Leu Leu Glu Phe Glu Asn Val Val Lys Val Lys Lys Gln
         80                  85                  90 act gtt gct ggc acg atg cac tac att aca atc cgg gtc act gaa ggt      398
Thr Val Ala Gly Thr Met His Tyr Ile Thr Ile Arg Val Thr Glu Gly
     95                 100                 105 ggg gcc aag aag ctc tat gaa gct aag gtg tgg gag aaa cca tgg gag      446
Gly Ala Lys Lys Leu Tyr Glu Ala Lys Val Trp Glu Lys Pro Trp Glu
110                 115                 120                 125 aac ttt aag aag ctc gag gag ttc aag ctg gtg gag gac gtt cca agc      494
Asn Phe Lys Lys Leu Glu Glu Phe Lys Leu Val Glu Asp Val Pro Ser
                130                 135                 140 gca taa ctcataaggc gcgtcccagc tttgcaagga tctgcagcta tggtgttgat      550
Ala * gtagctatct atcggacatg gtttagcgtg ttctcgtgta atatcaagaa taagtccgct      610
tcttgcaagt tgtttt                                                    626

<210> SEQ ID NO 58
<211> LENGTH: 142
<212> TYPE: PRT
<213> ORGANISM: Triticum aestivum
<220> FEATURE:
<221> NAME/KEY: DOMAIN
<222> LOCATION: (66)...(75)
<223> OTHER INFORMATION: N-terminal alpha-1 helix domain
<220> FEATURE:
<221> NAME/KEY: DOMAIN
<222> LOCATION: (93)...(103)
<223> OTHER INFORMATION: First hairpin loop domain
<220> FEATURE:
<221> NAME/KEY: DOMAIN
<222> LOCATION: (116)...(124)
<223> OTHER INFORMATION: Second hairpin loop domain

<400> SEQUENCE: 58

Met Glu Met Trp Lys Tyr Arg Val Val Gly Ser Val Ala Ala Leu Leu
  1               5                  10                  15

Leu Leu Leu Ala Ile Val Val Pro Phe Thr Gln Thr Gln Thr Gln Ser
```

```
                    20                  25                  30
Ala Arg Asp Lys Ala Ala Met Ala Glu Asp Ala Gly Pro Leu Val Gly
         35                  40                  45

Gly Ile Ser Asp Ser Pro Met Gly Gln Glu Asn Asp Leu Asp Val Ile
     50                  55                  60

Ala Leu Ala Arg Phe Ala Val Ser Glu His Asn Asn Lys Ala Asn Ala
 65                  70                  75                  80

Leu Leu Glu Phe Glu Asn Val Val Lys Val Lys Gln Thr Val Ala
                 85                  90                  95

Gly Thr Met His Tyr Ile Thr Ile Arg Val Thr Glu Gly Gly Ala Lys
                100                 105                 110

Lys Leu Tyr Glu Ala Lys Val Trp Glu Lys Pro Trp Glu Asn Phe Lys
            115                 120                 125

Lys Leu Glu Glu Phe Lys Leu Val Glu Asp Val Pro Ser Ala
            130                 135                 140
```

<210> SEQ ID NO 59
<211> LENGTH: 609
<212> TYPE: DNA
<213> ORGANISM: Triticum aestivum
<220> FEATURE:
<221> NAME/KEY: CDS
<222> LOCATION: (1)...(378)

<400> SEQUENCE: 59

```
cta ctc gcc atc gtc gtg ccg ttt act cag acc cgg acg cag agc gca      48
Leu Leu Ala Ile Val Val Pro Phe Thr Gln Thr Arg Thr Gln Ser Ala
 1               5                  10                  15 cgg gac aag gct gcc atg gcg gaa gac gcg ggg ccg ctg gtg gga ggc      96
Arg Asp Lys Ala Ala Met Ala Glu Asp Ala Gly Pro Leu Val Gly Gly
                 20                  25                  30 atc aag gac tca ccg atg ggc cag gag aac gac ctc gac gtc atc gcg     144
Ile Lys Asp Ser Pro Met Gly Gln Glu Asn Asp Leu Asp Val Ile Ala
             35                  40                  45 ctc gcc cgc ttc gcc gtc tcc gag cac aac aac aag gcc aat gcc ctg     192
Leu Ala Arg Phe Ala Val Ser Glu His Asn Asn Lys Ala Asn Ala Leu
         50                  55                  60 ctg gag ttc gag aat gtg gtg aag ctg aag aag caa act gtt gct ggc     240
Leu Glu Phe Glu Asn Val Val Lys Leu Lys Lys Gln Thr Val Ala Gly
 65                  70                  75                  80 acg atg cac tac att aca att cgg gtc act gaa ggt ggg gcc aag aag     288
Thr Met His Tyr Ile Thr Ile Arg Val Thr Glu Gly Gly Ala Lys Lys
                 85                  90                  95 ctc tat gaa gct aag gtg tgg gag aaa cca tgg gag aac ttt aag cag     336
Leu Tyr Glu Ala Lys Val Trp Glu Lys Pro Trp Glu Asn Phe Lys Gln
            100                 105                 110 ctc cag gag ttc aag ccg gtg gag gac gct gca atc gca tga             378
Leu Gln Glu Phe Lys Pro Val Glu Asp Ala Ala Ile Ala  *
        115                 120                 125 ggcgcgcccc agctttgcaa ggatctgcag ctatggtgtt gatgcaccta tcaatcggac    438
atggtttagc gtgttctcgt gtaatatcaa gaaagctgtc tcttgtgta atatcaagaa     498 caaatctgct tcttgcgagt tcttttttaag tccgcttctt gcaagttgtt ttaaccacgt    558
ctctaaataa aattctctgc agtattattg taaaaaaaaa aaaaaaaaaa a             609
```

<210> SEQ ID NO 60
<211> LENGTH: 125
<212> TYPE: PRT
<213> ORGANISM: Triticum aestivum

```
<220> FEATURE:
<221> NAME/KEY: DOMAIN
<222> LOCATION: (49)...(58)
<223> OTHER INFORMATION: N-terminal alpha-1 helix domain
<220> FEATURE:
<221> NAME/KEY: DOMAIN
<222> LOCATION: (76)...(86)
<223> OTHER INFORMATION: First hairpin loop domain
<220> FEATURE:
<221> NAME/KEY: DOMAIN
<222> LOCATION: (99)...(107)
<223> OTHER INFORMATION: Second hairpin loop domain

<400> SEQUENCE: 60

Leu Leu Ala Ile Val Val Pro Phe Thr Gln Thr Arg Thr Gln Ser Ala
 1               5                  10                  15

Arg Asp Lys Ala Ala Met Ala Glu Asp Ala Gly Pro Leu Val Gly Gly
             20                  25                  30

Ile Lys Asp Ser Pro Met Gly Gln Glu Asn Asp Leu Asp Val Ile Ala
         35                  40                  45

Leu Ala Arg Phe Ala Val Ser Glu His Asn Asn Lys Ala Asn Ala Leu
 50                  55                  60

Leu Glu Phe Glu Asn Val Val Lys Leu Lys Gln Thr Val Ala Gly
65                  70                  75                  80

Thr Met His Tyr Ile Thr Ile Arg Val Thr Glu Gly Gly Ala Lys Lys
                 85                  90                  95

Leu Tyr Glu Ala Lys Val Trp Glu Lys Pro Trp Glu Asn Phe Lys Gln
            100                 105                 110

Leu Gln Glu Phe Lys Pro Val Glu Asp Ala Ala Ile Ala
            115                 120                 125

<210> SEQ ID NO 61
<211> LENGTH: 557
<212> TYPE: DNA
<213> ORGANISM: Triticum aestivum
<220> FEATURE:
<221> NAME/KEY: CDS
<222> LOCATION: (57)...(443)

<400> SEQUENCE: 61
caaagtccca cataaatatc tcaagatcaa gaacccact agacaatcca atagcc atg     59
                                                            Met
                                                              1 agg aca tct agc ttc ctc ctc atc atc gtt gtt gcg ttc ctc tat gcc    107
Arg Thr Ser Ser Phe Leu Leu Ile Ile Val Val Ala Phe Leu Tyr Ala
        5                  10                  15 atc ggc tca ccc gcc ata ggc tgt ggg gaa cgg atg ggc aac caa ttg    155
Ile Gly Ser Pro Ala Ile Gly Cys Gly Glu Arg Met Gly Asn Gln Leu
     20                  25                  30 tgg aac acg gca ata gag aat gga tgg gaa cca atc gga aac atc aat    203
Trp Asn Thr Ala Ile Glu Asn Gly Trp Glu Pro Ile Gly Asn Ile Asn
 35                  40                  45 gac caa cac atc cag gag ctc ggc cgt tgg gcg gtg ttg gag ttc ggc    251
Asp Gln His Ile Gln Glu Leu Gly Arg Trp Ala Val Leu Glu Phe Gly
 50                  55                  60                  65 aag cat gtg aac tgc gtg ctc aag ttc aac aag gtg gta agt ggc agg    299
Lys His Val Asn Cys Val Leu Lys Phe Asn Lys Val Val Ser Gly Arg
                 70                  75                  80 caa caa ctt gtt tct gga atg aac tac gaa ctt atc atc gag gca tca    347
Gln Gln Leu Val Ser Gly Met Asn Tyr Glu Leu Ile Ile Glu Ala Ser
             85                  90                  95 gac att ggc ggg aaa gaa gac aag tac aag gca gag gtg tac gag cag    395
```

```
Asp Ile Gly Gly Lys Glu Asp Lys Tyr Lys Ala Glu Val Tyr Glu Gln
            100                 105                 110 acg tgg act cac aaa cgc cag ctc ctc tca ttc gcc aag gtg aaa tag    443
Thr Trp Thr His Lys Arg Gln Leu Leu Ser Phe Ala Lys Val Lys  *
        115                 120                 125 gcgagtggca ataacttcgg tagtaataat tgtgatgtac cagatttgtt agctgggttt   503
atttatcgac gaataattta tcgtcttgca ttgcaaaaaa aaaaaaaaaa aaaa         557

<210> SEQ ID NO 62
<211> LENGTH: 128
<212> TYPE: PRT
<213> ORGANISM: Triticum aestivum
<220> FEATURE:
<221> NAME/KEY: DOMAIN
<222> LOCATION: (56)...(65)
<223> OTHER INFORMATION: N-terminal alpha-1 helix domain
<220> FEATURE:
<221> NAME/KEY: DOMAIN
<222> LOCATION: (83)...(93)
<223> OTHER INFORMATION: First hairpin loop domain
<220> FEATURE:
<221> NAME/KEY: DOMAIN
<222> LOCATION: (107)...(115)
<223> OTHER INFORMATION: Second hairpin loop domain

<400> SEQUENCE: 62

Met Arg Thr Ser Ser Phe Leu Leu Ile Ile Val Val Ala Phe Leu Tyr
 1               5                  10                  15

Ala Ile Gly Ser Pro Ala Ile Gly Cys Gly Glu Arg Met Gly Asn Gln
            20                  25                  30

Leu Trp Asn Thr Ala Ile Glu Asn Gly Trp Glu Pro Ile Gly Asn Ile
        35                  40                  45

Asn Asp Gln His Ile Gln Glu Leu Gly Arg Trp Ala Val Leu Glu Phe
    50                  55                  60

Gly Lys His Val Asn Cys Val Leu Lys Phe Asn Lys Val Val Ser Gly
65                  70                  75                  80

Arg Gln Gln Leu Val Ser Gly Met Asn Tyr Glu Leu Ile Ile Glu Ala
                85                  90                  95

Ser Asp Ile Gly Gly Lys Glu Asp Lys Tyr Lys Ala Glu Val Tyr Glu
            100                 105                 110

Gln Thr Trp Thr His Lys Arg Gln Leu Leu Ser Phe Ala Lys Val Lys
        115                 120                 125

<210> SEQ ID NO 63
<211> LENGTH: 608
<212> TYPE: DNA
<213> ORGANISM: Triticum aestivum
<220> FEATURE:
<221> NAME/KEY: CDS
<222> LOCATION: (86)...(409)

<400> SEQUENCE: 63
ggactcacgg aacagatctg ttctctctca gactctctgc agcggccatc cgtcgtacaa    60
tccaccctcc ggacgcacgg cagcc atg gcc gag gcg gcg cag ggc ggg ggg    112
                            Met Ala Glu Ala Ala Gln Gly Gly Gly
                             1               5 cta cgc ggc cgc ggc gct ctg ctg ggc ggc gtc cag gac gcg ccg gcg    160
Leu Arg Gly Arg Gly Ala Leu Leu Gly Gly Val Gln Asp Ala Pro Ala
 10                  15                  20                  25 ggg cgg gag aac gac ctc gag acc atc gag ctc gcg cgc ttc gcc gtc    208
Gly Arg Glu Asn Asp Leu Glu Thr Ile Glu Leu Ala Arg Phe Ala Val
                30                  35                  40
```

```
gcc gag cac aac acc aag gcc aac gcg ctg ctg gag ttc gag agg ctg    256
Ala Glu His Asn Thr Lys Ala Asn Ala Leu Leu Glu Phe Glu Arg Leu
            45                  50                  55 gtg aag gtg agg cag cag gtg gtg gcc ggg tgc atg cac tac ttc acc    304
Val Lys Val Arg Gln Gln Val Val Ala Gly Cys Met His Tyr Phe Thr
        60                  65                  70 atc gag gtc aag gaa ggc ggc gcc aag aag ctc tac gag gcc aag gtg    352
Ile Glu Val Lys Glu Gly Gly Ala Lys Lys Leu Tyr Glu Ala Lys Val
    75                  80                  85 tgg gag aag gcc tgg gag aac ttc aag cag ctc cag gac ttc aag ccg    400
Trp Glu Lys Ala Trp Glu Asn Phe Lys Gln Leu Gln Asp Phe Lys Pro
90                  95                  100                 105 gcc gcc tga aaagatgtaa ataaatatgt tatgtgagct gaaccgctca             449
Ala Ala * agcttgtgga tggggcctat ccaacacgcc agcctcactg gatactggtg taatatgatg   509
aaataaacct gcttcctgcc atgtctatga ttcccacaag tattttgctt gtttgcacta   569
aacctcccac aaaaaaaaaa aaaaaaaaaa aaaaaaaa                           608

<210> SEQ ID NO 64
<211> LENGTH: 107
<212> TYPE: PRT
<213> ORGANISM: Triticum aestivum
<220> FEATURE:
<221> NAME/KEY: DOMAIN
<222> LOCATION: (36)...(45)
<223> OTHER INFORMATION: N-terminal alpha-1 helix domain
<220> FEATURE:
<221> NAME/KEY: DOMAIN
<222> LOCATION: (63)...(73)
<223> OTHER INFORMATION: First hairpin loop domain
<220> FEATURE:
<221> NAME/KEY: DOMAIN
<222> LOCATION: (86)...(94)
<223> OTHER INFORMATION: Second hairpin loop domain

<400> SEQUENCE: 64

Met Ala Glu Ala Ala Gln Gly Gly Gly Leu Arg Gly Arg Gly Ala Leu
1               5                   10                  15

Leu Gly Gly Val Gln Asp Ala Pro Ala Gly Arg Glu Asn Asp Leu Glu
            20                  25                  30

Thr Ile Glu Leu Ala Arg Phe Ala Val Ala Glu His Asn Thr Lys Ala
        35                  40                  45

Asn Ala Leu Leu Glu Phe Glu Arg Leu Val Lys Val Arg Gln Gln Val
    50                  55                  60

Val Ala Gly Cys Met His Tyr Phe Thr Ile Glu Val Lys Glu Gly Gly
65                  70                  75                  80

Ala Lys Lys Leu Tyr Glu Ala Lys Val Trp Glu Lys Ala Trp Glu Asn
                85                  90                  95

Phe Lys Gln Leu Gln Asp Phe Lys Pro Ala Ala
            100                 105

<210> SEQ ID NO 65
<211> LENGTH: 622
<212> TYPE: DNA
<213> ORGANISM: Triticum aestivum
<220> FEATURE:
<221> NAME/KEY: CDS
<222> LOCATION: (159)...(482)

<400> SEQUENCE: 65
tctatcccca cgtcgctata aagtcccgtc ccccacttcc ctcgatcaac atcgtctcgg   60
```

```
ctcacggaac agatctgttc tctctcagac tctcagcagc ggccatccgt cgtacactcc        120
tctctcgtct cagcgcaccc tccggacgca cggcggcg atg gcc gag gcg gcg cag       176
                                         Met Ala Glu Ala Ala Gln
                                          1               5 ggc ggg ggg ctg cgc ggc cgc ggc gtg ctg ctg ggc ggc gtc cag gac         224
Gly Gly Gly Leu Arg Gly Arg Gly Val Leu Leu Gly Gly Val Gln Asp
             10                  15                  20 gcg ccg gcg ggg cgg gag aac gac ctc gca acc atc gag ctc gcc cgc         272
Ala Pro Ala Gly Arg Glu Asn Asp Leu Ala Thr Ile Glu Leu Ala Arg
         25                  30                  35 ttc gcc gtc gcc gag cac aac acc aag gcc aac gcg ctg ctg gag ttc         320
Phe Ala Val Ala Glu His Asn Thr Lys Ala Asn Ala Leu Leu Glu Phe
     40                  45                  50 gag agg ctg gtg aag gtg agg cag cag gtg gtg gcc ggg tgc atg cac         368
Glu Arg Leu Val Lys Val Arg Gln Gln Val Val Ala Gly Cys Met His
 55                  60                  65                  70 tac ttc acc atc gag gtc aag gag ggc ggc gcc aag aag ctc tac gag         416
Tyr Phe Thr Ile Glu Val Lys Glu Gly Gly Ala Lys Lys Leu Tyr Glu
                 75                  80                  85 gcc aag gtg tgg gag aag gcc tgg gag aac ttc aag cag ctc cag gac         464
Ala Lys Val Trp Glu Lys Ala Trp Glu Asn Phe Lys Gln Leu Gln Asp
             90                  95                 100 ttc aag ccg gcc gcc tga aaagatgtaa ataaatatgt tatgtgagct                512
Phe Lys Pro Ala Ala *
        105 caactgctga agcttgtggc tggggcctat ccaacatgtc agcctcactg gatactggtg       572 taatatgatg aaataaacct gcttcctgcc tgaaaaaaaa aaaaaaaaaa                   622

<210> SEQ ID NO 66
<211> LENGTH: 107
<212> TYPE: PRT
<213> ORGANISM: Triticum aestivum
<220> FEATURE:
<221> NAME/KEY: DOMAIN
<222> LOCATION: (36)...(45)
<223> OTHER INFORMATION: N-terminal alpha-1 helix domain
<220> FEATURE:
<221> NAME/KEY: DOMAIN
<222> LOCATION: (63)...(73)
<223> OTHER INFORMATION: First hairpin loop domain
<220> FEATURE:
<221> NAME/KEY: DOMAIN
<222> LOCATION: (86)...(94)
<223> OTHER INFORMATION: Second hairpin loop domain

<400> SEQUENCE: 66

Met Ala Glu Ala Ala Gln Gly Gly Gly Leu Arg Gly Arg Gly Val Leu
 1               5                  10                  15

Leu Gly Gly Val Gln Asp Ala Pro Ala Gly Arg Glu Asn Asp Leu Ala
             20                  25                  30

Thr Ile Glu Leu Ala Arg Phe Ala Val Ala Glu His Asn Thr Lys Ala
         35                  40                  45

Asn Ala Leu Leu Glu Phe Glu Arg Leu Val Lys Val Arg Gln Gln Val
     50                  55                  60

Val Ala Gly Cys Met His Tyr Phe Thr Ile Glu Val Lys Glu Gly Gly
 65                  70                  75                  80

Ala Lys Lys Leu Tyr Glu Ala Lys Val Trp Glu Lys Ala Trp Glu Asn
                 85                  90                  95

Phe Lys Gln Leu Gln Asp Phe Lys Pro Ala Ala
            100                 105
```

<210> SEQ ID NO 67
<211> LENGTH: 750
<212> TYPE: DNA
<213> ORGANISM: Triticum aestivum
<220> FEATURE:
<221> NAME/KEY: CDS
<222> LOCATION: (62)...(520)

<400> SEQUENCE: 67

```
gcacagcgtc agtgctaagc agcatcagtg atctagctcg gatagacaca gtgcacgtga        60 a atg gct cgg gtg atc ggt gcc tcc ggc gcc tgc gcg ctg ttg gtc gtc      109
  Met Ala Arg Val Ile Gly Ala Ser Gly Ala Cys Ala Leu Leu Val Val
    1               5                  10                  15 ctg ctc gtg gcg tgc gcg gcg tcc gca gcg cgc acc gag ccg ggc gcc        157
Leu Leu Val Ala Cys Ala Ala Ser Ala Ala Arg Thr Glu Pro Gly Ala
                20                  25                  30 gcg cgg cag ctg tgg gag gac ggg agg aag gtg ggg gga agg acg gag        205
Ala Arg Gln Leu Trp Glu Asp Gly Arg Lys Val Gly Gly Arg Thr Glu
         35                  40                  45 gtg agg gac gtg gag agc gac agg gag gtg cag gag ctt ggg cgg tac        253
Val Arg Asp Val Glu Ser Asp Arg Glu Val Gln Glu Leu Gly Arg Tyr
 50                  55                  60 tcc gtc gaa gag cac aac cgg cgc cgg gag gag ggc tgc gag ggc ggc        301
Ser Val Glu Glu His Asn Arg Arg Arg Glu Glu Gly Cys Glu Gly Gly
 65                  70                  75                  80 ggc ggc gtc tgc ggc cgg ctg gag ttc gcc cgc gtg gtg tcg gcg cag        349
Gly Gly Val Cys Gly Arg Leu Glu Phe Ala Arg Val Val Ser Ala Gln
                 85                  90                  95 cgc cag gtg gtg tcc gga atc aag tac tac ctc cgc gtc gcg gcc gcc        397
Arg Gln Val Val Ser Gly Ile Lys Tyr Tyr Leu Arg Val Ala Ala Ala
            100                 105                 110 gag gag aac ggc gcg ggg agc aac gtc gtc agc gac ggc cgc gtg ttc        445
Glu Glu Asn Gly Ala Gly Ser Asn Val Val Ser Asp Gly Arg Val Phe
        115                 120                 125 gac gcc gtg gtg gtc gtc aag ccc tgg ctc cag tcc cgc gcg ctc gtc        493
Asp Ala Val Val Val Val Lys Pro Trp Leu Gln Ser Arg Ala Leu Val
    130                 135                 140 agg ttc gcg ccg gcc gac gcc aaa tga gcagttgcat gcgcgatccg              540
Arg Phe Ala Pro Ala Asp Ala Lys  *
145                 150 acgaacttgt gcgccagagt atgcaatgta cactcgaatg gcgaagtgtg agctagagtt      600
gaccgccaga gtatacaggc ggtcaaagtt ttgtaaggtc tcccggataa aaaagttttg      660
cgagaagaga tgagagtggc ggaataaata caatatacga taagaatgtt ttgcctctaa      720
aaaaaaaaaa aaaaaaaaaa aaaaaaaaaa                                       750
```

<210> SEQ ID NO 68
<211> LENGTH: 152
<212> TYPE: PRT
<213> ORGANISM: Triticum aestivum
<220> FEATURE:
<221> NAME/KEY: DOMAIN
<222> LOCATION: (61)...(70)
<223> OTHER INFORMATION: N-terminal alpha-1 helix domain
<220> FEATURE:
<221> NAME/KEY: DOMAIN
<222> LOCATION: (98)...(108)
<223> OTHER INFORMATION: First hairpin loop domain
<220> FEATURE:
<221> NAME/KEY: DOMAIN
<222> LOCATION: (129)...(137)
<223> OTHER INFORMATION: Second hairpin loop domain

<400> SEQUENCE: 68

| Met<br>1 | Ala | Arg | Val | Ile<br>5 | Gly | Ala | Ser | Gly | Ala<br>10 | Cys | Ala | Leu | Leu | Val<br>15 | Val |
|---|---|---|---|---|---|---|---|---|---|---|---|---|---|---|---|
| Leu | Leu | Val | Ala<br>20 | Cys | Ala | Ala | Ser | Ala<br>25 | Ala | Arg | Thr | Glu | Pro<br>30 | Gly | Ala |
| Ala | Arg | Gln<br>35 | Leu | Trp | Glu | Asp | Gly<br>40 | Arg | Lys | Val | Gly | Arg<br>45 | Thr | Glu |
| Val | Arg<br>50 | Asp | Val | Glu | Ser | Asp<br>55 | Arg | Glu | Val | Gln | Glu<br>60 | Leu | Gly | Arg | Tyr |
| Ser<br>65 | Val | Glu | Glu | His | Asn<br>70 | Arg | Arg | Arg | Glu | Glu<br>75 | Gly | Cys | Glu | Gly | Gly<br>80 |
| Gly | Gly | Val | Cys | Gly<br>85 | Arg | Leu | Glu | Phe | Ala<br>90 | Arg | Val | Val | Ser | Ala<br>95 | Gln |
| Arg | Gln | Val | Val<br>100 | Ser | Gly | Ile | Lys | Tyr<br>105 | Tyr | Leu | Arg | Val | Ala<br>110 | Ala | Ala |
| Glu | Glu | Asn<br>115 | Gly | Ala | Gly | Ser | Asn<br>120 | Val | Val | Ser | Asp | Gly<br>125 | Arg | Val | Phe |
| Asp | Ala<br>130 | Val | Val | Val | Val | Lys<br>135 | Pro | Trp | Leu | Gln | Ser<br>140 | Arg | Ala | Leu | Val |
| Arg<br>145 | Phe | Ala | Pro | Ala | Asp<br>150 | Ala | Lys | | | | | | | | |

<210> SEQ ID NO 69
<211> LENGTH: 801
<212> TYPE: DNA
<213> ORGANISM: Triticum aestivum
<220> FEATURE:
<221> NAME/KEY: CDS
<222> LOCATION: (80)...(538)

<400> SEQUENCE: 69

| cagcacagct ccagtactag taagtagcag cacttcatca tcagtgatct agctaagaga | 60 |
|---|---|
| cacacacagt gcacgtgaa atg gct cgg ctg gtc ggt gcc gcc ggc gcg tgc<br>                                Met Ala Arg Leu Val Gly Ala Ala Gly Ala Cys<br>                                 1              5                   10 | 112 |
| gcg ctc ctc gtc atc ctg ctc atg gcg tgc gcg gcg tcc gca gcg cgc<br>Ala Leu Leu Val Ile Leu Leu Met Ala Cys Ala Ala Ser Ala Ala Arg<br>                15                   20                   25 | 160 |
| agc gag cca ggc gcc gcg cgg cag ctg tgg gac gac ggg agg aag gtg<br>Ser Glu Pro Gly Ala Ala Arg Gln Leu Trp Asp Asp Gly Arg Lys Val<br>            30                        35                   40 | 208 |
| ggg gga cgg acg gag gtg acg gac gtg gag ggc gac agg gag gtg cag<br>Gly Gly Arg Thr Glu Val Thr Asp Val Glu Gly Asp Arg Glu Val Gln<br> 45                        50                        55 | 256 |
| gag ctg ggg cga tac tcc gtc gaa gag cac aac cgg cgc cgg gag gag<br>Glu Leu Gly Arg Tyr Ser Val Glu Glu His Asn Arg Arg Arg Glu Glu<br> 60                    65                        70                   75 | 304 |
| ggc tgc gag ggc ggc ggc ggt gtc tgc ggc cgg ctg gag ttc gcc cgc<br>Gly Cys Glu Gly Gly Gly Gly Val Cys Gly Arg Leu Glu Phe Ala Arg<br>                80                   85                   90 | 352 |
| gtg gtg tcg gcg cag cgc cag gtg gtc tcc gga atc aag tac tac ctc<br>Val Val Ser Ala Gln Arg Gln Val Val Ser Gly Ile Lys Tyr Tyr Leu<br>                95                 100                 105 | 400 |
| cgc gtc gcg gcc gcc gag gaa ggt ggc gcg ggg agc aac ggc gtc acc<br>Arg Val Ala Ala Ala Glu Glu Gly Gly Ala Gly Ser Asn Gly Val Thr<br>       110                   115                 120 | 448 |
| gac ggc cgc gtg ttc gac gcc gtg gtg gtc gtg aag ccc tgg ctc cag | 496 |

```
Asp Gly Arg Val Phe Asp Ala Val Val Val Lys Pro Trp Leu Gln
    125                 130                 135 tcc cgc gct ctg atc agg ttc gcg ccg gcc gac gcc aaa tga          538
Ser Arg Ala Leu Ile Arg Phe Ala Pro Ala Asp Ala Lys  *
140                 145                 150 gcagctgcat gcgcgatccg acgagaaccg ctgcgtgtct tctttgcgcg ccagagtacg  598
taatgtaagc tcgaataacg gagtgtgagg taccgaggta gggttgagcg ccagagtatg  658
gagaatgtat gtacgatgcg gcggtcgaag ttttgtgagg tctcccggat aaaaagtttt  718
gcaagaagag atgagagtgt cgaaataaat actaactagt atgacaagac tgttttttcc  778
cctgtaaaaa aaaaaaaaaa aaa                                         801

<210> SEQ ID NO 70
<211> LENGTH: 152
<212> TYPE: PRT
<213> ORGANISM: Triticum aestivum
<220> FEATURE:
<221> NAME/KEY: DOMAIN
<222> LOCATION: (61)...(70)
<223> OTHER INFORMATION: N-terminal alpha-1 helix domain
<220> FEATURE:
<221> NAME/KEY: DOMAIN
<222> LOCATION: (98)...(108)
<223> OTHER INFORMATION: First hairpin loop domain
<220> FEATURE:
<221> NAME/KEY: DOMAIN
<222> LOCATION: (129)...(137)
<223> OTHER INFORMATION: Second hairpin loop domain

<400> SEQUENCE: 70

Met Ala Arg Leu Val Gly Ala Ala Gly Ala Cys Ala Leu Leu Val Ile
1               5                   10                  15

Leu Leu Met Ala Cys Ala Ala Ser Ala Ala Arg Ser Glu Pro Gly Ala
            20                  25                  30

Ala Arg Gln Leu Trp Asp Asp Gly Arg Lys Val Gly Gly Arg Thr Glu
        35                  40                  45

Val Thr Asp Val Glu Gly Asp Arg Glu Val Gln Glu Leu Gly Arg Tyr
    50                  55                  60

Ser Val Glu Glu His Asn Arg Arg Arg Glu Glu Gly Cys Glu Gly Gly
65                  70                  75                  80

Gly Gly Val Cys Gly Arg Leu Glu Phe Ala Arg Val Val Ser Ala Gln
                85                  90                  95

Arg Gln Val Val Ser Gly Ile Lys Tyr Tyr Leu Arg Val Ala Ala Ala
            100                 105                 110

Glu Glu Gly Gly Ala Gly Ser Asn Gly Val Thr Asp Gly Arg Val Phe
        115                 120                 125

Asp Ala Val Val Val Lys Pro Trp Leu Gln Ser Arg Ala Leu Ile
    130                 135                 140

Arg Phe Ala Pro Ala Asp Ala Lys
145                 150

<210> SEQ ID NO 71
<211> LENGTH: 1149
<212> TYPE: DNA
<213> ORGANISM: Triticum aestivum
<220> FEATURE:
<221> NAME/KEY: CDS
<222> LOCATION: (140)...(871)

<400> SEQUENCE: 71
acgagacccc gactccacgc cccttgcgtt gcttacttcg gttccttctc ccttcctcgg  60
```

```
tacagaatcc aaaccccacc cacgcacacg cagtcatcgc gaagcaaagc gaaaccgcaa        120
aggactcctc cggcagagc atg cgc gtt gct gcg acg cgg ccc gcc tcc tcc        172
                    Met Arg Val Ala Ala Thr Arg Pro Ala Ser Ser
                     1               5                  10 gct ccc gtt gcc ctc ctc gcc gct cta gcc ctc ctc ttc ctc gtc ggc         220
Ala Pro Val Ala Leu Leu Ala Ala Leu Ala Leu Leu Phe Leu Val Gly
             15                  20                  25 tcc gcc tcg ctc gcc atc gga gcc atg gcc agc cac gtc ctc ggc ggc         268
Ser Ala Ser Leu Ala Ile Gly Ala Met Ala Ser His Val Leu Gly Gly
         30                  35                  40 aag agc gag aac ccc gac gcg gcc aac agc ctc gag acc gac ggc ctc         316
Lys Ser Glu Asn Pro Asp Ala Ala Asn Ser Leu Glu Thr Asp Gly Leu
     45                  50                  55 gcc cgc ttc gcc gtc gac gag cac aac aag cgc gag aac gcg ctg ctg         364
Ala Arg Phe Ala Val Asp Glu His Asn Lys Arg Glu Asn Ala Leu Leu
 60                  65                  70                  75 gag ttc gta cgg gtc gtg gag gcc aag gag cag acg gtg gcc ggc acg         412
Glu Phe Val Arg Val Val Glu Ala Lys Glu Gln Thr Val Ala Gly Thr
                 80                  85                  90 ctg cac cac ctc acg ctt gag gcg ctt gag gcc ggg cgg aag aag gtg         460
Leu His His Leu Thr Leu Glu Ala Leu Glu Ala Gly Arg Lys Lys Val
             95                 100                 105 tac gag gcc gag gtc tgg gtc aag ccg tgg ctc gac ttc aag gag ctg         508
Tyr Glu Ala Glu Val Trp Val Lys Pro Trp Leu Asp Phe Lys Glu Leu
         110                 115                 120 cag gag ttc cgc cac acc ggg gat gcc acc tcc ttc acc atc tcc gac         556
Gln Glu Phe Arg His Thr Gly Asp Ala Thr Ser Phe Thr Ile Ser Asp
125                 130                 135 ctc ggc gcc aag aga ggg gga cat gag cct gga tgg cgt gat gtg cct         604
Leu Gly Ala Lys Arg Gly Gly His Glu Pro Gly Trp Arg Asp Val Pro
140                 145                 150                 155 gtg cat gat cct gta gtc aaa gat gct gca agc cat gct gtg aaa tca         652
Val His Asp Pro Val Val Lys Asp Ala Ala Ser His Ala Val Lys Ser
                160                 165                 170 atc cag cag agg tcg aat tcc ctt ctc cca tat gaa ctt gtt gaa atc         700
Ile Gln Gln Arg Ser Asn Ser Leu Leu Pro Tyr Glu Leu Val Glu Ile
            175                 180                 185 gtt cgt gca aag gct gag gtg gtt gaa gac ttc gcg aag ttt gat atc         748
Val Arg Ala Lys Ala Glu Val Val Glu Asp Phe Ala Lys Phe Asp Ile
        190                 195                 200 ctc atg aaa ctg aag aga ggg acc aag gag gag aaa atg aaa gcc gag         796
Leu Met Lys Leu Lys Arg Gly Thr Lys Glu Glu Lys Met Lys Ala Glu
205                 210                 215 gtg cat aag aac ctc gag gga gct ttt gtg ctg aac cag atg cag cca         844
Val His Lys Asn Leu Glu Gly Ala Phe Val Leu Asn Gln Met Gln Pro
220                 225                 230                 235 gag cat gac gaa tct agc agc cag tga atctgacttg ttgagctcac               891
Glu His Asp Glu Ser Ser Ser Gln  *
                240 agtaatgtag tttgtactaa gaaataaaca gtaaacctgt ctctacatgg atattatgct       951 ttctgcaccg gcggttgttg aatgaagcac gatggaacta tgtgttcttg ctagctgaac       1011 cttatttggt tgctgttaat ggtggaatgt gcaaccaatc ttgtaactcg agggtaccgt       1071 tggatgcgat atacactgtc aatttcggtt actctgcaat atacactgtc aatttcggtt       1131 aaaaaaaaaa aaaaaaaa                                                     1149

<210> SEQ ID NO 72
```

-continued

```
<211> LENGTH: 243
<212> TYPE: PRT
<213> ORGANISM: Triticum aestivum
<220> FEATURE:
<221> NAME/KEY: DOMAIN
<222> LOCATION: (59)...(68)
<223> OTHER INFORMATION: N-terminal alpha-1 helix domain
<220> FEATURE:
<221> NAME/KEY: DOMAIN
<222> LOCATION: (86)...(96)
<223> OTHER INFORMATION: First hairpin loop domain
<220> FEATURE:
<221> NAME/KEY: DOMAIN
<222> LOCATION: (109)...(117)
<223> OTHER INFORMATION: Second hairpin loop domain

<400> SEQUENCE: 72

Met Arg Val Ala Ala Thr Arg Pro Ala Ser Ser Ala Pro Val Ala Leu
  1               5                  10                  15

Leu Ala Ala Leu Ala Leu Leu Phe Leu Val Gly Ser Ala Ser Leu Ala
             20                  25                  30

Ile Gly Ala Met Ala Ser His Val Leu Gly Gly Lys Ser Glu Asn Pro
         35                  40                  45

Asp Ala Ala Asn Ser Leu Glu Thr Asp Gly Leu Ala Arg Phe Ala Val
     50                  55                  60

Asp Glu His Asn Lys Arg Glu Asn Ala Leu Leu Glu Phe Val Arg Val
 65                  70                  75                  80

Val Glu Ala Lys Glu Gln Thr Val Ala Gly Thr Leu His His Leu Thr
                 85                  90                  95

Leu Glu Ala Leu Glu Ala Gly Arg Lys Lys Val Tyr Glu Ala Glu Val
            100                 105                 110

Trp Val Lys Pro Trp Leu Asp Phe Lys Glu Leu Gln Glu Phe Arg His
        115                 120                 125

Thr Gly Asp Ala Thr Ser Phe Thr Ile Ser Asp Leu Gly Ala Lys Arg
    130                 135                 140

Gly Gly His Glu Pro Gly Trp Arg Asp Val Pro Val His Asp Pro Val
145                 150                 155                 160

Val Lys Asp Ala Ala Ser His Ala Val Lys Ser Ile Gln Gln Arg Ser
                165                 170                 175

Asn Ser Leu Leu Pro Tyr Glu Leu Val Glu Ile Val Arg Ala Lys Ala
            180                 185                 190

Glu Val Val Glu Asp Phe Ala Lys Phe Asp Ile Leu Met Lys Leu Lys
        195                 200                 205

Arg Gly Thr Lys Glu Glu Lys Met Lys Ala Glu Val His Lys Asn Leu
    210                 215                 220

Glu Gly Ala Phe Val Leu Asn Gln Met Gln Pro Glu His Asp Glu Ser
225                 230                 235                 240

Ser Ser Gln

<210> SEQ ID NO 73
<211> LENGTH: 959
<212> TYPE: DNA
<213> ORGANISM: Triticum aestivum
<220> FEATURE:
<221> NAME/KEY: CDS
<222> LOCATION: (64)...(606)

<400> SEQUENCE: 73
cagacagcca ccacacgccg acgccaaact cgccaaccaa tcgaaggctc gggaggagcg      60 acg atg gtc cgc cgc tgc ggc tgc tcc ggt gcc atg ctc ctc gcc ctc      108
```

```
        Met Val Arg Arg Cys Gly Cys Ser Gly Ala Met Leu Leu Ala Leu
        1               5                   10                  15 tcc ctt gcc gtc ctc ctc gcc gcc tcg gcc gtc ccc ggg gcc gcc ggg         156
Ser Leu Ala Val Leu Leu Ala Ala Ser Ala Val Pro Gly Ala Ala Gly
            20                  25                  30 ttc cac ctc ggc ggc gac gag agc ggc ctc gtg cgg ggc atg ctc gcc         204
Phe His Leu Gly Gly Asp Glu Ser Gly Leu Val Arg Gly Met Leu Ala
                35                  40                  45 gcc gtc cgc gag cgg gct gag gcc gag gac gcc gcg cgc ttc gcc gtc         252
Ala Val Arg Glu Arg Ala Glu Ala Glu Asp Ala Ala Arg Phe Ala Val
            50                  55                  60 gcc gag cat aac agg aag cag ggt tct gca ttg gag ttt aca cgg gtt         300
Ala Glu His Asn Arg Lys Gln Gly Ser Ala Leu Glu Phe Thr Arg Val
65                  70                  75 gtg aac gcg aaa agg caa gtg gtt gct ggg acc ttg cat gac ctg atg         348
Val Asn Ala Lys Arg Gln Val Val Ala Gly Thr Leu His Asp Leu Met
80                  85                  90                  95 gtg gag gta gtg gat tct gga aag aaa agt atg tac aag gca aag gtc         396
Val Glu Val Val Asp Ser Gly Lys Lys Ser Met Tyr Lys Ala Lys Val
                100                 105                 110 tgg gtg aag ccg tgg caa aat ttc aag gcg gtt gtc gag ttc cgt cat         444
Trp Val Lys Pro Trp Gln Asn Phe Lys Ala Val Val Glu Phe Arg His
            115                 120                 125 gca ggg gac ttc cag tct gag tct tcc gtt gct tct gat ggt agc act         492
Ala Gly Asp Phe Gln Ser Glu Ser Ser Val Ala Ser Asp Gly Ser Thr
        130                 135                 140 ggg caa gct atc ctc aag ctg tct ctt caa acc gac atg gca cca aag         540
Gly Gln Ala Ile Leu Lys Leu Ser Leu Gln Thr Asp Met Ala Pro Lys
145                 150                 155 atg cac agc aac gag aat act gga ctt tct gtt gac tca tcc tct tct         588
Met His Ser Asn Glu Asn Thr Gly Leu Ser Val Asp Ser Ser Ser Ser
160                 165                 170                 175 cag gca cac acg gtg tga aggttgcttc catagagtat ggaactggaa                636
Gln Ala His Thr Val *
                180 ggcgtgaagg tcggagcatg aggctctgaa atgtagctgc cagcaacctg tgaacttaag       696 tactactagt agtttcccct gtgcaaagtt cttatcctcc gttagtctgt ttaccaaatg       756 gcatctagtg atctagtccc atcgtcatcc gctgttagat agtatactat atgctgtcac       816 acggacatgc tttgagcctt tgacagtttg acgtctgaac tctgtatatt tgttttgaaa       876 catggggact ctgtatattg tattcagttc atgttcaggt atgtacatta aaaaaaaaaa       936 aaaaaaaaaa aaaaaaaaaa aaa                                               959

<210> SEQ ID NO 74
<211> LENGTH: 180
<212> TYPE: PRT
<213> ORGANISM: Triticum aestivum
<220> FEATURE:
<221> NAME/KEY: DOMAIN
<222> LOCATION: (85)...(95)
<223> OTHER INFORMATION: First hairpin loop domain
<220> FEATURE:
<221> NAME/KEY: DOMAIN
<222> LOCATION: (57)...(67)
<223> OTHER INFORMATION: N-terminal alpha-1 helix domain
<220> FEATURE:
<221> NAME/KEY: DOMAIN
<222> LOCATION: (108)...(116)
<223> OTHER INFORMATION: Second hairpin loop domain

<400> SEQUENCE: 74
```

```
Met Val Arg Arg Cys Gly Cys Ser Gly Ala Met Leu Leu Ala Leu Ser
  1               5                  10                  15

Leu Ala Val Leu Leu Ala Ala Ser Ala Val Pro Gly Ala Ala Gly Phe
             20                  25                  30

His Leu Gly Gly Asp Glu Ser Gly Leu Val Arg Gly Met Leu Ala Ala
         35                  40                  45

Val Arg Glu Arg Ala Glu Ala Glu Asp Ala Ala Arg Phe Ala Val Ala
 50                  55                  60

Glu His Asn Arg Lys Gln Gly Ser Ala Leu Glu Phe Thr Arg Val Val
 65                  70                  75                  80

Asn Ala Lys Arg Gln Val Val Ala Gly Thr Leu His Asp Leu Met Val
                 85                  90                  95

Glu Val Val Asp Ser Gly Lys Lys Ser Met Tyr Lys Ala Lys Val Trp
            100                 105                 110

Val Lys Pro Trp Gln Asn Phe Lys Ala Val Val Glu Phe Arg His Ala
        115                 120                 125

Gly Asp Phe Gln Ser Glu Ser Ser Val Ala Ser Asp Gly Ser Thr Gly
    130                 135                 140

Gln Ala Ile Leu Lys Leu Ser Leu Gln Thr Asp Met Ala Pro Lys Met
145                 150                 155                 160

His Ser Asn Glu Asn Thr Gly Leu Ser Val Asp Ser Ser Ser Ser Gln
                165                 170                 175

Ala His Thr Val
            180

<210> SEQ ID NO 75
<211> LENGTH: 518
<212> TYPE: DNA
<213> ORGANISM: Triticum aestivum
<220> FEATURE:
<221> NAME/KEY: CDS
<222> LOCATION: (3)...(386)

<400> SEQUENCE: 75 tc tcg ctc gtg gct gcc ctg ctc ata ctg ctt gcc ctc gcc gta tcg        47
   Ser Leu Val Ala Ala Leu Leu Ile Leu Leu Ala Leu Ala Val Ser
    1               5                  10                  15 tcc acc cgc aac gca cag gag gat tcc atg gcc gac aac acc ggg acg       95
Ser Thr Arg Asn Ala Gln Glu Asp Ser Met Ala Asp Asn Thr Gly Thr
                 20                  25                  30 ttg gcg ggc ggc atc aag gac gtg ccg ggg aac gag aac gac ctt cac      143
Leu Ala Gly Gly Ile Lys Asp Val Pro Gly Asn Glu Asn Asp Leu His
         35                  40                  45 ctc cag gaa ctc gcc cgc ttc gcc gtc gat gag cac aac aag aag gcc      191
Leu Gln Glu Leu Ala Arg Phe Ala Val Asp Glu His Asn Lys Lys Ala
 50                  55                  60 aat gct ctt ctg ggg ttc gag aag ctt gtg aag gcc aag aca caa gtg      239
Asn Ala Leu Leu Gly Phe Glu Lys Leu Val Lys Ala Lys Thr Gln Val
 65                  70                  75 gtt gct ggc acg atg tac tat ctc act att gaa gtg aag gat ggc gaa      287
Val Ala Gly Thr Met Tyr Tyr Leu Thr Ile Glu Val Lys Asp Gly Glu
 80                  85                  90                  95 gtg aag aag ctc tac gaa gct aag gtc tgg gag aag cca tgg gag aac      335
Val Lys Lys Leu Tyr Glu Ala Lys Val Trp Glu Lys Pro Trp Glu Asn
                100                 105                 110 ttc aag gag ctg cag gaa ttc aag cct gtt gaa gag ggt gct agc gcc      383
Phe Lys Glu Leu Gln Glu Phe Lys Pro Val Glu Glu Gly Ala Ser Ala
        115                 120                 125
```

```
taa ggatctctcc ttctccatgt gcgaacctga agctcaaagc aaattgcaag        436
* aataaggagc actccaacat gctagacatg ctcccttgtg taattcataa agactacaac  496
cttttagggc tgttcgtttg tt                                           518
```

```
<210> SEQ ID NO 76
<211> LENGTH: 127
<212> TYPE: PRT
<213> ORGANISM: Triticum aestivum
<220> FEATURE:
<221> NAME/KEY: DOMAIN
<222> LOCATION: (51)...(60)
<223> OTHER INFORMATION: N-terminal alpha-1 helix domain
<220> FEATURE:
<221> NAME/KEY: DOMAIN
<222> LOCATION: (78)...(88)
<223> OTHER INFORMATION: First hairpin loop domain
<220> FEATURE:
<221> NAME/KEY: DOMAIN
<222> LOCATION: (101)...(109)
<223> OTHER INFORMATION: Second hairpin loop domain

<400> SEQUENCE: 76
```

Ser Leu Val Ala Ala Leu Leu Ile Leu Leu Ala Leu Ala Val Ser Ser
 1               5                  10                  15

Thr Arg Asn Ala Gln Glu Asp Ser Met Ala Asp Asn Thr Gly Thr Leu
            20                  25                  30

Ala Gly Gly Ile Lys Asp Val Pro Gly Asn Glu Asn Asp Leu His Leu
        35                  40                  45

Gln Glu Leu Ala Arg Phe Ala Val Asp Glu His Asn Lys Lys Ala Asn
    50                  55                  60

Ala Leu Leu Gly Phe Glu Lys Leu Val Lys Ala Lys Thr Gln Val Val
65                  70                  75                  80

Ala Gly Thr Met Tyr Tyr Leu Thr Ile Glu Val Lys Asp Gly Glu Val
                85                  90                  95

Lys Lys Leu Tyr Glu Ala Lys Val Trp Glu Lys Pro Trp Glu Asn Phe
            100                 105                 110

Lys Glu Leu Gln Glu Phe Lys Pro Val Glu Glu Gly Ala Ser Ala
        115                 120                 125

```
<210> SEQ ID NO 77
<211> LENGTH: 5
<212> TYPE: PRT
<213> ORGANISM: Artificial Sequence
<220> FEATURE:
<223> OTHER INFORMATION: consensus sequence showing glycine residues in
      N-terminal region of plant cysteine proteinases
<220> FEATURE:
<221> NAME/KEY: VARIANT
<222> LOCATION: 2, 4
<223> OTHER INFORMATION: Xaa = any amino acid

<400> SEQUENCE: 77
```

Gln Xaa Val Xaa Gly
 1               5

```
<210> SEQ ID NO 78
<211> LENGTH: 10
<212> TYPE: PRT
<213> ORGANISM: Artificial Sequence
<220> FEATURE:
<223> OTHER INFORMATION: consensus sequence showing N-terminal alpha-1
      helix domain of plant cysteine proteinases
<220> FEATURE:
<221> NAME/KEY: VARIANT
```

```
<222> LOCATION: (4)...(4)
<223> OTHER INFORMATION: Xaa = Phe or Tyr
<220> FEATURE:
<221> NAME/KEY: VARIANT
<222> LOCATION: (6)...(6)
<223> OTHER INFORMATION: Xaa = Val or Ile
<220> FEATURE:
<221> NAME/KEY: VARIANT
<222> LOCATION: 7, 8, 9
<223> OTHER INFORMATION: Xaa = any amino acid

<400> SEQUENCE: 78

Leu Ala Arg Xaa Ala Xaa Xaa Xaa Xaa Asn
 1               5                  10

<210> SEQ ID NO 79
<211> LENGTH: 10
<212> TYPE: PRT
<213> ORGANISM: Artificial Sequence
<220> FEATURE:
<223> OTHER INFORMATION: consensus sequence showing N-terminal alpha-1
      helix domain of plant cysteine proteinases
<220> FEATURE:
<221> NAME/KEY: VARIANT
<222> LOCATION: (1)...(1)
<223> OTHER INFORMATION: Xaa = Leu or Val or Ile
<220> FEATURE:
<221> NAME/KEY: VARIANT
<222> LOCATION: (2)...(2)
<223> OTHER INFORMATION: Xaa = Ala or Gly or Thr
<220> FEATURE:
<221> NAME/KEY: VARIANT
<222> LOCATION: (3)...(3)
<223> OTHER INFORMATION: Xaa = Arg or Lys or Glu
<220> FEATURE:
<221> NAME/KEY: VARIANT
<222> LOCATION: (4)...(4)
<223> OTHER INFORMATION: Xaa = Phe or Tyr
<220> FEATURE:
<221> NAME/KEY: VARIANT
<222> LOCATION: (5)...(5)
<223> OTHER INFORMATION: Xaa = Ala or Ser
<220> FEATURE:
<221> NAME/KEY: VARIANT
<222> LOCATION: (6)...(6)
<223> OTHER INFORMATION: Xaa = Val or Ile
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (8)...(8)
<223> OTHER INFORMATION: Xaa = Glu or Asp or Gln or Val
<220> FEATURE:
<221> NAME/KEY: VARIANT
<222> LOCATION: (9)...(9)
<223> OTHER INFORMATION: Xaa = His or Tyr or Phe or Gln

<400> SEQUENCE: 79

Xaa Xaa Xaa Xaa Xaa Xaa Xaa Xaa Xaa Asn
 1               5                  10

<210> SEQ ID NO 80
<211> LENGTH: 6
<212> TYPE: PRT
<213> ORGANISM: Artificial Sequence
<220> FEATURE:
<223> OTHER INFORMATION: consensus sequence showing first hairpin loop
      domain of plant cysteine proteinases

<400> SEQUENCE: 80

Thr Met Tyr Tyr Ile Thr
 1               5
```

```
<210> SEQ ID NO 81
<211> LENGTH: 6
<212> TYPE: PRT
<213> ORGANISM: Artificial Sequence
<220> FEATURE:
<223> OTHER INFORMATION: consensus sequence showing first hairpin loop
      domain of plant cysteine proteinases

<400> SEQUENCE: 81

Thr Leu Tyr Tyr Leu Thr
1               5

<210> SEQ ID NO 82
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys1

<400> SEQUENCE: 82

Gln Val Val Ala Gly Thr Leu His His Leu Thr
1               5                   10

<210> SEQ ID NO 83
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys2

<400> SEQUENCE: 83

Gln Val Val Ser Gly Thr Leu Tyr Thr Ile Thr
1               5                   10

<210> SEQ ID NO 84
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys3

<400> SEQUENCE: 84

Gln Val Val Ser Gly Thr Leu Tyr Tyr Ile Thr
1               5                   10

<210> SEQ ID NO 85
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys4

<400> SEQUENCE: 85

Gln Val Val Glu Gly Phe Ile Tyr Tyr Ile Thr
1               5                   10

<210> SEQ ID NO 86
<211> LENGTH: 11
<212> TYPE: PRT
```

```
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys5

<400> SEQUENCE: 86

Gln Val Val Ser Gly Thr Asn Tyr Arg Leu Val
 1               5                  10

<210> SEQ ID NO 87
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys6

<400> SEQUENCE: 87

Gln Val Val Ser Gly Met Lys Tyr Tyr Leu Lys
 1               5                  10

<210> SEQ ID NO 88
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys7

<400> SEQUENCE: 88

Gln Val Val Ser Gly Thr Leu Tyr Thr Ile Thr
 1               5                  10

<210> SEQ ID NO 89
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys8

<400> SEQUENCE: 89

Gln Val Val Ser Gly Met Lys Tyr Tyr Leu Lys
 1               5                  10

<210> SEQ ID NO 90
<211> LENGTH: 11
<212> TYPE: PRT
<213> ORGANISM: Glycine max
<220> FEATURE:
<221> NAME/KEY: DOMAIN
<222> LOCATION: (0)...(0)
<223> OTHER INFORMATION: First hairpin loop domain of gm-cys9

<400> SEQUENCE: 90

Gln Val Val Ala Gly Leu Asn Tyr Arg Leu Ser
 1               5                  10

<210> SEQ ID NO 91
<211> LENGTH: 11
<212> TYPE: PRT
<213> ORGANISM: Oryza sativa
<220> FEATURE:
<221> NAME/KEY: DOMAIN
<222> LOCATION: (0)...(0)
```

<223> OTHER INFORMATION: First hairpin loop domain of os-cys1

<400> SEQUENCE: 91

Gln Val Val Ala Gly Thr Leu Tyr Tyr Phe Thr
 1               5                  10

<210> SEQ ID NO 92
<211> LENGTH: 11
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: First hairpin loop domain of os-cys2

<400> SEQUENCE: 92

Gln Val Val Ala Gly Thr Leu His His Leu Thr
 1               5                  10

<210> SEQ ID NO 93
<211> LENGTH: 11
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: First hairpin loop domain of os-cys3

<400> SEQUENCE: 93

Gln Val Val Gly Gly Phe Met His Tyr Leu Thr
 1               5                  10

<210> SEQ ID NO 94
<211> LENGTH: 11
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: First hairpin loop domain of os-cys4

<400> SEQUENCE: 94

Gln Val Val Thr Gly Thr Leu His Asp Leu Met
 1               5                  10

<210> SEQ ID NO 95
<211> LENGTH: 11
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: First hairpin loop domain of os-cys5

<400> SEQUENCE: 95

Gln Val Val Ser Asp Val Ala Tyr Tyr Leu Lys
 1               5                  10

<210> SEQ ID NO 96
<211> LENGTH: 11
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: First hairpin loop domain of os-cys6

<400> SEQUENCE: 96

```
Gln Val Val Ser Gly Met Asn Tyr Arg Leu Val
1               5                   10
```

<210> SEQ ID NO 97
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys1

<400> SEQUENCE: 97

```
Gln Thr Val Ala Gly Thr Met His Tyr Ile Thr
1               5                   10
```

<210> SEQ ID NO 98
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys10

<400> SEQUENCE: 98

```
Gln Thr Val Ala Gly Thr Val His His Leu Thr
1               5                   10
```

<210> SEQ ID NO 99
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys11

<400> SEQUENCE: 99

```
Gln Val Val Ala Gly Thr Leu His Asp Leu Met
1               5                   10
```

<210> SEQ ID NO 100
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys13

<400> SEQUENCE: 100

```
Gln Val Val Ala Gly Thr Met Tyr Tyr Leu Thr
1               5                   10
```

<210> SEQ ID NO 101
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys2

<400> SEQUENCE: 101

```
Gln Thr Val Ala Gly Thr Met His Tyr Ile Thr
1               5                   10
```

```
<210> SEQ ID NO 102
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys3

<400> SEQUENCE: 102

Gln Leu Val Ser Gly Met Asn Tyr Glu Leu Ile
1               5                   10

<210> SEQ ID NO 103
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys4

<400> SEQUENCE: 103

Gln Val Val Ala Gly Cys Met His Tyr Phe Thr
1               5                   10

<210> SEQ ID NO 104
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys6

<400> SEQUENCE: 104

Gln Val Val Ala Gly Cys Met His Tyr Phe Thr
1               5                   10

<210> SEQ ID NO 105
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys8

<400> SEQUENCE: 105

Gln Val Val Ser Gly Ile Lys Tyr Tyr Leu Arg
1               5                   10

<210> SEQ ID NO 106
<211> LENGTH: 11
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: First hairpin loop domain of ta-cys9

<400> SEQUENCE: 106

Gln Val Val Ser Gly Ile Lys Tyr Tyr Leu Arg
1               5                   10

<210> SEQ ID NO 107
<211> LENGTH: 11
<212> TYPE: PRT
<213> ORGANISM: Zea mays
```

```
<220> FEATURE:
<221> NAME/KEY: DOMAIN
<222> LOCATION: (0)...(0)
<223> OTHER INFORMATION: First hairpin loop domain of zm-cys1

<400> SEQUENCE: 107

Gln Val Val Ala Gly Thr Met Tyr Tyr Leu Thr
 1               5                  10

<210> SEQ ID NO 108
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys10

<400> SEQUENCE: 108

Gln Val Val Thr Gly Thr Leu His Asp Leu Ile
 1               5                  10

<210> SEQ ID NO 109
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys11

<400> SEQUENCE: 109

Gln Val Val Ala Gly Thr Asn Tyr Lys Leu Asn
 1               5                  10

<210> SEQ ID NO 110
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys12

<400> SEQUENCE: 110

Gln Val Val Ala Gly Thr Leu His His Leu Thr
 1               5                  10

<210> SEQ ID NO 111
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys13

<400> SEQUENCE: 111

Gln Ile Val Ala Gly Lys Asn Tyr Arg Leu Arg
 1               5                  10

<210> SEQ ID NO 112
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys14
```

```
<400> SEQUENCE: 112

Gln Val Val Ser Gly Leu Lys Tyr Tyr Leu Arg
1               5                   10

<210> SEQ ID NO 113
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys3

<400> SEQUENCE: 113

Gln Val Val Ala Gly Thr Met Tyr Tyr Leu Thr
1               5                   10

<210> SEQ ID NO 114
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys4

<400> SEQUENCE: 114

Gln Val Val Ala Gly Thr Met Tyr Tyr Leu Thr
1               5                   10

<210> SEQ ID NO 115
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys5

<400> SEQUENCE: 115

Gln Val Val Ala Gly Thr Leu His His Leu Thr
1               5                   10

<210> SEQ ID NO 116
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys6

<400> SEQUENCE: 116

Gln Val Val Thr Gly Thr Leu His Asp Leu Ile
1               5                   10

<210> SEQ ID NO 117
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys7

<400> SEQUENCE: 117

Gln Val Val Ser Gly Met Asn Tyr Lys Leu Val
```

<210> SEQ ID NO 118
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys8

<400> SEQUENCE: 118

Gln Val Val Ala Gly Thr Leu His His Phe Thr
 1               5                  10

<210> SEQ ID NO 119
<211> LENGTH: 11
<212> TYPE: PRT
<213> ORGANISM: Zea mays
<220> FEATURE:
<221> NAME/KEY: DOMAIN
<222> LOCATION: (0)...(0)
<223> OTHER INFORMATION: First hairpin loop domain of zm-cys9

<400> SEQUENCE: 119

Gln Val Val Ser Gly Met Asn Tyr Arg Leu Tyr
 1               5                  10

<210> SEQ ID NO 120
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys1

<400> SEQUENCE: 120

Glu Ala Lys Val Trp Val Lys Pro Trp
 1               5

<210> SEQ ID NO 121
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys2

<400> SEQUENCE: 121

Glu Ala Lys Val Trp Glu Lys Ser Trp
 1               5

<210> SEQ ID NO 122
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys3

<400> SEQUENCE: 122

Glu Thr Lys Val Leu Glu Lys Pro Trp
 1               5

<210> SEQ ID NO 123

```
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys4

<400> SEQUENCE: 123

Glu Thr Lys Val Trp Val Arg Ser Trp
 1               5

<210> SEQ ID NO 124
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys5

<400> SEQUENCE: 124

Glu Ala Ile Val Trp Glu Lys Pro Trp
 1               5

<210> SEQ ID NO 125
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys6

<400> SEQUENCE: 125

Thr Ser Val Val Val Val Lys Pro Trp
 1               5

<210> SEQ ID NO 126
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys7

<400> SEQUENCE: 126

Glu Ala Lys Val Trp Glu Lys Ala Trp
 1               5

<210> SEQ ID NO 127
<211> LENGTH: 9
<212> TYPE: PRT
<213> ORGANISM: Glycine max
<220> FEATURE:
<221> NAME/KEY: DOMAIN
<222> LOCATION: (0)...(0)
<223> OTHER INFORMATION: Second hairpin loop domain of gm-cys8

<400> SEQUENCE: 127

Asn Ser Val Val Val Val Lys Pro Trp
 1               5

<210> SEQ ID NO 128
<211> LENGTH: 9
<212> TYPE: PRT
<213> ORGANISM: Glycine max
<220> FEATURE:
```

```
<221> NAME/KEY: DOMAIN
<222> LOCATION: (0)...(0)
<223> OTHER INFORMATION: Second hairpin loop domain of gm-cys9

<400> SEQUENCE: 128

Gln Ala Ile Val Tyr Glu Lys Ala Trp
 1               5

<210> SEQ ID NO 129
<211> LENGTH: 9
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: Second hairpin loop domain of os-cys1

<400> SEQUENCE: 129

Glu Ala Lys Val Trp Glu Lys Pro Trp
 1               5

<210> SEQ ID NO 130
<211> LENGTH: 9
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: Second hairpin loop domain of os-cys2

<400> SEQUENCE: 130

Glu Ala Lys Val Trp Val Lys Pro Trp
 1               5

<210> SEQ ID NO 131
<211> LENGTH: 9
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: Second hairpin loop domain of os-cys3

<400> SEQUENCE: 131

Glu Ala Lys Val Trp Glu Arg Ala Trp
 1               5

<210> SEQ ID NO 132
<211> LENGTH: 9
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: Second hairpin loop domain of os-cys4

<400> SEQUENCE: 132

Ser Ala Lys Val Trp Val Lys Pro Trp
 1               5

<210> SEQ ID NO 133
<211> LENGTH: 9
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: Second hairpin loop domain of os-cys5
```

```
<400> SEQUENCE: 133

Asp Ala Val Val Val Lys Ala Trp
1               5

<210> SEQ ID NO 134
<211> LENGTH: 9
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: Second hairpin loop domain of os-cys6

<400> SEQUENCE: 134

Val Ala Val Val Tyr Glu Gln Ser Trp
1               5

<210> SEQ ID NO 135
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys-1

<400> SEQUENCE: 135

Glu Ala Lys Val Trp Glu Lys Pro Trp
1               5

<210> SEQ ID NO 136
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys10

<400> SEQUENCE: 136

Glu Ala Lys Val Trp Val Lys Pro Trp
1               5

<210> SEQ ID NO 137
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys11

<400> SEQUENCE: 137

Thr Thr Gln Ser Leu Gly Glu Ala Trp
1               5

<210> SEQ ID NO 138
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys13

<400> SEQUENCE: 138

Glu Ala Lys Val Trp Glu Lys Pro Trp
1               5
```

```
<210> SEQ ID NO 139
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys2

<400> SEQUENCE: 139

Glu Ala Lys Val Trp Glu Lys Pro Trp
 1               5

<210> SEQ ID NO 140
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys3

<400> SEQUENCE: 140

Lys Ala Glu Val Tyr Glu Gln Thr Trp
 1               5

<210> SEQ ID NO 141
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys4

<400> SEQUENCE: 141

Glu Ala Lys Val Trp Glu Lys Ala Trp
 1               5

<210> SEQ ID NO 142
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys6

<400> SEQUENCE: 142

Glu Ala Lys Val Trp Glu Lys Ala Trp
 1               5

<210> SEQ ID NO 143
<211> LENGTH: 9
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys8

<400> SEQUENCE: 143

Asp Ala Val Val Val Val Lys Pro Trp
 1               5

<210> SEQ ID NO 144
<211> LENGTH: 9
```

```
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: Second hairpin loop domain of ta-cys9

<400> SEQUENCE: 144

Asp Ala Val Val Val Lys Pro Trp
 1               5

<210> SEQ ID NO 145
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys1

<400> SEQUENCE: 145

Glu Ala Lys Val Trp Glu Lys Pro Trp
 1               5

<210> SEQ ID NO 146
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys10

<400> SEQUENCE: 146

Arg Ala Lys Val Trp Val Lys Ser Trp
 1               5

<210> SEQ ID NO 147
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys11

<400> SEQUENCE: 147

Gln Ala Val Val Phe Asp Pro Leu Pro
 1               5

<210> SEQ ID NO 148
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys12

<400> SEQUENCE: 148

Glu Ala Lys Val Trp Val Lys Pro Trp
 1               5

<210> SEQ ID NO 149
<211> LENGTH: 9
<212> TYPE: PRT
<213> ORGANISM: Zea mays
<220> FEATURE:
<221> NAME/KEY: DOMAIN
```

```
<222> LOCATION: (0)...(0)
<223> OTHER INFORMATION: Second hairpin loop domain of zm-cys13

<400> SEQUENCE: 149

Arg Ala Val Val Tyr Glu Gln Leu Thr
 1               5

<210> SEQ ID NO 150
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys14

<400> SEQUENCE: 150

Asp Ala Val Val Val Lys Pro Trp
 1               5

<210> SEQ ID NO 151
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys3

<400> SEQUENCE: 151

Glu Ala Lys Val Trp Glu Lys Pro Trp
 1               5

<210> SEQ ID NO 152
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys4

<400> SEQUENCE: 152

Glu Ala Lys Val Trp Glu Lys Pro Trp
 1               5

<210> SEQ ID NO 153
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys5

<400> SEQUENCE: 153

Glu Ala Lys Val Trp Val Lys Pro Trp
 1               5

<210> SEQ ID NO 154
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys6

<400> SEQUENCE: 154
```

Arg Ala Lys Val Trp Val Lys Pro Trp
1               5

<210> SEQ ID NO 155
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys7

<400> SEQUENCE: 155

Gly Ala Phe Val Tyr Glu Gln Ser Trp
1               5

<210> SEQ ID NO 156
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys8

<400> SEQUENCE: 156

Glu Ala Lys Val Trp Glu Lys Ala Trp
1               5

<210> SEQ ID NO 157
<211> LENGTH: 9
<212> TYPE: PRT
<213> ORGANISM: Zea mays
<220> FEATURE:
<221> NAME/KEY: DOMAIN
<222> LOCATION: (0)...(0)
<223> OTHER INFORMATION: Second hairpin loop domain of zm-cys9

<400> SEQUENCE: 157

Val Ala Val Val Tyr Glu Gln Val Trp
1               5

<210> SEQ ID NO 158
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys1

<400> SEQUENCE: 158

Leu Ala Arg Phe Ala Val Asp Glu His Asn
1               5                   10

<210> SEQ ID NO 159
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys2

<400> SEQUENCE: 159

Leu Ala Arg Phe Ala Val Glu Glu His Asn
1               5                   10

```
<210> SEQ ID NO 160
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys3

<400> SEQUENCE: 160

Leu Ala Arg Phe Ala Val Asp Glu His Asn
 1               5                  10

<210> SEQ ID NO 161
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys4

<400> SEQUENCE: 161

Leu Ala Arg Phe Ala Val Glu Glu Gln Asn
 1               5                  10

<210> SEQ ID NO 162
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys5

<400> SEQUENCE: 162

Ile Ala Asn Tyr Ala Leu Ser Glu Tyr Asp
 1               5                  10

<210> SEQ ID NO 163
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys6

<400> SEQUENCE: 163

Leu Gly Arg Phe Ala Val Glu Glu Tyr Asn
 1               5                  10

<210> SEQ ID NO 164
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys7

<400> SEQUENCE: 164

Leu Ala Arg Phe Ala Val Glu Glu His Asn
 1               5                  10

<210> SEQ ID NO 165
<211> LENGTH: 10
<212> TYPE: PRT
```

<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys8

<400> SEQUENCE: 165

Leu Gly Arg Phe Ala Val Glu Glu Tyr Asn
 1               5                  10

<210> SEQ ID NO 166
<211> LENGTH: 10
<212> TYPE: PRT
<213> ORGANISM: Glycine max
<220> FEATURE:
<221> NAME/KEY: DOMAIN
<222> LOCATION: (0)...(0)
<223> OTHER INFORMATION: N-terminal alpha-1 helix domain of gm-cys9

<400> SEQUENCE: 166

Ile Ala Asn Phe Ala Val Thr Glu Tyr Asp
 1               5                  10

<210> SEQ ID NO 167
<211> LENGTH: 10
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: N-terminal alpha-1 helix domain of os-cys1

<400> SEQUENCE: 167

Leu Ala Arg Phe Ala Val Thr Glu His Asn
 1               5                  10

<210> SEQ ID NO 168
<211> LENGTH: 10
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: N-terminal alpha-1 helix domain of os-cys2

<400> SEQUENCE: 168

Leu Ala Arg Phe Ala Val Asp Glu His Asn
 1               5                  10

<210> SEQ ID NO 169
<211> LENGTH: 10
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: N-terminal alpha-1 helix domain of os-cys3

<400> SEQUENCE: 169

Leu Ala Arg Phe Ala Val Ala Glu His Asn
 1               5                  10

<210> SEQ ID NO 170
<211> LENGTH: 10
<212> TYPE: PRT
<213> ORGANISM: Oryza sativa
<220> FEATURE:
<221> NAME/KEY: DOMAIN
<222> LOCATION: (0)...(0)

<223> OTHER INFORMATION: N-terminal alpha-1 helix domain of os-cys4

<400> SEQUENCE: 170

Ala Ala Arg Phe Ala Val Ala Glu Tyr Asn
1               5                   10

<210> SEQ ID NO 171
<211> LENGTH: 10
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: N-terminal alpha-1 helix domain of os-cys5

<400> SEQUENCE: 171

Leu Gly Arg Phe Ala Val Ala Glu His Asn
1               5                   10

<210> SEQ ID NO 172
<211> LENGTH: 10
<212> TYPE: PRT
<213> ORGANISM: Oryza sativa
<220> FEATURE:
<221> NAME/KEY: DOMAIN
<222> LOCATION: (0)...(0)
<223> OTHER INFORMATION: N-terminal alpha-1 helix domain of os-cys6

<400> SEQUENCE: 172

Leu Gly Gly Trp Ala Val Glu Arg His Ala
1               5                   10

<210> SEQ ID NO 173
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys1

<400> SEQUENCE: 173

Leu Ala Arg Phe Ala Val Ser Glu His Asn
1               5                   10

<210> SEQ ID NO 174
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys10

<400> SEQUENCE: 174

Ala Ala Arg Phe Ala Val Ala Glu His Asn
1               5                   10

<210> SEQ ID NO 175
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys11
<220> FEATURE:
<221> NAME/KEY: VARIANT
<222> LOCATION: 5

```
<223> OTHER INFORMATION: Xaa = Any Amino Acid

<400> SEQUENCE: 175

Ala Ala Arg Phe Xaa Val Ala Glu His Asn
 1               5                  10

<210> SEQ ID NO 176
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys13

<400> SEQUENCE: 176

Leu Ala Arg Phe Ala Val Asp Glu His Asn
 1               5                  10

<210> SEQ ID NO 177
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys2

<400> SEQUENCE: 177

Leu Ala Arg Phe Ala Val Ser Glu His Asn
 1               5                  10

<210> SEQ ID NO 178
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys3

<400> SEQUENCE: 178

Leu Gly Arg Trp Ala Val Leu Glu Phe Gly
 1               5                  10

<210> SEQ ID NO 179
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys4

<400> SEQUENCE: 179

Leu Ala Arg Phe Ala Val Ala Glu His Asn
 1               5                  10

<210> SEQ ID NO 180
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys6

<400> SEQUENCE: 180
```

-continued

```
Leu Ala Arg Phe Ala Val Ala Glu His Asn
1               5                   10

<210> SEQ ID NO 181
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys8

<400> SEQUENCE: 181

Leu Gly Arg Tyr Ser Val Glu Glu His Asn
1               5                   10

<210> SEQ ID NO 182
<211> LENGTH: 10
<212> TYPE: PRT
<213> ORGANISM: Triticum aestivum
<220> FEATURE:
<221> NAME/KEY: DOMAIN
<222> LOCATION: (0)...(0)
<223> OTHER INFORMATION: N-terminal alpha-1 helix domain for ta-cys9

<400> SEQUENCE: 182

Leu Gly Arg Tyr Ser Val Glu Glu His Asn
1               5                   10

<210> SEQ ID NO 183
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys1

<400> SEQUENCE: 183

Leu Ala Arg Phe Ala Val Asn Glu His Asn
1               5                   10

<210> SEQ ID NO 184
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys10

<400> SEQUENCE: 184

Ala Ala Arg Phe Ala Val Ala His Tyr Asn
1               5                   10

<210> SEQ ID NO 185
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys11

<400> SEQUENCE: 185

Val Gly Glu Trp Ala Val Lys Glu His Asn
1               5                   10
```

```
<210> SEQ ID NO 186
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys12

<400> SEQUENCE: 186

Leu Gly Arg Phe Ala Val Asp Glu His Asn
 1               5                  10

<210> SEQ ID NO 187
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys13

<400> SEQUENCE: 187

Ile Gly Arg Trp Ala Val Ser Glu His Ile
 1               5                  10

<210> SEQ ID NO 188
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys14

<400> SEQUENCE: 188

Leu Gly Arg Phe Ser Val Ala Glu Tyr Asn
 1               5                  10

<210> SEQ ID NO 189
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys3

<400> SEQUENCE: 189

Leu Ala Arg Phe Ala Val Asp Glu His Asn
 1               5                  10

<210> SEQ ID NO 190
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys4

<400> SEQUENCE: 190

Leu Ala Arg Phe Ala Val Asp Glu His Asn
 1               5                  10

<210> SEQ ID NO 191
<211> LENGTH: 10
<212> TYPE: PRT
<213> ORGANISM: Zea mays
```

```
<220> FEATURE:
<221> NAME/KEY: DOMAIN
<222> LOCATION: (0)...(0)
<223> OTHER INFORMATION: N-terminal alpha-1 helix domain for zm-cys5

<400> SEQUENCE: 191

Leu Gly Arg Phe Ala Val Asp Glu His Asn
 1               5                  10

<210> SEQ ID NO 192
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys6

<400> SEQUENCE: 192

Ala Ala Arg Phe Ala Val Ala Tyr His Asn
 1               5                  10

<210> SEQ ID NO 193
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys7

<400> SEQUENCE: 193

Leu Gly Gly Trp Ala Val Thr Glu His Val
 1               5                  10

<210> SEQ ID NO 194
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys8

<400> SEQUENCE: 194

Leu Ala Arg Phe Ala Val Ala Glu His Asn
 1               5                  10

<210> SEQ ID NO 195
<211> LENGTH: 10
<212> TYPE: PRT
<213> ORGANISM: Zea mays
<220> FEATURE:
<221> NAME/KEY: DOMAIN
<222> LOCATION: (0)...(0)
<223> OTHER INFORMATION: N-terminal alpha-1 helix domain for zm-cys9

<400> SEQUENCE: 195

Leu Gly Gly Trp Ala Leu Gly Gln Ala Lys
 1               5                  10
```